US012617814B2

(12) United States Patent
Martinez Botella et al.

(10) Patent No.: US 12,617,814 B2
(45) **Date of Patent: *May 5, 2026**

(54) NEUROACTIVE STEROIDS AND METHODS OF USE THEREOF

(71) Applicant: Sage Therapeutics, LLC, Wilmington, DE (US)

(72) Inventors: Gabriel Martinez Botella, Wayland, MA (US); Boyd L. Harrison, Princeton Junction, NJ (US); Albert Jean Robichaud, Boston, MA (US); Francesco G. Salituro, Marlborough, MA (US)

(73) Assignee: SAGE THERAPEUTICS, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/405,657

(22) Filed: Jan. 5, 2024

(65) Prior Publication Data

US 2024/0287125 A1 Aug. 29, 2024

Related U.S. Application Data

(63) Continuation of application No. 17/381,829, filed on Jul. 21, 2021, now Pat. No. 11,905,309, which is a continuation of application No. 16/227,013, filed on Dec. 20, 2018, now Pat. No. 11,104,701, which is a continuation of application No. 15/917,263, filed on Mar. 9, 2018, now Pat. No. 10,227,375, which is a continuation of application No. 15/588,305, filed on May 5, 2017, now abandoned, which is a continuation of application No. 14/775,678, filed as application No. PCT/US2014/026784 on Mar. 13, 2014, now abandoned.

(60) Provisional application No. 61/779,735, filed on Mar. 13, 2013.

(51) Int. Cl.

| | |
|---|---|
| ***C07J 9/00*** | (2006.01) |
| ***A61K 31/575*** | (2006.01) |
| *C07J 13/00* | (2006.01) |
| *C07J 21/00* | (2006.01) |
| *C07J 41/00* | (2006.01) |

(52) U.S. Cl.

CPC ................. *C07J 9/00* (2013.01); *C07J 9/005* (2013.01); *C07J 13/005* (2013.01); *C07J 13/007* (2013.01); *C07J 21/008* (2013.01); *C07J 41/0061* (2013.01)

(58) Field of Classification Search

CPC ................................ C07J 9/00; A61K 31/575

See application file for complete search history.

(56) References Cited

U.S. PATENT DOCUMENTS

| | | | |
|---|---|---|---|
| 2,259,698 | A | 10/1941 | Johannessohn et al. |
| 2,594,323 | A | 4/1952 | Levin et al. |
| 2,673,206 | A | 3/1954 | Ryer |
| 3,079,385 | A | 2/1963 | Bertin et al. |
| 3,206,459 | A | 9/1965 | Cross |
| 4,071,625 | A | 1/1978 | Grunwell et al. |
| 4,174,345 | A | 11/1979 | Kaiser |
| 4,183,852 | A | 1/1980 | Kaiser |
| 4,358,406 | A | 11/1982 | De Luca et al. |
| 4,868,165 | A | 9/1989 | Ikekawa |
| 5,232,917 | A | 8/1993 | Bolger et al. |
| 5,376,645 | A | 12/1994 | Stella et al. |
| 5,512,570 | A | 4/1996 | Dorn et al. |
| 5,595,996 | A | 1/1997 | Graham et al. |
| 5,843,953 | A | 12/1998 | Tolman et al. |
| 5,888,996 | A | 3/1999 | Farb |
| 5,925,630 | A | 7/1999 | Upasani et al. |
| 6,407,086 | B2 | 6/2002 | Faarup et al. |
| 6,645,953 | B2 | 11/2003 | Gronvald et al. |
| 6,780,853 | B1 | 8/2004 | Upasani et al. |
| 6,884,796 | B2 | 4/2005 | Faarup et al. |
| 6,933,312 | B2 | 8/2005 | Price et al. |
| 8,034,798 | B2 | 10/2011 | Baulieu et al. |

(Continued)

FOREIGN PATENT DOCUMENTS

| | | |
|---|---|---|
| AU | 728843 | 1/2001 |
| CN | 1257077 | 6/2000 |

(Continued)

OTHER PUBLICATIONS

Berardelli et al., "EFNS/MDS-ES/ENS [corrected] recommendations for the diagnosis of Parkinson's disease," European Journal of Neurology, 20(1):16-34 (2013).

(Continued)

*Primary Examiner* — Brenda L Coleman

(74) *Attorney, Agent, or Firm* — Leason Ellis LLP; Karen Mangasarian; Mihaela Diana Danca

(57) ABSTRACT

3beta, 17beta disubstituted steroidal compounds, pharmaceutically acceptable salts thereof, and pharmaceutical compositions thereof, are provided for the prevention and treatment of a variety of CNS-related conditions.

(I)

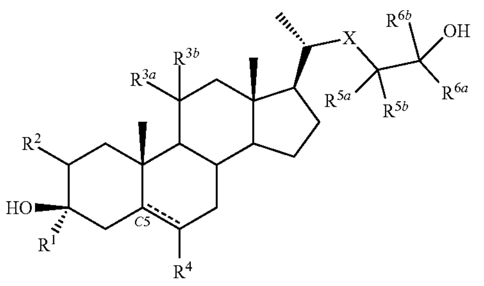

12 Claims, No Drawings

(56) References Cited

U.S. PATENT DOCUMENTS

| | | | |
|---|---|---|---|
| 8,247,436 | B2 | 8/2012 | Baettig et al. |
| 8,604,011 | B2 | 12/2013 | Mellon |
| 8,673,843 | B2 | 3/2014 | Moskal et al. |
| 8,829,213 | B2 | 9/2014 | Peng et al. |
| 10,201,550 | B2 | 2/2019 | Salituro et al. |
| 10,227,375 | B2 | 3/2019 | Botella et al. |
| 10,259,840 | B2 | 4/2019 | Harrison et al. |
| 11,104,701 | B2 | 8/2021 | Botella et al. |
| 11,111,266 | B2 | 9/2021 | Salituro et al. |
| 11,149,054 | B2 | 10/2021 | Salituro et al. |
| 2004/0048838 | A1 | 3/2004 | Gronvald et al. |
| 2005/0101573 | A1 | 5/2005 | Faarup et al. |
| 2006/0142241 | A1 | 6/2006 | Yoo |
| 2006/0199790 | A1 | 9/2006 | Baulieu et al. |
| 2007/0032464 | A1 | 2/2007 | Lia et al. |
| 2007/0292405 | A1 | 12/2007 | Seckl et al. |
| 2008/0193423 | A1 | 8/2008 | Brunton et al. |
| 2008/0269183 | A1 | 10/2008 | Mellon et al. |
| 2008/0319026 | A1 | 12/2008 | Gant et al. |
| 2010/0034781 | A1 | 2/2010 | Parhami et al. |
| 2010/0087411 | A1 | 4/2010 | Barraclough et al. |
| 2010/0330197 | A1 | 12/2010 | Naruto-shi et al. |
| 2011/0112077 | A1 | 5/2011 | Kuduk et al. |
| 2011/0160223 | A1 | 6/2011 | Dingledine et al. |
| 2011/0190249 | A1 | 8/2011 | Rees et al. |
| 2011/0207230 | A1 | 8/2011 | Chung et al. |
| 2012/0035156 | A1 | 2/2012 | Alberati et al. |
| 2012/0040916 | A1 | 2/2012 | Moon et al. |
| 2012/0041016 | A1 | 2/2012 | Frincke |
| 2012/0115169 | A1 | 5/2012 | Mullenix et al. |
| 2013/0210792 | A1 | 8/2013 | Song et al. |
| 2014/0045943 | A1 | 2/2014 | Khan et al. |
| 2014/0148412 | A1 | 5/2014 | Hogenkamp |
| 2014/0235600 | A1 | 8/2014 | Covey et al. |
| 2014/0335050 | A1 | 11/2014 | Haggerty et al. |
| 2015/0158903 | A1 | 6/2015 | Upasani et al. |
| 2015/0291654 | A1 | 10/2015 | Upasani et al. |
| 2015/0376225 | A1 | 12/2015 | Dugar et al. |
| 2016/0022701 | A1 | 1/2016 | Reddy et al. |
| 2016/0031930 | A1 | 2/2016 | Botella et al. |
| 2016/0083418 | A1 | 3/2016 | Martinez et al. |
| 2017/0247405 | A1 | 8/2017 | Harrison et al. |
| 2017/0304321 | A1 | 10/2017 | Quirk et al. |
| 2017/0342103 | A1 | 11/2017 | Upasani et al. |
| 2018/0194797 | A1 | 7/2018 | Salituro et al. |
| 2018/0200267 | A1 | 7/2018 | Salituro et al. |
| 2018/0201643 | A1 | 7/2018 | Salituro et al. |
| 2018/0371009 | A1 | 12/2018 | Pellicciari et al. |
| 2019/0125764 | A1 | 5/2019 | Salituro et al. |
| 2019/0160078 | A1 | 5/2019 | Masuoka et al. |
| 2019/0233465 | A1 | 8/2019 | Robichaud et al. |
| 2019/0248829 | A1 | 8/2019 | Salituro et al. |
| 2019/0330259 | A1 | 10/2019 | Robichaud et al. |
| 2019/0359646 | A1 | 11/2019 | Botella et al. |
| 2020/0002371 | A1 | 1/2020 | Salituro et al. |
| 2020/0024300 | A1 | 1/2020 | Salituro et al. |
| 2020/0123195 | A1 | 4/2020 | Salituro et al. |

FOREIGN PATENT DOCUMENTS

| | | | |
|---|---|---|---|
| CN | 1254716 | | 5/2008 |
| CN | 111825735 | A | 10/2020 |
| FR | 2850023 | | 7/2004 |
| GB | 1564806 | | 4/1980 |
| JP | 50140435 | | 11/1975 |
| JP | 53082766 | | 7/1978 |
| JP | 54163565 | | 12/1979 |
| JP | 57035597 | | 2/1982 |
| JP | 61254599 | | 11/1986 |
| JP | 62187485 | | 8/1987 |
| JP | 08268917 | | 10/1996 |
| JP | 09328498 | | 12/1997 |
| JP | H11509844 | A | 8/1999 |
| JP | 2005508368 | | 3/2005 |
| JP | 2009545535 | | 12/2009 |
| RU | 2194712 | C2 | 12/2002 |
| RU | 2458065 | C2 | 8/2012 |
| RU | 2665571 | | 8/2018 |
| WO | WO1980002562 | | 11/1980 |
| WO | WO1989002272 | | 3/1989 |
| WO | WO1994027608 | | 12/1994 |
| WO | WO1995002409 | | 1/1995 |
| WO | WO1995013287 | | 5/1995 |
| WO | WO1995021617 | | 8/1995 |
| WO | WO1996012705 | | 5/1996 |
| WO | WO1996016076 | | 5/1996 |
| WO | WO1996040043 | | 12/1996 |
| WO | WO1996040151 | | 12/1996 |
| WO | WO1997000884 | | 1/1997 |
| WO | WO1997003677 | | 2/1997 |
| WO | WO1997042215 | | 11/1997 |
| WO | WO1998005337 | | 2/1998 |
| WO | WO1998007740 | | 2/1998 |
| WO | WO1999058497 | | 11/1999 |
| WO | WO2000063228 | | 10/2000 |
| WO | WO2000066614 | | 11/2000 |
| WO | WO2000068246 | | 11/2000 |
| WO | WO2001049703 | | 7/2001 |
| WO | WO2002011708 | | 2/2002 |
| WO | WO2002053577 | | 7/2002 |
| WO | WO2002079221 | | 10/2002 |
| WO | WO2002090375 | | 11/2002 |
| WO | WO2003039480 | | 5/2003 |
| WO | WO2003049685 | | 6/2003 |
| WO | WO2003082893 | | 10/2003 |
| WO | WO2004055201 | | 7/2004 |
| WO | WO2005079810 | | 9/2005 |
| WO | WO2008041003 | | 4/2008 |
| WO | WO2008063128 | | 5/2008 |
| WO | WO2009001097 | | 12/2008 |
| WO | WO2009059239 | | 5/2009 |
| WO | WO2009059961 | | 5/2009 |
| WO | WO2009073186 | | 6/2009 |
| WO | WO2009090063 | | 7/2009 |
| WO | WO2010075282 | | 7/2010 |
| WO | WO2010088414 | | 8/2010 |
| WO | WO2011014661 | | 2/2011 |
| WO | WO2011028794 | | 3/2011 |
| WO | WO2011067501 | | 6/2011 |
| WO | WO2011092127 | | 8/2011 |
| WO | WO2012064501 | | 5/2012 |
| WO | WO2012142039 | | 10/2012 |
| WO | WO2013019711 | | 2/2013 |
| WO | WO2013036835 | | 3/2013 |
| WO | WO2013054822 | | 4/2013 |
| WO | WO2013056181 | | 4/2013 |
| WO | WO2013163455 | | 10/2013 |
| WO | WO2014025942 | | 2/2014 |
| WO | WO2014115167 | | 7/2014 |
| WO | WO2014120786 | | 8/2014 |
| WO | WO2014160441 | | 10/2014 |
| WO | WO2014160480 | | 10/2014 |
| WO | WO2015195967 | | 12/2015 |
| WO | WO2016007762 | | 1/2016 |
| WO | WO2016057713 | | 4/2016 |
| WO | WO2017007832 | | 1/2017 |
| WO | WO2017007836 | | 1/2017 |
| WO | WO2017007840 | | 1/2017 |
| WO | WO2017037465 | | 3/2017 |
| WO | WO2017173358 | | 10/2017 |
| WO | WO2018064649 | | 4/2018 |
| WO | WO2018075698 | | 4/2018 |
| WO | WO2018075699 | | 4/2018 |
| WO | WO2018170336 | | 9/2018 |

OTHER PUBLICATIONS

Berge et al., "Pharmaceutical salts," Journal of Pharmaceutical Sciences, 66(1):1-19 (1977).

Bjorkhem et al., "Oxysterols in the circulation of patients with the Smith-Lemli-Opitz syndrome: abnormal levels of 24S- and 27-hydroxycholesterol," Journal of Lipid Research, 42(3):366-371 (2001).

(56) References Cited

OTHER PUBLICATIONS

Bukelis et al., "Smith-Lemli-Opitz syndrome and autism spectrum disorder," American Journal of Psychiatry, 164(11):1655-1661 (2007).
Cais et al., "Temperature dependence of NR1/NR2B NMDA receptor channels," Neuroscience, 151(2):428-438 (2008).
Cancer [online], [retrieved on Jul. 6, 2007]. Retrieved from the internet, URL http://www.nlm.nih.gov/medlineplus/ cancer.html> (11 pages).
Chen et al., "The chemical biology of clinically tolerated NMDA receptor antagonists," Journal of Neurochemistry, 97(6):1611-1626 (2006).
Citraro et al., "Effects of some neurosteroids injected into some brain areas of WAG/Rij rats, an animal model of generalized absence epilepsy," Neuropharmacology, 50(8):1059-1071 (2006).
Collingridge et al., "The NMDA receptor as a target for cognitive enhancement," Neuropharmacology, 64:13-26 (2013).
Connick et al., "Program No. 613 1/B86," 2009 Neuroscience Meeting Planner, Chicago, IL: Society for Neuroscience (2009) (2 pages).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metabolism and Disposition, 37(10):2069-2078 (2009).
Corman et al., "Structure-activity relationships for side chain oxysterol agonists of the hedgehog signaling pathway," ACS Medicinal Chemistry Letters, 3(10):828-833 (2012).
Costa et al., "A novel family of negative and positive allosteric modulators of NMDA receptors," Journal of Pharmacology and Experimental Therapeutics, 335(3):614-621 (2010).
Cross et al., "Steroids CCLXXIN[1]. Biologically-active labile ethers IV[2]. The synthesis of 22-oxa-25-azacholesterol and related compounds," Steroids, 5(5):585-598 (1965).
Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).
Dayal et al., "Stereospecific synthesis of 3 beta-hydroxylated bile alcohols," Journal of Lipid Research, 25(6):646-650 (1984).
Deng et al., "Fluoro analogs of bioactive oxy-steroids: Synthesis of an $EBI_2$ agonist with enhanced metabolic stability," Bioorganic and Medicinal Chemistry Letters, 26(2):4888-4891 (2016).
Domasio, "Alzheimer's disease and related dementias," Cecil Textbook of Medicine, 20th edition, 2:1992-1996 (1996).
Dubois et al., "Research criteria for the diagnosis of Alzheimer's disease: revising the NINCDS-ADRDA criteria," Lancet Neurology, 6(8):734-746 (2007).
Dubois et al., "Revising the definition of Alzheimer's disease: a new lexicon," Lancet Neurology, 9(11):1118-27 (2010).
EESR for European Application No. 14774060.9, dated Aug. 17, 2016 (11 pages).
EESR for European Application No. 14775126.7, dated Sep. 14, 2016 (7 pages).
EESR for European Application No. 14775126.7, Dec. 15, 2016 (7 pages).
EESR for European Application No. 15809462.3, dated Nov. 29, 2017 (8 pages).
EESR for European Application No. 15849514.3, dated May 23, 2018 (7 pages).
EESR for European Application No. 16821920.2, dated Jan. 31, 2019 (12 pages).
EESR for European Application No. 16821924.4, dated Jan. 31, 2019 (12 pages).
EESR for European Application No. 16821926.9, dated Jan. 31, 2019 (10 pages).
Elbarbry et al., "Cyclosporine-induced changes in drug metabolizing enzymes in hyperlipemic rabbit kidneys could explain its toxicity," Xenobiotica, 40(11):772-781 (2010).
FDA mulls drug to slow late-stage Alzheimer's [online] (cnn.com/health), [retrieved on Sep. 23, 2003]. Retrieved from the Internet, URL; http://www.cnn.com/2003/HEALTH/conditions/09/24/alzheimers.drug.ap/indexhtml> (2 pages).
Ferriz et al., "Prodrug Design of Phenolic Drugs", Current Pharmaceutical Designs 16: 2033-2052 (2010).
Festa et al., "Exploitation of cholane scaffold for the discovery of potent and selective farnesoid X receptor (FXR) and G-protein coupled bile acid receptor 1 ($GP-BAR_1$) ligands," Journal of Medicinal Chemistry, 57(20):8477-8495 (2014).
Foster et al., "Effect of steroids on beta-adrenoceptor-mediated relaxation of pig bronchus," British Journal of Pharmacology, 78(2):441-445 (1983).
Fukuto et al., "Determination of the Mechanism of Demethlenation of (methylenedioxy)phenyl compounds by cytochrome P450 using deuterium isotope effects," Journal of Medicinal Chemistry, 34(9):2871-2876 (1991).
Gee et al., "GABA-dependent modulation of the Cl-ionophore by steroids in rat brain," European Journal of Pharmacology, 136(3):419-423 (1987).
Golub et al., "Molecular classification of cancer: class discovery and class prediction by gene expression monitoring," Science, 286(5439):531-537 (1999).
Groden et al., "Determination of Fura-2 dissociation constants following adjustment of the apparent Ca-EGTA association constant for temperature and ionic strength," Cell Calcium, 12(4):279-287 (1991).
Grynkiewicz et at., "A new generation of Ca2+ indicators with greatly improved fluorescence properties," Journal of Biological Chemistry, 260(6):3440-3345 (1985).
Gunatilaka et al., "Bioactive ergost-5-ene-3 beta, 7 alpha-diol derivatives from *Pseudobersama mossambicensis,*" Journal of Natural Products, 55(11):1648-1654 (1992).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistry, 50(23):4508-4514 (1985).
Hoffmeister et al., "Zur chemie des ecdysons, III: Vergleichende spektrometrische untersuchungen an a.b-ungesättigten steroidketonen," Chemische Berichte, 98(7):2361-2375 (1965).
Hogg et al., "An automated system for intracellular and intranuclear injection," Journal of Neuroscience, Methods, 169(1):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs—from serendipity to rational design," Pharmacological Reviews, 63(3):750-771 (2011).
Iida et al., "An improved method for the capillary gas chromatographic derivatization of polyhydroxylated steroids having tert-hydroxyl groups," Analytical Sciences, 19(9):1317-1321 (2003).
Iida et al., "Preparation of glycine-conjugated bile acids and their gas/liquid chromatographic analysis on an aluminum-clad flexible fused silica capillary column," Biomed Chromatography, 6(1):4-8 (1992).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jack et al., "Hypothetical model of dynamic biomarkers of the Alzheimer's pathological cascade," Lancet Neurology, 9(1):119-128 (2010).
Jack et al., "Introduction to the recommendations from the National Institute on Aging-Alzheimer's Association workgroups on diagnostic guidelines for Alzheimer's disease," Alzheimer's & Dementia, 7(3):257-62 (2011).
Jurman et al., "Visual identification of individual transfected cells for electrophysiology using antibody-coated beads," Biotechniques, 17(5):876-881 (1994).

(56) References Cited

OTHER PUBLICATIONS

Karaki et al., "Structure-activity relationship studies of Niemann-Pick type C1-like 1 (NPC1L1) ligands identified by screening assay monitoring pharmacological chaperone effect," Bioorganic and Medicinal Chemistry, 21(17):5297-5309 (2013).
Khripach et al., "Synthesis of (24S)-hydroxy-and (24S)-24,25-epoxycholesterol analogues, potential agonists of nuclear LXR receptors," Russian Journal of Bioorganic Chemistry, 32(6):586-594 (2006).
Knoppert et al., "Position paper: Paediatric age categories to be used in differentiating between listing on a model essential medicines list for children," pp. 1-5 (2007).
Kurosawa et al., "Synthesis of 19-hydroxylated bile acids and identification of 3 alpha,7 alpha,12 alpha,19-tetrahydroxy-5 beta-cholan-24oic acid in human neonatal urine," Chemical and Pharmaceutical Bulletin, 43(9):1551-1557 (1995).
Lakhan et al., "NMDA receptor activity in neuropsychiatric disorders," Frontiers in Psychiatry, 4:1-7 (2013).
Lala et al., "Role of nitric oxide in tumor progression: Lessons from experimental tumors," Cancer and Metastasis Reviews, 17(1):91-106 (1998).
Layzer, "Section five-degenerative diseases of the nervous system," Cecil Textbook of Medicine, 20th edition, 2:2050-2057 (1996).
Leoni et al., "Changes in human plasma levels of the brain specific oxysterol 24S-hydroxycholesterol during progression of multiple sclerosis," Neuroscience Letters, 331(3):163-166 (2002).
Leoni et al., "Oxysterols as biomarkers in neurodegenerative diseases," Chemistry and Physics of Lipids, 164(6):515-524 (2011).
Lettré et al., "Mehrwertige alkohole aus sterinen und sterinderivaten, VI Steroide mit strukturmerkmalen des ecdysons und der elatericine," Justus Liebigs Annalen der Chemie, 758:89-110 (1972) (English Abstract).
Li et al., "Synthesis of 7alpha-hydroxy derivatives of regulatory oxysterols," Steroids, 65(9):529-535 (2000).
Linsenbardt et al., "Different oxysterols have opposing actions at N-methyl-D-aspartate receptors," Neuropharmacology, 85:232-242 (2014).
Litvan et al., "Diagnostic criteria for mild cognitive impairment in Parkinson's disease: Movement Disorder Society Task Force guidelines," Movement Disorders, 27(3):349-56 (2012).
Litvan et al., "MDS Task Force on mild cognitive impairment in Parkinson's disease: critical review of PD-MCI," Movement Disorders, 26(10):1814-1824 (2011).
Lutjohann et al., "Cholesterol homeostasis in human brain: evidence for an age-dependent flux of 24S-hydroxycholesterol from the brain into the circulation," PNAS, 93(18):9799-804 (1996).
Luu et al., "Oxysterols: Old Tale, New Twists," Annual Review of Pharmacology and Toxicology, 56:447-467 (2016).
Madau et al, Program No. 613.2/B87. 2009 Neuroscience Meeting Planner. Chicago, IL: Society for Neuroscience (2009) (3 pages).
Magyar et al., "Stereoselective reactions of (20R)-3,20-dihydroxy-(3',4'-dihydro-2'H-pyranyl)-5-pregnene derivatives form 27-nor-3,20,23,26-tetrahydroxy-cholesten-22-ones and related bromo ketones," Steroids, 69(1):35-42 (2004).
Mateos et al., "Activity-regulated cytoskeleton-associated protein in rodent brain is down regulated by high fat diet in vivo and by 27-hydroxycholesterol in vitro," Brain Pathology, 19(1):69-80 (2009).
Meljon et al., "Analysis by liquid chromatography-mass spectrometry of sterols and oxysterols in brain of the newborn Dher7(Δ3-5/T93M) mouse: a model of Smith-Lemli-Opitz syndrome," Biochemical Pharmacology, 86(1):43-55 (2013).
Monyer et al., "Heteromeric NMDA receptors: molecular and functional distinction of subtypes," Science, 256(5060):1217-1221 (1992).
Mourino et al., "Studies on vitamin D (calciferol) and its analogs. 15. 24-nor-1a,25-dihydroxyvitamin D3 and 24-nor-25-hydroxy-5,6-trans-vitamin D3," Journal of Medicinal Chemistry, 21(10):1025-1029 (1978).
Nagano et al., "Chemistry and biochemistry of Chinese drugs. Part II. Hydroxylated sterols, cytotoxic towards cancerous cells: synthesis and testing," Journal of Chemical Research, 9:218 (1977).
Nagasaka et al., "Oxysterol changes along with cholesterol and vitamin D changes in adult phenylketonuric patients diagnosed by newborn mass-screening," Clinica Chimica Acta, 416:54-59 (2013).
Nasreddine et al., "The Montreal Cognitive Assessment, MoCA: a brief screening tool for mild cognitive impairment," Journal of the American Geriatrics Society, 53(4):695-699 (2005).
Niemann-Pick diagnosis-treatment [online] retrieved from the internet on Jul. 17, 2021 (URL: https://www.mayoclinic.org/diseases-conditions/niemann-pick/diagnosis-treatment/drc-20355890) (2 pages).
Niemann-Pick overview [online] retrieved from the internet on Jul. 17, 2021 (URL: https://www.mayoclinic.org/diseases-conditions/niemann-pick/symptoms-causes/syc-20355887) (4 pages).
Olkkonen et al., "Oxysterols and their cellular effectors," Biomolecules, 2(1):76-103 (2012).
Papassotiropoulos, et al., "Plasma 24S-hydroxycholesterol a peripheral indicator of neuronal degeneration and potential state marker for Alzheimer's disease", NeuroReport 11(9): 1959-1962 (2000).
Park-Chung et al., "Distinct sites for inverse modulation of N-methyl-D-aspartate receptors by sulfated steroids," Molecular Pharmacology, 52(6):1113-1123 (1997).
Paul et al., "The major brain cholesterol metabolite 24(S)-hydroxycholesterol is a potent allosteric modulator of N-methyl-D-aspartate receptors," The Journal of Neuroscience, 33(44):17290-17300 (2013).
PCT International Search Report and Written Opinion for corresponding International Application No. PCT/US2012/054261, dated Nov. 28, 2012 (10 pages).
PCT International Search Report and Written Opinion for corresponding International Application No. PCT/US2014/026633, dated Jul. 14, 2014 (6 pages).
PCT International Search Report and Written Opinion for corresponding International Application No. PCT/US2014/026784, dated Jul. 8, 2014 (13 pages).
PCT International Search Report and Written Opinion for corresponding International Application No. PCT/US2015/036510, dated Sep. 15, 2015 (7 pages).
PCT International Search Report and Written Opinion for corresponding International Application No. PCT/US2015/054551, dated Jan. 8, 2016 (10 pages).
PCT International Search Report and Written Opinion for corresponding International Application No. PCT/US2016/041160, dated Oct. 28, 2016 (7 pages).
PCT International Search Report and Written Opinion for corresponding International Application No. PCT/US2016/041168, dated Sep. 15, 2016 (6 pages).
PCT International Search Report and Written Opinion for corresponding International Application No. PCT/US2016/041175, dated Sep. 16, 2016 (6 pages).
PCT International Search Report and Written Opinion for corresponding International Application No. PCT/US2017/025535, dated Jul. 3, 2017 (7 pages).
PCT International Search Report and Written Opinion for corresponding International Application No. PCT/US2017/031374, dated Aug. 14, 2017 (8 pages).
PCT International Search Report and Written Opinion for corresponding International Application No. PCT/US2017/041199, dated Aug. 29, 2017 (12 pages).
PCT International Search Report and Written Opinion for corresponding International Application No. PCT/US2017/054657, dated Nov. 21, 2017 (18 pages).
PCT International Search Report and Written Opinion for corresponding International Application No. PCT/US2017/057276, dated Dec. 11, 2017 (13 pages).
PCT International Search Report and Written Opinion for corresponding International Application No. PCT/US2017/057277, dated Feb. 20, 2018 (19 pages).
PCT Invitation to Correct Fees and Partial International Search Report and Provisional Opinion for corresponding International Application No. PCT/US2017/057277, dated Dec. 20, 2017 (13 pages).

(56) References Cited

OTHER PUBLICATIONS

Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883):1306-1308 (1988).
Pubchem, CID 00065094, 25-Hydroxycholesterol, Nov. 18, 2016 (17 pages).
Pubchem, CID 0132021, Ergostan-3,24-diol, Mar. 5, 2018 (15 pages).
Pubchem, CID 54083335, Schembl4961477, Nov. 8, 2016 (13 pages).
Pubchem, CID 54160779, Schembl4961477, Nov. 8, 2016 (13 pages).
Pubchem, CID 58455549, Schembl12198161, Nov. 8, 2016 (13 pages).
Pubchem, CID 66966798, Cholane-3alpha,24,-diol, Nov. 8, 2016 (11 pages).
Pubchem, CID 70604305, Schembl11528874, Nov. 8, 2016 (13 pages).
Pubchem, CID 71508953, Mar. 5, 2018 (13 pages).
Reddy, "Pharmacology of endogenous neuroactive steroids," Critical Reviews in Neurobiology, 15(3-4):197-234 (2013).
Registry (STN) [online] CAS Registration No. 1392266-35-1; 13392266-34-0; 1271523-00-2; 185138-08-3; 185138-00-5; 1851387-82-0; 66450-87-1 (2012).
Roh et al., "Neuroprotective effects of ginsenoside Rg3 against 24-OH-cholesterol-induced cytotoxicity in cortical neurons," Journal of Ginseng Research, 34(3):246-253 (2010).
Schmidt et al., "Inhibitory effect of oxygenated cholestan-3b-ol derivatives on the growth of *Mycobacterium tuberculosis,*" Bioorganic & Medicinal Chemistry Letters, 23(22):6111-6113 (2013).
Segal, "Pat hippocampal Neurons in Culture: Responses to Electrical and Chemical Stimuli," Journal of Neurophysiology, 50(6):1249-1264 (1983).
Sepe et al., "Total synthesis and pharmacological characterization of solomonsterol A, a potent marine pregnane-X-receptor agonist endowed with anti-inflammatory activity," Journal of Medicinal Chemistry, 54:4590-4599 (2011).
Solomon, et al., "Plasma levels of 24S-hydroxycholesterol reflect brain volumes in patients without objective cognitive impairment but not in those with Alzheimer's disease", Neuroscience Letters 462(1): 89-93 (2009).
Stamp et al., "Plasma levels and therapeutic effect of 25-hydroxycholecalciferol in epileptic patients taking anticonvulsant drugs," British Medical Journal 4(5831): 9-12 (1972).
Stastna et al., "Synthesis of C3, C5, and C7 pregnane derivatives and their effect on NMDA receptor responses in cultured rat hippocampal neurons," Steroids, 74(2):256-263 (2008).
Steinrauf et al., "Synthesis and evaluation of sulfur-containing steroids against methylmercuric chloride toxicity," Journal of Pharmaceutical Sciences, 67(12):1739-1743 (1978).
Svoboda et al., "Treatment of Smith-Lemli-Opitz syndrome and other sterol disorders," American Journal of Medical Genetics Part C: Seminars in Medical Genetics, 160C(4): 285-294 (2012).
Takahashi et al., "Stereochemistry of reduction of the C-24,25 double bond in the conversion of desmosterol into cholesterol," Tetrahedron Letters, 44(2):341-344 (2003).
Takano et al., "Simple synthesis of 3b,24-dihydroxychol-5-en-7-one by oxidative cleavage of the side chain of cholesterol," Chemistry Letters, 14(8):1265-1266 (1985).
Tierney et al., "Abnormalities of cholesterol metabolism in autism spectrum disorders," American Journal of Medical Genetics Part B: Neuropsychiatric Genetics, 141B(6):666-668 (2006).
Tomek et al., "NMDA receptor modulators in the treatment of drug addiction," Pharmaceuticals (Basel), 6(2):251-258 (2013).
Verdoorn et al., "Functional properties of recombinant rat GABAA receptors depend upon subunit composition," Neuron, 4(6):919-928 (1990).
Vyklicky et al., "Calcium-mediated modulation of N-methyl-D-aspartate (NMDA) responses in cultured rat hippocampal neurones," Journal of Physiology, 470:575-600 (1993).
Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).
Wilen et al., "Strategies in Optical Resolutions," Tetrahedron, 33:2725-2736 (1977).
Wolozin et al., "The cellular biochemistry of cholesterol and statins: Insights into the pathophysiology and therapy of Alzheimer's disease," CNS Drug Review, 10(2):127-146 (2004).
Wong et al., "An efficient and convenient transformation of a-haloketones to a-hydroxyketones using cesium formate," Journal of Organometallic Chemistry, 694(21):3452-3455 (2004).
Xiangdong et al., "Highly stereoselective synthesis of 24R,25- and 24S, 25-dihydroxysteroid," Database Chemical Abstracts Service, Database accession No. 2001:174431 (2000) (4 pages).
Xilouri et al., "Neuroprotective effects of steroid analogues on P19-N neurons," Neurochemistry International, 50(4):660-670 (2007).
Yang et al., "New cytotoxic oxygenated sterols from marine bryozoan *Bugula neritina,*" Natural Product Research, 25(16):1505-1511 (2011).
Zhou et al., "Properties of HERG channels stably expressed in HEK 293 cells studied at physiological temperature," Biophysical Journal, 74(1):230-241 (1998).
Zuliani et al., "Plasma 24S-hydroxycholesterol levels in elderly subjects with late onset Alzheimer's disease or vascular dementia: a case-control study," BMC Neurology 11(121): 1-8 (2011).
Bjorkhem et al., "Oxysterols and Alzheimer's disease," Acta Neurologica Scandinavica, 114(Suppl. 195):43-49 (2006).
Eguchi et al., "Synthesis and determination of configuration of natural 25-hydroxyvitamin D3 26,23-lactone," PNAS, 78(11):6579-6583 (1981).
Eguchi et al., "Synthesis of Four Isomers of 25-Hydroxyvitamin D3-26,23-Lactone," Hetercyles, 17:359-375 (1982).
Guntert et al., "Synthese eines homologen steroidischen 17-Pyrrolinons Partialsynthetische Versuche in der Reihe der Herzgifte, 9. Mitteilung," Helvetica Chimica Acta, 59(6)2138-2148 (1976).
Koizumi et al., "Stereoselective Introduction of Hydroxy Groups into the Cholesterol Side Chain. Preparation of (24R)- and (24S)-24,25-Dihydroxy- and (25R)- and (25S)-25,26-Dihydroxyvitamin D3 by Asymmetric Synthesis," Journal of the Chemical Society, Perkin Transactions 1:1401-1410 (1983).
Koldamova et al., "22R-Hydroxycholesterol and 9-cis-Retinoic Acid Induce ATP-binding Cassette Transporter Al Expression and Cholesterol Efflux in Brain Cells and Decrease Amyloid Beta Secretion," Journal of Biological Chemistry, 278(15):13244-13256 (2003).
Matsumori et al., "An amphotericin B-ergosterol covalent conjugate with powerful membrane permeabilizing activity," Chemistry & Biology, 11(5):673-679 (2004).
Morisaki et al, "Nutritional effect of possible intermediates of phytosterol dealkylation in the silkworm, Bombyx Mori," Steroids, 24(2):165-176 (1974).
Schubring et al., "The bile steroid chenodeoxycholate is a potent antagonist at NMDA and GABAA receptors," Neuroscience Letters, 506(2):322-326 (2012).
Bretillon et al., "Plasma levels of 24S-hydroxycholesterol in patients with neurological diseases", Neuroscience Letters, 293:87-90 (2000).
Khan, "Putative Molecular Interactions Involving Naturally Occurring Steroidal Alkaloids from Sarcococca hookeriana Against Acetyl- and Butyryl-Cholinesterase," Current Bioinformatics, 8(4):416-428 (2013).
Leoni et al., "Plasma 24S-hydroxycholesterol correlation with markers of Huntington disease progression", Neurobiology of Disease, 55:37-43 (2013).
Singh et al, "Bile Acid-Based 1,2,4-Trioxanes: Synthesis and Antimalarial Assessment," Journal of Medicinal Chemistry, 55(23):10662-10673 (2012).
U.S. Appl. No. 14/343,603, filed Nov. 25, 2014, Abandoned.
U.S. Appl. No. 14/775,401, filed Sep. 11, 2015, Abandoned.
U.S. Appl. No. 14/775,678, filed Sep. 12, 2015, Abandoned.

(56) References Cited

OTHER PUBLICATIONS

U.S. Appl. No. 15/319,504, filed Dec. 16, 2016, U.S. Pat. No. 10,259,840, Apr. 16, 2019, Issued.
U.S. Appl. No. 15/517,886, filed Apr. 7, 2017, Abandoned.
U.S. Appl. No. 15/588,305, filed May 5, 2017, Abandoned.
U.S. Appl. No. 15/742,422, filed Jan. 5, 2018, U.S. Pat. No. 10,696,712, Jun. 30, 2020, Issued.
U.S. Appl. No. 15/742,424, filed Jan. 5, 2018, U.S. Pat. No. 11,117,924, Sep. 14, 2021, Issued.
U.S. Appl. No. 15/742,425, filed Jan. 5, 2018, U.S. Pat. No. 10,201,550, Feb. 12, 2019, Issued.
U.S. Appl. No. 15/917,263, filed Mar. 9, 2018, U.S. Pat. No. 10,227,375, Mar. 12, 2019, Issued.
U.S. Appl. No. 15/917,272, filed Mar. 9, 2018, Abandoned.
U.S. Appl. No. 16/028,790, filed Jul. 6, 2018, U.S. Pat. No. 10,723,758, Jul. 28, 2020, Issued.
U.S. Appl. No. 16/089,896, filed Sep. 28, 2018, Abandoned.
U.S. Appl. No. 16/099,122, filed Nov. 5, 2018, U.S. Pat. No. 10,752,653, Aug. 25, 2020, Issued.
U.S. Appl. No. 16/114,791, filed Aug. 28, 2018, U.S. Pat. No. 10,759,828, Sep. 1, 2020, Issued.
U.S. Appl. No. 16/227,013, filed Dec. 20, 2018, U.S. Pat. No. 11,104,701, Aug. 31, 2021, Issued.
U.S. Appl. No. 16/227,099, filed Dec. 20, 2018, U.S. Pat. No. 10,765,685, Sep. 8, 2020, Issued.
U.S. Appl. No. 16/315,250, filed Jan. 4, 2019, U.S. Pat. No. 10,781,231, Sep. 22, 2020, Issued.
U.S. Appl. No. 16/338,315, filed Mar. 29, 2019, U.S. Pat. No. 11,149,056, Oct. 19, 2021, Issued.
U.S. Appl. No. 16/343,235, filed Apr. 18, 2019, U.S. Pat. No. 11,149,054, Oct. 19, 2021, Issued.
U.S. Appl. No. 16/343,238, filed Apr. 18, 2019, U.S. Pat. No. 11,111,266, Sep. 7, 2021, Issued.
U.S. Appl. No. 16/879,460, filed May 20, 2020, Abandoned.
U.S. Appl. No. 16/902,730, filed Jun. 16, 2020, Abandoned.
U.S. Appl. No. 16/930,047, filed Jul. 15, 2020, U.S. Pat. No. 11,407,782, Aug. 9, 2022, Issued.
U.S. Appl. No. 16/938,348, filed Jul. 24, 2020, Abandoned.
U.S. Appl. No. 16/942,235, filed Jul. 29, 2020, Abandoned.
U.S. Appl. No. 16/942,245, filed Jul. 29, 2020, Abandoned.
U.S. Appl. No. 16/943,649, filed Jul. 30, 2020, U.S. Pat. No. 11,279,730, Mar. 22, 2022, Issued.
U.S. Appl. No. 17/242,860, filed Apr. 28, 2021, U.S. Pat. No. 11,884,697, Jan. 30, 2024, Issued.
U.S. Appl. No. 17/381,829, filed Jul. 21, 2021, U.S. Pat. No. 11,905,309, Feb. 20, 2024, Issued.
U.S. Appl. No. 17/386,364, filed Jul. 27, 2021, U.S. Pat. No. 11,613,556, Mar. 28, 2023, Issued.
U.S. Appl. No. 17/395,155, filed Aug. 5, 2021, U.S. Pat. No. 11,851,457, Dec. 26, 2023, Issued.
U.S. Appl. No. 17/396,034, filed Aug. 6, 2021, U.S. Pat. No. 11,732,000, Aug. 22, 2023, Issued.
U.S. Appl. No. 17/476,153, filed Sep. 15, 2021, U.S. Pat. No. 11,926,646, Mar. 12, 2024, Issued.
U.S. Appl. No. 17/707,303, filed Mar. 29, 2022, U.S. Pat. No. 12,129,275, Oct. 29, 2024, Issued.
U.S. Appl. No. 17/749,976, filed May 20, 2022, Abandoned.
U.S. Appl. No. 17/860,816, filed Jul. 8, 2022, U.S. Pat. No. 11,878,995, Jan. 23, 2024, Issued.
U.S. Appl. No. 17/947,844, filed Sep. 19, 2022, Pending.
U.S. Appl. No. 18/077,031, filed Dec. 7, 2022, Pending.
U.S. Appl. No. 18/106,073, filed Feb. 6, 2023, U.S. Pat. No. 12,180,247, Dec. 31, 2024, Issued.
U.S. Appl. No. 18/116,557, filed Mar. 2, 2023, U.S. Pat. No. 12,129,276, Oct. 29, 2024, Issued.
U.S. Appl. No. 18/216,057, filed Jun. 29, 2023, Pending.
U.S. Appl. No. 18/289,550, filed Nov. 3, 2023, Pending.
U.S. Appl. No. 18/388,390, filed Nov. 9, 2023, Pending.
U.S. Appl. No. 18/430,056, filed Feb. 1, 2024, U.S. Pat. No. 12,331,070, Jun. 17, 2025, Issued.
U.S. Appl. No. 18/532,752, filed Dec. 7, 2023, Abandoned.
U.S. Appl. No. 18/535,256, filed Dec. 11, 2023, Allowed.
U.S. Appl. No. 18/568,624, filed Dec. 8, 2023, Pending.
U.S. Appl. No. 18/603,816, filed Mar. 13, 2024, U.S. Pat. No. 12,268,697, Apr. 9, 2025, Patent.
U.S. Appl. No. 18/685,603, filed Feb. 22, 2024, Pending.
U.S. Appl. No. 18/694,572, filed Mar. 22, 2024, Pending.
U.S. Appl. No. 18/719,143, filed Jun. 12, 2024, Pending.
U.S. Appl. No. 18/719,194, filed Jun. 12, 2024, Pending.
U.S. Appl. No. 18/746,388, filed Jun. 18, 2024, Pending.
U.S. Appl. No. 18/813,962, filed Aug. 23, 2024, Pending.
U.S. Appl. No. 18/813,999, filed Aug. 23, 2024, Pending.
U.S. Appl. No. 18/814,031, filed Aug. 23, 2024, Pending.
U.S. Appl. No. 18/814,049, filed Aug. 23, 2024, Pending.
U.S. Appl. No. 18/877,746, filed Dec. 20, 2024, Pending.
U.S. Appl. No. 18/893,387, filed Sep. 23, 2024, Pending.
U.S. Appl. No. 18/893,565, filed Sep. 23, 2024, Pending.
U.S. Appl. No. 18/945,876, filed Nov. 13, 2024, Pending.
U.S. Appl. No. 18/993,172, filed Jan. 10, 2025, Pending.
U.S. Appl. No. 19/025,497, filed Jan. 16, 2025, Pending.
U.S. Appl. No. 19/068,855, filed Mar. 3, 2025, Pending.
U.S. Appl. No. 19/131,145, filed May 19, 2025, Pending.
U.S. Appl. No. 19/206,490, filed May 13, 2025, Pending.
U.S. Appl. No. 19/301,383, filed Aug. 15, 2025, Pending.

NEUROACTIVE STEROIDS AND METHODS OF USE THEREOF

RELATED APPLICATIONS

The present application is a continuation of U.S. patent application Ser. No. 17/381,829, filed Jul. 21, 2021, which is a continuation of U.S. patent application Ser. No. 16/227,013, filed Dec. 20, 2018, now U.S. Pat. No. 11,104,701, which is a continuation of U.S. patent application Ser. No. 15/917,263, filed Mar. 9, 2018, now U.S. Pat. No. 10,227,375, which is a continuation of Ser. No. 15/588,305, filed May 5, 2017 (now abandoned), which is a continuation of Ser. No. 14/775,678, filed Sep. 12, 2015 (now abandoned), which is a U.S. National Stage Application under 35 U.S.C. § 371 of International Application PCT/US2014/026784, filed Mar. 13, 2014 and published as International Publication No. WO2014/160480 on Oct. 2, 2014, which claims claim priority and the benefit under 35 U.S.C. § 119(e) to U.S. provisional patent application U.S.S.N. Provisional Patent Application No. 61/779,735, filed Mar. 13, 2013, which is the disclosures of each of which are incorporated herein by reference in their entireties.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion (K+, Na+, Cl−, organic anions) balance across the neuronal semipermeable membrane. Neurotransmitters are stored in presynaptic vesicles and are released as a result of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase the membrane permeability of Na+ ions. The reduced membrane potential increases the probability of generating a postsynaptic action potential, which amounts to an increase in neuronal excitability.

NMDA receptors are highly expressed in the CNS and are involved in excitatory synaptic transmission. Activating these receptors contributes to synaptic plasticity in some circumstances and excitotoxicity in others. These receptors are ligand-gated ion channels that admit Ca2+ after binding of the neurotransmitters glutamate and glycine, and are fundamental to excitatory neurotransmission and normal CNS function. NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Neuroactive steroids such as pregnenolone sulfate (PS) have been shown to exert direct modulatory effects on several types of neurotransmitter receptors, such as GABAA, glycine, AMPA, kainate, and NMDA receptors. NMDA receptors are positively modulated by PS; however, the degree of modulation varies considerably, e.g., depending upon the subunit composition of the receptor.

In addition to PS, several other 3β-hydroxy steroids have been shown to potentiate NMDA receptors (see, e.g., Paul et al., J. Pharm. and Exp. Ther. 1994, 271, 677-682). Recently, a 3β-hydroxy-ergost-5-ene steroid derivative, referred to as Org-1, was reported as positive modulator of NMDA (NR1a/NR2A). Org-1 was found to selectively modulate NMDA over GABAA (see, e.g., Madau et al., Program No. 613.2/B87. 2009 Neuroscience Meeting Planner. Chicago, IL: Society for Neuroscience, 2009; Connick et al., Program No. 613.1/B86. 2009 Neuroscience Meeting Planner. Chicago, IL: Society for Neuroscience, 2009; Paul el al., J. Neurosci. 2013, 33, 17290-17300).

Org-1

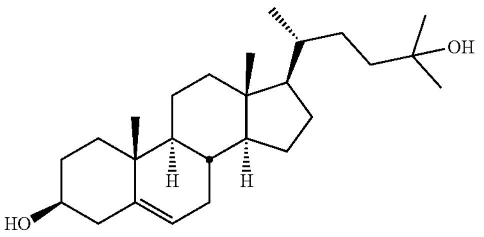

New and improved neuroactive steroids are needed that modulate brain excitability for the prevention and treatment of CNS-related conditions. The compounds, compositions, and methods described herein are directed toward this end.

SUMMARY OF THE INVENTION

The inventors of the present invention, during an ongoing exploration of Org-1 analogs for NMDA modulation, a portion of which is described in PCT/US2012/054261, incorporated herein by reference, discovered several specific combination of elements which provides NMDA modulators with comparatively superior properties. For example, as shown in Table 1, compounds bearing a beta-hydrogen at $C_5$ are disfavored compared to compounds bearing either alpha-hydrogen $C_5$ or double bond across $C_5$-$C_6$ due to loss of potentiation of the NMDA receptor. The removal of the methyl at $C_{21}$ also results in significant loss of NMDA potentiation. Disubstitution at $C_3$ is expected to increase metabolic stability of these compounds and is thus a preferred feature of the invention. Fluorination on the $C_{17}$ side chain has been shown to improve potency and limit maximum potentiation of the NMDA receptor when tested as high as 1 μM concentration of compound. A secondary or tertiary terminal alcohol on the $C_{17}$ side chain has been shown to improve potency and limit maximum potentiation of the NMDA receptor when tested as high as 1 μM concentration of compound, and is thus a preferred feature of the invention, with a preference for bulkier groups at the terminating end containing 2-3 carbons, or a group comprising fluorine substitution. Such properties are expected limit the risk of inducing glutamate driven neurotoxicity relative to compounds that achieve a greater maximum potentiation of the NMDA receptor. Compounds of the present invention encompass various combinations of these specified features to provide superior NMDA modulators.

Thus, in one aspect, provided are compounds of Formula (I),

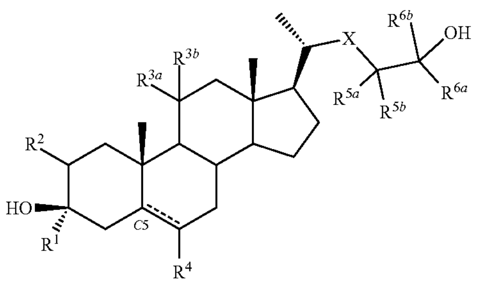

(I)

and pharmaceutically acceptable salts thereof;

wherein:

$R^1$ is substituted or unsubstituted aliphatic;

$R^2$ is hydrogen, halogen, substituted or unsubstituted $C_{1-6}$alkyl, substituted or unsubstituted cyclopropyl, or —$OR^{A2}$, wherein $R^{A2}$ is hydrogen or substituted or unsubstituted alkyl;

$R^{3a}$ is hydrogen or —$OR^{A3}$, wherein $R^{A3}$ is hydrogen or substituted or unsubstituted alkyl, and $R^{3b}$ is hydrogen; or $R^{3a}$ and $R^{3b}$ are joined to form an oxo (=O) group;

$R^4$ is hydrogen, substituted or unsubstituted alkyl, or halogen;

X is —$C(R^X)_2$— or —O—, wherein $R^X$ is hydrogen or fluorine, or one $R^X$ group and $R^{5b}$ are joined to form a double bond;

each instance of $R^{5a}$ and $R^{5b}$ is independently hydrogen or fluorine;

$R^{6a}$ is a non-hydrogen group selected from the group consisting of substituted and unsubstituted alkyl, substituted and unsubstituted alkenyl, substituted and unsubstituted alkynyl, substituted and unsubstituted carbocyclyl, substituted and unsubstituted heterocyclyl, substituted and unsubstituted aryl, and substituted and unsubstituted heteroaryl group, wherein the non-hydrogen group is optionally substituted with fluorine; and $R^{6b}$ is hydrogen or a substituted or unsubstituted alkyl group optionally substituted with fluorine;

----- represents a single or double bond, provided if a single bond is present, then the hydrogen at C5 is in the alpha configuration;

and further provided that:

(1) at least one of $R^X$, $R^{5a}$, and $R^{5b}$ is fluorine; or (2) at least one of $R^{6a}$ and $R^{6b}$ is a non-hydrogen group substituted with a fluorine; or (3) $R^{6a}$ is a non-hydrogen group comprising between two and ten carbon atoms.

In another aspect, provided are pharmaceutical compositions comprising a compound of Formula (I), or a pharmaceutically acceptable salt thereof, and a pharmaceutically acceptable excipient.

In yet another aspect, provided is a method for treating or preventing a CNS-related condition associated with NMDA modulation comprising administering to a subject in need thereof an effective amount of a compound or pharmaceutically acceptable salt thereof, or pharmaceutical composition thereof. In certain embodiments, the CNS-related condition is an adjustment disorder, anxiety disorder (including obsessive-compulsive disorder, posttraumatic stress disorder, social phobia, and generalized anxiety disorder), cognitive disorder (including Alzheimer's disease and other forms of dementia), dissociative disorder, eating disorder, mood disorder (including depression, bipolar disorder, and dysthymic disorder), schizophrenia or other psychotic disorder (including schizoaffective disorder), sleep disorder (including insomnia), substance abuse-related disorder, personality disorder (including obsessive-compulsive personality disorder), autism spectrum disorders (including those involving mutations to the Shank group of proteins), neurodevelopmental disorder (including Rett syndrome), pain (including acute and chronic pain), seizure disorder (including status epilepticus and monogenic forms of epilepsy such as Dravet's disease, and Tuberous Sclerosis complex (TSC)), stroke, traumatic brain injury, movement disorder (including Huntington's disease and Parkinson's disease) and tinnitus. In certain embodiments, these compounds can be used to induce sedation or anesthesia.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, *Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_1$ 9 alkyl"). In some embodiments, an alkyl group has 1 to 8 carbon atoms ("$C_{1-5}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., $—CH_3$). In certain embodiments, the alkyl group is substituted $C_{1-10}$ alkyl. Common alkyl abbreviations include Me ($—CH_3$), Et ($—CH_2CH_3$), iPr ($—CH(CH_3)_2$), nPr ($—CH_2CH_2CH_3$), n-Bu ($—CH_2CH_2CH_2CH_3$), or i-Bu ($—CH_2CH(CH_3)_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene ($—CH_2—$), ethylene ($—CH_2CH_2—$), propylene ($—CH_2CH_2CH_2—$), butylene ($—CH_2CH_2CH_2CH_2—$), pentylene ($—CH_2CH_2CH_2CH_2CH_2—$), hexylene ($—CH_2CH_2CH_2CH_2CH_2CH_2—$), and the like. Exemplary substituted alkylene groups, e.g., substituted with one or more alkyl (methyl) groups, include but are not limited to, substituted methylene ($—CH(CH_3)—$, ($—C(CH_3)_2—$), substituted ethylene ($—CH(CH_3)CH_2—$, $—CH_2CH(CH_3)—$, $—C(CH_3)_2CH_2—$, $—CH_2C(CH_3)_2—$), substituted propylene ($—CH(CH_3)CH_2CH_2—$, $—CH_2CH(CH_3)CH_2—$, $—CH_2CH_2CH(CH_3)—$, $—C(CH_3)_2CH_2CH_2—$, $—CH_2C(CH_3)_2CH_2—$, $—CH_2CH_2C(CH_3)_2—$), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl (C), and the like. Additional examples of alkenyl include heptenyl ($C_7$), octenyl ($C_5$), octatrienyl ($C_5$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene ($—CH{=}CH—$) and propenylene (e.g., $—CH{=}CHCH_2—$, $—CH_2—CH{=}CH—$). Exemplary substituted alkenylene groups, e.g., substituted with one or more alkyl (methyl) groups, include but are not limited to, substituted ethylene ($—C(CH_3){=}CH—$, $—CH{=}C(CH_3)—$), substituted propylene (e.g., $—C(CH_3)$ $=CHCH_2-$, $-CH=C(CH_3)CH_2-$, $-CH=CHCH(CH_3)-$, $-CH=CHC(CH_3)_2-$, $-CH(CH_3)-CH=CH-$, $-C(CH_3)_2-CH=CH-$, $-CH_2-C(CH_3)=CH-$, $-CH_2-CH=C(CH_3)-$), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl (C), and the like. Additional examples of alkynyl include heptynyl ($C_7$), octynyl ($C_5$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("hetero$C_{2-10}$ alkenyl"). In some embodiments, a heteroalkenyl group has 2 to 9 carbon atoms at least one double bond, and 1, 2, 3, or 4 heteroatoms ("hetero$C_{2-9}$ alkenyl"). In some embodiments, a heteroalkenyl group has 2 to 8 carbon atoms, at least one double bond, and 1, 2, 3, or 4 heteroatoms ("hetero$C_{2-8}$ alkenyl"). In some embodiments, a heteroalkenyl group has 2 to 7 carbon atoms, at least one double bond, and 1, 2, 3, or 4 heteroatoms ("hetero$C_{2-7}$ alkenyl"). In some embodiments, a heteroalkenyl group has 2 to 6 carbon atoms, at least one double bond, and 1, 2, or 3 heteroatoms ("hetero$C_{2-6}$ alkenyl"). In some embodiments, a heteroalkenyl group has 2 to 5 carbon atoms, at least one double bond, and 1 or 2 heteroatoms ("hetero$C_{2-5}$ alkenyl"). In some embodiments, a heteroalkenyl group has 2 to 4 carbon atoms, at least one double bond, and 1 or 2 heteroatoms ("hetero$C_{2-4}$ alkenyl"). In some embodiments, a heteroalkenyl group has 2 to 3 carbon atoms, at least one double bond, and 1 heteroatom ("hetero$C_{2-3}$ alkenyl"). In some embodiments, a heteroalkenyl group has 2 to 6 carbon atoms, at least one double bond, and 1 or 2 heteroatoms ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("hetero$C_{2-10}$ alkynyl"). In some embodiments, a heteroalkynyl group has 2 to 9 carbon atoms, at least one triple bond, and 1, 2, 3, or 4 heteroatoms ("hetero$C_{2-9}$ alkynyl"). In some embodiments, a heteroalkynyl group has 2 to 8 carbon atoms, at least one triple bond, and 1, 2, 3, or 4 heteroatoms ("hetero$C_{2-8}$ alkynyl"). In some embodiments, a heteroalkynyl group has 2 to 7 carbon atoms, at least one triple bond, and 1, 2, 3, or 4 heteroatoms ("hetero$C_{2-7}$ alkynyl"). In some embodiments, a heteroalkynyl group has 2 to 6 carbon atoms, at least one triple bond, and 1, 2, or 3 heteroatoms ("hetero$C_{2-6}$ alkynyl"). In some embodiments, a heteroalkynyl group has 2 to 5 carbon atoms, at least one triple bond, and 1 or 2 heteroatoms ("hetero$C_{2-5}$ alkynyl"). In some embodiments, a heteroalkynyl group has 2 to 4 carbon atoms, at least one triple bond, and 1 or 2 heteroatoms ("hetero$C_{2-4}$ alkynyl"). In some embodiments, a heteroalkynyl group has 2 to 3 carbon atoms, at least one triple bond, and 1 heteroatom ("hetero$C_{2-3}$ alkynyl"). In some embodiments, a heteroalkynyl group has 2 to 6 carbon atoms, at least one triple bond, and 1 or 2 heteroatoms ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

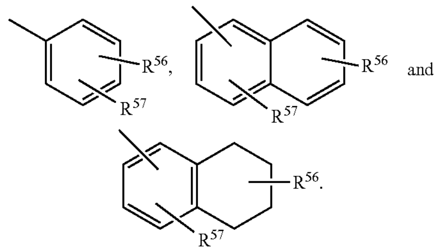

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

Other representative aryl groups having a fused heterocyclyl group include the following:

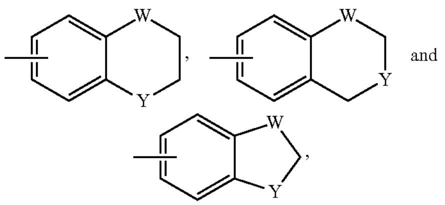

wherein each W is selected from $C(R^{66})_2$, $NR^{66}$, O, and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

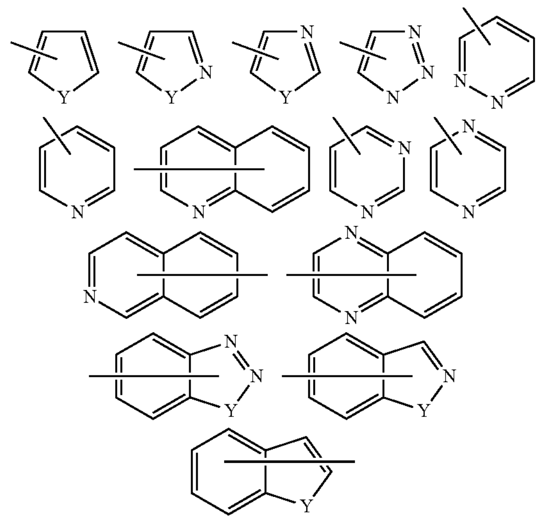

wherein each Y is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_5$), cyclooctenyl ($C_5$), bicyclo[2.2.1]heptanyl ($C_7$), bicyclo[2.2.2]octanyl ($C_5$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-4}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

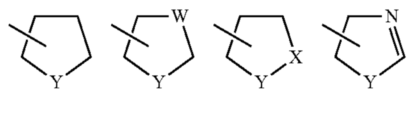

-continued

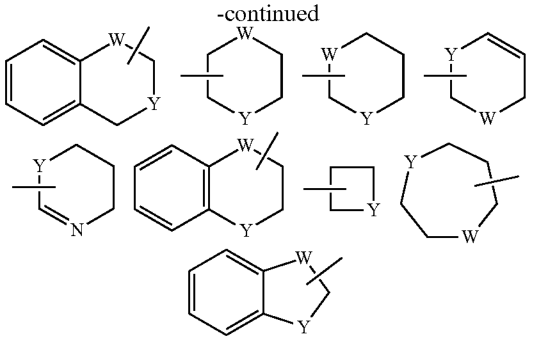

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, 5-10 membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —$S(O)_2$-alkyl, and —$S(O)_2$-aryl. Substituting groups include carbonyl or thiocarbonyl which provide, for example, lactam and urea derivatives.

“Hetero” when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

“Acyl” refers to a radical —$C(O)R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. “Alkanoyl” is an acyl group wherein $R^{20}$ is a group other than hydrogen. Representative acyl groups include, but are not limited to, formyl (—CHO), acetyl (—$C(=O)CH_3$), cyclohexylcarbonyl, cyclohexylmethylcarbonyl, benzoyl (—C(=O)Ph), benzylcarbonyl (—$C(=O)CH_2Ph$), C(O)—$C_1$-$C_8$ alkyl, —C(O)—$(CH_2)_t$($C_6$-$C_{10}$ aryl), —C(O)—$(CH_2)_t$(5-10 membered heteroaryl), —C(O)—$(CH_2)_t$($C_3$-$C_{10}$ cycloalkyl), and —C(O)—$(CH_2)_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

“Acylamino” refers to a radical —$NR^{22}C(O)R^{23}$, where each instance of $R^{22}$ and $R^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or $R^{22}$ is an amino protecting group. Exemplary “acylamino” groups include, but are not limited to, formylamino, acetylamino, cyclohexylcarbonylamino, cyclohexylmethyl-carbonylamino, benzoylamino and benzylcarbonylamino. Particular exemplary “acylamino” groups are —$NR^{24}C(O)$—$C_1$-$C_8$ alkyl, —$NR^{24}C(O)$—$(CH_2)_t$($C_6$-$C_{10}$ aryl), —$NR^{24}C(O)$—$(CH_2)_t$(5-10 membered heteroaryl), —$NR^{24}C(O)$—$(CH_2)$($C_3$-$C_{10}$ cycloalkyl), and —$NR^{24}C(O)$—$(CH_2)_t$(4-10 membered heterocyclyl), wherein t is an integer from 0 to 4, and each $R^{24}$ independently represents H or $C_1$-$C_8$ alkyl. In certain embodiments, $R^{25}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is H, $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl; provided at least one of $R^{25}$ and $R^{26}$ is other than H.

“Acyloxy” refers to a radical —$OC(O)R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_1$-$C_8$ alkyl, substituted with halo or hydroxy; $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

“Alkoxy” refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-$S(O)_2$— and aryl-$S(O)_2$—. Exemplary ‘substituted alkoxy’ groups include, but are not limited to, —O—$(CH_2)_t$($C_6$-$C_{10}$ aryl), —O—$(CH_2)_t$(5-10 membered heteroaryl), —O—$(CH_2)_t$($C_3$-$C_{10}$ cycloalkyl), and —O—$(CH_2)$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —$OCF_3$, —$OCH_2CF_3$, —$OCH_2Ph$, —$OCH_2$-cyclopropyl, —$OCH_2CH_2OH$, and —$OCH_2CH_2NMe_2$.

"Amino" refers to the radical —$NH_2$.

"Substituted amino" refers to an amino group of the formula —$N(R^{38})_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{31}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)$($C_6$-$C_{10}$ aryl), —$(CH_2)$(5-10 membered heteroaryl), —$(CH_2)_t$($C_3$-$C_{10}$ cycloalkyl), or —$(CH_2)$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t$($C_6$-$C_{10}$ aryl), —$NR^{39}$—$(CH_2)_t$(5-10 membered heteroaryl), —$NR^{39}$—$(CH_2)$($C_3$-$C_{10}$ cycloalkyl), and —$NR^{39}$—$(CH_2)$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —C(O)$NH_2$.

"Substituted carbamoyl" or "substituted amido" refers to the radical —C(O)$N(R^{62})_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary "substituted carbamoyl" groups include, but are not limited to, —C(O) $NR^{64}$—$C_1$-$C_8$ alkyl, —C(O)$NR^{64}$—$(CH_2)_t$($C_6$-$C_{10}$ aryl), —C(O)$N^{64}$—$(CH_2)_t$(5-10 membered heteroaryl), —C(O)$NR^{64}$—$(CH_2)_t$($C_3$-$C_{10}$ cycloalkyl), and —C(O)$NR^{64}$—$(CH_2)_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —$NO_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethenyl" refers to substituted or unsubstituted —(C═C)—.

"Ethylene" refers to substituted or unsubstituted —(C—C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group ═S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R$—, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R')_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R^{aa}$, —$OP(=O)_2R^{aa}$, —$P(=O)(R')_2$, —$OP(=O)(R^{aa})_2$, —$OP(=O)(OR^{cc})_2$, —$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R$—, =$NR^{bb}$, or =$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{a}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(RC)_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —$C(=O)R^{ee}$, —$CO_2H$, —$CO_2R^{cc}$, —$OC(=O)R^{ee}$, —$OCO_2R^{ee}$, —$C(=O)N(R^{ff})_2$, —$OC(=O)N(R^{ff})_2$, —$NR^{ff}C(=O)R^{ee}$, —$NR^{ff}CO_2R^{ee}$, —$NR^{ff}C(=O)N(R^{ff})_2$, —$C(=NR^{ff})OR^{ee}$, —$OC(=NR^{ff})R^{ee}$, —$OC(=NR^{ff})OR^{ee}$, —$C(=NR^{ff})N(R^{ff})_2$, —$OC(=NR^{ff})N(R^{ff})_2$, —$NR^{ff}C(=NR^{ff})N(R^{ff})_2$, —$NR^{ff}SO_2R^{ee}$, —$SO_2N(R^{f})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)_2R^{ee}$, —$P(=O)(R^{ee})_2$—$OP(=O)(R^{ee})_2$—$OP(=O)(OR^{ee})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl$)(C_{1-6}$ alkyl), —$N(OH)(C_{1-6}$ alkyl), —NH(OH), —SH, —$SC_{1-6}$ alkyl, —SS($C_{1-6}$ alkyl), —C(═O)($C_{1-6}$ alkyl), —$CO_2$H, —$CO_2$($C_{1-6}$ alkyl), —OC(═O)($C_{1-6}$ alkyl), —$OCO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)O$C_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —$NHSO_2$($C_{1-6}$ alkyl), —$SO_2$N($C_{1-6}$ alkyl)$_2$, —$SO_2$NH($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$-C(═S)N($C_{1-6}$ alkyl)$_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)$_2$($C_{1-6}$ alkyl), —P(═O)($C_{1-6}$ alkyl)$_2$, —OP(═O)($C_{1-6}$ alkyl)$_2$, —OP(═O)($OC_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, $SO_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═$NR^{bb}$)$R^{aa}$, —C(═$NR^{cc}$)$OR^{aa}$, —C(═$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(═S)N($R^{cc}$)$_2$, —C(═O)$SR^{cc}$, —C(═S)$SR^{cc}$, —P(═O)$_2R^{aa}$, —P(═O)($R^{aa}$)$_2$, —P(═O)$_2$N($R^{cc}$)$_2$, —P(═O)($NR^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N+($C_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

The inventors of the present invention, during an ongoing exploration of Org-1 analogs for NMDA modulation, a portion of which is described in PCT/US2012/054261, incorporated herein by reference, discovered several specific combination of elements which provides NMDA modulators with comparatively superior properties. For example, as shown in Table 1, compounds bearing a beta-hydrogen at $C_5$ are disfavored compared to compounds bearing either alpha-hydrogen $C_5$ or double bond across $C_5$-$C_6$ due to loss of potentiation of the NMDA receptor. The removal of the methyl at $C_{21}$ also results in significant loss of NMDA potentiation. Disubstitution at $C_3$ is expected to increase metabolic stability of these compounds and is thus a preferred feature of the invention. Fluorination on the $C_{17}$ side chain has been shown to improve potency and limit maximum potentiation of the NMDA receptor when tested as high as 1 μM concentration of compound. A secondary or tertiary terminal alcohol on the $C_{17}$ side chain has been shown to improve potency and limit maximum potentiation of the NMDA receptor when tested as high as 1 μM concentration of compound, and is thus a preferred feature of the invention, with a preference for bulkier groups at the terminating end containing 2-3 carbons, or a group comprising fluorine substitution. Such properties are expected limit the risk of inducing glutamate driven neurotoxicity relative to compounds that achieve a greater maximum potentiation of the NMDA receptor. Compounds of the present invention encompass various combinations of these specified features to provide superior NMDA modulators.

Compounds

In one aspect, provided herein are compounds according to Formula (I):

(I)

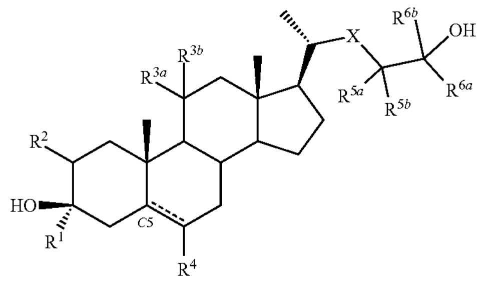

and pharmaceutically acceptable salts thereof;

$R^1$ is substituted or unsubstituted aliphatic;

$R^2$ is hydrogen, halogen, substituted or unsubstituted $C_{1-6}$alkyl, substituted or unsubstituted cyclopropyl, or —$OR^{A2}$, wherein $R^{A2}$ is hydrogen or substituted or unsubstituted alkyl;

$R^{3a}$ is hydrogen or —$OR^{A3}$, wherein $R^{A3}$ is hydrogen or substituted or unsubstituted alkyl, and $R^{3b}$ is hydrogen; or $R^{3a}$ and $R^{3b}$ are joined to form an oxo (═O) group;

$R^4$ is hydrogen, substituted or unsubstituted alkyl, or halogen;

X is —$C(R^X)_2$— or —O—, wherein $R^X$ is hydrogen or fluorine, or one $R^X$ group and $R^{5b}$ are joined to form a double bond;

each instance of $R^{5a}$ and $R^{5b}$ is independently hydrogen or fluorine;

$R^{6a}$ is a non-hydrogen group selected from the group consisting of substituted and unsubstituted alkyl, substituted and unsubstituted alkenyl, substituted and unsubstituted alkynyl, substituted and unsubstituted carbocyclyl, substituted and unsubstituted heterocyclyl, substituted and unsubstituted aryl, and substituted and unsubstituted heteroaryl group, wherein the non-hydrogen group is optionally substituted with fluorine; and $R^{6b}$ is hydrogen or a substituted or unsubstituted alkyl group optionally substituted with fluorine;

----- represents a single or double bond, provided if a single bond is present, then the hydrogen at $C_5$ is in the alpha configuration;

and further provided that:

(1) at least one of $R^X$, $R^{5a}$, and $R^{5b}$ is fluorine; or (2) at least one of $R^{6a}$ and $R^{6b}$ is a non-hydrogen group substituted with a fluorine; or (3) $R^{6a}$ is a non-hydrogen group comprising between two and ten carbon atoms.

As generally described herein, compounds wherein the hydrogen at $C_5$ is provided in the beta configuration demonstrate loss of NMDA potentiation compared to compounds wherein the hydrogen at $C_5$ is alpha, or wherein a double bond is present at $C_5$-$C_6$. Thus, the compound of Formula (I) encompasses only compounds of Formula (I-A) and (I-B):

(I-A)

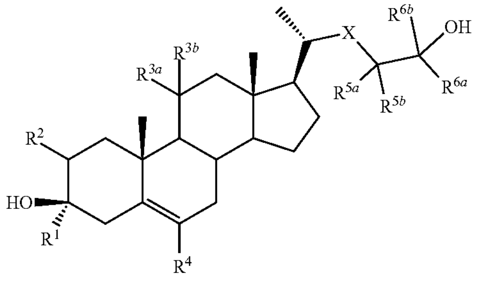

(I-B)

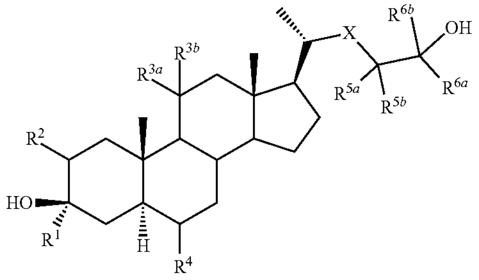

and pharmaceutically acceptable salts thereof.

Group $R^1$

As generally defined herein, $R^1$ is substituted or unsubstituted alphatic, i.e., substituted or unsubstituted alkyl, substituted or unsubstituted alkenyl, substituted or unsubstituted alkynyl, or substituted or unsubstituted carbocyclyl.

In certain embodiments, $R^1$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^1$ $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), $C_{1-6}$ alkyl substituted with 1, 2, 3, 4, 5, 6, 7, 8, 9, 10, or more fluoro groups (e.g., $-CF_3$, $-CH_2F$, $-CHF_2$, difluoroethyl, and 2,2,2-trifluoro-1,1-dimethyl-ethyl), $C_{1-6}$ alkyl substituted with 1, 2, 3, 4, 5, 6, 7, 8, 9, 10, or more chloro groups (e.g., $-CH_2Cl$, $-CHCl_2$), and $C_{1-6}$ alkyl substituted with alkoxy groups (e.g., $-CH_2OCH_3$, $-CH_2OCH_2CH_3$, $-CH_2O$-cyclopropyl). In certain embodiments, $R^1$ is substituted alkyl, e.g., $R^1$ is haloalkyl, alkoxyalkyl, or aminoalkyl. In certain embodiments, $R^1$ is Me, Et, n-Pr, n-Bu, i-Bu, fluoromethyl, chloromethyl, difluoromethyl, trifluoromethyl, trifluoroethyl, difluoroethyl, 2,2,2-trifluoro-1,1-dimethyl-ethyl, methoxymethyl, methoxyethyl, or ethoxymethyl.

In certain embodiments, $R^1$ is unsubstituted $C_{1-3}$ alkyl, e.g., $R^1$ is $-CH_3$, $-CH_2CH_3$, or $-CH_2CH_2CH_3$.

In certain embodiments, $R^1$ is alkyl substituted with one or more fluorine atoms; e.g., $R^1$ is $-CH_2F$, $-CHF_2$, or $-CF_3$.

In certain embodiments, $R^1$ is alkyl substituted with one or more $-OR^{A1}$ groups, wherein $R^{A1}$ is hydrogen or substituted or unsubstituted alkyl. In certain embodiments, $R^1$ is $-CH_2OR^{A1}$, e.g., wherein $R^{A1}$ is hydrogen, $-CH_3$, $-CH_2CH_3$, or $-CH_2CH_2CH_3$.

In certain embodiments, $R^1$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl. In certain embodiments, $R^1$ is ethenyl ($C_2$), propenyl ($C_3$), or butenyl ($C_4$), unsubstituted or substituted with one or more substituents selected from the group consisting of alkyl, halo, haloalkyl, alkoxyalkyl, or hydroxyl. In certain embodiments, $R^1$ is ethenyl, propenyl, or butenyl, unsubstituted or substituted with alkyl, halo, haloalkyl, alkoxyalkyl, or hydroxy. In certain embodiments, $R^1$ is ethenyl.

In certain embodiments, $R^1$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl. Exemplary substituted or unsubstituted $R^1$ alkynyl groups include, but are not limited to, ethynyl, propynyl, or butynyl, unsubstituted or substituted with alkyl, halo, haloalkyl (e.g., $CF_3$), alkoxyalkyl, cycloalkyl (e.g., cyclopropyl or cyclobutyl), or hydroxyl. In certain embodiments, $R^1$ is selected from the group consisting of trifluoroethynyl, cyclopropylethynyl, cyclobutylethynyl, and propynyl, fluoropropynyl, and chloroethynyl. In certain embodiments, $R^1$ is ethynyl ($C_2$), propynyl ($C_3$), or butynyl ($C_4$), unsubstituted or substituted with one or more substituents selected from the group consisting of substituted or unsubstituted aryl, substituted or unsubstituted heteroaryl, substituted or unsubstituted carbocyclyl, and substituted or unsubstituted heterocyclyl. In certain embodiments, $R^1$ is ethynyl ($C_2$), propynyl ($C_3$), or butynyl ($C_4$) substituted with substituted phenyl. In certain embodiments, the phenyl substitutent is further substituted with one or more substituents selected from the group consisting of halo, alkyl, trifluoroalkyl, alkoxy, acyl, amino or amido. In certain embodiments, $R^1$ is ethynyl ($C_2$), propynyl ($C_3$), or butynyl ($C_4$) substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, or tetrazolyl.

In certain embodiments, $R^1$ is ethynyl, propynyl, or butynyl, unsubstituted or substituted with alkyl, halo, haloalkyl, alkoxyalkyl, or hydroxyl. In certain embodiments, $R^1$ is ethynyl or propynyl, substituted with substituted or unsubstituted aryl. In certain embodiments, $R^1$ is ethynyl or propynyl, substituted with phenyl unsubstituted or substituted with halo, alkyl, alkoxy, haloalkyl, trihaloalkyl, or acyl. In certain embodiments, $R^1$ is ethynyl or propynyl, substituted with substituted or unsubstituted carbocyclyl. In certain embodiments, $R^{3a}$ is ethynyl or propynyl, substituted with substituted or unsubstituted cyclopropyl, cyclobutyl, cyclopentyl, or cyclohexyl. In certain embodiments, $R^1$ is ethynyl or propynyl, substituted with substituted or unsubstituted heteroaryl. In certain embodiments, $R^1$ is ethynyl or propynyl, substituted with substituted or unsubstituted pyridinyl, or pyrimidinyl. In certain embodiments, $R^1$ is ethynyl or propynyl, substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, tetrazolyl. In certain embodiments, $R^1$ is ethynyl or propynyl, substituted with substituted or unsubstituted heterocyclyl. In certain embodiments, $R^1$ is ethynyl or propynyl, substituted with substituted or unsubstituted pyrrolidinyl, piperidinyl, piperazinyl, or mopholinyl. In certain embodiments, $R^1$ is propynyl or butynyl, substituted with hydroxyl or alkoxy. In certain embodiments, $R^1$ is propynyl or butynyl, substituted with methoxy or ethoxy. In certain embodiments, $R^1$ is ethynyl or propynyl, substituted with chloro. In certain embodiments, $R^1$ is ethynyl or propynyl, substituted with trifluoromethyl.

In certain embodiments, $R^1$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl. In certain embodiments, $R^1$ is substituted or unsubstituted cyclopropyl or substituted or unsubstituted cyclobutyl.

Groups $R^2$, $R^{3a}$, $R^{3b}$, and $R^4$

As generally defined herein, $R^2$ is hydrogen, halogen, substituted or unsubstituted $C_{1-6}$alkyl, substituted or unsubstituted cyclopropyl, or —$OR^{A2}$, wherein $R^{A2}$ is hydrogen or substituted or unsubstituted alkyl. In certain embodiments, $R^2$ is hydrogen. In certain embodiments, $R^2$ is halogen, e.g., fluoro, chloro, bromo, or iodo. In certain embodiments, $R^2$ is fluoro or chloro. In certain embodiments, $R^2$ is substituted or unsubstituted $C_{1-6}$alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, $R^2$ is —$CH_3$, —$CH_2CH_3$, —$CH_2CH_2CH_3$, or cyclopropyl. In certain embodiments, $R^2$ is —$OR^{A2}$. In certain embodiments, $R^{A2}$ is hydrogen. In certain embodiments, $R^{A2}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_3$-4alkyl, substituted or unsubstituted $C_{4-5}$alkyl, or substituted or unsubstituted $C_{5-6}$alkyl. In certain embodiments, $R^{A2}$ is hydrogen, —$CH_3$, —$CH_2CH_3$, or —$CH_2CH_2CH_3$, i.e., to provide a group $R^2$ of formula —OH, —$OCH_3$, —$OCH_2CH_3$, or —$OCH_2CH_2CH_3$. In certain embodiments, $R^2$ is a non-hydrogen substituent in the alpha configuration. In certain embodiments, $R^2$ is a non-hydrogen substituent in the beta configuration.

As generally defined herein, $R^{3a}$ is hydrogen or —$OR^{A3}$, wherein $R^{A3}$ is hydrogen or substituted or unsubstituted alkyl, and $R^{3b}$ is hydrogen; or $R^{3a}$ and $R^{3b}$ are joined to form an oxo (=O) group.

In certain embodiments, both $R^{3a}$ and $R^{3b}$ are both hydrogen.

In certain embodiments, $R^{3a}$ and $R^{3b}$ are joined to form an oxo (=O) group.

In certain embodiments, $R^{3a}$ is —$OR^{A3}$ and $R^{3b}$ is hydrogen. In certain embodiments, wherein $R^{3a}$ is —$OR^{A3}$, $R^{3a}$ is in the alpha or beta configuration. In certain embodiments, wherein $R^{3a}$ is —$OR^{A3}$, $R^{3a}$ is in the alpha configuration. In certain embodiments, wherein $R^{3a}$ is —$OR^{A3}$, $R^{3a}$ is in the beta configuration. In certain embodiments, $R^{A3}$ is hydrogen. In certain embodiments, $R^{A3}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, $R^{A3}$ is hydrogen, —$CH_3$, —$CH_2CH_3$, or —$CH_2CH_2CH_3$, i.e., to provide a group $R^{3a}$ of formula —OH, —$OCH_3$, —$OCH_2CH_3$, or —$OCH_2CH_2CH_3$.

As generally defined herein, $R^4$ is hydrogen, substituted or unsubstituted alkyl, or halogen. In certain embodiments, $R^4$ is hydrogen. In certain embodiments, $R^4$ is halogen, e.g., fluoro. In certain embodiments, $R^4$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. In certain embodiments, $R^4$ is $C_1$ alkyl, e.g., —$CH_3$ or —$CF_3$. In certain embodiments, $R^4$ is hydrogen, —$CH_3$, or —F. In certain embodiments, wherein ----- represents a single bond, $R^4$ is a non-hydrogen substitutent in the alpha configuration. In certain embodiments, wherein ----- represents a single bond, $R^4$ is a non-hydrogen substituent in the beta configuration.

Group X, $R^{5a}$, $R^{5b}$, $R^{6a}$, and $R^{6b}$

As generally defined herein, X is —$C(R^X)_2$— or —O—, wherein $R^X$ is hydrogen or fluorine, or one $R^X$ group and $R^{5b}$ are joined to form a double bond; each of $R^{5a}$ and $R^{5b}$ is independently hydrogen or fluorine; $R^{6a}$ is a non-hydrogen group selected from the group consisting of substituted and unsubstituted alkyl, substituted and unsubstituted alkenyl, substituted and unsubstituted alkynyl, substituted and unsubstituted carbocyclyl, substituted and unsubstituted heterocyclyl, substituted and unsubstituted aryl, and substituted and unsubstituted heteroaryl group, wherein the non-hydrogen group is optionally substituted with fluorine; and $R^{6b}$ is hydrogen or a substituted or unsubstituted alkyl group optionally substituted with fluorine; provided: (1) at least one of $R^X$, $R^{5a}$, and $R^{5b}$ is fluorine; or (2) at least one of $R^{6a}$ and $R^{6b}$ is a non-hydrogen group substituted with fluorine; or (3) $R^{6a}$ is a non-hydrogen group comprising between two and ten carbon atoms.

In certain embodiments, X is —O—. In certain embodiments, X is —$CH_2$—. In certain embodiments, X is —$CF_2$—.

In certain embodiments, at least one of $R^{5a}$ and $R^{5b}$ is hydrogen. In certain embodiments, at least one of $R^{5a}$ and $R^{5b}$ is fluorine. In certain embodiments, $R^{5a}$ and $R^{5b}$ are both hydrogen. In certain embodiments, $R^{5a}$ and $R^{5b}$ are both fluorine. In certain embodiments, $R^X$ and $R^{5b}$ are joined to form a double bond, e.g., cis or trans double bond.

In certain embodiments, $R^{6a}$ is a non-hydrogen group, as described herein, which is not substituted with fluorine. In certain embodiments, $R^{6a}$ is substituted or unsubstituted alkyl (e.g., —$CH_3$, —$CH_2CH_3$, —$CH(CH_3)_2$), substituted or unsubstituted alkenyl, substituted or unsubstituted alkynyl, or substituted or unsubstituted carbocyclyl (e.g., isopropanol). In certain embodiments, $R^{6a}$ is a non-hydrogen group, as described herein, which is substituted with fluorine.

In certain embodiments, $R^{6a}$ is a non-hydrogen group, as described herein, and $R^{6b}$ is hydrogen. In certain embodiments, $R^{6a}$ is a non-hydrogen group, as described herein, and $R^{6b}$ is a substituted or unsubstituted alkyl group optionally substituted by fluorine. In certain embodiments, $R^{6b}$ is an alkyl group which is not substituted with fluorine. In certain embodiments, $R^{6a}$ is an alkyl group which is substituted with fluorine.

In certain embodiments, $R^{6b}$ is hydrogen. In certain embodiments, $R^{6b}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, optionally substituted by fluorine. In certain embodiments, $R^{6b}$ is $C_1$ alkyl optionally substituted by fluorine, e.g., —$CH_3$ or —$CF_3$.

In certain embodiments, $R^{6a}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^{6a}$ $C_{1-6}$alkyl groups include, but are not limited to, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), substituted or unsubstituted n-hexyl ($C_6$). In certain embodiments, $R^{6a}$ is alkyl, as described above, substituted with one or more fluorines, e.g., 1, 2, 3, 4, or more fluorines. In certain embodiments, $R^{6a}$ is —$CF_3$, —$CH_2F$, —$CHF_2$, difluoroethyl, or 2,2,2-trifluoro-1,1-dimethyl-ethyl). In certain embodiments, $R^{6a}$ is alkyl, as described above, substituted with one or more —$OR^{A6}$ groups, wherein $R^{A6}$ is hydrogen or substituted or unsubstituted alkyl. In certain embodiments, $R^{6a}$ is —$CH_2OR^{A6}$, —$CH_2CH_2OR^{A6}$, or —$CH_2CH_2CH_2OR^{A6}$, e.g., —$CH_2OCH_3$, —$CH_2CH_2OCH_3$, or —$CH_2CH_2CH_2OCH_3$.

In certain embodiments, $R^{6a}$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl, optionally substituted with fluorine. In certain embodiments, $R^{6a}$ is substituted or unsubstituted vinyl ($C_2$) or substituted or unsubstituted allyl ($C_3$).

In certain embodiments, $R^{6a}$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl, optionally substituted with fluorine. In certain embodiments, $R^{6a}$ is substituted or unsubstituted ethynyl ($C_2$) or substituted or unsubstituted propargyl ($C_3$).

In certain embodiments, $R^{6a}$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl, optionally substituted with fluorine. In certain embodiments, $R^{6a}$ is substituted or unsubstituted cyclopropyl.

In certain embodiments, $R^{6a}$ is substituted or unsubstituted heterocyclyl, e.g., substituted or unsubstituted $C_{3-6}$ heterocyclyl, substituted or unsubstituted $C_{3-4}$ heterocyclyl, substituted or unsubstituted $C_{4-5}$ heterocyclyl, or substituted or unsubstituted $C_{5-6}$ heterocyclyl, optionally substituted with fluorine.

In certain embodiments, $R^{6a}$ is substituted or unsubstituted aryl, e.g., substituted or unsubstituted phenyl, optionally substituted with fluorine.

In certain embodiments, $R^{6a}$ is substituted or unsubstituted heteroaryl, e.g., optionally substituted 5- to 6-membered heteroaryl, optionally substituted with fluorine.

In certain embodiments, $R^{6a}$ is a non-hydrogen group comprising between two and ten carbon atoms, e.g., between two and nine, two and eight, two and seven, two and six, two and five, two and four, or two and three carbon atoms, inclusive. For example, in certain embodiments, $R^{6a}$ is substituted or unsubstituted $C_{2-3}$ alkyl, substituted or unsubstituted $C_{2-3}$ alkenyl, substituted or unsubstituted $C_{2-3}$ alkynyl, or substituted or unsubstituted $C_3$ carbocyclyl.

In certain embodiments, wherein at least one of $R^X$, $R^{5a}$, and $R^{5b}$ is fluorine; or at least one of $R^{6a}$ and $R^{6b}$ is a non-hydrogen group substituted with fluorine; $R^{6a}$ is substituted or unsubstituted $C_{1-3}$ alkyl, substituted or unsubstituted $C_{1-3}$ alkenyl, substituted or unsubstituted $C_1$. 3 alkynyl, or substituted or unsubstituted $C_3$ carbocyclyl.

In certain embodiments, $R^{6a}$ and $R^{6b}$ are the same group. In certain embodiments, $R^{6a}$ and $R^{6b}$ are different groups, and the carbon to $R^{6a}$ is attached is in the (S) or (R) configuration. In certain embodiments, the carbon to which $R^{6a}$ is attached is in the (S) configuration. In certain embodiments, the carbon to which $R^{6a}$ is attached is in the (R) configuration. In certain embodiments, $R^{6a}$ is —$CF_3$ and $R^{6b}$ is hydrogen or $C_{1-4}$ alkyl. In certain embodiments, $R^{6a}$ is a non-hydrogen group substituted with fluorine, and $R^{6b}$ is —$CH_3$. In certain embodiments, $R^{6a}$ is substituted with one or more —$OR^{A6}$ groups, wherein $R^{A6}$ is hydrogen or substituted or unsubstituted alkyl. In certain embodiments, $R^{6a}$ is a substituted or unsubstituted $C_{2-4}$ alkyl, substituted or unsubstituted $C_{2-3}$ alkenyl, substituted or unsubstituted $C_{2-3}$ alkynyl, or substituted or unsubstituted $C_3$ carbocyclyl, and $R^{6b}$ is —$CH_3$. In certain embodiments, $R^{6a}$ is a unsubstituted $C_{2-4}$ alkyl, unsubstituted $C_{2-3}$ alkenyl, or unsubstituted $C_{2-3}$ alkynyl, or unsubstituted $C_3$ carbocyclyl, and $R^{6b}$ is —$CH_3$. In certain embodiments, $R^{6a}$ is a non-hydrogen group substituted with fluorine, and $R^{6b}$ is —$CH_3$.

Various Combinations of Certain Embodiments

Various combinations of certain embodiments are father contemplated herein.

For example, in certain embodiments, wherein X is —$CH_2$— and $R^{5a}$ and $R^{5b}$ are both hydrogen, provided is a compound of Formula (I-a):

(I-a)

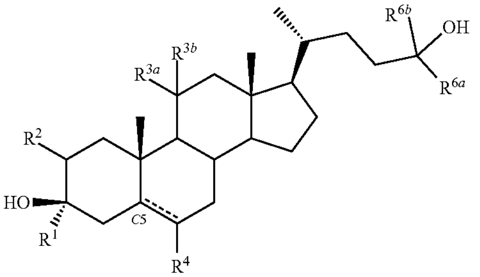

or a pharmaceutically acceptable salt thereof. In certain embodiments, $R^{6a}$ is a non-hydrogen group comprising between two and ten carbon atoms. In certain embodiments, at least one of $R^{6a}$ and $R^{6b}$ is a non-hydrogen group substituted with fluorine. In certain embodiments, the carbon to which $R^{6a}$ is attached is in the (S) configuration. In certain embodiments, the carbon to which $R^{6a}$ is attached is in the (R) configuration. In certain embodiments, $R^{6a}$ is methyl ($C_1$) optionally substituted with one or more fluorines, e.g., —$CH_3$ or —$CF_3$. In certain embodiments, $R^{6a}$ is substituted or unsubstituted ethyl ($C_2$), substituted or unsubstituted n-propyl ($C_3$), or substituted or unsubstituted isopropyl ($C_3$). In certain embodiments, $R^{6a}$ is —$CH_2OR^{A6}$, —$CH_2CH_2OR^{A6}$, or —$CH_2CH_2CH_2OR^{A6}$. In certain embodiments, $R^{6a}$ is substituted or unsubstituted vinyl ($C_2$) or substituted or unsubstituted allyl ($C_3$). In certain embodiments, $R^{6a}$ is substituted or unsubstituted ethynyl ($C_2$) or substituted or unsubstituted propargyl ($C_3$). In certain embodiments, $R^{6a}$ is substituted or unsubstituted cyclopropyl. In certain embodiments, $R^{6b}$ is ----- hydrogen. In certain embodiments, $R^{6b}$ is —$CH_3$ or —$CF_3$. In certain embodiments, ----- represents a single bond, and the hydrogen at $C_5$ is alpha. In certain embodiments, ----- represents a double bond. In certain embodiments, $R^1$ is $—CH_3$ or $—CH_2CH_3$. In certain embodiments, $R^2$ is hydrogen, —OH, $—OCH_3$, $—OCH_2CH_3$, $—OCH_2CH_2CH_3$, $—CH_3$, $—CH_2CH_3$, $—CH_2CH_2CH_3$, cyclopropyl, fluoro, or chloro. In certain embodiments, $R^2$ is a non-hydrogen substitutent in the alpha configuration. In certain embodiments, $R^2$ is a non-hydrogen substituent in the beta configuration. In certain embodiments, $R^{3a}$ and $R^{3b}$ are both hydrogen. In certain embodiments, $R^{3a}$ and $R^{3b}$ are joined to form =O (oxo). In certain embodiments, $R^4$ is hydrogen.

In certain embodiments, wherein X is $—CH_2—$ and $R^{5a}$ and $R^{5b}$ are both fluorine, provided is a compound of Formula (I-b):

(I-b)

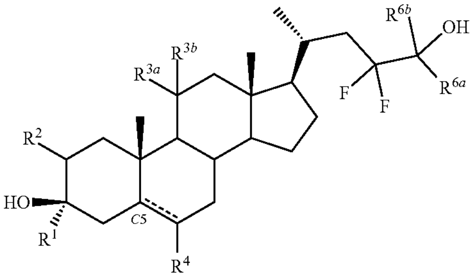

or a pharmaceutically acceptable salt thereof. In certain embodiments, $R^{6a}$ is a non-hydrogen group comprising between two and ten carbon atoms. In certain embodiments, at least one of $R^{6a}$ and $R^{6b}$ is a non-hydrogen group substituted with fluorine. In certain embodiments, the carbon to which $R^{6a}$ is attached is in the (S) configuration. In certain embodiments, the carbon to which $R^{6a}$ is attached is in the (R) configuration. In certain embodiments, $R^{6a}$ is methyl ($C_1$), optionally substituted with one or more fluorines, e.g., $—CH_3$ or $—CF_3$. In certain embodiments, $R^{6a}$ is substituted or unsubstituted ethyl ($C_2$), substituted or unsubstituted n-propyl ($C_3$), or substituted or unsubstituted isopropyl ($C_3$). In certain embodiments, $R^{6a}$ is $—CH_2OR^{A6}$, $—CH_2CH_2OR^{A6}$, or $—CH_2CH_2CH_2OR^{A6}$. In certain embodiments, $R^{6a}$ is substituted or unsubstituted vinyl ($C_2$) or substituted or unsubstituted allyl ($C_3$). In certain embodiments, $R^{6a}$ is substituted or unsubstituted ethynyl ($C_2$) or substituted or unsubstituted propargyl ($C_3$). In certain embodiments, $R^{6a}$ is substituted or unsubstituted cyclopropyl. In certain embodiments, $R^{6b}$ is hydrogen. In certain embodiments, $R^{6b}$ is $—CH_3$ or $—CF_3$. In certain embodiments, ----- represents a single bond, and the hydrogen at C5 is alpha. In certain embodiments, ----- represents a double bond. In certain embodiments, $R^1$ is $—CH_3$ or $—CH_2CH_3$ In certain embodiments, $R^2$ is hydrogen, —OH, $—OCH_3$, $—OCH_2CH_3$, $—OCH_2CH_2CH_3$, $—CH_3$, $—CH_2CH_3$, $—CH_2CH_2CH_3$, cyclopropyl, fluoro, or chloro. In certain embodiments, $R^2$ is a non-hydrogen substitutent in the alpha configuration. In certain embodiments, $R^2$ is a non-hydrogen substituent in the beta configuration. In certain embodiments, $R^{3a}$ and $R^{3b}$ are both hydrogen. In certain embodiments, $R^{3a}$ and $R^{3b}$ are joined to form =O (oxo). In certain embodiments, $R^4$ is hydrogen.

In certain embodiments, wherein X is $—C(R^X)_2—$ and one $R^X$ group and $R^{5b}$ are joined to form a trans double bond, provided is a compound of Formula (I-c).

(I-c)

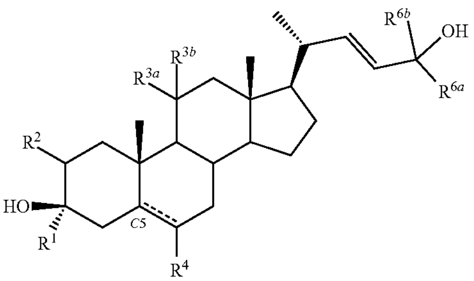

or a pharmaceutically acceptable salt thereof. In certain embodiments, $R^{6a}$ is a non-hydrogen group comprising between two and ten carbon atoms. In certain embodiments, at least one of $R^{6a}$ and $R^{6b}$ is a non-hydrogen group substituted with fluorine. In certain embodiments, the carbon to which $R^{6a}$ is attached is in the (S) configuration. In certain embodiments, the carbon to which $R^{6a}$ is attached is in the (R) configuration. In certain embodiments, $R^{6a}$ is methyl ($C_1$) optionally substituted with one or more fluorines, e.g., $—CH_3$ or $—CF_3$. In certain embodiments, $R^{6a}$ is substituted or unsubstituted ethyl ($C_2$), substituted or unsubstituted n-propyl ($C_3$), or substituted or unsubstituted isopropyl ($C_3$). In certain embodiments, $R^{6a}$ is $—CH_2OR^{A6}$, $—CH_2CH_2OR^{A6}$, or $—CH_2CH_2CH_2OR^{A6}$. In certain embodiments, $R^{6a}$ is substituted or unsubstituted vinyl ($C_2$) or substituted or unsubstituted allyl ($C_3$). In certain embodiments, $R^{6a}$ is substituted or unsubstituted ethynyl ($C_2$) or substituted or unsubstituted propargyl ($C_3$). In certain embodiments, $R^{6a}$ is substituted or unsubstituted cyclopropyl. In certain embodiments, $R^{6b}$ is hydrogen. In certain embodiments, $R^{6b}$ is $—CH_3$ or $—CF_3$. In certain embodiments ----- represents a single bond, and the hydrogen at $C_5$ is alpha. In certain embodiments, ----- represents a double bond. In certain embodiments, $R^1$ is $—CH_3$ or $—CH_2CH_3$. In certain embodiments, $R^2$ is hydrogen, —OH, $—OCH_3$, $—OCH_2CH_3$, $—OCH_2CH_2CH_3$, $—CH_3$, $—CH_2CH_3$, $—CH_2CH_2CH_3$, cyclopropyl, fluoro, or chloro. In certain embodiments, $R^2$ is a non-hydrogen substitutent in the alpha configuration. In certain embodiments, $R^2$ is a non-hydrogen substituent in the beta configuration. In certain embodiments, $R^{3a}$ and $R^{3b}$ are both hydrogen. In certain embodiments, $R^{3a}$ and $R^{3b}$ are joined to form =O (oxo). In certain embodiments, $R^4$ is hydrogen.

In certain embodiments, the compound of Formula (I) is selected from a compound of Formula (II):

(II)

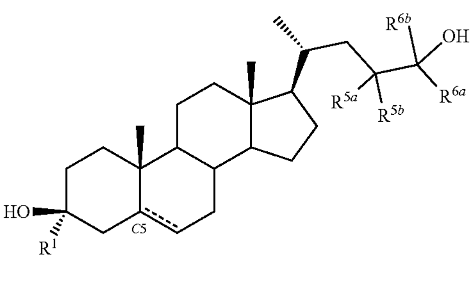

or a pharmaceutically acceptable salt thereof. In certain embodiments, $R^{6a}$ is a non-hydrogen group comprising between two and ten carbon atoms. In certain embodiments, at least one of $R^{6a}$ and $R^{6b}$ is a non-hydrogen group substituted with fluorine. In certain embodiments, the carbon to which $R^{6a}$ is attached is in the (S) configuration. In certain embodiments, the carbon to which $R^{6a}$ is attached is in the (R) configuration. In certain embodiments, $R^{6a}$ is methyl ($C_1$) optionally substituted with one or more fluorines, e.g., $—CH_3$ or $—CF_3$. In certain embodiments, $R^{6a}$ is substituted or unsubstituted ethyl ($C_2$), substituted or unsubstituted n-propyl ($C_3$), or substituted or unsubstituted isopropyl ($C_3$). In certain embodiments, $R^{6a}$ is $—CH_2OR^{A6}$, $—CH_2CH_2OR^{A6}$, or $—CH_2CH_2CH_2OR^{A6}$. In certain embodiments, $R^{6a}$ is substituted or unsubstituted vinyl ($C_2$) or substituted or unsubstituted allyl ($C_3$). In certain embodiments, $R^{6a}$ is substituted or unsubstituted ethynyl ($C_2$) or substituted or unsubstituted propargyl ($C_3$). In certain embodiments, $R^{6a}$ is substituted or unsubstituted cyclopropyl. In certain embodiments, $R^{6b}$ is hydrogen. In certain embodiments, $R^{6b}$ is $—CH_3$ or $—CF_3$. In certain embodiments, ---- represents a single bond, and the hydrogen at $C_5$ is alpha. In certain embodiments, ---- represents a double bond. In certain embodiments, $R^1$ is $—CH_3$ or $—CH_2CH_3$.

In certain embodiments, the compound of Formula (I) is selected from a compound of Formula (II-A):

(II-A)

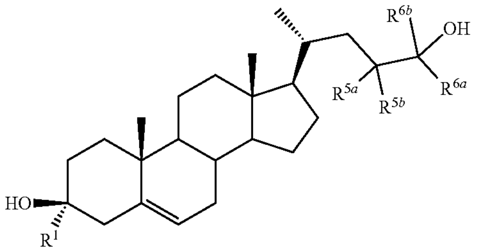

or a pharmaceutically acceptable salt thereof. In certain embodiments, $R^{6a}$ is a non-hydrogen group comprising between two and ten carbon atoms. In certain embodiments, at least one of $R^{6a}$ and $R^{6b}$ is a non-hydrogen group substituted with fluorine. In certain embodiments, the carbon to which $R^{6a}$ is attached is in the (S) configuration. In certain embodiments, the carbon to which $R^{6a}$ is attached is in the (R) configuration. In certain embodiments, $R^{6a}$ is methyl ($C_1$) optionally substituted with one or more fluorines, e.g., $—CH_3$ or $—CF_3$. In certain embodiments, $R^{6a}$ is substituted or unsubstituted ethyl ($C_2$), substituted or unsubstituted n-propyl ($C_3$), or substituted or unsubstituted isopropyl ($C_3$). In certain embodiments, $R^{6a}$ is $—CH_2OR^{A6}$, $—CH_2CH_2OR^{A6}$, or $—CH_2CH_2CH_2OR^{A6}$. In certain embodiments, $R^{6a}$ is substituted or unsubstituted vinyl ($C_2$) or substituted or unsubstituted allyl ($C_3$). In certain embodiments, $R^{6a}$ is substituted or unsubstituted ethynyl ($C_2$) or substituted or unsubstituted propargyl ($C_3$). In certain embodiments, $R^{6a}$ is substituted or unsubstituted cyclopropyl. In certain embodiments, $R^{6b}$ is hydrogen. In certain embodiments, $R^{6b}$ is $—CH_3$ or $—CF_3$. In certain embodiments, $R^1$ is $—CH_3$ or $—CH_2CH_3$.

In certain embodiments, the compound of Formula (I) is selected from a compound of Formula (II-B):

(II-B)

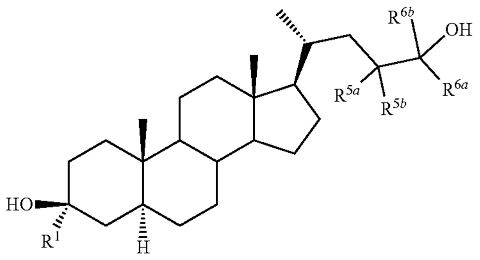

or a pharmaceutically acceptable salt thereof. In certain embodiments, $R^{6a}$ is a non-hydrogen group comprising between two and ten carbon atoms. In certain embodiments, at least one of $R^{6a}$ and $R^{6b}$ is a non-hydrogen group substituted with fluorine. In certain embodiments, the carbon to which $R^{6a}$ is attached is in the (S) configuration. In certain embodiments, the carbon to which $R^{6a}$ is attached is in the (R) configuration. In certain embodiments, $R^{6a}$ is methyl ($C_1$) optionally substituted with one or more fluorines, e.g., $—CH_3$ or $—CF_3$. In certain embodiments, $R^{6a}$ is substituted or unsubstituted ethyl ($C_2$), substituted or unsubstituted n-propyl ($C_3$), or substituted or unsubstituted isopropyl ($C_3$). In certain embodiments, $R^{6a}$ is $—CH_2OR^{A6}$, $—CH_2CH_2OR^{A6}$, or $—CH_2CH_2CH_2OR^{A6}$. In certain embodiments, $R^{6a}$ is substituted or unsubstituted vinyl ($C_2$) or substituted or unsubstituted allyl ($C_3$). In certain embodiments, $R^{6a}$ is substituted or unsubstituted ethynyl ($C_2$) or substituted or unsubstituted propargyl ($C_3$). In certain embodiments, $R^{6a}$ is substituted or unsubstituted cyclopropyl. In certain embodiments, $R^{6b}$ is hydrogen. In certain embodiments, $R^{6b}$ is $—CH_3$ or $—CF_3$. In certain embodiments, $R^1$ is $—CH_3$ or $—CH_2CH_3$.

In certain embodiments, a compound of Formula (I) is selected from the group consisting of:

1-11

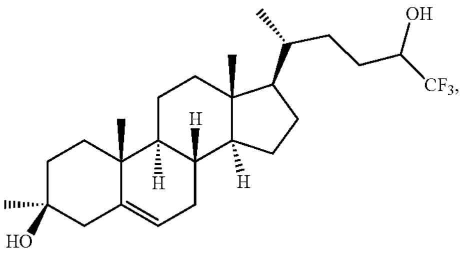

1-12

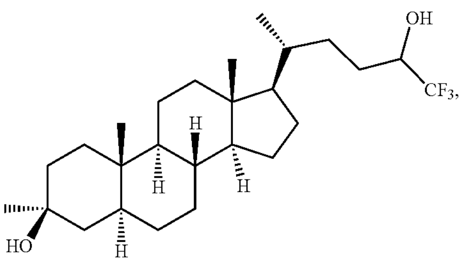

-continued
1-15
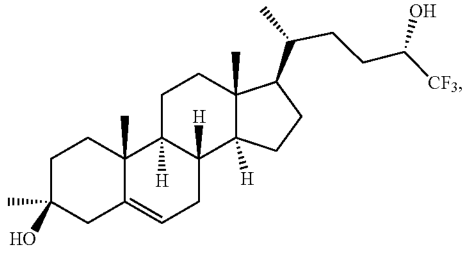
1-16
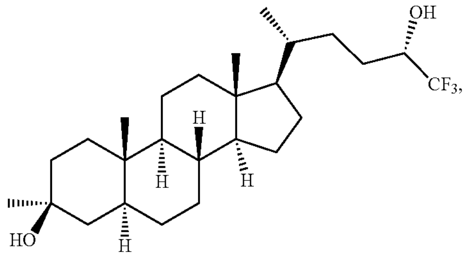
1-17
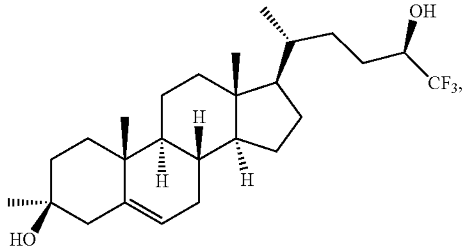
1-18
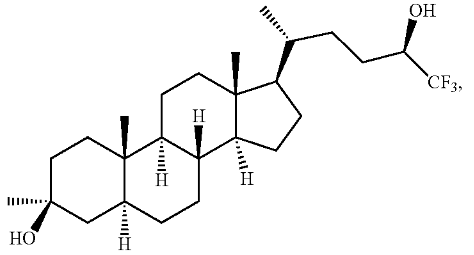
2-4
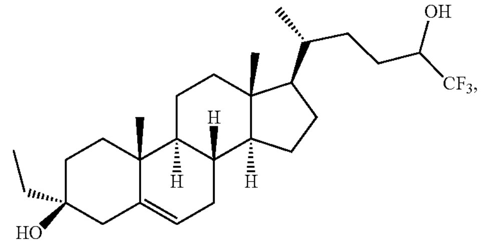
2-5
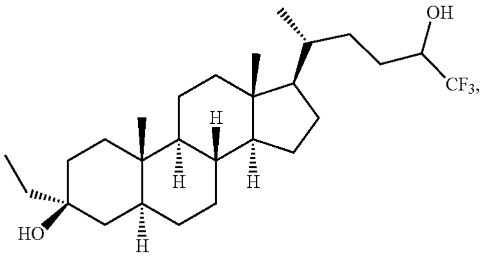
-continued
2-7
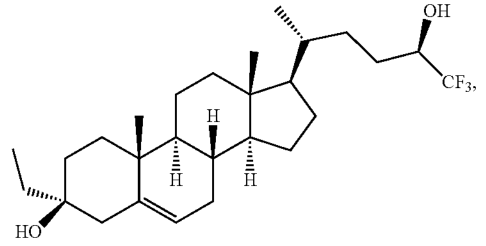
2-8
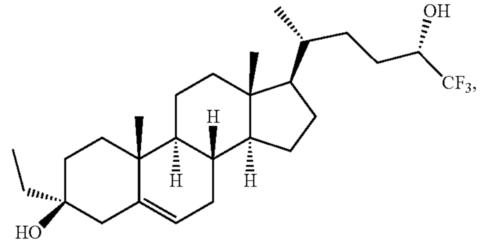
2-9
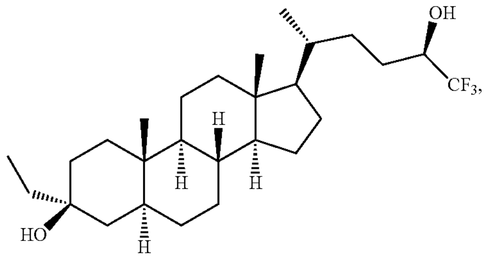
2-10
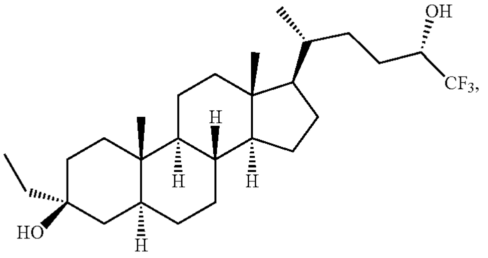
3-2
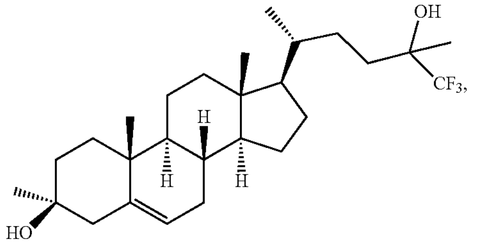
3-3
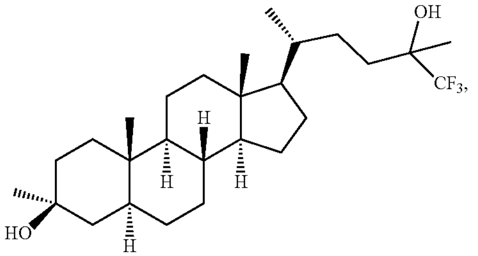

-continued
3-5
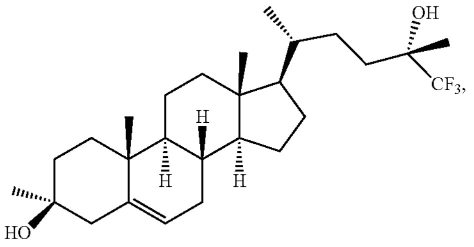
3-6
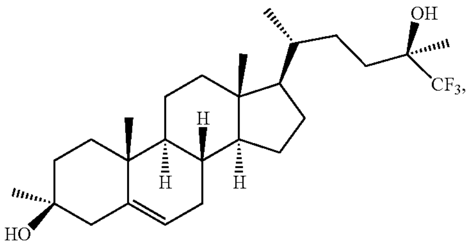
3-7
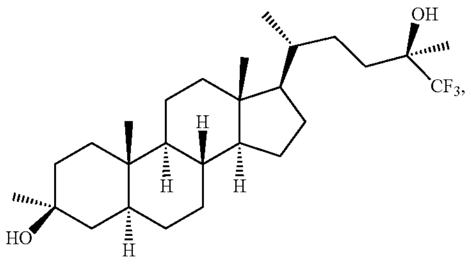
3-8
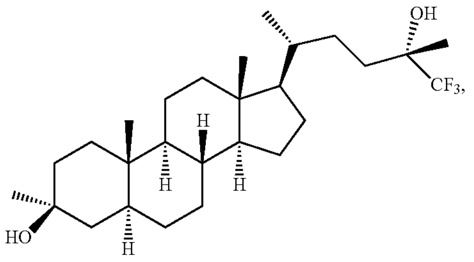
4-6
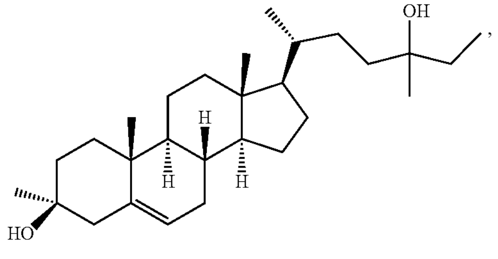
4-7
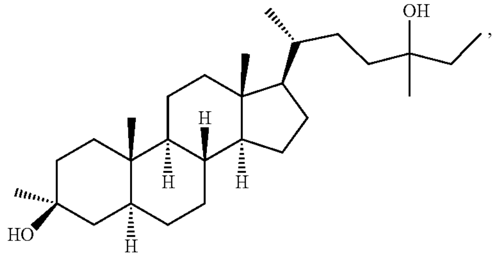
-continued
4-9
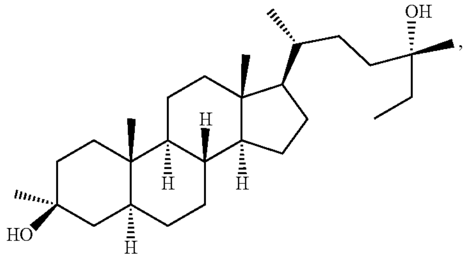
4-10
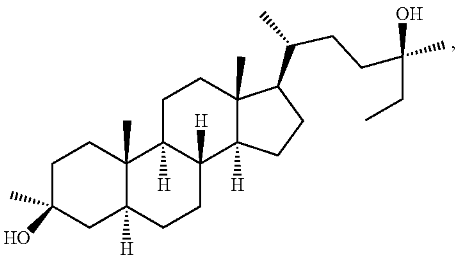
4-11
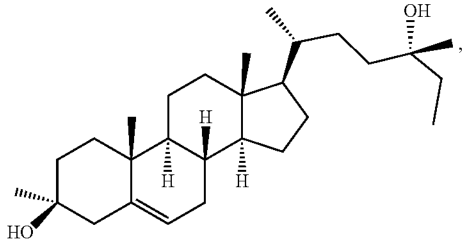
4-12
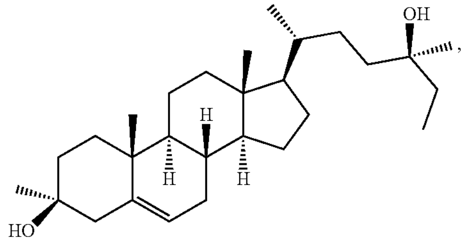
5-2
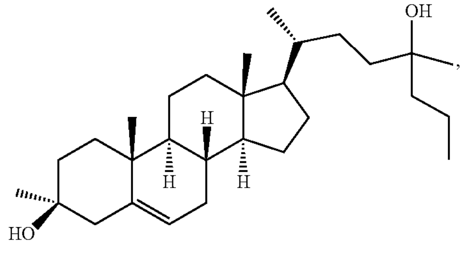
5-3
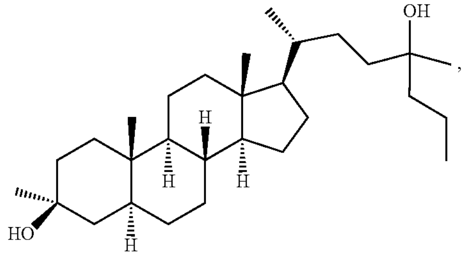

-continued
5-5
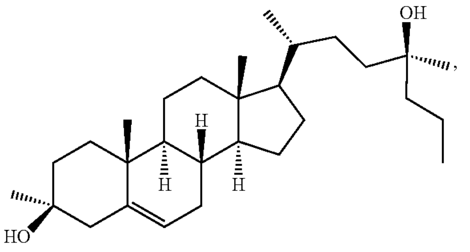
5-6
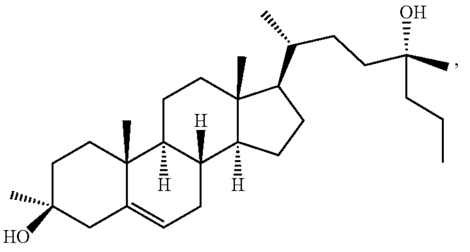
5-7
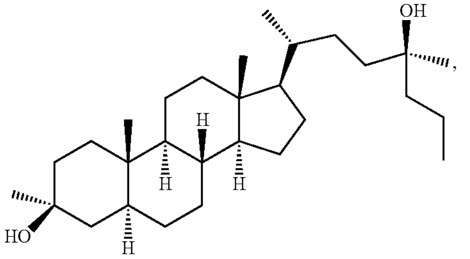
5-8
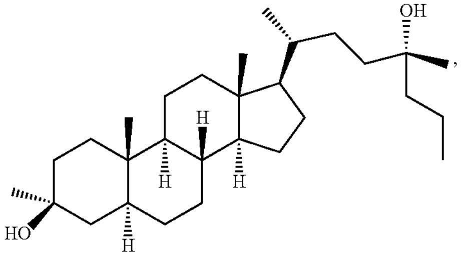
6-2
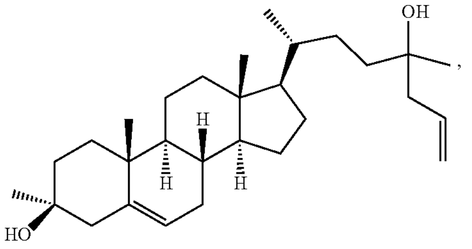
6-3
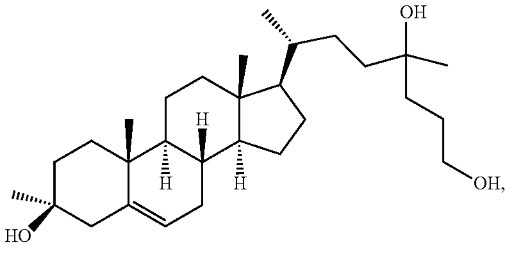
-continued
6-6
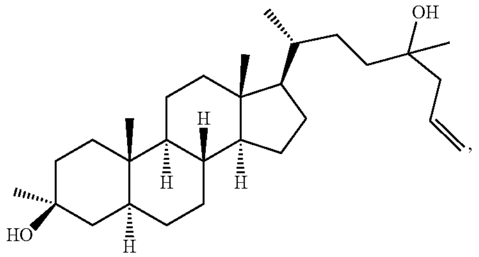
6-11
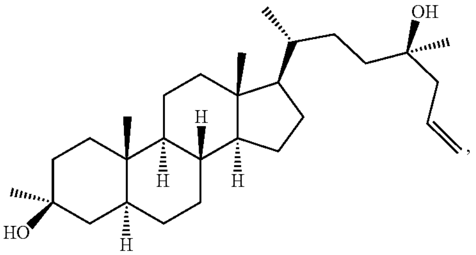
6-12
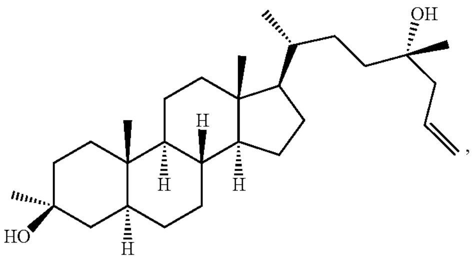
6-7
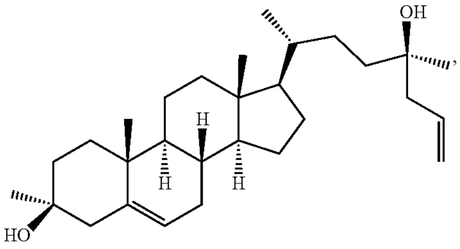
6-8
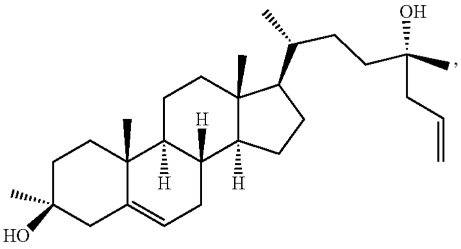
6-9
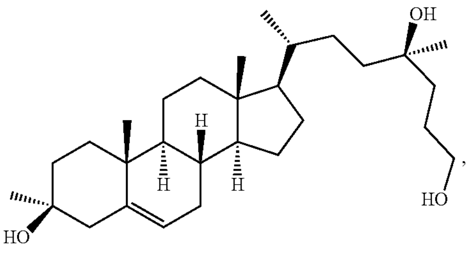

-continued
6-10
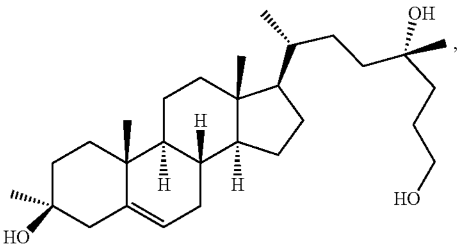
6-11
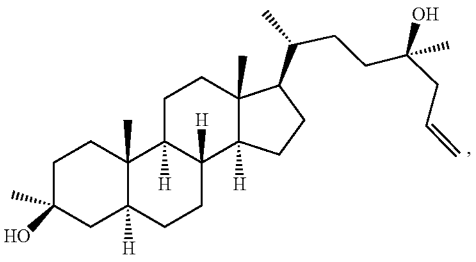
6-12
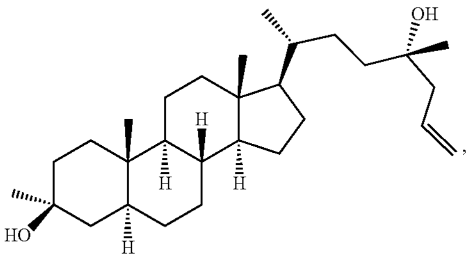
6-13
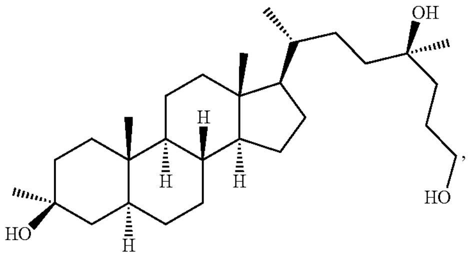
6-14
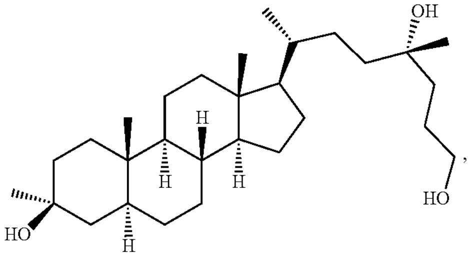
6-15
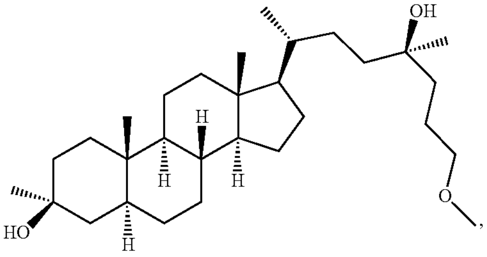
-continued
6-16
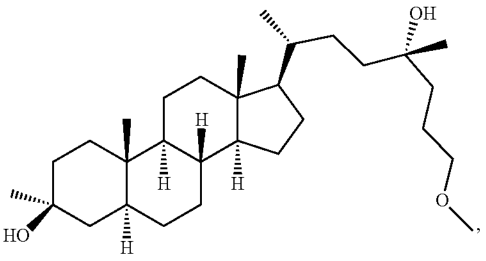
6-17
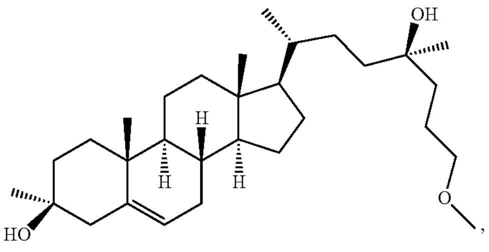
6-18
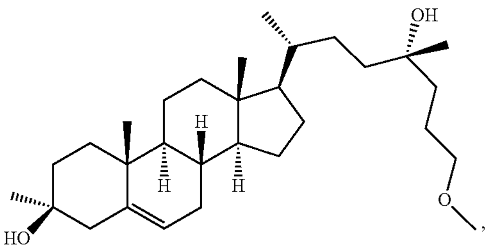
7-2
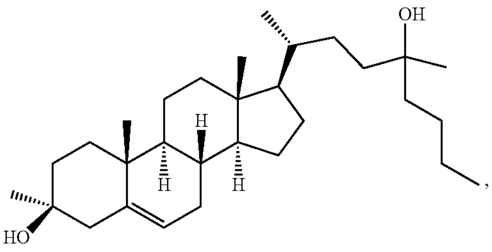
7-3
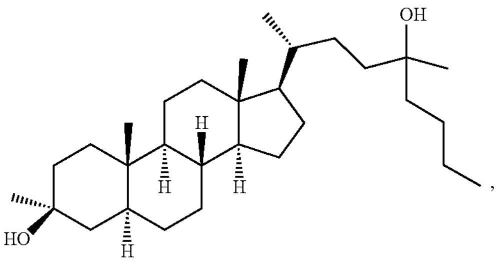
7-4
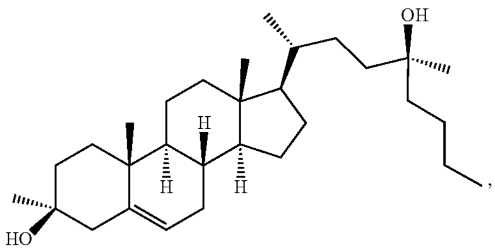

-continued
7-5
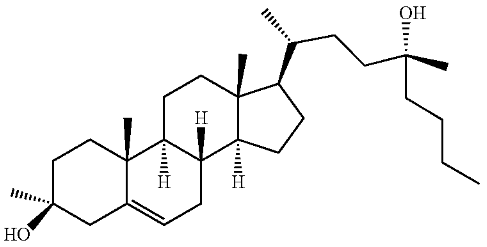,
7-6
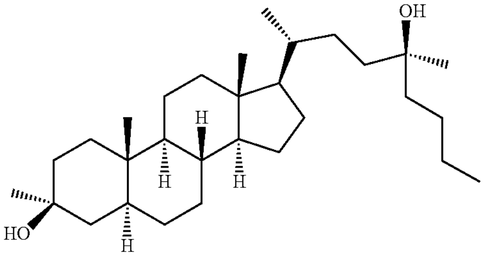,
7-7
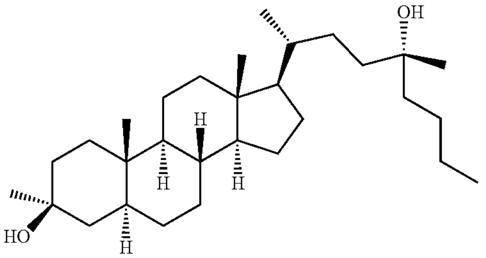,
8-2
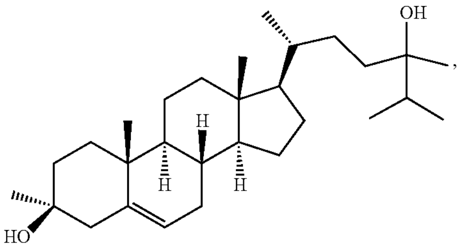,
8-3
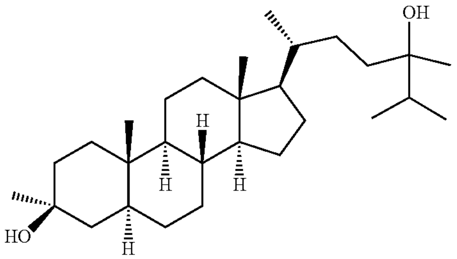,
8-5
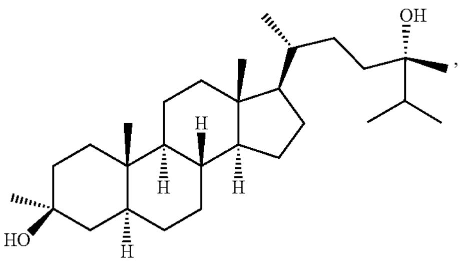,
-continued
8-6
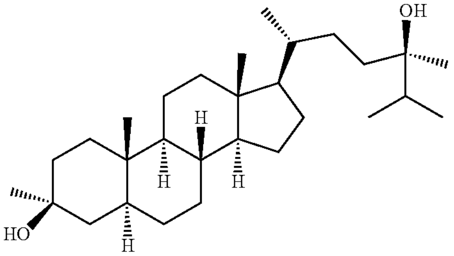,
8-7
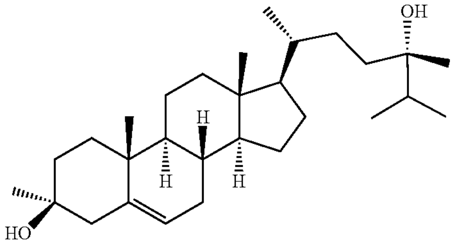,
8-8
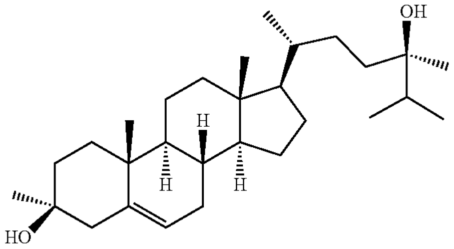,
9-2
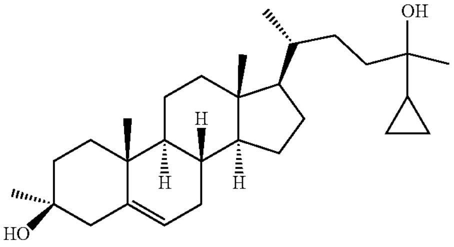,
9-3
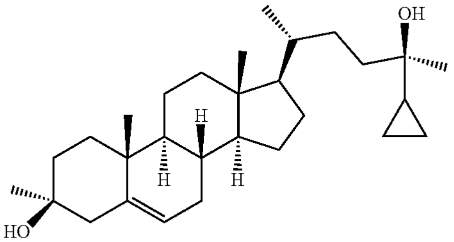,
9-4
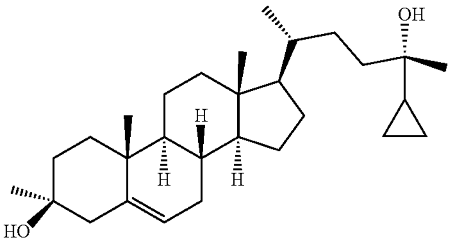, 9-6
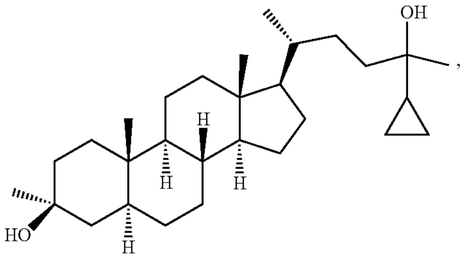
9-7
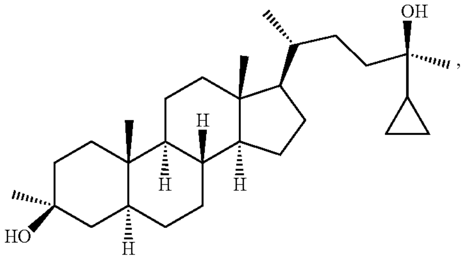
9-8
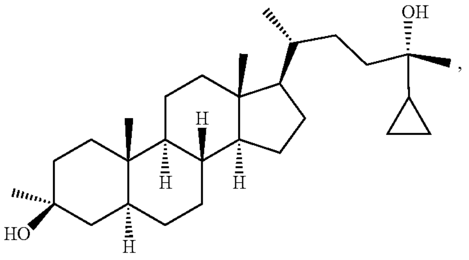
10-2
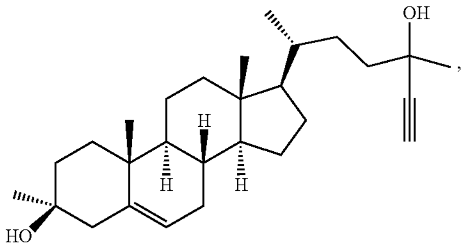
10-3
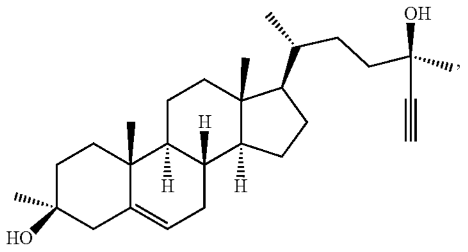
10-4
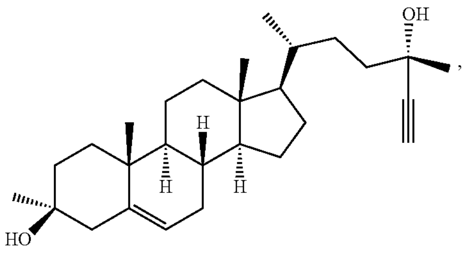
10-6
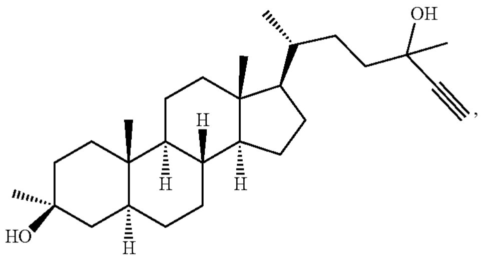
10-8
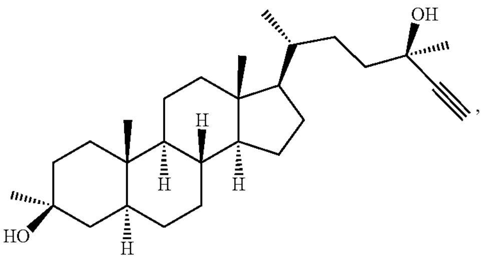
10-9
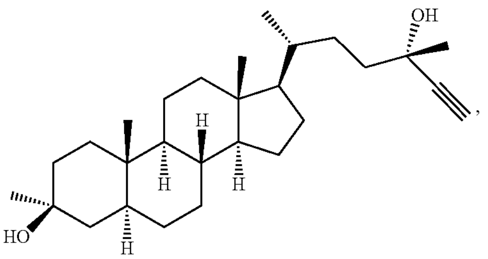
10-7
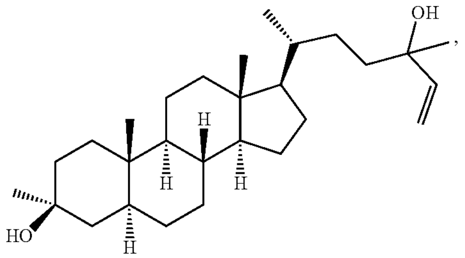
10-10
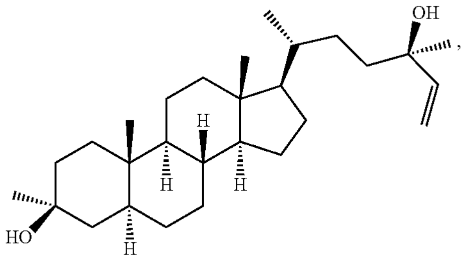
10-11
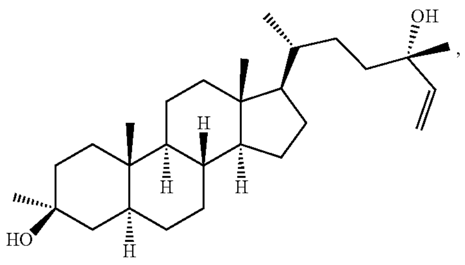

-continued
10-12
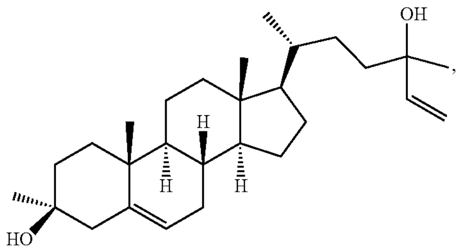
10-12A
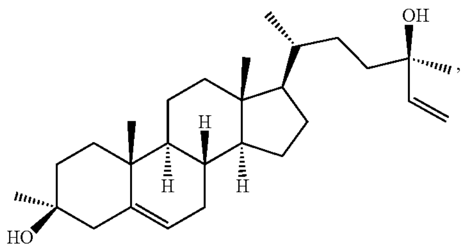
10-12B
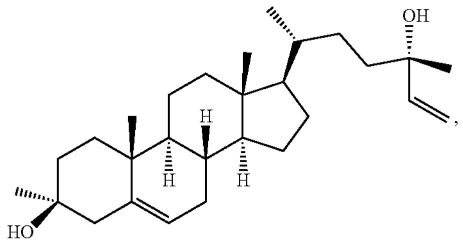
10-13
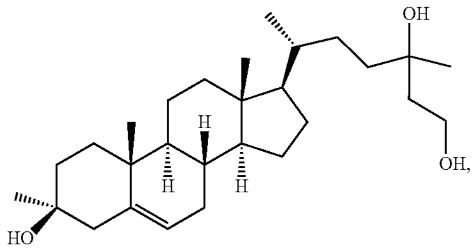
10-14
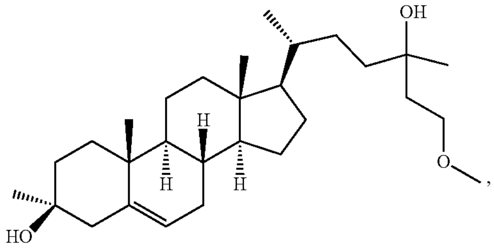
10-16
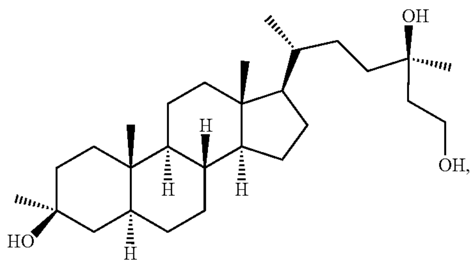
-continued
10-15
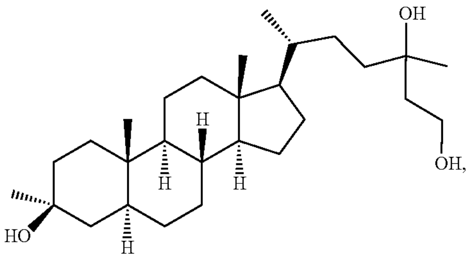
10-17
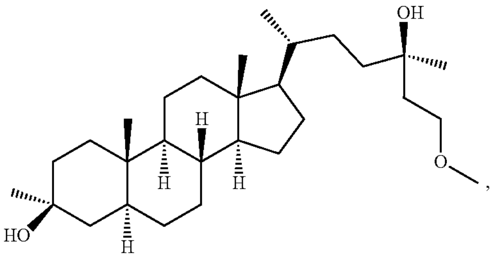
10-18
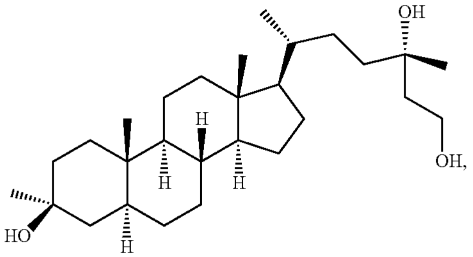
10-19
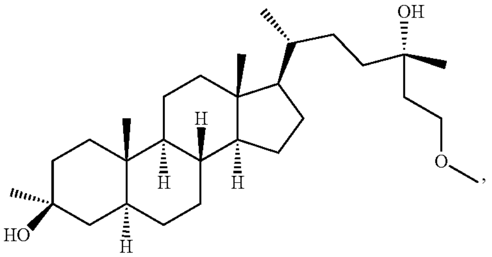
10-20
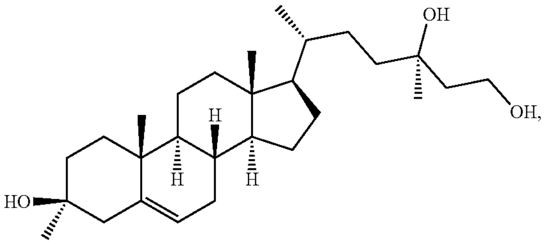
10-21
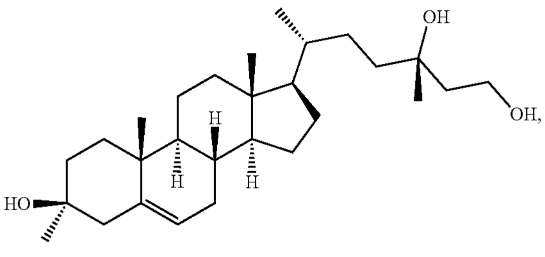

-continued 10-22

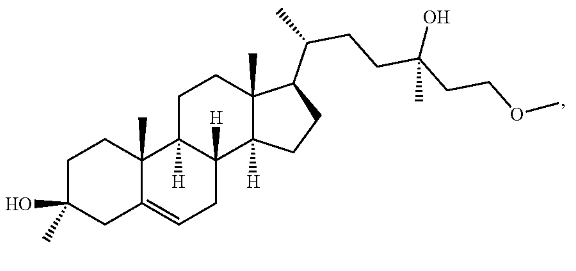

10-23

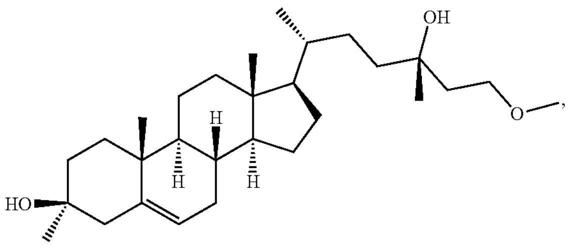

11-13

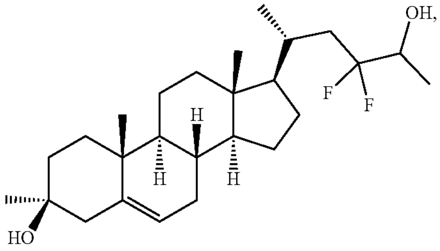

11-14

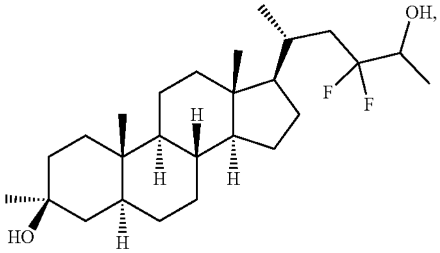

11-15

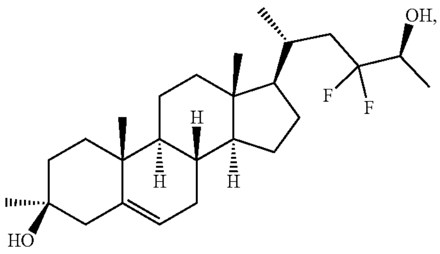

11-16

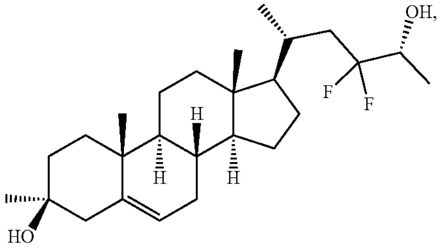

-continued 11-17

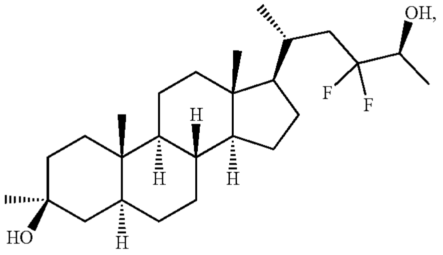

11-18

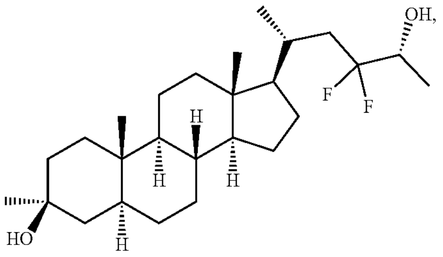

11-19

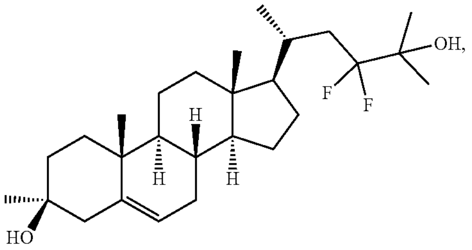

11-20

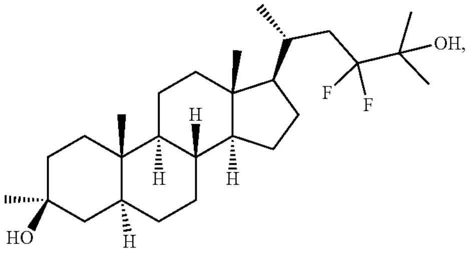

and pharmaceutically acceptable salts thereof.

Pharmaceutical Compositions

In another aspect, the invention provides a pharmaceutical composition comprising a pharmaceutically acceptable carrier and a effective amount of a compound of Formula (I).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of Formula (I) or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound of Formula (I). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether O-cyclodextrin, e.g., for example, sulfobutyl ether O-cyclodextrin, also known as Captisol®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of Formula (I). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of Formula (I), or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid: A compound of Formula (I), or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of Formula (I), or pharmaceutically acceptable salt thereof, may be dissolved or suspended in a buffered sterile saline injectable aqueous medium to a concentration of approximately 5 mg/mL.

Exemplary Formulation 6—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: v may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of Formula (I), and pharmaceutically acceptable salts thereof, as described herein, are generally designed to modulate NMDA function, and therefore to act as neuroactive steroids for the treatment and prevention of CNS-related conditions in a subject. Modulation, as used herein, refers to the inhibition or potentiation of NMDA receptor function. In certain embodiments, the compound of Formula (I), or pharmaceutically acceptable salt thereof, may act as a negative allosteric modulator (NAM) of NMDA, and inhibit NMDA receptor function. In certain embodiments, the compound of Formula (I), or pharmaceutically acceptable salt thereof, may act as positive allosteric modulators (PAM) of NMDA, and potentiate NMDA receptor function.

Exemplary CNS conditions related to NMDA-modulation include, but are not limited to, adjustment disorders, anxiety disorders (including obsessive-compulsive disorder, post-traumatic stress disorder, social phobia, generalized anxiety disorder), cognitive disorders (including Alzheimer's disease and other forms of dementia), dissociative disorders, eating disorders, mood disorders (including depression, bipolar disorder, and dysthymic disorder), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins), neurodevelopmental disorders (including Rett syndrome), pain (including acute and chronic pain), seizure disorders (including status epilepticus and monogenic forms of epilepsy such as Dravet's disease, and Tuberous Sclerosis Complex (TSC)), stroke, traumatic brain injury, movement disorders (including Huntington's disease and Parkinson's disease) and tinnitus. In certain embodiments, the compound of Formula (I), or pharmaceutically acceptable salt thereof, can be used to induce sedation or anesthesia. In certain embodiments, the compound of Formula (I), or pharmaceutically acceptable salt thereof, is useful in the treatment or prevention of adjustment disorders, anxiety disorders, cognitive disorders, dissociative disorders, eating disorders, mood disorders, schizophrenia or other psychotic disorders, sleep disorders, substance-related disorders, personality disorders, autism spectrum disorders, neurodevelopmental disorders, pain, seizure disorders, stroke, traumatic brain injury, movement disorders and tinnitus.

In another aspect, provided is a method of treating or preventing brain excitability in a subject susceptible to or afflicted with a condition associated with brain excitability, comprising administering to the subject an effective amount of a compound of Formula (I), or a pharmaceutically acceptable salt thereof.

In yet another aspect, the present invention provides a combination of a compound of Formula (I), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative substituted biarylamides that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

General method for supercritical fluid chromatography (SFC): SFC purification was carried out using a Thar 200 preparative SFC instrument equipped with a ChiralPak AD-10 μM, 200×50 mm ID. The compounds were separated eluting with mixtures of carbon dioxide and methanol or ethanol (e.g., 20-35% methanol or ethanol and 0.1% ammonium hydroxide) at a flow rate of 55-200 mL/min and monitored at 220 nm wavelength.

Single pure isomers were obtained after SFC chromatographic separation, yielding two isomers with a diasteriomeric ratio ≥95:5, as determined by SFC chromatography.

The configuration of the steroid C-24 stereocenter of 1-13 and 1-14, and 2-20 and 2-21 isomers was determined by the Mosher Method (Dale, J. A., Dull, D. L., and Mosher, H. S. (1969) J. Org. Chem. 34, 2543). The C-24 configuration of subsequent derivatives that employed such intermediates, for example 1-15 and 1-17, were assigned accordingly.

For all other single diastereomers, for which the C-24 stereocenter was not determined by the Mosher Method, the first eluting diastereomer from the SFC was tentatively assigned to be attached in the (R) configuration at C-24, whereas the second eluting diastereomer from the SFC was tentatively assigned to be attached in the (S) configuration at C-24. The assignments were not unambiguously confirmed by the Mosher Method or other techniques.

Example 1

(a)

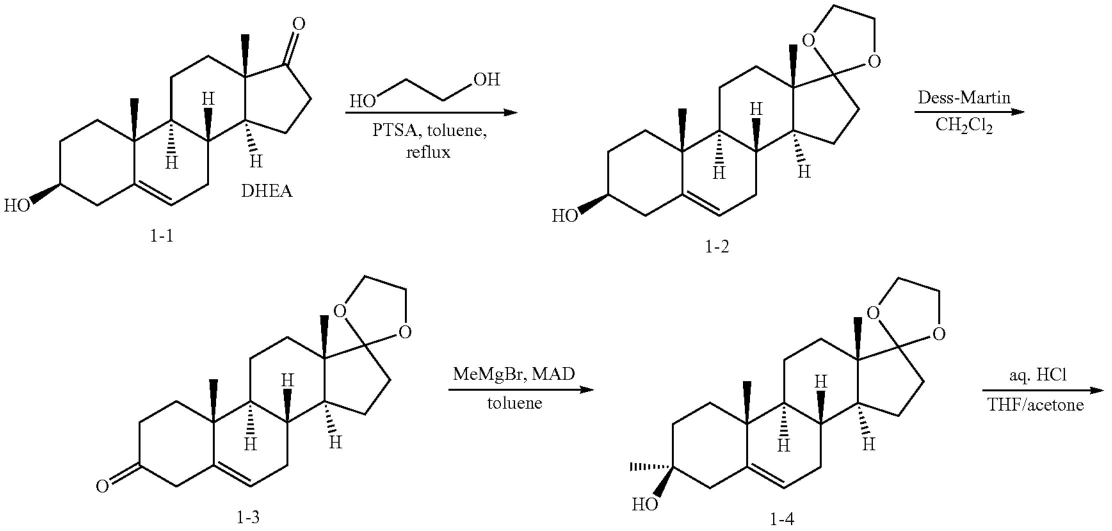

-continued
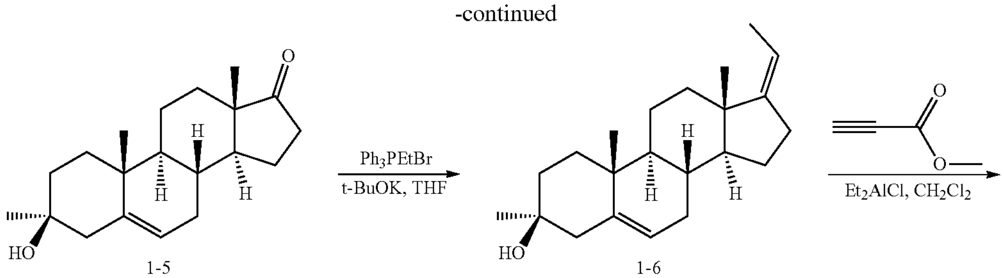
1-5 1-6
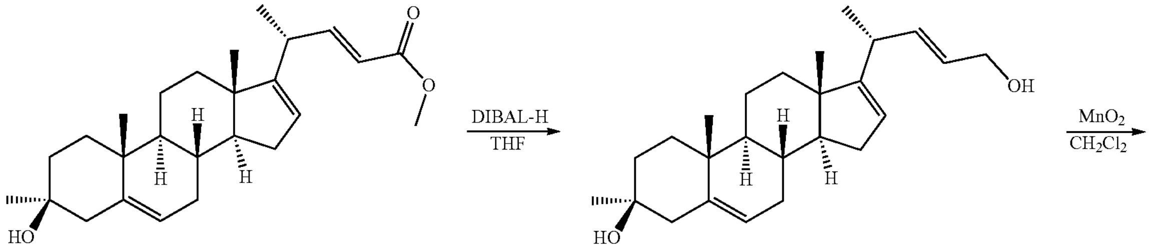
1-7 1-8
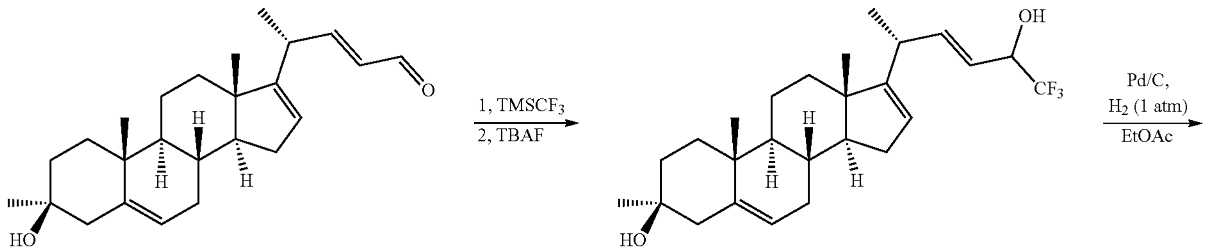
1-9 1-10
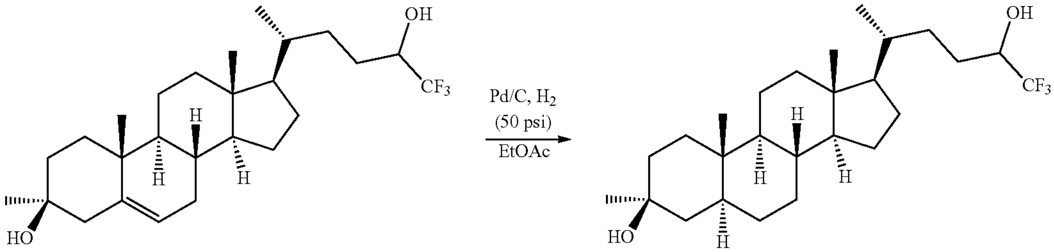
1-11 1-12
(b)
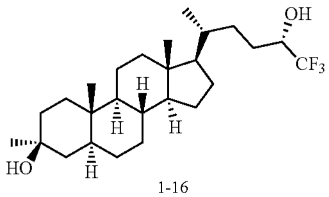
1-16

-continued

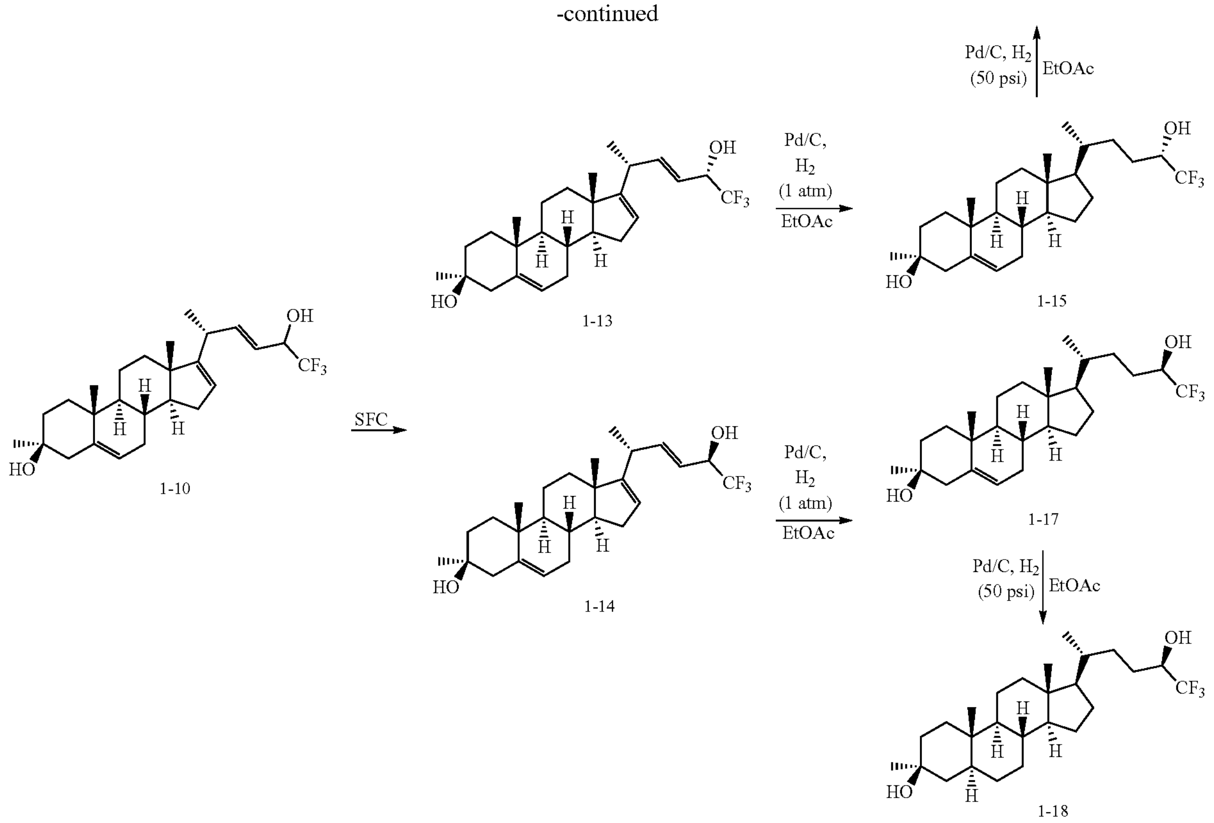

1-10

1-13

1-14

1-15

1-17

1-18

Preparation of Compound 1-2. To a solution of ketone 1-1 (50.0 g, 0.17 mol) and ethylene glycol (62 mL) in toluene (600 mL) was added p-toluenesulfonic acid (1.4 g, 7.28 mmol). The reaction mixture was refluxed overnight with a Dean-Stark trap. The mixture was cooled to room temperature, diluted with ethyl acetate (500 mL), and washed with saturated aqueous sodium bicarbonate (300 mL×2) and brine (300 mL×2). The organic phase was dried over sodium sulfate and concentrated in vacuum to afford crude product 1-2 (64.0 g, 100%) which was directly used in the next step without further purification. $^1$H NMR: (400 MHz, CDC13) δ 5.35 (d, J=5.6 Hz, 1H), 3.97-3.82 (m, 4H), 3.59-3.47 (m, 1H), 2.34-2.21 (m, 2H), 2.06-1.94 (m, 2H), 1.90-1.74 (m, 3H), 1.73-1.64 (m, 1H), 1.63-1.33 (m, 10H), 1.32-1.19 (m, 1H), 1.14-1.03 (m, 1H), 1.01 (s, 3H), 0.99-0.93 (m, 1H), 0.86 (s, 3H).

Preparation of Compound 1-3. To a solution of compound 1-2 (32 g, 96 mmol) in dry $CH_2Cl_2$ (1200 mL) was added Dess-Martin reagent (81 g, 192 mmol) in portions at 0° C. Then the reaction mixture was stirred at room temperature for 3 h. TLC (petroleum ether:ethyl acetate=3:1) showed the starting material was consumed completely. The mixture was quenched with saturated aqueous $NaHCO_3$/$Na_2S_2O_3$=1:3 (1 L). The organic phase was washed with brine (500 mL) and dried over $Na_2SO_4$, and the solvent was evaporated to afford crude product 1-3 (33.0 g, 100%), which was directly used in the next step without further purification. $^1$H NMR: (400 MHz, CDC13) δ 5.34 (d, J=5.2 Hz, 1H), 3.77-4.00 (m, 4H), 3.19-3.39 (m, 1H), 2.83 (dd, J=16.44, 2.13 Hz, 1H), 2.38-2.59 (m, 1H), 2.21-2.37 (m, 1H), 1.95-2.09 (m, 3H), 1.54-1.73 (m, 4H), 1.74-1.90 (m, 2H), 1.37-1.51 (m, 3H), 1.21-1.34 (m, 2H), 1.19 (s, 3H), 0.98-1.12 (m, 1H), 0.83-0.93 (m, 3H).

Preparation of MAD. To a solution of 2,6-di-tert-butyl-4-methylphenol (40 g, 180 mmol) in toluene (200 mL) was added a solution of $AlMe_3$ (45 mL, 90 mmol, 2 M in hexane) at room temperature. The resulting mixture was stirred at room temperature for 1 h and used as a solution of MAD in toluene in the next step without any purification.

Preparation of Compound 1-4. To a solution of MAD (90 mmol, freshly prepared) in toluene (200 mL) was added dropwise a solution of compound 1-3 (10 g, 30 mmol) in toluene (80 mL) at −78° C. during a period of 1 h under nitrogen. Then the reaction mixture was stirred for 30 min, a solution of $CH_3MgBr$ (30 mL, 90 mmol, 1.0 M in toluene) was added dropwise at −78° C. The reaction mixture was warmed to −40° C. and stirred at this temperature for 3 h. TLC (petroleum ether:ethyl acetate=3:1) showed that the starting material was consumed completely. The mixture was poured into saturated aqueous $NH_4Cl$ solution (200 mL) and extracted with EtOAc (150 mL×2). The combined organic phases were dried over $Na_2SO_4$, and the solvent was evaporated to afford crude product, which was purified by column chromatography on silica gel (eluent: petroleum ether:ethyl acetate=15:1) to give compound 1-4 (4 g, 38%) as white powder. $^1$H NMR: (400 MHz, CDC13) δ 5.30 (d, J=5.2 Hz, 1H), 3.75-4.04 (m, 4H), 2.42 (d, J=13.6 Hz, 1H), 1.88-2.12 (m, 3H), 1.73-1.86 (m, 2H), 1.64-1.72 (m, 2H), 1.52-1.63 (m, 4H), 1.35-1.51 (m, 4H), 1.19-1.32 (m, 1H), 1.12-1.18 (m, 1H), 1.10 (s, 3H), 0.99-1.03 (m, 3H), 0.92-0.98 (m, 1H), 0.86 (s, 3H).

Preparation of Compound 1-5. To a solution of compound 1-4 (6.0 g, 17.3 mmol) in THE (200 mL) was added aqueous HCl solution (35 mL, 1 M) and acetone (35 mL). The reaction mixture was stirred for 20° C. at room temperature. TLC (petroleum ether:ethyl acetate=3:1) indicated that the reaction was complete. Then the reaction mixture was diluted with EtOAc (200 mL), washed with saturated aqueous $NaHCO_3$ solution (200 mL), dried over $Na_2SO_4$ and evaporated under reduced pressure to give 1-5 (5.2 g, 99.2%). $^1$H NMR: (400 MHz, CDCl3) δ 5.27 (d, J=6.8 Hz, 1H), 2.45-2.35 (m, 2H), 2.09-1.84 (m, 4H), 1.82-1.57 (m, 6H), 1.50-1.35 (m, 4H), 1.26-1.08 (m, 4H), 1.05 (s, 3H), 0.95 (s, 3H), 0.86 (s, 3H).

Preparation of Compound 1-6. To a solution of $Ph_3PEtBr$ (12.25 g, 33.00 mmol) in dry THE (15 mL) was added dropwise a solution of t-BuOK (3.70 g, 33.00 mmol) in dry THE (10 mL) under $N_2$ at 0° C. The mixture was stirred at room temperature for 1.5 h. Then a solution of 1-5 (1.00 g, 3.31 mmol) in THF (10 mL) was added dropwise and the resulting mixture was stirred at 70° C. for 4 h. TLC (petroleum ether:ethyl acetate=3:1) indicated that the starting material was consumed completely. The reaction was quenched with saturated aqueous $NH_4Cl$ solution (50 mL) and extracted with EtOAc (30 mL×2). The combined organic phases were dried over $Na_2SO_4$ and concentrated in vacuum. The residue was purified by column chromatography on silica gel (eluent: petroleum ether:ethyl acetate=12:1) to give 1-6 (900 mg, 90.9%) as white powder. $^1$H NMR: (400 MHz, CDCl3) δ 5.32 (d, J=5.2 Hz, 1H), 5.15-5.12 (m, 1H), 2.44-2.30 (m, 3H), 2.29-2.21 (m, 1H), 2.05-1.97 (m, 2H), 1.81-1.45 (m, 14H), 1.30-1.15 (m, 3H), 1.12 (s, 3H), 1.02 (s, 3H), 0.95-1.01 (m, 1H), 0.90 (s, 3H).

Preparation of Compound 1-7. To a solution of compound 1-6 (1.00 g, 3.20 mmol) and methyl propiolate (0.67 g, 8.00 mmol) in dry $CH_2Cl_2$ (15 mL) was added dropwise a solution of $Et_2AlCl$ (12.8 mL, 12.8 mmol, 1 M in toluene) with stirring at 0° C. Then the reaction was warmed to room temperature and stirred for 20 h. TLC (petroleum ether:ethyl acetate=5:1) indicated that the starting material was consumed completely. The mixture was quenched with saturated aqueous $NaHCO_3$ solution (30 mL) and extracted with $CH_2Cl_2$ (30 mL×2). The combined organic phases were dried over $Na_2SO_4$ and concentrated in vacuum. The residue was purified by column chromatography on silica gel (eluent: petroleum ether:ethyl acetate=10:1) to give 1-7 (1.00 g, 78.7%) as white powder. $^1$H NMR: (400 MHz, CDCl3) δ 6.97-6.91 (m, 1H) 5.82 (d, J=16 Hz, 1H), 5.42-5.41 (m, 1H), 5.32 (d, J=5.2 Hz, 1H), 3.73 (s, 3H), 3.04-3.00 (m, 1H), 2.43 (d, J=12.8 Hz, 1H), 2.11-1.97 (m, 3H), 1.88-1.50 (m, 12H), 1.40-1.20 (m, 3H), 1.21-1.26 (m, 1H), 1.18 (d, J=6.78 Hz, 3H), 1.12 (s, 3H), 1.04 (s, 3H), 0.82 (s, 3H).

Preparation of Compound 1-8. To a solution of compound 1-7 (1.75 g, 4.4 mmol) in dry THE (20 mL), DIBAL-H (1 M in THF, 22 mL, 22.0 mmol) was added dropwise at −78° C. under nitrogen. The reaction mixture was warmed to 30° C. and then stirred for 2 h at 30° C. The reaction was quenched with addition of $H_2O$ (2 mL), diluted with EtOAc (200 mL) and dried over anhydrous $Na_2SO_4$, filtered through a pad of celite and the pad was washed with EtOAc (50 mL×3). The combined filtrates were concentrated in vacuum to give the crude product 1-8 (1.6 g, 98%) which was directly used in the next step without further purification.

Preparation of Compound 1-9. A mixture of 1-8 (1.6 g, 4.3 mmol) and $MnO_2$ (7.5 g, 86.0 mmol) in $CH_2Cl_2$ (50 mL) was stirred at 30° C. for 20 h. The reaction mixture was filtered through a pad of celite and the pad was washed with $CH_2Cl_2$ (50 mL×3). The combined filtrates were concentrated to dryness to give the crude product 1-9 (1.3 g, 82%) which was directly used in the next step without purification. $^1$H NMR: (400 MHz, CDCl3) δ 9.54 (d, J=7.6 Hz, 1H), 6.84-6.78 (dd, $J_1$=15.6 Hz, $J_2$=7.6 Hz, 1H), 5.54-5.49 (dd, $J_1$=15.6 Hz, $J_2$=7.6 Hz, 1H), 5.45-5.44 (m, 1H), 5.32 (d, J=5.2 Hz, 1H), 3.19-3.12 (m, 1H), 2.42 (d, J=12.8 Hz, 1H), 2.14-2.08 (m, 1H), 2.00-1.52 (m, 13H), 1.42-1.35 (m, 3H), 1.24 (d, J=6.8 Hz, 3H), 1.12 (s, 3H), 1.05 (s, 3H), 0.80 (s, 3H).

Preparation of Compound 1-10. To a suspension of 1-9 (600 mg, 1.63 mmol) and CsF (120 mg, 0.82 mmol) in toluene/THF (18 mL, 8/1) was added $TMSCF_3$ (2.4 mL, 16.3 mmol) and the mixture was stirred for 20° C. at room temperature under nitrogen. TLC (petroleum ether:ethyl acetate=3/1) showed the starting material was consumed completely. A solution of TBAF (6.8 mL, 1 M in THF) was added and the mixture was stirred for 4 h at room temperature. The mixture was diluted with MTBE (200 mL), washed with a saturated $NaHCO_3$ solution (30 mL×3) and concentrated in vacuum. The residue was purified by column chromatography on silica gel (eluent: petroleum ether:ethyl acetate=12/1) to afford 1-10 (300 mg, 42%) as white solid. $^1$H NMR: (400 MHz, CDCl3) δ 5.97-5.91 (dd, $J_1$=15.6 Hz, $J_2$=7.6 Hz, 1H), 5.54-5.49 (dd, $J_1$=15.6 Hz, $J_2$=6.8 Hz, 1H), 5.42-5.38 (m, 1H), 5.30 (d, J=5.2 Hz, 1H), 4.44-4.36 (m, 1H), 2.97-2.94 (m, 1H), 2.42 (d, J=12.0 Hz, 1H), 2.01-1.98 (m, 2H), 1.88-1.64 (m, 6H), 1.40-1.32 (m, 3H), 1.26-1.21 (m, 2H), 1.17 (d, J=6.8 Hz, 3H), 1.12 (s, 3H), 1.05 (s, 3H), 1.00-0.95 (m, 2H), 0.79 (s, 3H).

Preparation of Compound 1-11. A mixture of 1-10 (40 mg, 0.09 mmol) and 5% Pd/C (10 mg) in EA (10 mL) was hydrogenated for 2 h at 30° C. under 1 atm of hydrogen pressure. The reaction mixture was filtered through a pad of celite and the pad was washed with EA (10 mL×3). The combined filtrates were concentrated. The residue was purified by column chromatography on silica gel (eluent: PE/EA=8/1) to afford 1-11 (20 mg, 50%) as white solid. $^1$H NMR: (400 MHz, CDCl3) δ 5.31 (d, J=5.2 Hz, 1H), 3.87-3.86 (m, 1H), 2.42 (d, J=12.8 Hz, 1H), 2.15-2.12 (m, 1H), 2.05-1.96 (m, 3H), 1.86-1.41 (m, 16H), 1.38-1.11 (m, 5H), 1.11 (s, 3H), 1.08-1.04 (m, 1H), 1.01 (s, 3H), 0.95 (d, J=6.6 Hz, 3H), 0.69 (s, 3H).

Preparation of Compound 1-13 and 1-14. 1-13 (120 mg, 40%) and 1-14 (120 mg, 40%) were obtained by SFC purification from 1-10 (300 mg, 0.814 mmol). The configuration of 1-13 and 1-14 was confirmed by Mosher method.

Preparation of Compound 1-15. A mixture of 1-13 (120 mg, 0.27 mmol) and 5% Pd/C (20 mg) in EtOAc (10 mL) was hydrogenated for 20 b at room temperature under $H_2$ (1 atm). The reaction mixture was filtered through a pad of celite and the pad was washed with EtOAc (10 mL×3). The combined filtrates were concentrated. The residue was purified by column chromatography on silica gel (eluent: petroleum ether:ethyl acetate=8/I) to afford 1-15 (70 mg, 59%) as white powder. $^1$H NMR: (400 MHz, CDCl3) δ 5.30 (d, J=5.2 Hz, 1H), 4.00-3.90 (m, 1H), 2.42 (d, J=13.2 Hz, 1H), 2.02-1.29 (m, 18H), 1.28-1.08 (m, 6H), 1.03 (s, 3H), 1.02 (s, 3H), 0.97 (d, J=6.8 Hz, 3H), 0.73 (s, 3H).

Preparation of Compound 1-17. A mixture of 1-14 (120 mg, 0.27 mmol) and 5% Pd/C (20 mg) in EtOAc (10 mL) was hydrogenated for 20 h at room temperature under $H_2$ (1 atm). The reaction mixture was filtered through a pad of celite and the pad was washed with EtOAc (10 mL×3). The combined filtrates were concentrated. The residue was purified by column chromatography on silica gel (eluent: petroleum ether:ethyl acetate=8/1) to afford 1-17 (71 mg, 59%) as white powder. $^1$H NMR: (400 MHz, CDCl3) δ 5.27 (d, J=5.6 Hz, 1H), 4.00-3.90 (m, 1H), 2.42 (d, J=13.2 Hz, 1H), 2.03-1.28 (m, 19H), 1.25-1.03 (m, 5H), 1.03 (s, 3H), 1.02 (s, 3H), 0.97 (d, J=6.4 Hz, 3H), 0.73 (s, 3H).

Example 2
(a)
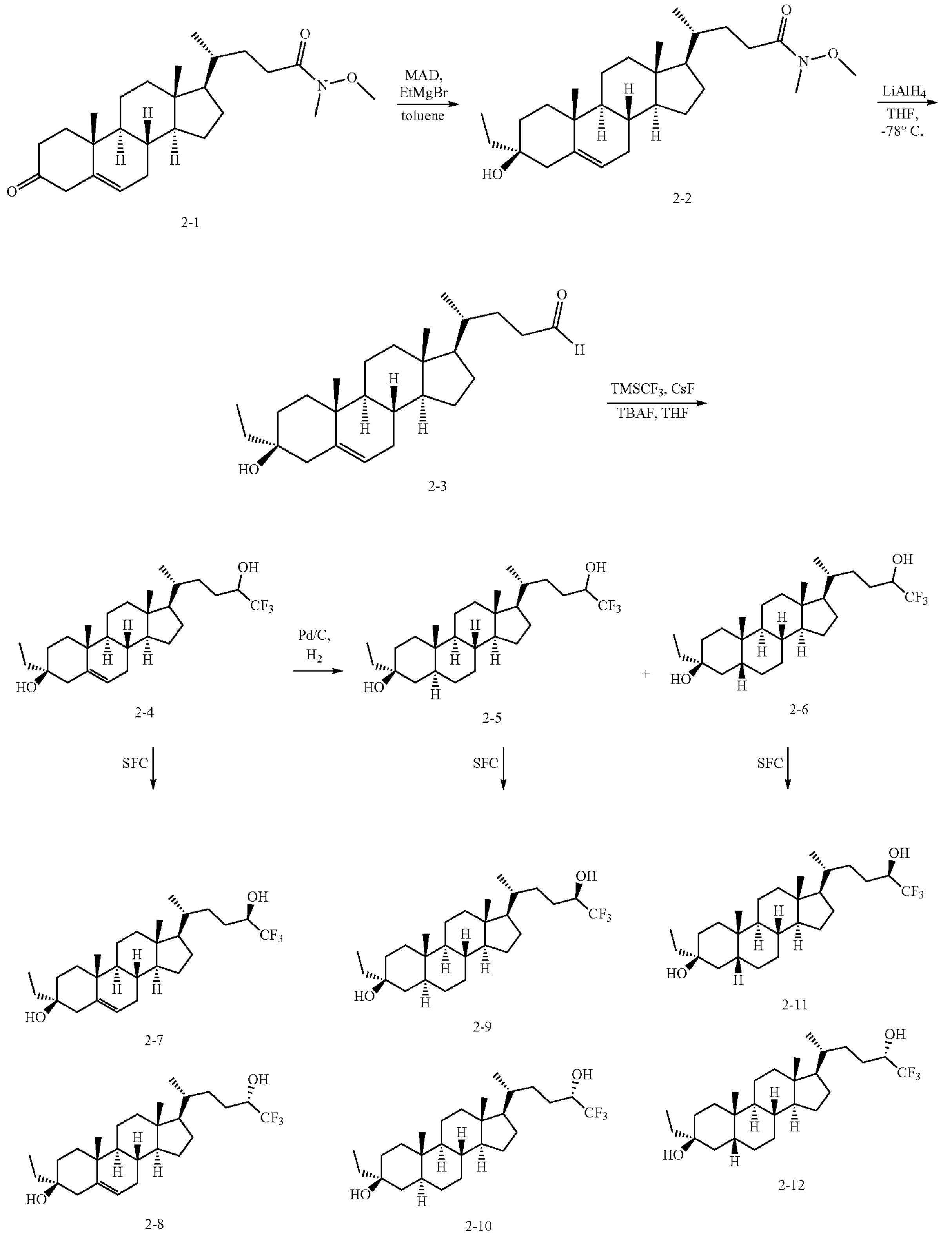

-continued
(b)
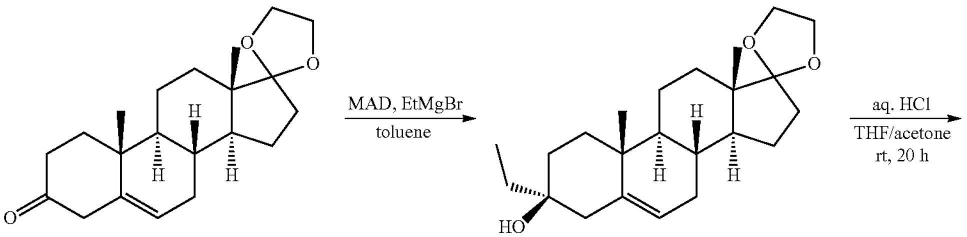
2-13 2-14
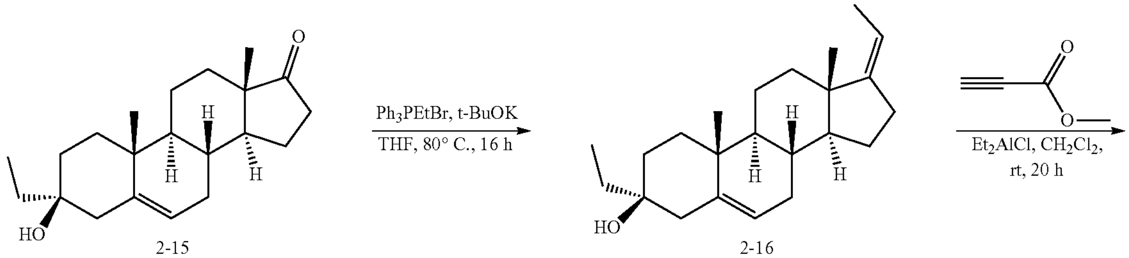
2-15 2-16
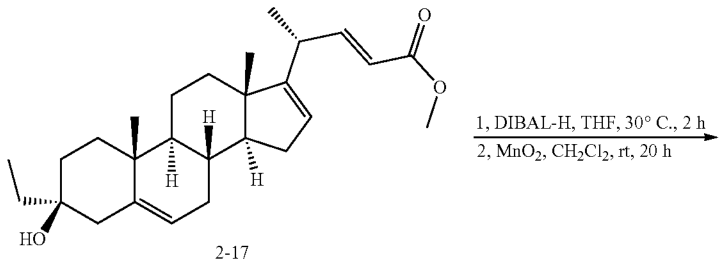
2-17
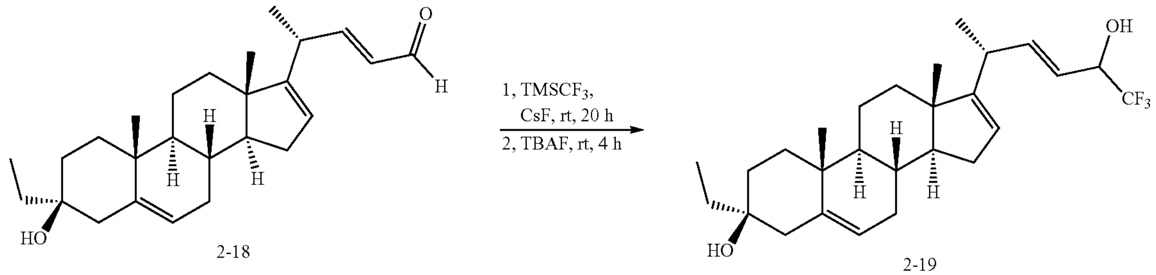
2-18 2-19
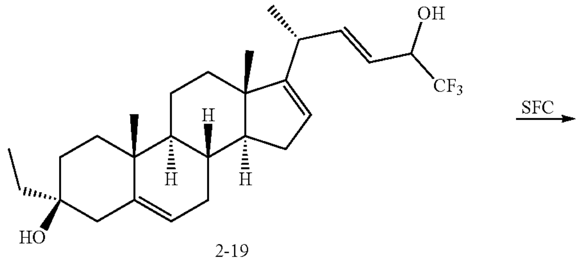
2-19

-continued

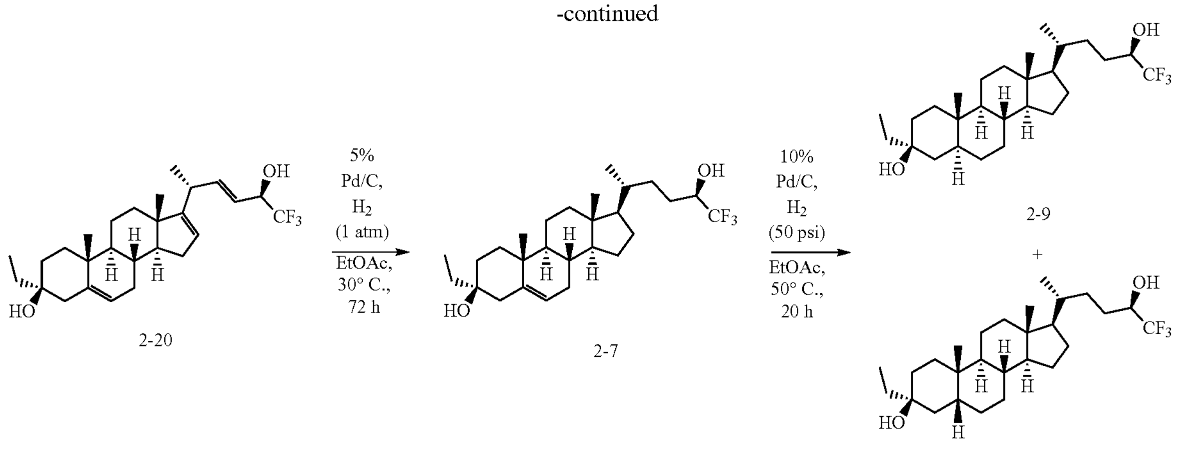

2-20 2-7 2-9 + 2-11

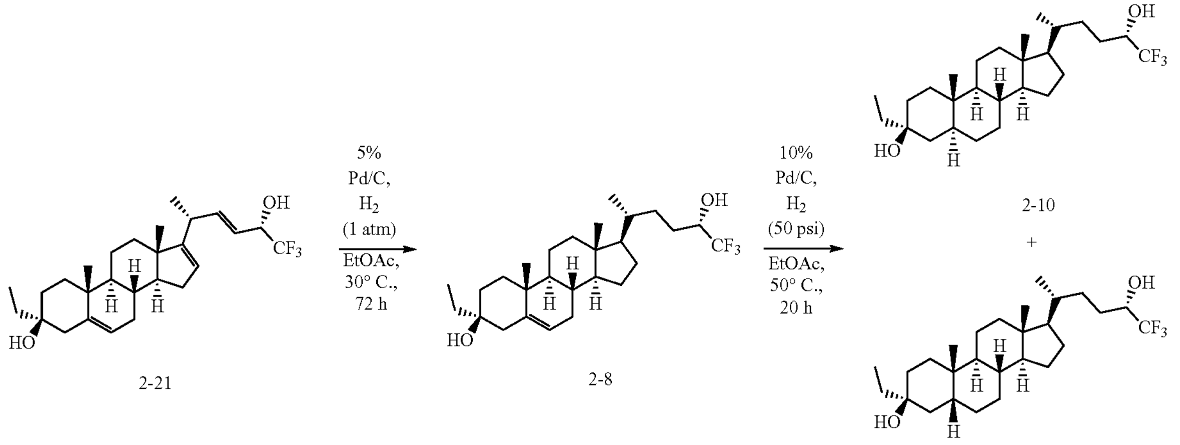

2-21 2-8 2-10 + 2-12

Preparation of 2-2. To a solution of MAD (28.87 mmol, freshly prepared) in toluene (20 mL) was added dropwise a solution of 2-1 (4 g, 9.62 mmol) in toluene (20 mL) at −78° C. during a period of 1 h under nitrogen. Then the reaction mixture was stirred for 30 min, a solution of EtMgBr (29 mL, 28.87 mmol, 1.0 M in toluene) was added dropwise at −78° C. The reaction mixture was warmed to −40° C. and stirred at this temperature for 3 hours. TLC (petroleum ether:ethyl acetate=3:1) showed that the starting material was consumed completely. The mixture was poured into aqueous saturated $NH_4Cl$ solution (200 mL) and extracted with EtOAc (150 mL×2). The combined organic phases were dried over $Na_2SO_4$, and the solvent was evaporated to afford crude product. The crude product was purified by column chromatography on silica gel (eluent: petroleum ether:ethyl acetate=15:1) to give the product 2-2 (2.0 g, 47.6%) as white powder. $^1H$ NMR: (400 MHz, CDCl3) δ 5.28 (d, J=5.2 Hz, 1H), 3.69 (s, 3H), 3.17 (s, 3H), 2.45-2.34 (m, 3H), 2.04-1.95 (m, 3H), 1.94-1.61 (m, 4H), 1.62-1.60 (m, 2H), 1.53-1.26 (m, 10H), 1.19-1.01 (m, 4H), 1.10 (s, 3H), 0.98-0.90 (m, 4H), 0.85 (t, J=6.8 Hz, 3H), 0.68 (s, 3H).

Preparation of 2-3. To a suspension of $LiAlH_4$ (852.6 mg, 22.43 mmol) in THF (20 ml) was added 2-2 (2.0 g, 4.48 mmol) at −78° C., then the solution was stirred at −78° C. for 2 hours. The mixture was poured into aqueous saturated NaOH solution (2 mL) and extracted with EtOAc (50 mL×2). The combined organic phases were dried over $Na_2SO_4$, and the solvent was evaporated to afford crude product. The crude product was purified by column chromatography on silica gel (eluent: petroleum ether:ethyl acetate=20:1) to give the product 2-3 (600 mg, 35%) as white powder. $^1H$ NMR: (400 MHz, CDCl3) δ 9.78 (s, 1H), 5.28 (d, J=5.2 Hz, 1H), 2.51-2.22 (m, 3H), 2.03-1.91 (m, 3H), 1.89-1.73 (m, 3H), 1.67-1.61 (m, 2H), 1.65-1.629 (m, 1H), 1.50-1.21 (m, 10H), 1.19-1.06 (m, 4H), 1.02 (s, 3H), 1.01-0.99 (m, 1H), 0.98-0.93 (m, 4H), 0.87 (t, J=6.8 Hz, 3H), 0.68 (s, 3H).

Preparation of 2-4. To a mixture of 2-3 (0.3 g, 0.78 mmol) and CsF (0.06 g, 039 mmol) in toluene/THF (18 mL, 8/1) was added $TMSCF_3$ (1.2 mL, 7.8 mmol) and the reaction mixture was stirred at room temperature overnight under nitrogen. TLC (petroleum ether:ethyl acetate=3/1) showed the starting material was consumed completely. A solution of TBAF (7.8 mL, 7.8 mmol, 1 M in THF) was added and the mixture was stirred for 4 h at room temperature. The reaction mixture was diluted with tert-Butyl methyl ether (30 mL), washed with aq. saturated $NaHCO_3$ solution (10 mL×3) and concentrated in vacuum. The residue was purified by column chromatography on silica gel (eluent: petroleum ether:ethyl acetate:=20:1) to afford 2-4 (80 mg, 22%) as white powder. $^1H$ NMR: (400 MHz, CDCl3) δ 5.29 (d, J=5.2 Hz, 1H), 3.87-3.84 (m, 1H), 2.36 (d, J=13.2 Hz, 1H), 2.05-1.95 (m, 3H), 1.86-1.61 (m, 6H), 1.54-1.06 (m, 17H), 1.03 (s, 3H), 1.02-0.91 (m, 5H), 0.85 (t, J=6.8 Hz, 3H), 0.68 (s, 3H).

Preparation of 2-5 and 2-6. A mixture of 2-4 (0.07 g, 0.15 mmol) and 10% Pd/C (20 mg) in EtOAc (10 mL) was hydrogenated for 36 h at 50° C. under $H_2$ (50 psi). The reaction mixture was filtered through a pad of celite and the pad was washed with EtOAc (20 mL×3). The combined filtrates were concentrated. The residue was purified by column chromatography on silica gel (eluent: petroleum ether:ethyl acetate=25/1) to give 2-5 (25 mg, 35.7%) and 2-6 (20 mg, 28.6%) as white powder. $^1$H NMR (2-5): (400 MHz, CDCl3) δ 3.87-3.82 (m, 1H), 2.05-1.94 (m, 2H), 1.86-1.58 (m, 6H), 1.56-1.17 (m, 16H), 1.13-0.96 (m, 6H), 0.93 (d, J=6.8 Hz, 3H), 0.88 (t, J=6.8 Hz, 3H), 0.86-0.84 (m, 1H), 0.83 (s, 3H), 0.67-0.61 (m, 4H). $^1$H NMR (2-6): (400 MHz, CDCl3) δ 3.83-3.76 (m, 1H), 1.95-1.52 (m, 10H), 1.43-0.98 (m, 22H), 0.89 (s, 3H), 0.88-0.82 (m, 6H), 0.59 (s, 3H).

Preparation of 2-14. To a solution of MAD (91 mmol, freshly prepared) in toluene (200 mL) was added dropwise a solution of compound 2-13 (10 g, 30 mmol) in toluene (80 mL) at −78° C. during a period of 1 h under nitrogen. Then the reaction mixture was stirred for 30 min, a solution of EtMgBr (91 mL, 91 mmol, 1.0 M THF) was added dropwise at −78° C. The reaction mixture was warmed to −40° C. and stirred at this temperature for 3 h. TLC (petroleum ether: ethyl acetate=3:1) showed that the starting material was consumed completely. The mixture was poured into saturated aqueous $NH_4Cl$ solution (200 mL) and extracted with EtOAc (150 mL×2). The combined organic phases were dried over $Na_2SO_4$, and the solvent was evaporated to afford crude product, which was purified by column chromatography on silica gel (eluent: petroleum ether:ethyl acetate=15:1) to give compound 2-14 (4 g, 40%) as white powder.

Preparation of 2-15. To a solution of 2-14 (4.0 g, 111 mmol) in THE (200 mL) was added aqueous HCl solution (35 mL, 1 M) and acetone (35 mL). The reaction mixture was stirred for 20° C. at room temperature. TLC (petroleum ether:ethyl acetate=3:1) indicated that the reaction was complete. Then the reaction mixture was diluted with EtOAc (200 mL), washed with saturated aqueous $NaHCO_3$ solution (200 mL), dried over $Na_2SO_4$ and evaporated under reduced pressure to give 2-15 (3 g, 88%) as white solid.

Preparation of 2-16. To a solution of $Ph_3PEtBr$ (15.8 g, 42.6 mmol) in dry THE (50 mL) was added dropwise a solution of t-BuOK (4.8 g, 42.6 mmol) in dry THE (20 mL) under $N_2$ at 0° C. The mixture was stirred at room temperature for 1.5 h. Then a solution of 2-15 (2.7 g, 8.5 mmol) in THE (20 mL) was added dropwise and the resulting mixture was stirred at 80° C. for 16 h. TLC (petroleum ether:ethyl acetate=3:1) indicated that the starting material was consumed completely. The reaction was quenched with saturated aqueous $NH_4Cl$ solution (100 mL) and extracted with EtOAc (30 mL×2). The combined organic phases were dried over $Na_2SO_4$ and concentrated in vacuum. The residue was purified by column chromatography on silica gel (eluent: petroleum ether:ethyl acetate=12:1) to give 2-16 (1.8 g, 64%) as white solid.

Preparation of 2-17. To a solution of compound 2-16 (1.8 g, 5.5 mmol) and methyl propiolate (1.1 g, 13.7 mmol) in dry $CH_2Cl_2$ (20 mL) was added dropwise a solution of $Et_2AlCl$ (22 mL, 22 mmol, 1 M in toluene) with stirring at 0° C. Then the reaction was warmed to room temperature and stirred for 20 h. TLC (petroleum ether:ethyl acetate=5:1) indicated that the starting material was consumed completely. The mixture was quenched with saturated aqueous $NaHCO_3$ solution (30 mL) and extracted with $CH_2Cl_2$ (30 mL×2). The combined organic phases were dried over $Na_2SO_4$ and concentrated in vacuum. The residue was purified by column chromatography on silica gel (eluent: petroleum ether:ethyl acetate=10:1) to give 2-17 (2.0 g, 88%) as white powder. $^1$H NMR: (300 MHz, CDCl3) δ 6.99-6.92 (m, 1H) 5.84 (d, J=10.5 Hz, 1H), 5.45-5.41 (m, 1H), 5.32 (d, J=5.2 Hz, 1H), 3.75 (s, 3H), 3.06-2.99 (m, 1H), 2.38 (d, J=12.6 Hz, 1H), 2.14-1.67 (m, 10H), 1.54-1.25 (m, 7H), 1.21 (d, J=6.8 Hz, 3H), 1.15-0.99 (m, 5H), 0.87 (t, J=7.2 Hz, 3H), 0.80 (s, 3H).

Preparation of 2-18. To a solution of compound 2-17 (2.2 g, 5.3 mmol) in dry THF (20 mL), DIBAL-H (1 M in THF, 27 mL, 27.0 mmol) was added dropwise at −78° C. under nitrogen. The reaction mixture was warmed to 30° C. and then stirred for 2 h at 30° C. The reaction was quenched with addition of water (3 mL), diluted with EtOAc (200 mL) and dried over anhydrous $Na_2SO_4$, filtered through a pad of celite and the pad was washed with EtOAc (50 mL×3). The combined filtrates were concentrated in vacuum to give 1.9 g of the crude product, which was directly used in the next step without further purification. A mixture of the crude product (1.9 g, 4.9 mmol) and $MnO_2$ (8.6 g, 98 mmol) in $CH_2Cl_2$ (50 mL) was stirred at room temperature for 20 h. The reaction mixture was filtered through a pad of celite and the pad was washed with $CH_2Cl_2$ (50 mL×3). The combined filtrates were concentrated. The residue was purified by column chromatography on silica gel (eluent: petroleum ether:ethyl acetate=15:1) to give 2-18 (1.5 g, 79%) as white solid. $^1$H NMR: (400 MHz, CDCl3) δ 9.55-9.53 (m, 1H), 6.84-6.78 (m, 1H), 6.15-6.09 (m, 1H), 5.45-5.41 (m, 1H), 5.30 (d, J=5.2 Hz, 1H), 3.15-3.14 (m, 1H), 2.36 (d, J=13.2 Hz, 1H), 2.10-2.03 (m, 3H), 1.90-1.60 (m, 9H), 1.59-1.27 (m, 7H), 1.24 (d, J=6.8 Hz, 3H), 1.10-1.22 (m, 6H), 0.87-0.83 (m, 4H), 0.80 (s, 3H).

Preparation of 2-19. To a suspension of 2-18 (1.5 g, 3.92 mmol) and CsF (0.3 g, 1.96 mmol) in toluene/THE (22 mL, 9/1) was added $TMSCF_3$ (5.8 mL, 39.2 mmol) and the mixture was stirred for 20 h at room temperature under nitrogen. TLC (petroleum ether:ethyl acetate=3/1) showed the starting material was consumed completely. A solution of TBAF (39.2 mL, 39.2 mmol, 1 M in THF) was added and the mixture was stirred for 4 h at room temperature. The mixture was diluted with MTBE (200 mL), washed with a saturated $NaHCO_3$ solution (30 mL×3) and concentrated in vacuum. The residue was purified by column chromatography on silica gel (eluent: petroleum ether:ethyl acetate=25/1) to afford 2-19 (0.65 g, 37%) as white solid.

Preparation of 2-20 & 2-21. 2-20 (210 mg, 32%) and 2-21 (210 mg, 32%) were obtained by SFC purification from 2-19 (650 mg, 1.44 mmol). The configuration of 2-20 and 2-21 was confirmed by Mosher method. $^1$H NMR (2-20): (400 MHz, CDCl3) δ 5.92 (dd, $J_1$=15.6 Hz, $J_2$=7.2 Hz, 1H), 5.53 (dd, $J_1$=15.6 Hz, $J_2$=7.2 Hz, 1H), 5.40-5.37 (m, 1H), 5.30 (d, J=5.2 Hz, 1H), 4.43-4.40 (m, 1H), 2.95-2.94 (m, 1H), 2.37 (d, J=13.6 Hz, 1H), 2.09-1.98 (m, 4H), 1.87-1.18 (m, 18H), 1.16 (d, J=6.8 Hz, 3H), 1.12-0.97 (m, 6H), 0.85 (t, J=6.8 Hz, 3H), 0.78 (s, 3H). $^1$H NMR (2-21): (400 MHz, CDCl3) δ 5.95 (dd, $J_1$=15.6 Hz, $J_2$=7.2 Hz, 1H), 5.53 (dd, $J_1$=15.6 Hz, $J_2$=6.8 Hz, 1H), 5.39-5.36 (m, 1H), 5.30 (d, J=5.2 Hz, 1H), 4.44-4.41 (m, 1H), 2.99-2.92 (m, 1H), 2.37 (d, J=13.2 Hz, 1H), 2.10-1.98 (m, 4H), 1.87-1.25 (m, 18H), 1.16 (d, J=6.8 Hz, 3H), 1.09-0.99 (m, 6H), 0.85 (t, J=7.2 Hz, 3H), 0.80 (s, 3H).

Preparation of 2-7. A mixture of 2-20 (200 mg, 0.44 mmol) and 5% Pd/C (50 mg) in EtOAc (20 mL) was hydrogenated for 72 b at 30° C. under $H_2$ (1 atm). The reaction mixture was filtered through a pad of celite and the pad was washed with EtOAc (10 mL×3). The combined filtrates were concentrated. The residue was purified by column chromatography on silica gel (eluent: petroleum ether:ethyl acetate=25/1) to afford crude 2-7, which was purified by pre-HPLC to afford 2-7 (64 mg, 52%) as white powder. $^1$H NMR (2-7): (400 MHz, CDCl3) δ 5.29 (d, J=4.8

Hz, 1H), 3.90-3.80 (m, 1H), 2.36 (d, J=13.6 Hz, 1H), 2.05-1.60 (m, 11H), 1.53-1.06 (m, 15H), 1.03 (s, 3H), 1.02-0.89 (m, 5H), 0.85 (t, $J_1$=14.8 Hz, $J_2$=7.2 Hz, 3H), 0.69 (s, 3H).

Preparation of 2-8. A mixture of 2-21 (200 mg, 0.44 mmol) and 5% Pd/C (50 mg) in EtOAc (20 nL) was hydrogenated for 72 b at 30° C. under $H_2$ (1 atm). The reaction mixture was filtered through a pad of celite and the pad was washed with EtOAc (10 mL×3). The combined filtrates were concentrated. The residue was purified by column chromatography on silica gel (eluent: petroleum ether:ethyl acetate=25/1) to afford 2-8 (105 mg, 52%) as white powder. $^1$H NMR: (400 MHz, $CDCl_3$) δ 5.29 (d, J=4.8 Hz, 1H), 3.86-3.83 (m, 1H), 2.36 (d, J=13.2 Hz, 1H), 2.05-1.95 (m, 4H), 1.86-1.60 (m, 7H), 1.54-1.08 (m, 15H), 1.03 (s, 3H), 1.01-0.90 (m, 5H), 0.85 (t, J=6.8 Hz, 3H), 0.68 (s, 3H).

Preparation of 2-10 and 2-12. A mixture of 2-8 (30 mg, 0.067 mmol) and 10% Pd/C (10 mg) in EtOAc (10 mL) was hydrogenated for 20 h at 50° C. under $H_2$ (50 psi). The reaction mixture was filtered through a pad of celite and the pad was washed with EtOAc (20 mL×3). The combined filtrates were concentrated. The residue was purified by column chromatography on silica gel (eluent: petroleum ether:ethyl acetate=25/1) to give 2-10 (11 mg, 37%) and 2-12 (7 mg, 23%) as white powder. $^1$H NMR (2-10): (400 MHz, CDCl3) δ 3.85-3.82 (m, 1H), 2.04-1.93 (m, 2H), 1.84-1.59 (m, 6H), 1.56-1.20 (m, 14H), 1.14-0.96 (m, 7H), 0.93 (d, J=6.8 Hz, 3H), 0.88-0.84 (m, 4H), 0.83 (s, 3H) 0.67-0.61 (m, 4H). $^1$H NMR (2-12): (400 MHz, CDCl3) δ 3.89-3.80 (m, 1H), 2.08-1.93 (m, 2H), 1.91-1.66 (m, 6H), 1.52-1.01 (m, 23H), 0.97 (s, 3H), 0.95-0.90 (m, 6H), 0.66 (s, 3H).

Example 3

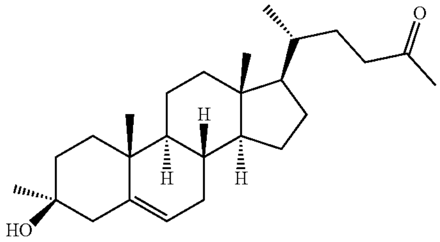

3-1

TMSCF3, CsF

TBAF, THF

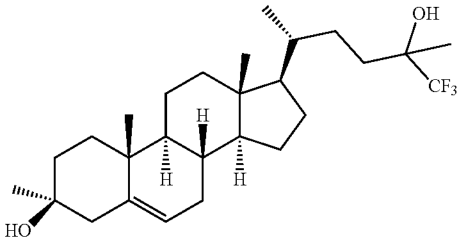

3-2

SFC

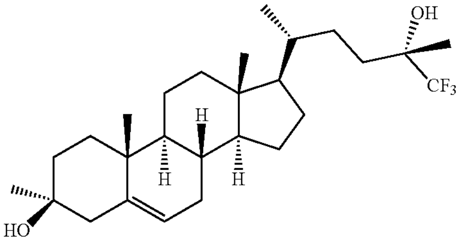

3-5

Pd/C, $H_2$ (50 psi)

EtOAc, 50° C.

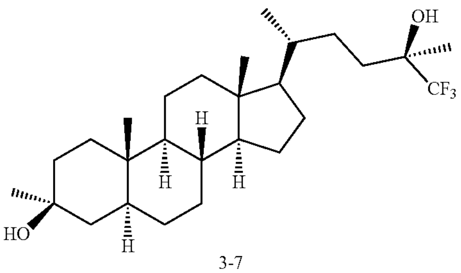

3-7

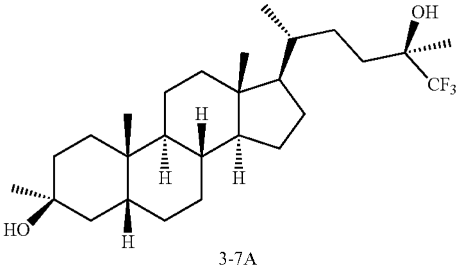

3-7A

-continued

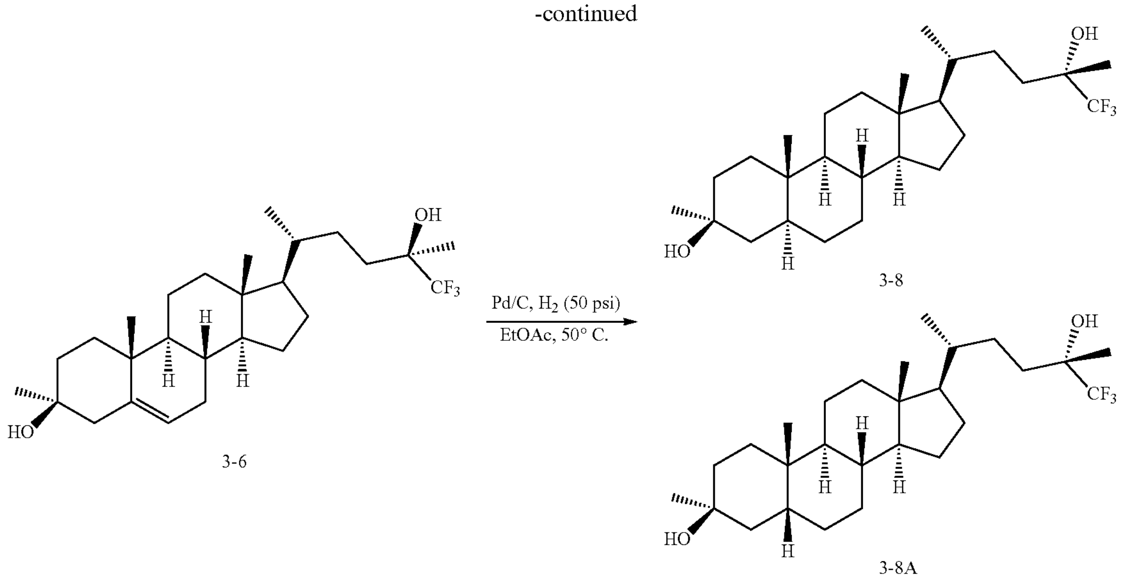

3-6

3-8

3-8A

Preparation of 3-2. To a suspension of 3-1 (400 mg, 1.035 mmol) and CsF (76 mg) in toluene/THF (20 mL, 8/1) was added $TMSCF_3$ (1.53 mL, 10.35 mmol) and the mixture was stirred for 20° C. at room temperature under nitrogen. TLC (petroleum ether:ethyl acetate=3/1) showed the starting material was consumed completely. A solution of TBAF (6.8 mL, 1 M in THF) was added and the mixture was stirred for 4 h at room temperature. The mixture was diluted with MTBE (200 mL), washed with aq. saturated $NaHCO_3$ solution (30 mL×3) and concentrated in vacuum. The residue was purified by column chromatography on silica gel (eluent: petroleum ether:ethyl acetate=20:1) to afford 3-2 (220 mg, 46%) as white solid. $^1H$ NMR: (400 MHz, CDCl3) δ 5.31 (d, J=2.0 Hz, 1H), 2.44-2.41 (m, 1H), 2.04-1.96 (m, 3H), 1.81-1.67 (m, 5H), 1.65-1.39 (m, 11H), 1.34-1.32 (m, 3H), 1.31-1.25 (m, 1H), 1.21-1.10 (m, 3H), 1.12-0.98 (m, 4H), 0.96 (s, 3H), 0.98-0.90 (m, 4H), 0.68 (s, 3H.)

Preparation of 3-3 and 3-4. To a solution of compound 3-2 (220 mg, 0.569 mmol) in EtOAc (10 mL) was added Pd/C (20 mg), then the mixture was stirred under hydrogen (50 psi) at 50° C. overnight. The mixture was filtered through a pad of celite and the filtrate was evaporated under reduced pressure. The residue was purified by column chromatography on silica gel (eluent: petroleum ether:ethyl acetate=20:1) to afford the pure product 3-3 (100 mg, 38.5%) and 3-4 (51 mg, 19.3%) as white powder. $^1H$ NMR (3-3): (400 MHz, CDCl3) δ 2.01-1.95 (m, 1H), 1.89-1.75 (m, 2H), 1.69-1.55 (m, 9H), 1.52-1.43 (m, 5H), 1.32-1.28 (m, 4H), 1.27-1.20 (m, 7H), 1.17-1.08 (m, 4H), 1.06-0.96 (m, 3H), 0.96-0.91 (m, 3H), 0.80 (s, 3H), 0.68-0.49 (m, 4H). $^1H$ NMR (3-4): (400 MHz, CDCl3) δ 2.01-1.95 (m, 1H), 1.89-1.67 (m, 5H), 1.66-1.60 (m, 2H), 1.63-1.36 (m, 8H), 1.35-1.31 (m, 4H), 1.29-1.24 (m, 4H), 1.22 (s, 3H), 1.28-1.06 (m, 6H), 0.96 (s, 3H), 0.95-0.92 (m, 3H), 0.68 (s, 3H).

Preparation of 3-5 and 3-6. Compound 3-2 (1.2 g, 2.63 mmol) was split by SFC to get Product 3-5 (400 mg) and 3-6 (400 mg) as white powder (total yield: 66.7%). $^1H$ NMR (3-5): (400 MHz, $CDCl_3$) δ 5.32 (d, J=4.0 Hz, 1H), 2.50-2.40 (m, 1H), 2.08-1.95 (m, 3H), 1.90-0.90 (m, 35H), 0.70 (s, 3H). $^1H$ NMR (3-6): (400 MHz, $CDCl_3$) δ 5.32 (d, J=4.0 Hz, 1H), 2.50-2.40 (m, 1H), 2.08-1.95 (m, 3H), 1.90-0.92 (m, 35H), 0.70 (s, 3H).

Preparation of 3-7 To a solution of compound 3-6 (300 mg, 0.66 mmol) in EtOAc (8 mL) was added Pd/C (10%, 200 mg) under $N_2$. The suspension was degassed under vacuum and purged with $H_2$ several times. Then the mixture was stirred under $H_2$ (50 psi) at 50° C. for 24 h. The suspension was filtered through a pad of celite and the pad was washed with EtOAc (50 mL×2). The combined filtrates were concentrated to dryness to give the crude product, which was purified by column chromatography on silica gel (petroleum ether:ethyl acetate=20:1) to afford 3-7 (142 mg, 47%) as white solid. $^1H$ NMR: (3-7) (400 MHz, $CDCl_3$) δ 1.96-1.92 (m, 1H), 1.90-1.75 (m, 1H), 1.70-1.57 (m, 5H), 1.55-1.35 (m, 6H), 1.30-1.20 (m, 12H), 1.20-1.06 (m, 12H), 1.19-0.81 (m, 11H), 0.80 (s, 3H), 0.70-0.60 (m, 4H). $^1H$ NMR: (3-7A) (400 MHz, $CDCl_3$) δ 1.96-1.92 (m, 1H), 1.90-1.75 (m, 3H), 1.70-1.57 (m, 2H), 1.55-1.25 (m, 13H), 1.21-1.00 (m, 15H), 0.96-0.86 (m, 8H), 0.65 (s, 3H)

Preparation of 3-8 To a solution of compound 3-5 (300 mg, 0.66 mmol) in EtOAc (8 mL) was added Pd/C (10%, 200 mg) under $N_2$. The suspension was degassed under vacuum and purged with $H_2$ several times. Then the mixture was stirred under $H_2$ (50 psi) at 50° C. for 24 h. The suspension was filtered through a pad of celite and the pad was washed with EtOAc (50 mL×2). The combined filtrates were concentrated to dryness to give the crude product, which was purified by column chromatography on silica gel (petroleum ether:ethyl acetate=20:1) to afford 3-8 (141.6 mg, 47%) as white solid. $^1H$ NMR: (3-8) (400 MHz, $CDCl_3$) δ 1.96-1.92 (m, 1H), 1.90-1.70 (m, 2H), 1.69-1.57 (m, 5H), 1.55-1.20 (m, 18H), 1.19-0.81 (m, 10H), 0.80 (s, 3H), 0.70-0.60 (m 4H). $^1H$ NMR: (3-8A) (400 MHz, $CDCl_3$) δ 1.97-1.70 (m, 6H), 1.70-1.57 (m, 2H), 1.50-1.30 (m 13H), 1.25-1.05 (m, 15H), 1.00-0.86 (m, 7H), 0.65 (s, 3H)

Example 4
(a)
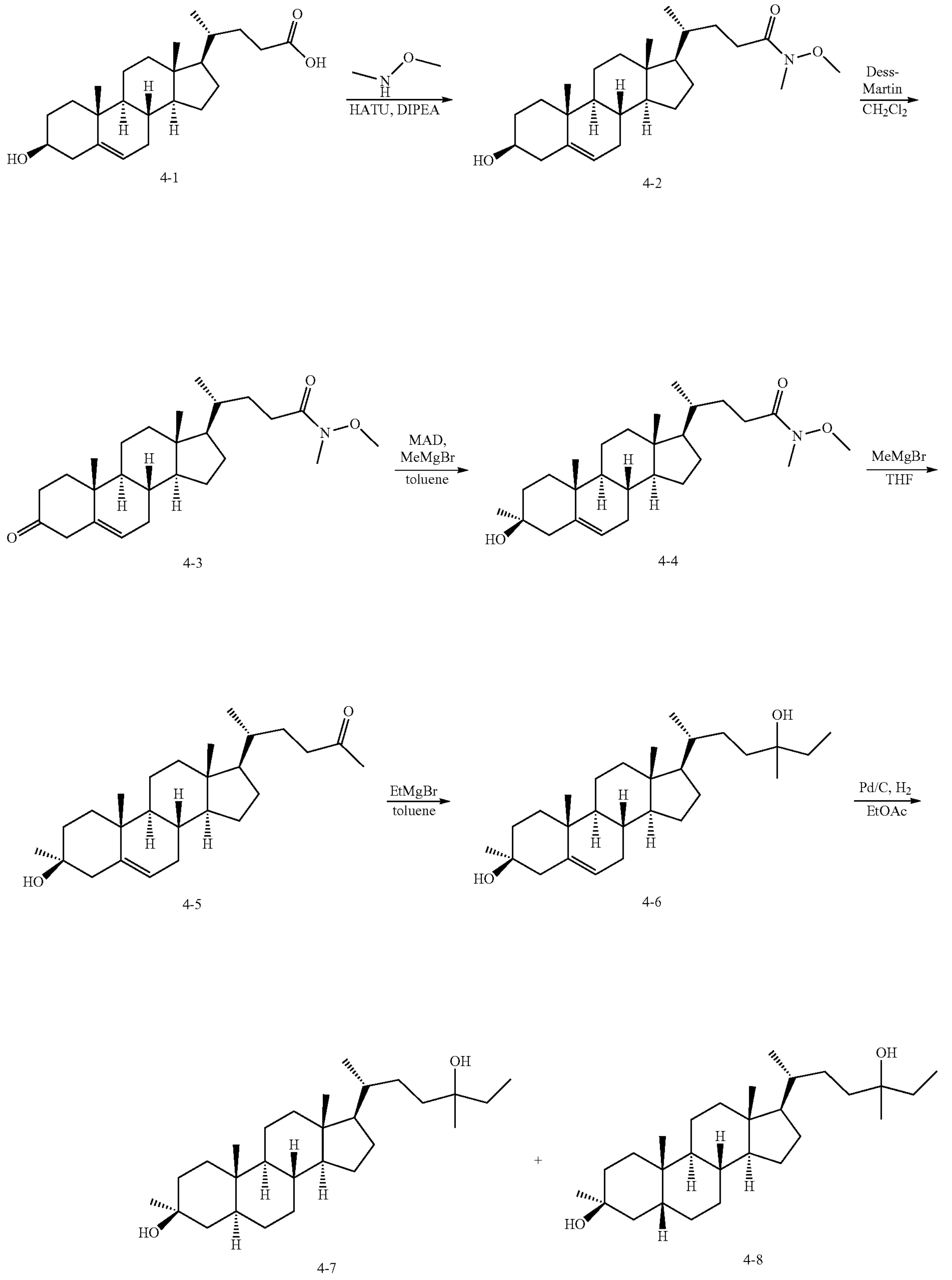

-continued (b)

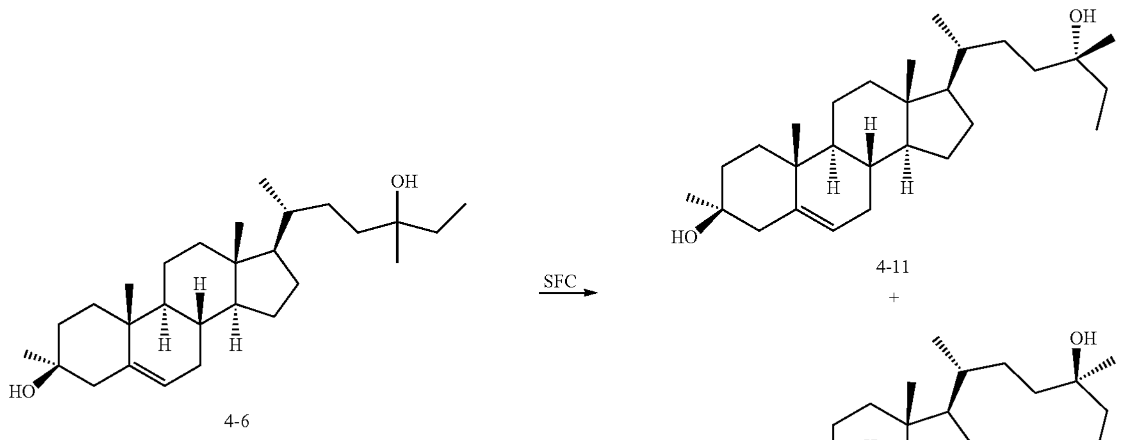

4-6

4-11

+

4-12

(c)

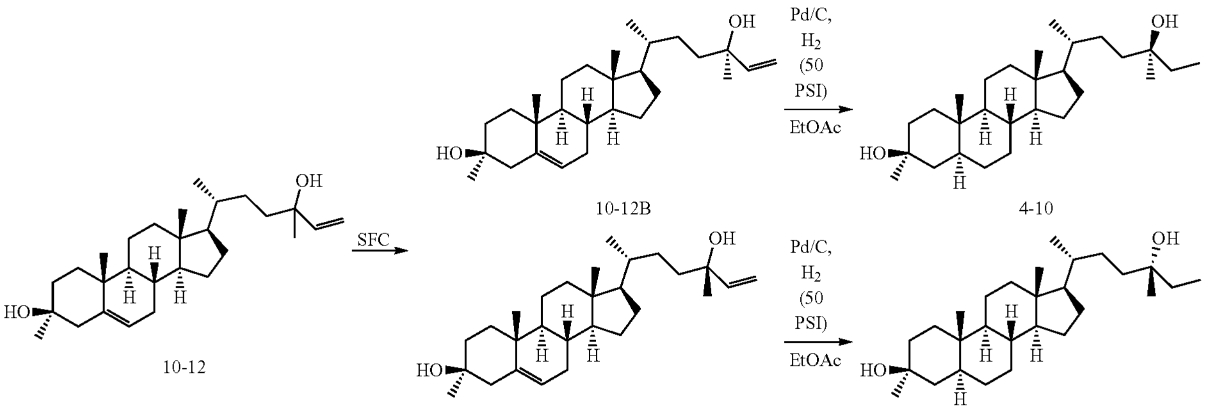

10-12

10-12B 10-12A 4-10

4-9

Preparation of Compound 4-2. To a solution of 4-1 (38 g, 101.5 mmol) in THF (400 mL) at room temperature was added HATU (46.3 g, 121.8 mmol), DIPEA (45.9 g, 355.2 mmol). The mixture was stirred for 1 h, and N,O-dimethylhydroxylamine hydrochloride (19.8 g, 203 mmol) was added. The mixture was stirred at room temperature for another 6 h. The reaction mixture was concentrated, poured into water, extracted with EtOAc, washed with water, dried over $Na_2SO_4$, and concentrated to give crude product. The crude product was purified by column chromatography on silica gel (eluent: PE:EA=3:1) to afford the desired product 4-2 (24 g, 57%) as white solid. $^1H$ NMR: (300 MHz, CDCl3) δ: ppm 5.25 (d, J=5.2 Hz, 1H), 3.59 (s, 3H), 3.46-3.37 (m, 1H), 3.07 (s, 3H), 2.70 (s, 1H), 2.40-2.09 (m, 4H), 1.92-1.63 (m, 6H), 1.44-1.33 (m, 6H), 1.29-1.15 (m, 3H), 1.11-0.93 (m, 5H), 0.90 (s, 3H), 0.85 (d, J=6.4 Hz, 3H), 0.82-0.78 (m, 1H), 0.58 (s, 3H).

Preparation of Compound 4-3. To a solution of compound 4-2 (14 g, 33.52 mmol, 1.0 eq) in dry $CH_2Cl_2$ (600 mL) was added Dess-Martin (28 g, 67.04 mmol, 2.0 eq) in portions at 0° C. Then the reaction mixture was stirred at room temperature for 6.5 h. TLC (PE:EA=3:1) showed the starting material was consumed completely. The mixture was quenched with saturated aqueous $NaHCO_3/Na_2S_2O_3$=1:3 (800 mL). The organic phase was washed with brine (500 mL) and dried over $Na_2SO_4$, and the solvent was evaporated to afford crude product 4-3 (14.0 g, 100%), which was directly used in the next step without further purification.

Preparation of Compound 4-4. To a solution of MAD (101 mmol, 3.0 eq) in toluene, freshly prepared by addition of a solution of $Me_3Al$ (50.5 mL, 101.00 mmol, 2 M in hexane) to a stirred solution of 2,6-di-tert-butyl-4-methylphenol (44.4 g, 202 mmol) in toluene (200 mL) followed by stirring for 1 h at room temperature, was added dropwise a solution of 4-3 (14.0 g, 33.7 mmol, 1.0 eq) in toluene (10 mL) at −78° C. under nitrogen. Then the reaction mixture was stirred for 30 min, a solution of MeMgBr (33.7 mL, 101 mmol, 3.0 eq, 3 M in ether) was added dropwise at −78° C. The reaction mixture was warmed to 25° C. and stirred at this temperature for 12 h. TLC (PE:EA=3:1) showed that the starting material was consumed completely. The mixture was poured into aqueous saturated $NH_4Cl$ solution (200 mL) and extracted with EtOAc (200 mL×2). The combined organic phases were dried over $Na_2SO_4$, and the solvent was evaporated to afford crude product. The crude product was purified by column chromatography on silica gel (eluent: PE:EA=3:1) to give the pure target (7.5 g, 52%) as white powder. $^1H$ NMR: (400 MHz, CDCl3) δ 5.30 (d, J=5.2 Hz, 1H), 3.69 (s, 3H), 3.17 (s, 3H), 2.50-2.30 (m, 3H), 2.05-1.70 (m, 7H), 1.52-1.30 (m, 9H), 1.20-0.90 (m, 15H), 0.68 (s, 3H).

Preparation of Compound 4-5. To a solution of compound 4-4 (7.5 g, 17.4 mmol, 1.0 eq) in THE (150 mL) was added dropwise a solution of MeMgBr (29 mL, 87 mmol, 5.0 eq, 3 M in THF) at room temperature during a period of 30 min under nitrogen. Then the reaction mixture was stirred at room temperature for 12 h. TLC (PE:EA=1:1) showed that the starting material was consumed completely. The mixture was poured into aqueous saturated $NH_4Cl$ solution (200 mL) and extracted with EtOAc (150 mL×2). The combined organic phases were dried over $Na_2SO_4$, and the solvent was evaporated to afford crude product. The crude product was purified by column chromatography on silica gel (eluent: PE:EA=4:1) to give the product 4-5 (5.2 g, 77%) as white powder. $^1H$ NMR: (400 MHz, CDCl3) δ 5.30 (d, J=5.2 Hz, 1H), 2.50-2.30 (m, 3H), 2.14 (s, 3H) 2.03-1.93 (m, 3H), 1.87-1.68 (m, 4H), 1.60-1.18 (m, 12H), 1.12 (s, 3H), 1.11-1.03 (m, 1H), 1.01 (s, 3H), 1.00-0.94 (m, 1H), 0.91 (d, J=6.4 Hz, 3H), 0.68 (s, 3H).

Preparation of 4-6. To a solution of compound 4-5 (300 mg, 0.777 mmol, 1.0 eq) in toluene (5 mL) was added dropwise a solution of EtMgBr (4.5 mL, 4.5 mmol, 6.0 eq, 1 M in THF) at room temperature during a period of 10 min under nitrogen. Then the reaction mixture was stirred at room temperature for 12 h. TLC (PE:EA=3:1) showed that the starting material was consumed completely. The mixture was poured into aqueous saturated $NH_4Cl$ solution (20 mL) and extracted with EtOAc (50 mL×2). The combined organic phases were dried over $Na_2SO_4$, and the solvent was evaporated to afford crude product. The crude product purified by column chromatography on silica gel (eluent: PE:EA=8:1) to give the product 4-6 (200 mg, 62%) as white powder. $^1H$ NMR: (400 MHz, CDCl3) δ 5.23 (d, J=5.6 Hz, 1H), 2.40-2.30 (m, 1H), 2.00-1.55 (m, 7H), 1.50-1.98 (m, 25H), 0.95 (s, 3H), 0.94-0.80 (m, 8H), 0.62 (s, 3H).

Preparation of 4-7 and 4-8. To a solution of compound 4-6 (175 mg, 0.42 mmol) in EtOAc (10 mL) was added 10% Pd/C (40 mg) under argon. The suspension was degassed under vacuum and purged with $H_2$ several times. The mixture was stirred under $H_2$ (50 Psi) at 50° C. overnight. The suspension was filtered through a pad of celite and the pad was washed with EA (20 mL×3). The combined filtrates were concentrated in vacuum and the residue was purified by column chromatography on silica gel (eluent: PE:EA=8:1) to give 4-7 (84 mg, 48%) and 4-8 (25 mg, 14%) as white powder. $^1H$ NMR (4-7): (400 MHz, CDCl3) δ 1.98-1.92 (m, 1H), 1.87-1.78 (m, 1H), 1.70-1.60 (m, 2H), 1.58-1.20 (m, 21H), 1.20-0.97 (m, 11H), 0.95-0.82 (m, 7H), 0.80 (s, 3H), 0.70-0.61 (m, 4H). $^1H$ NMR (4-8): (400 MHz, CDCl3) δ 2.00-1.78 (m, 4H), 1.68-1.63 (m, 1H), 1.57-1.55 (m, 1H), 1.53-1.35 (m, 10H), 1.32-1.12 (m, 16H), 1.11-0.99 (m, 5H), 0.97 (s, 3H), 0.95-0.83 (m, 6H), 0.67 (s, 3H).

Preparation of 4-9 To a solution of compound 10-12B (80 mg, 0.193 mmol) in EtOAc (20 mL) was added 10% Pd/C (20 mg) under $N_2$. The suspension was degassed under vacuum and purged with $H_2$ several times. Then the mixture was stirred under $H_2$ (50 psi) at 50° C. for 12 hours. The mixture was filtered through a pad of celite and the pad was washed with EtOAc (5 mL×2). The combined filtrates were concentrated to dryness to give the product, which was purified by column chromatography on silica gel (eluent: petroleum ether:ethyl acetate=12:1 to 10:1) to afford the 4-9 (40 mg, 50%) as white powder. $^1H$ NMR (4-9): (400 MHz, $CDCl_3$) δ 2.02-1.93 (m, 1H), 1.92-1.80 (m, 1H), 1.70-0.85 (m, 41H), 0.82 (s, 3H), 0.67 (s, 3H).

Preparation of 4-10 To a solution of compound 10-12A (80 mg, 0.193 mmol) in EtOAc (20 mL) was added 10% Pd/C (20 mg) under $N_2$. The suspension was degassed under vacuum and purged with $H_2$ several times. Then the mixture was stirred under $H_2$ (50 psi) at 50° C. for 48 hours. The mixture was filtered through a pad of celite and the pad was washed with EtOAc (5 mL×2). The combined filtrates were concentrated to dryness to give the product, which was purified by column chromatography on silica gel (eluent: petroleum ether:ethyl acetate=12:1 to 10:1) to afford the 4-10 (40 mg, 50%) as white powder. $^1H$ NMR (4-10): (400 MHz, $CDCl_3$) δ 2.02-1.93 (m, 1H), 1.92-1.80 (m, 1H), 1.70-0.85 (m, 41H), 0.82 (s, 3H), 0.67 (s, 3H).

Preparation of 4-11 and 4-12. 4-11 (100 mg, 15.38%) and 4-12 (90 mg, 13.85%) were obtained by SFC purification from 4-6 (600 mg, 1.55 mmol). $^1H$ NMR (Isomer 1): (400 MHz, CDCl3) δ 5.30 (m, 1H), 2.43-2.40 (d, J=12.4 Hz, 1H), 2.14-1.99 (m, 3H), 1.96-1.68 (m, 3H), 1.68-1.52 (m, 5H), 1.51-1.24 (m, 13H), 1.19-1.09 (m, 8H), 1.02 (s, 3H), 0.96-0.93 (m, 3H), 0.93-0.87 (m, 3H), 0.69 (s, 3H). $^1H$ NMR (Isomer 2): (400 MHz, CDCl3) δ 5.30 (m, 1H), 2.44-2.40 (d, J=14 Hz, 1H), 2.17-1.96 (m, 3H), 1.96-1.67 (m, 3H), 1.67-1.18 (m, 18H), 1.16-1.09 (m, 8H), 1.06 (s, 3H), 0.96-0.93 (m, 3H), 0.93-0.87 (m, 3H), 0.69 (s, 3H).

Example 5

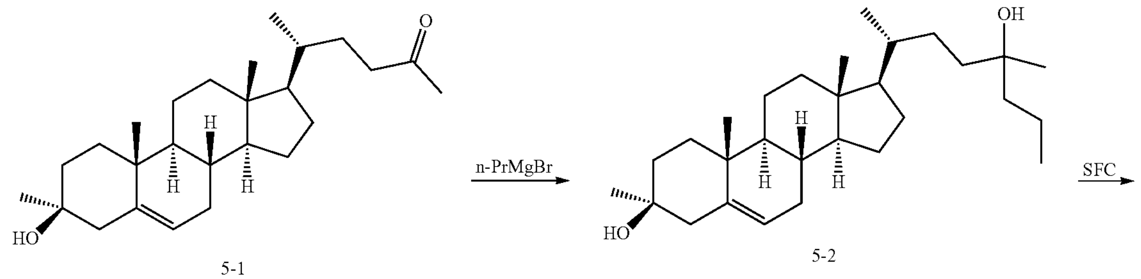

5-1 5-2

-continued

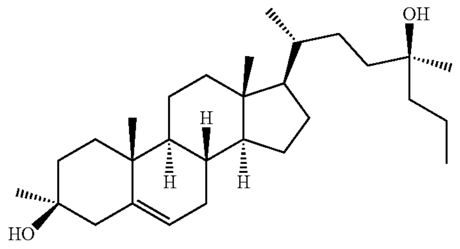

5-5

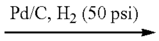

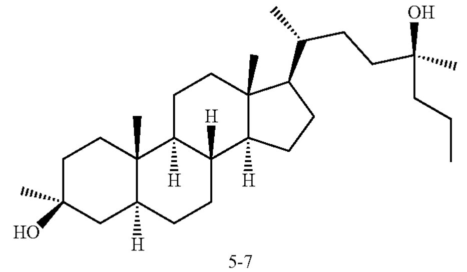

5-7

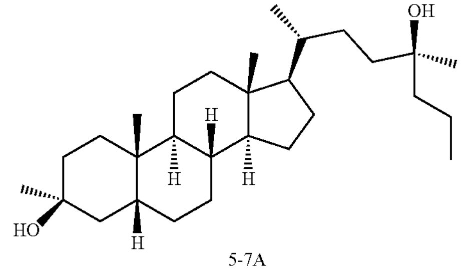

5-7A

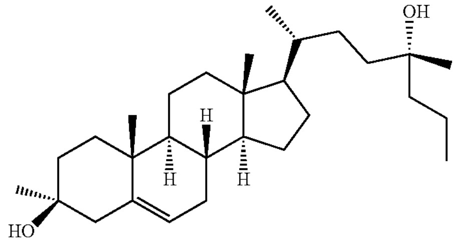

5-6

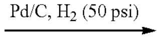

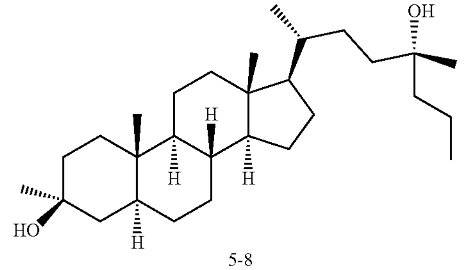

5-8

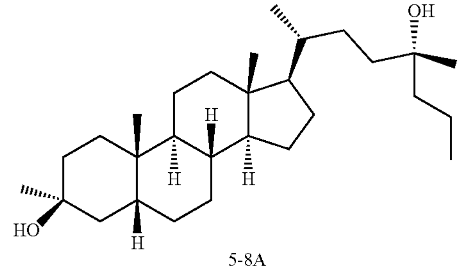

5-8A

Preparation of Compound 5-2. To a solution of 5-1 (200 mg, 0.52 mmol) in toluene (5 mL) at −78° C. was added n-PrMgBr (1.3 mL, 2 M in THF, 2.6 mmol) dropwise. The mixture was warmed up to room temperature gradually and stirred for 6 h. The reaction mixture was quenched with $NH_4Cl$ aqueous, extracted with EtOAc. The organic layer was dried over $Na_2SO_4$, and concentrated to give crude product. The crude product was purified by column chromatography on silica gel (eluent: PE:EA=15:1) to afford 5-2 (130 mg, 58%) as white solid. $^1H$ NMR: (300 MHz, CDCl3) δ: ppm 5.30 (d, J=4.8 Hz, 1H), 2.48-2.38 (m, 1H), 2.02-1.95 (m, 3H), 1.88-1.66 (m, 3H), 1.63-1.52 (m, 5H), 1.52-1.46 (m, 4H), 1.43-1.41 (m, 1H), 1.41-1.35 (m, 4H), 1.30-1.22 (m, 3H), 1.20-1.14 (m, 4H), 1.13-1.08 (m, 4H), 1.03 (s, 3H), 0.95-0.90 (m, 3H), 0.90-0.87 (m, 3H), 0.87-0.85 (m, 1H) 0.68 (s, 3H).

Preparation of 5-3 and 5-4. To a solution of compound 5-2 (400 mg, 0.93 mmol) in EtOAc (20 mL) was added 10% Pd/C (100 mg). Then the mixture was stirred under hydrogen (50 psi) at 50° C. overnight. The mixture was filtered through a pad of celite and the filtrate was evaporated under reduced pressure. The residue was purified by column chromatography on silica gel (eluent: petroleum ether:ethyl acetate=15:1) to afford the pure product 5-3 (150 mg, 37.3%) and 5-4 (27 mg, 6.7%) as white powder. $^1H$ NMR (5-3): (300 MHz, CDCl3) δ 1.97-1.94 (m, 1H), 1.93-1.77 (m, 1H), 1.67-1.62 (m, 3H), 1.56-1.51 (m, 6H), 1.47-1.30 (m, 11H), 1.24 (s, 6H), 1.20 (s, 1H), 1.13 (s, 5H), 1.09-0.99 (m, 4H), 0.94-0.90 (m, 6H), 0.80 (s, 3H), 0.65 (s, 3H). $^1H$ NMR (5-4): (300 MHz, CDCl3) δ 1.98-1.94 (m, 2H), 1.91-1.78 (m, 5H), 1.65-1.51 (m, 5H), 1.47-1.46 (m, 3H), 1.38-1.35 (m, 9H), 1.32-1.30 (m, 2H), 1.25 (s, 3H), 1.22 (s, 6H), 1.16-1.10 (m, 4H), 1.06-1.04 (m, 4H), 0.98-0.94 (m, 4H), 0.92-0.89 (m, 6H), 0.86-0.83 (m, 1H), 0.64 (s, 3H).

Preparation of 5-5 and 5-6 To a solution of compound 5-1 (1500 mg, 3.88 mmol) in dry THE (30 mL) was added a solution of n-PrMgBr (11.6 mL, 23.3 mmol) dropwise at 0° C. The mixture was stirred at 40° C. for 16 h. TLC (PE/EtOAc=2/1) showed the reaction was complete. Saturated aqueous $NH_4Cl$ (5 mL) was added slowly to quench the reaction. The resulting solution was separated between EtOAc (30 mL×3) and $H_2O$ (30 mL). The combined organic layers were concentrated in vacuum and the residue was purified by silica gel column eluted with PE/EtOAc=10/1 to give the mixture of the diastereomeric pair (1.1 g) as white power. The diastereimeric pair was separated by prep-SFC to give 5-6 (380 mg, 22.8%) as a white solid and 5-5 (385 mg, 23.1%) as a white solid. $^1$H NMR (5-5): (400 MHz, $CDCl_3$) δ 5.31-5.30 (m, 1H), 2.44-2.41 (d, 1H, J=12.8 Hz), 2.01-1.96 (m, 3H), 1.86-1.69 (m, 3H), 1.58-1.25 (m, 16H), 1.14-1.08 (m, 11H), 1.06-0.99 (m, 4H), 0.94-0.91 (m, 6H), 0.68 (s, 3H). $^1$H NMR (5-6): (400 MHz, $CDCl_3$) δ 5.31-5.30 (m, 1H), 2.44-2.41 (d, 1H, J=12.4 Hz), 2.02-1.96 (m, 3H), 1.87-1.68 (m, 3H), 1.57-1.25 (m, 16H), 1.18-1.08 (m, 10H), 1.02-0.99 (m, 4H), 0.94-0.91 (m, 6H), 0.68 (s, 3H).

Preparation of 5-8 A mixture of 5-6 (200 mg, 0.464 mmol) and Pd/C (100 mg, cat.) in EtOAc (30 mL) was hydrogenated under 50 psi of hydrogen for 48 h at 50° C. The reaction mixture was filtered through a celite pad. The pad was washed with EtOAc (50 mL). The filtrate was concentrated in vacuum and the residue was purified by silica gel column eluted with PE/EtOAc=20/1 to give 5-8 (111.3 mg, 55.4%) as a white solid. $^1$H NMR (5-8) (400 MHz, $CDCl_3$), δ (ppm) 1.97-1.94 (d, 1H, J=12.0 Hz), 1.83-1.78 (m, 1H), 1.65-1.61 (m, 3H), 1.50-1.24 (m, 20H), 1.13-1.00 (m, 11H), 0.94-0.85 (m, 7H), 0.80 (s, 3H), 0.68-0.65 (m, 4H). $^1$H NMR (5-8A) (400 MHz, $CDCl_3$), δ (ppm) 1.98-1.95 (d, 1H, J=11.2 Hz), 1.88-1.80 (m, 3H), 1.65-1.60 (m, 1H), 1.51-1.47 (m, 1H), 1.40-1.31 (m, 12H), 1.28-1.20 (m, 8H), 1.16-1.01 (m, 11H), 0.96-0.80 (m, 10H), 0.65 (s, 3H).

Preparation of 5-7 A mixture of 5-5 (200 mg, 0.464 mmol) and Pd/C (100 mg, cat.) in EtOAc (30 mL) was hydrogenated under 50 psi of hydrogen for 48 h at 50° C. The reaction mixture was filtered through a celite pad. The pad was washed with EtOAc (50 mL). The filtrate was concentrated in vacuum and the residue was purified by silica gel column eluted with PE/EtOAc=20/1 to give 5-7 (118.5 mg, 59.0%) as a white solid. $^1$H NMR (5-7) (400 MHz, $CDCl_3$), δ (ppm) 1.97-1.94 (d, 1H, J=12.8 Hz), 1.88-1.79 (m, 1H), 1.71-1.61 (m, 3H), 1.51-1.24 (m, 20H), 1.13-1.00 (m, 11H), 0.94-0.85 (m, 7H), 0.80 (s, 3H), 0.68-0.65 (m, 4H). $^1$H NMR (5-7A) (400 MHz, $CDCl_3$), δ (ppm) 1.98-1.95 (d, 1H, J=11.2 Hz), 1.88-1.79 (m, 3H), 1.65-1.59 (m, 1H), 1.52-1.47 (m, 1H), 1.41-1.31 (m, 11H), 1.27-1.22 (m, 9H), 1.13-1.11 (m, 7H), 1.06-1.01 (m, 4H), 0.96-0.90 (m, 10H), 0.65 (s, 3H).

Example 6

(a)

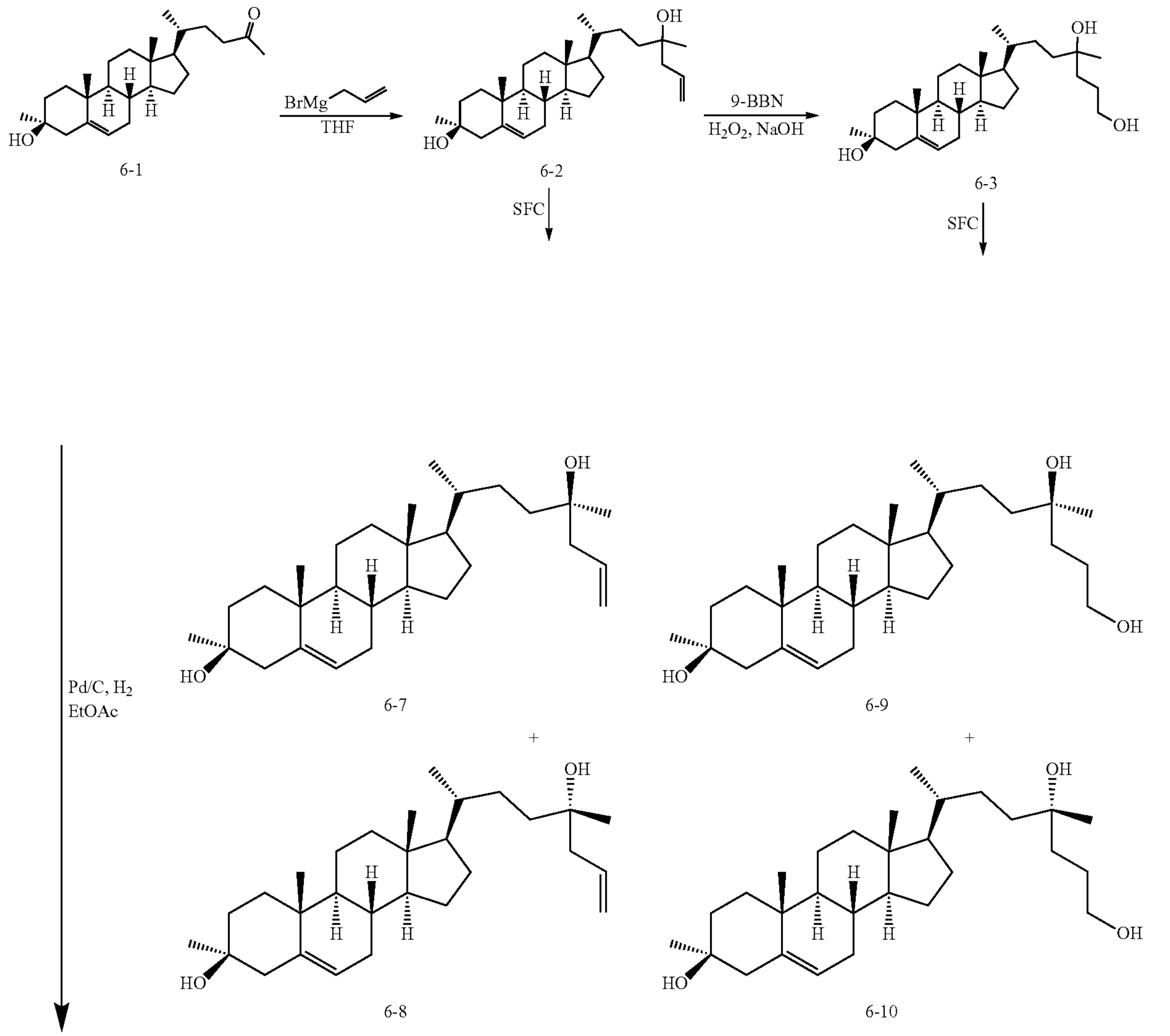

-continued
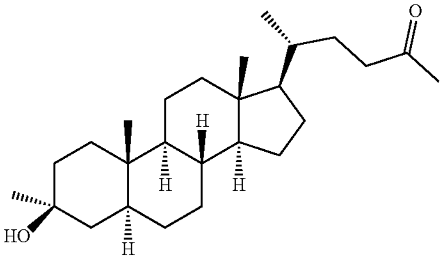
6-4
+
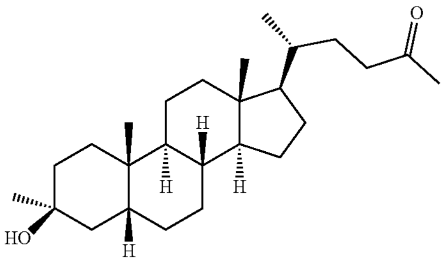
6-5
(b)
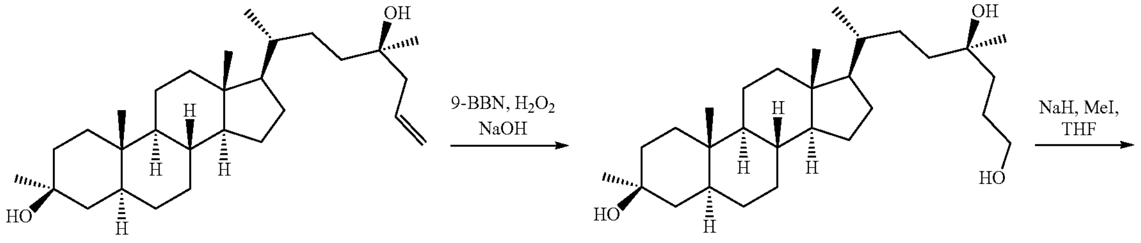
6-11
6-13
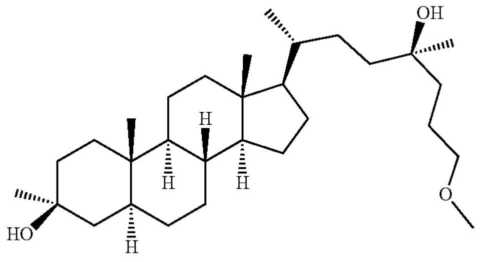
6-15
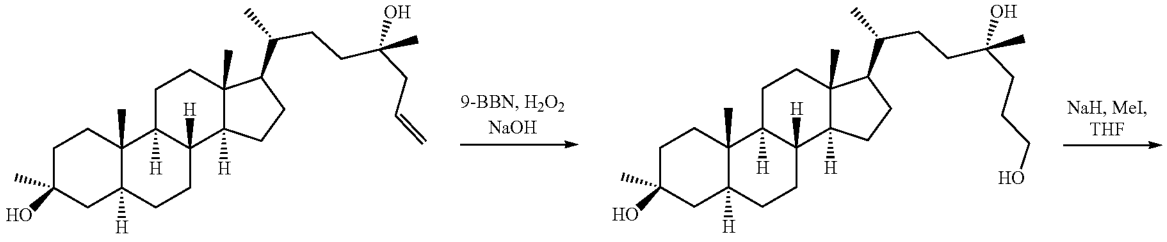
6-12
6-14
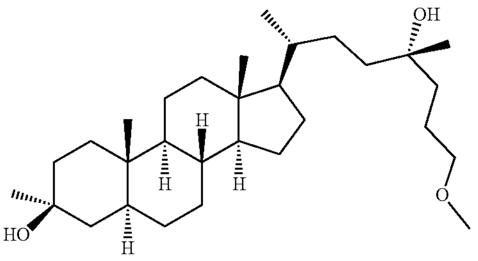
6-16

-continued
(c)
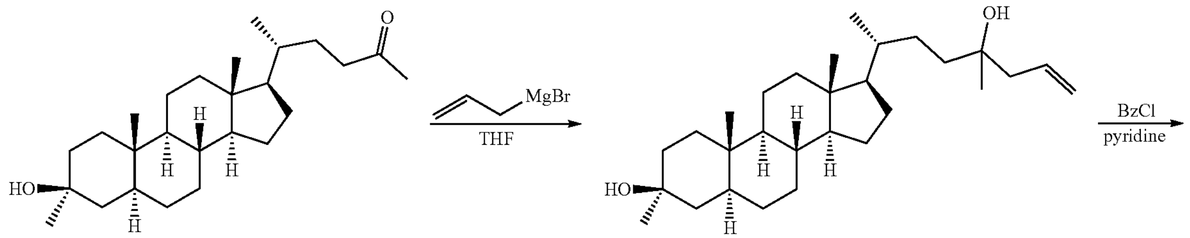
6-4
6-6
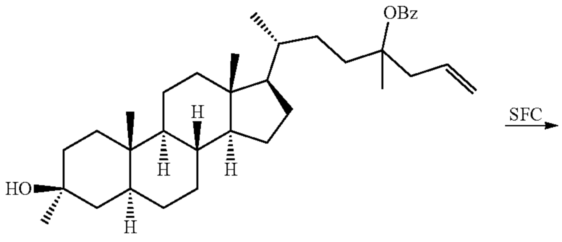
6-6-Bz
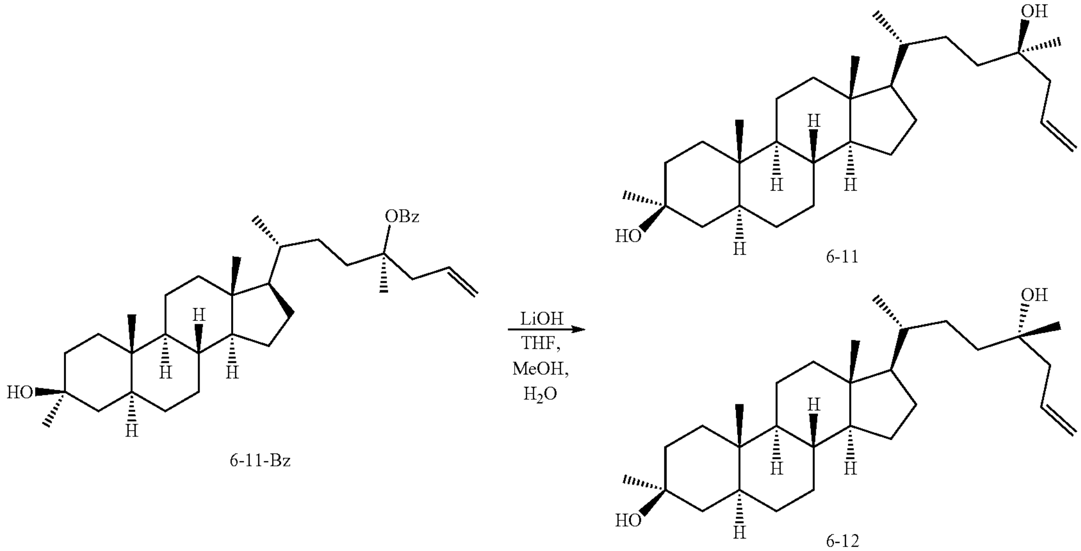
6-11-Bz
6-11
6-12
(d)
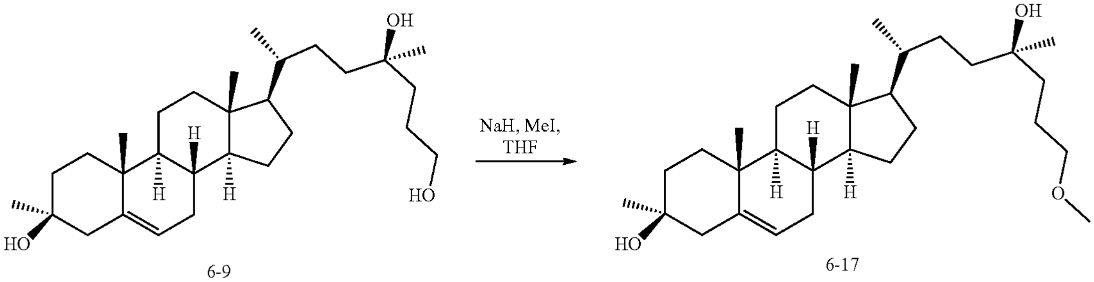
6-9
6-17

-continued

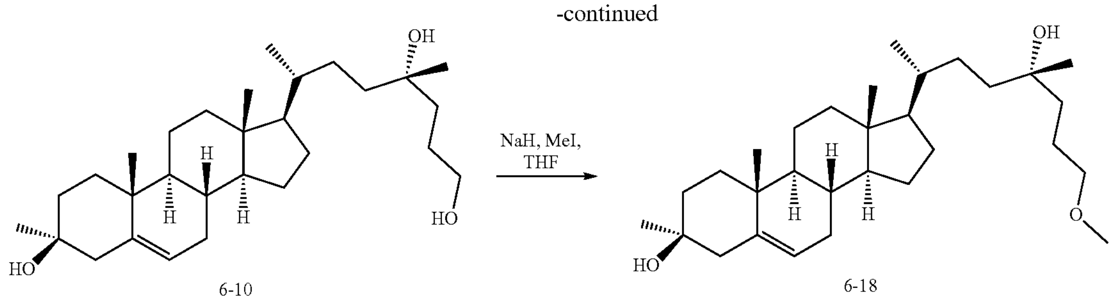

6-10

6-18

Preparation of 6-2. To a solution of 6-1 (150 mg, 0.39 mmole) in THE (4 mL) was added allylmagnesium bromide (2.34 mL, 2.34 mmole, 1M in ether) at −78° C. Then the reaction mixture was warmed to room temperature and stirred for 12 hours. The mixture was quenched with $NH_4Cl$ (20 mL) solution and extracted with EtOAc (10 mLx2). The organic phase was dried by $Na_2SO_4$ and purified by column chromatography on silica gel (eluent: PE:EA=10:1) to get the 6-2 (100 mg, 59%). $^1$H NMR: (400 MHz, $CDCl_3$) δ 5.89-5.82 (m, 1H), 5.31 (d, J=5.2 Hz, 2H), 5.15-5.09 (m, 2H), 2.43-2.40 (m, 1H), 2.22-2.20 (d, J=7.6 Hz, 2H), 2.04-1.96 (m, 3H), 1.95-1.57 (m, 3H), 1.54-1.24 (m, 12H), 1.19-1.11 (m, 5H), 1.09-1.05 (m, 6H), 1.03 (s, 3H), 0.98-0.92 (m, 5H), 0.68 (s, 3H).

Preparation of 6-3. To a solution of 9-BBN (3.2 mL, 1.6 mmol, 2M in THF) was added dropwise a solution of 6-2 (70 mg, 0.16 mmol) in THE (2 mL) at 0° C. The reaction mixture was heated at 60° C. and stirred for 12 hours. The mixture was cooled to 0° C. and aq. NaOH (10%) solution (2 mL) was added followed by $H_2O_2$ (30%, 1 mL). The mixture was stirred for 2 hours at 0° C. and then extracted with EtOAc. The combined organic layer was washed with brine, dried over $Na_2SO_4$ and concentrated to give crude product. The crude product was purified by column chromatography on silica gel (eluent: petroleum ether:ethyl acetate=2:1) to afford 6-3 (30 mg, 42%) as white solid. $^1$H NMR: (300 MHz, CDCl3) δ: 5.30 (d, J=5.2 Hz, 1H), 3.68-3.65 (m, 2H), 2.43-2.39 (m, 1H), 2.03-1.80 (m, 6H), 1.79-1.62 (m, 6H), 1.47-1.36 (m, 5H), 1.32-1.25 (m, 7H), 1.17-1.13 (m, 4H), 1.11-1.07 (m, 6H), 10.5-0.98 (m, 4H), 0.94-0.90 (m, 5H), 0.68 (s, 3H).

Preparation of 6-4 and 6-5. A mixture of 6-1 (1.0 g, 2.59 mmol) and 10% Pd/C (140 mg) in EtOAc (30 mL) was hydrogenated for 16 h at 50° C. under $H_2$ (50 psi). The reaction mixture was filtered through a pad of celite and the pad was washed with EtOAc (20 mLx3). The combined filtrates were concentrated. The residue was purified by column chromatography on silica gel (eluent: petroleum ether:ethyl acetate=15:1) to afford 6-4 (500 mg, 49.5%) and 6-5 (200 mg, 19.8%) as white solid.

Preparation of 6-6. To a solution of 6-4 (70 mg, 0.18 mmol) in dry THF (2 mL) at −78° C. was added $C_3H_5MgBr$ (1.1 mL, 1.08 mmol) dropwise under $N_2$. The mixture was warmed up to room temperature gradually and stirred for 12 h. The reaction was quenched with $NH_4Cl$ aqueous and extracted by EtOAc. The organic layer was dried over $Na_2SO_4$, filtered and concentrated to give crude product. The crude product was purified by column chromatography on silica gel (eluent: petroleum ether:ethyl acetate=15:1) to afford the pure product 6-6 (40 mg, 51.9%) as white powder. $^1$H NMR: (300 MHz, CDCl3) δ: ppm 5.92-5.79 (m, 1H), 5.15 (d, J=4.2 Hz, 1H), 5.11 (d, J=13.2 Hz, 1H), 2.21 (d, J=7.5 Hz, 2H), 1.97-1.75 (m, 5H), 1.67-1.34 (m, 19H), 1.30-0.94 (m, 11H), 0.91 (d, J=6.3 Hz, 3H), 0.80 (s, 3H), 0.69-0.61 (m, 4H).

Preparation of 6-7 and 6-8 Compound 6-2 (400 mg, 0.849 mmol) was split by SFC to get 6-7 (96 mg) and 6-8 (162 mg) as white powder (total yield: 65%). $^1$H NMR (6-7) (400 MHz, $CDCl_3$), δ 5.90-5.81 (m, 1H), 5.31 (d, J=5.2 Hz, 1H), 5.20-5.09 (m, 2H), 2.45-2.35 (m, 1H), 2.25-2.15 (m, 2H), 2.04-0.90 (m, 36H), 0.68 (s, 3H). $^1$H NMR (6-8) (400 MHz, $CDCl_3$), δ 5.90-5.80 (m, 1H), 5.31 (d, J=5.2 Hz, 1H), 5.21-5.09 (m, 2H), 2.45-2.34 (m, 1H), 2.25-2.15 (m, 2H), 2.04-0.89 (m, 36H), 0.68 (s, 3H).

Preparation of 6-6-Bz To a solution of 6-6 (100 mg, 0.23 mmol) in pyridine (3 mL) was added BzCl (64.4 mg, 0.46 mmol) dropwise at room temperature. Then the reaction mixture was stirred at 40° C. for 12 hours. TLC showed the starting material was consumed completely. The mixture was quenched by saturated aqueous water and extracted with EtOAc. The combined organic phase was washed with 1 M HCl (30 mL) and brine, dried over anhydrous $Na_2SO_4$ then concentrated in vacuum. The residue was purified by column chromatography on silica gel (petroleum ether:ethyl acetate=80:1) to afford 6-8-Bz (60 mg, 48%) as a white solid.

Preparation of 6-11-Bz Compound 6-6-Bz (60 mg, 0.11 mmol) was split by SFC to get 6-11-Bz (40 mg, 66%) as a white solid. $^1$H NMR: (400 MHz, $CDCl_3$) δ 7.99-7.98 (d, J=7.2 Hz, 2H), 7.53-7.49 (t, J=7.2 Hz, 1H), 7.42-7.38 (t, J=7.2 Hz, 2H), 2.22-2.20 (d, J=7.6 Hz, 2H), 1.98-1.57 (m, 11H), 1.54-1.26 (m, 16H), 1.15 (s, 3H), 1.12-1.10 (m, 6H), 0.92-0.91 (d, J=6.0 Hz, 3H), 0.80 (s, 3H), 0.64-0.60 (m, 4H)

Preparation of 6-11 To a solution of compound 6-11-Bz (40 mg, 0.075 mmol) in a mixture solvent of THE (2 mL) and MeOH (1 mL) was added a solution of LiOH (90 mg, 3.75 mmol) in $H_2O$ (1 mL). The mixture was stirred at 40° C. for 3 days. TLC showed the starting material was consumed completely. The reaction mixture was treated with water and extracted with EtOAc. The combined organic phase was washed with brine, dried over anhydrous $Na_2SO_4$ then concentrated by vacuum. The residue was purified by column chromatography on silica gel (petroleum ether:ethyl acetate=8:1) to afford 6-11 (23 mg, 71%) as a white solid. $^1$H NMR: (400 MHz, $CDCl_3$) δ 5.86-5.84 (m, 1H), 5.13-5.09 (m, 2H), 2.21-2.19 (d, J=7.6 Hz, 2H), 1.84-1.25 (m, 19H), 1.24 (s, 3H), 1.14 (s, 3H), 1.13-1.09 (m, 7H), 0.91-0.90 (d, J=6.8 Hz, 3H), 0.80 (s, 3H), 0.64-0.60 (m, 4H)

Example 7

(a)

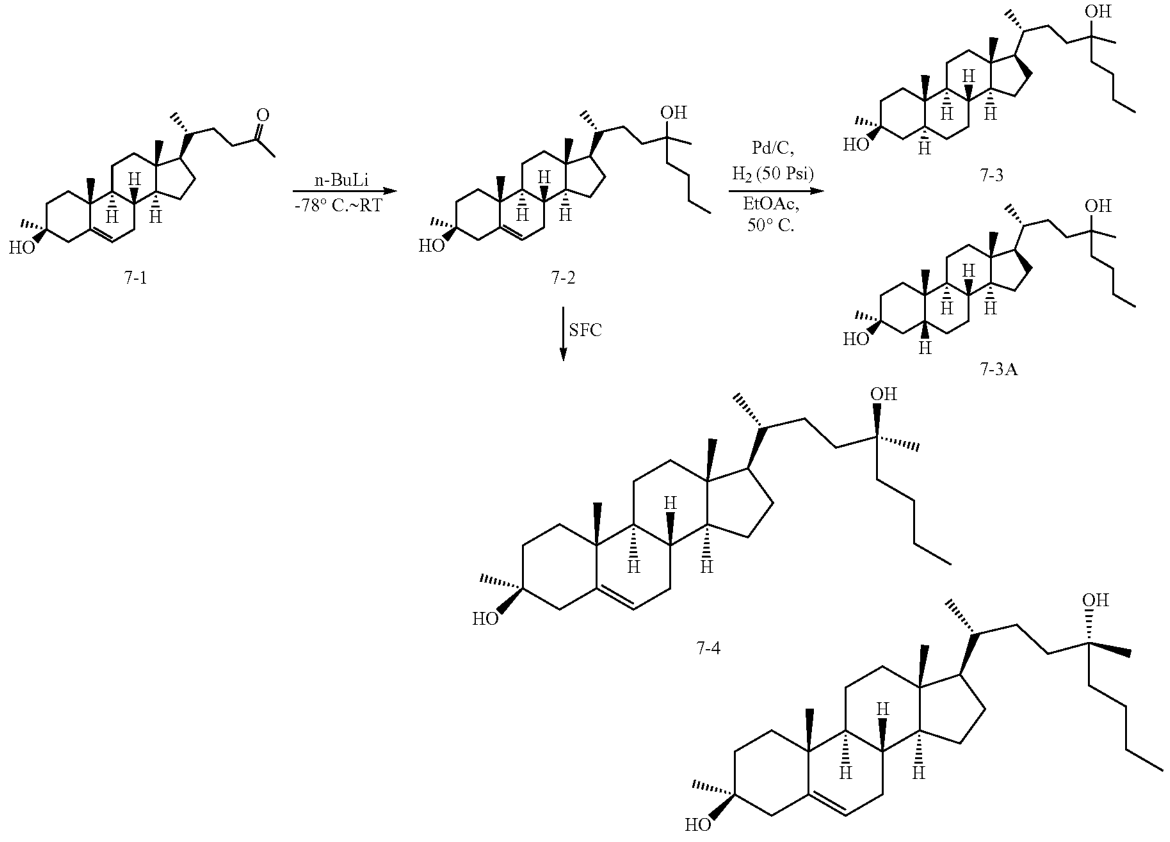

7-1 7-2 7-3 7-3A 7-4 7-5

(b)

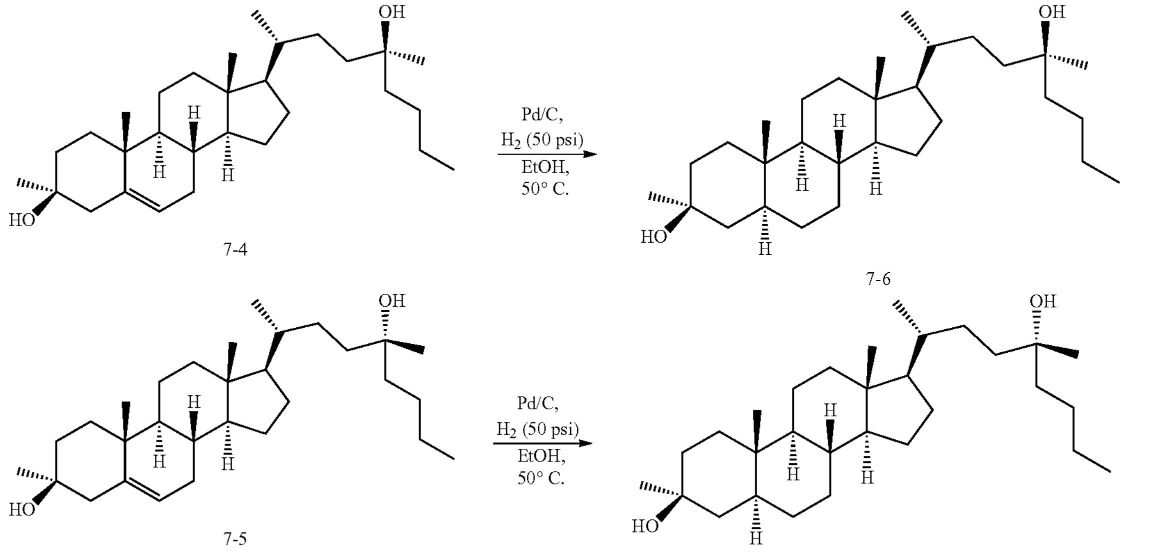

7-4 7-6 7-5 7-7

Preparation of Compound 7-2. To a solution of 7-1 (193 mg, 0.5 mmol, 1.0 eq) in dry THE (3 mL), n-BuLi (1.6 mL, 4 mmol, 8.0 eq) was added dropwise at −78° C. The resulting mixture was stirred at this temperature for 0.5 h, and then the temperature was allowed to warm to room temperature and stirred at this temperature for another 18 h. TLC (PE/EA=5/1) showed the reaction was complete. The mixture was quenched with saturated aqueous $NH_4Cl$ and extracted with EtOAc (10 mL×3). The combined organic layers were washed with brine (10 mL), dried over sodium sulfate and concentrated in vacuum. The residue was purified by column chromatography on silica gel (eluent: PE:EA=20:1) to give the product 7-2 (85 mg, 38.6%) as white powder. $^1$H NMR: (400 MHz, $CDCl_3$) δ 5.31 (d, J=5.2 Hz, 1H), 2.41 (d, J=13.2 Hz, 1H), 2.10-1.95 (m, 3H), 1.94-1.62 (m, 42H), 1.52-1.22 (m, 17H), 1.22-1.20 (m, 1H), 1.15 (s, 3H), 1.10 (s, 3H), 1.05 (s, 3H), 1.04-1.00 (m, 3H), 1.00-0.85 (m, 9H), 0.67 (s, 3H).

Preparation of Compound 7-3. A mixture of 7-2 (100 mg, 2.59 mmol) and 10% Pd/C (140 mg) in EtOAc (30 mL) was hydrogenated for 16 h at 50° C. under Hz (50 psi). The reaction mixture was filtered through a pad of celite and the pad was washed with EtOAC (20 mL×3). The combined filtrates were concentrated. The residue was purified by column chromatography on silica gel (eluent: petroleum ether:ethyl acetate=15:1) to afford 7-3 (35 mg, 35%) and 7-3A (19 mg, 19%) as white powder. $^1$H NMR (7-3): (400 MHz, CDC13) δ 2.02-1.92 (m, 1H), 1.90-1.77 (m, 1H), 1.70-1.38 (m, 14H), 1.36-1.29 (m, 6H), 1.28-1.20 (m, 8H), 1.20-1.08 (m, 6H), 1.07-0.96 (m, 4H), 0.96-0.84 (m, 7H), 0.82 (s, 3H), 0.70-0.60 (m, 4H). $^1$H NMR (7-3A): (400 MHz, CDC13) δ 1.98-1.80 (m, 4H), 1.67-1.48 (m, 6H), 1.45-1.33 (m, 9H), 1.32-1.23 (m, 10H), 1.22-1.18 (m, 4H), 1.17-1.10 (m, 6H), 1.10-0.97 (m, 4H), 0.94 (s, 3H), 0.93-0.87 (m, 6H), 0.64 (s, 3H).

Preparation of 7-4 and 7-5 To a solution of compound 7-1 (1.5 g, 3.88 mmol) in dry THE (15 mL) was added n-BuLi (12.5 mL, 31 mmol, 2.5 M in THF) dropwise at −78° C. The resulting mixture was stirred at this temperature for 0.5 h, and then the temperature was allowed to warm to room temperature and stirred at this temperature for another 18 h. TLC (PE/EA=5/1) showed the reaction was complete. The mixture was quenched with saturated aqueous $NH_4Cl$ and extracted with EtOAc (30 mL×3). The combined organic layers were washed with brine (10 mL), dried over sodium sulfate and concentrated in vacuum. The residue was purified by column chromatography on silica gel (eluent: PE:EA=20:1) to give 7-2 (800 mg, 46.4%) as white powder, which was split by SFC to give 7-4 (207 mg) and 7-5 (360 mg) as white powder. $^1$H NMR (7-4): (400 MHz, CDC13) δ 5.38-5.29 (m, 1H), 2.44 (d, 1H, J=12.5 Hz), 2.04-1.69 (m, 6H), 1.57-1.25 (m, 18H), 1.20-0.89 (m, 23H), 0.70 (s, 3H). $^1$H NMR (7-5): (400 MHz, CDC13) δ 5.32 (s, 1H), 2.44 (d, 1H, J=12.3 Hz), 2.08-1.68 (m, 6H), 2.55-1.25 (m, 17H), 2.22-0.85 (m, 24H), 0.70 (s, 3H).

Preparation of 7-6 To a solution of 7-4 (0.17 g, 0.38 mmol) in 15 mL EtOH was added Pd/C (100 mg) then the reaction mixture was stirred under hydrogen (50 psi) at 50° C. for 24 h. The resulting solution was filtered and concentrated. The product was purified by column chromatograph on silica gel elude with (PE:EA=20:1) to give 7-6 (40 mg, yield: 23.42%) as white solid. $^1$H NMR (7-6) (400 MHz, $CDCl_3$), δ 1.97-1.94 (m, 1H), 1.88-1.76 (m, 1H), 1.71-1.59 (m, 3H), 1.56-1.23 (m, 21H), 1.23-0.86 (m, 19H), 0.81 (s, 3H), 0.65 (s, 3H).

Preparation of 7-7 To a solution of 7-5 (0.23 g, 0.52 mmol) in 15 mL EtOH was added Pd/C (200 mg), then the reaction mixture was stirred under hydrogen (50 psi) at 50° C. for 24 h. The resulting solution was filtered and concentrated. The product was purified by column chromatograph on silica gel elude with (PE:EA=20:1) to give 7-7 (70 mg, yield: 30.3%) as white solid. $^1$H NMR (7-7) (400 MHz, $CDCl_3$), δ (ppm) 1.99-1.92 (m, 1H), 1.88-1.78 (m, 1H), 1.70-1.52 (m, 61H) 1.46-1.20 (m, 21H), 1.18-0.87 (m, 20H), 0.81 (s, 3H), 0.65 (s, 3H).

Example 8

(a)

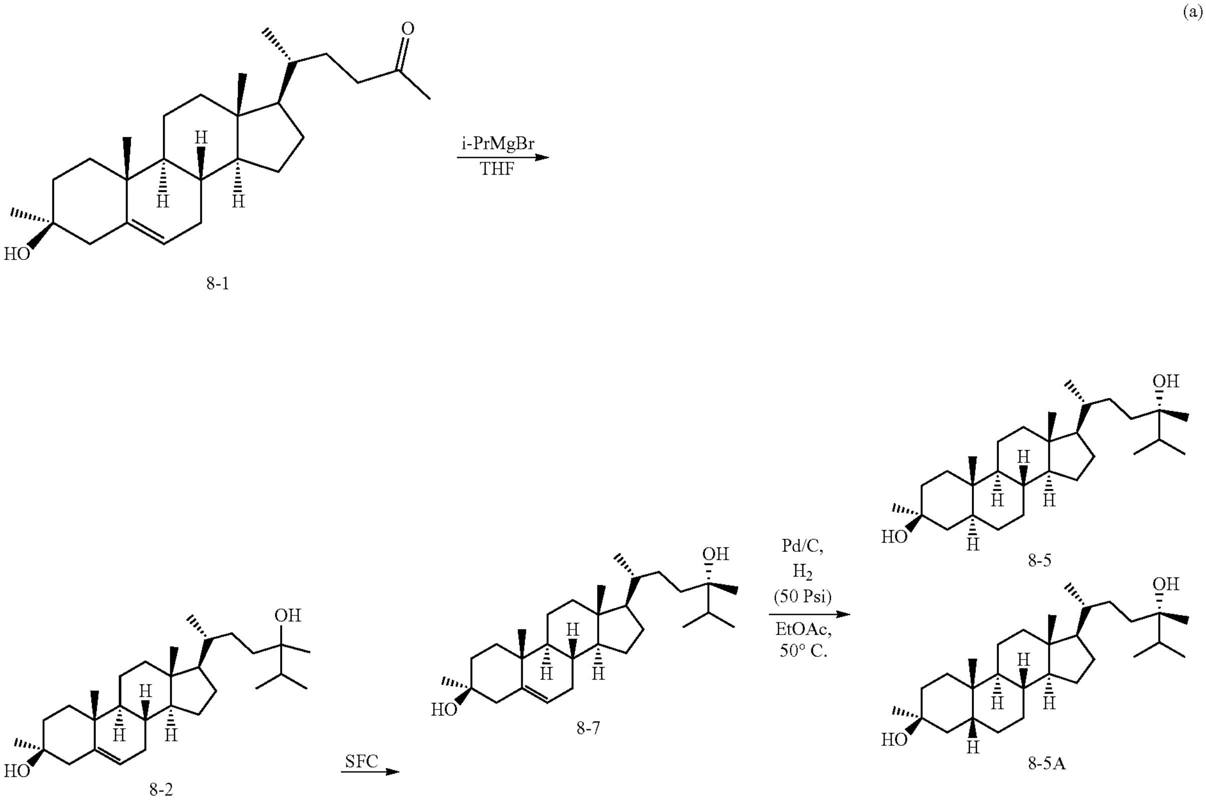

8-1

8-2

8-7

8-5

8-5A

-continued

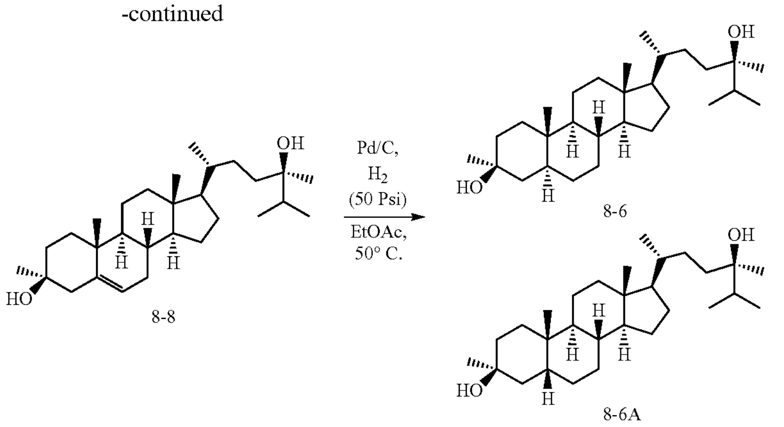

8-8

8-6

8-6A (b)

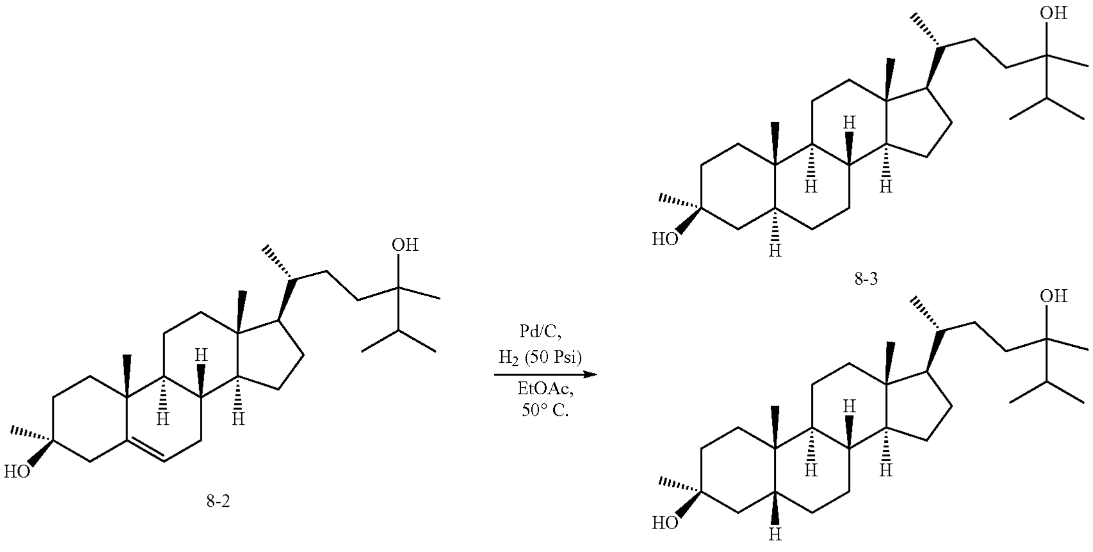

8-2

8-3

8-4

Preparation of 8-2. To a solution of compound 8-1 (100 mg, 0.25 mmol) in toluene (8 mL) was added dropwise a solution of i-PrMgBr (1.5 mL, 1.5 mmol, 1 M in THF) at room temperature during a period of 10 min under nitrogen. Then the reaction mixture was stirred at room temperature for 12 h. TLC showed that the starting material was consumed completely. The mixture was poured into aqueous saturated $NH_4Cl$ solution (20 mL) and extracted with EtOAc (50 mL×2). The combined organic phases were dried over $Na_2SO_4$, and the solvent was evaporated to afford crude product. The crude product purified by column chromatography on silica gel (eluent: petroleum ether:ethyl acetate=8:1) to give the product 8-2 (66 mg, 59.46%) as white powder. $^1$H NMR: (400 MHz, CDCl3) δ 5.30 (d, J=5.2 Hz, 1H), 2.43-2.40 (m, 1H), 2.04-1.55 (m, 3H), 1.88-1.66 (m, 5H), 1.58-1.13 (m, 15H), 1.11 (s, 3H), 1.08 (s, 3H), 1.01 (s, 3H), 0.96-0.90 (m, 6H), 0.90-0.86 (m, 3H), 0.68 (s, 3H).

Preparation of 8-3 and 8-4. To a solution of compound 8-2 (60 mg, 0.14 mmol) in EtOAc (15 mL) was added 10% Pd/C (20 mg) under argon. The suspension was degassed under vacuum and purged with $H_2$ several times. The mixture was stirred under $H_2$ (50 Psi) at 50° C. overnight. The suspension was filtered through a pad of celite and the pad was washed with EA (20 mL×3). The combined filtrates were concentrated in vacuum and the residue was purified by column chromatography on silica gel (eluent: petroleum ether:ethyl acetate=10:1) to give 8-3 (27 mg, 45%) and 8-4 (9 mg, 15%) as white powder. $^1$H NMR (8-3): (400 MHz, CDCl3) δ 1.97-1.94 (m, 1H), 1.85-1.78 (m, 2H), 1.74-1.42 (m, 12H), 1.48-1.20 (m, 12H), 1.18-1.09 (m, 3H), 1.07 (s, 3H), 1.02-0.98 (m, 2H), 0.93-0.88 (m, 6H), 0.88-0.86 (m, 3H), 0.80 (s, 3H), 0.63 (s, 3H). $^1$H NMR (8-4): (400 MHz, CDCl3) δ1.98-1.95 (m, 1H), 1.89-1.79 (m, 3H), 1.75-1.54 (m, 7H), 1.48-1.24 (m, 16H), 1.23 (s, 3H), 1.19-1.11 (m, 4H), 1.08 (s, 4H), 0.95 (s, 3H), 0.94-0.88 (m, 6H), 0.88-0.86 (m, 3H), 0.63 (s, 3H).

Preparation of 8-7 and 8-8. To a solution of compound 8-1 (1500 mg, 3.88 mmol) in dry THF (30 mL) was added a solution of i-PrMgCl (11.6 mL, 23.3 mmol) dropwise at 0° C. The mixture was stirred at 40° C. for 16 h. TLC (PE/EtOAc=2/1) showed the reaction was complete. Saturated aqueous $NH_4Cl$ (5 mL) was added slowly to quench the reaction. The resulting solution was separated between EtOAc (30 mL×3) and $H_2O$ (30 mL). The combined organic layers were concentrated in vacuum and the residue was purified by silica gel column eluted with PE/EtOAc=10/1 to give the mixture of the diastereomeric pair (800 mg) as white power. The diastereimeric pair was separated by prep-SFC to give 8-8 (317 mg, 19.0%) and 8-7 (250 mg, 15.0%) as white solid. $^1$H NMR (8-8): (400 MHz, $CDCl_3$)

δ 5.30 (s, 1H), 2.42 (d, J=12.4 Hz, 1H), 2.01-1.99 (m, 3H), 1.89-1.65 (m, 4H), 1.59-1.58 (m, 1H), 1.51-1.26 (m, 9H), 1.20-1.05 (m, 12H), 1.04-0.99 (m, 4H), 0.94-0.88 (m, 10H), 0.68 (s, 3H). $^1$H NMR (8-7): (400 MHz, $CDCl_3$) δ 5.30 (d, J=3.6 Hz, 1H), 2.42 (d, J=12.4 Hz, 1H), 2.00-1.97 (m, 3H), 1.89-1.68 (m, 4H), 1.58-1.25 (m, 10H), 1.19-1.08 (m, 10H), 1.03-0.98 (m, 4H), 0.95-0.88 (m, 10H), 0.68 (s, 3H).

Preparation of 8-6. A mixture of 8-8 (200 mg, 0.464 mmol) and Pd/C (100 mg, cat.) in EtOAc (30 mL) was hydrogenated under 50 psi of hydrogen for 48 h at 50° C. The reaction mixture was filtered through a celite pad. The pad was washed with EtOAc (50 mL). The filtrate was concentrated in vacuum and the residue was purified by silica gel column eluted with PE/EtOAc=20/1 to give 8-6 (85.9 mg, 42.8%) as a white solid and 8-6A (17.6 mg, 8.8%) as a white solid. $^1$H NMR (8-6) (400 MHz, $CDCl_3$), δ (ppm) 1.97-1.94 (d, 1H, J=12.8 Hz), 1.88-1.79 (m, 1H), 1.71-1.61 (m, 3H), 1.54-1.45 (m, 3H), 1.36-1.19 (m, 13H), 1.16-0.96 (m, 12H), 0.92-0.87 (m, 10H), 0.80 (s, 3H), 0.68-0.65 (m, 4H). $^1$H NMR (8-6A) (400 MHz, $CDCl_3$), δ (ppm) 1.98-1.95 (d, 1H, J=10.8 Hz), 1.88-1.79 (m, 3H), 1.71-1.59 (m, 3H), 1.53-1.48 (m, 2H), 1.42-1.31 (m, 6H), 1.27-0.96 (m, 20H), 0.92-0.87 (m, 12H), 0.80 (s, 3H), 0.64 (s, 3H).

Preparation of 8-5 A mixture of 8-7 (150 mg, 0.348 mmol, 1.0 eq) and Pd/C (75 mg, cat.) in EtOAc (20 mL) was hydrogenated under 50 psi of hydrogen for 48 h at 50° C. The reaction mixture was filtered through a celite pad. The pad was washed with EtOAc (50 mL). The filtrate was concentrated in vacuum and the residue was purified by silica gel column eluted with PE/EtOAc=20/1 to give 8-5 (89.0 mg, 44.3%) as a white solid and 8-5A (4.6 mg, 2.3%) as a white solid. $^1$H NMR (8-5) (400 MHz, $CDCl_3$), δ (ppm) 1.97-1.94 (d, 1H, J=12.8 Hz), 1.88-1.79 (m, 1H), 1.71-1.61 (m, 3H), 1.54-1.45 (m, 3H), 1.36-1.19 (m, 13H), 1.16-0.96 (m, 12H), 0.92-0.87 (m, 10H), 0.80 (s, 3H), 0.68-0.65 (m, 4H). $^1$H NMR (8-5A) (400 MHz, $CDCl_3$), δ (ppm) 1.98-1.95 (d, 1H, J=10.8 Hz), 1.91-1.79 (m, 3H), 1.72-1.64 (m, 2H), 1.54-1.50 (m, 1H), 1.46-1.00 (m, 28H), 0.96-0.87 (m, 12H), 0.64 (s, 3H).

Example 9

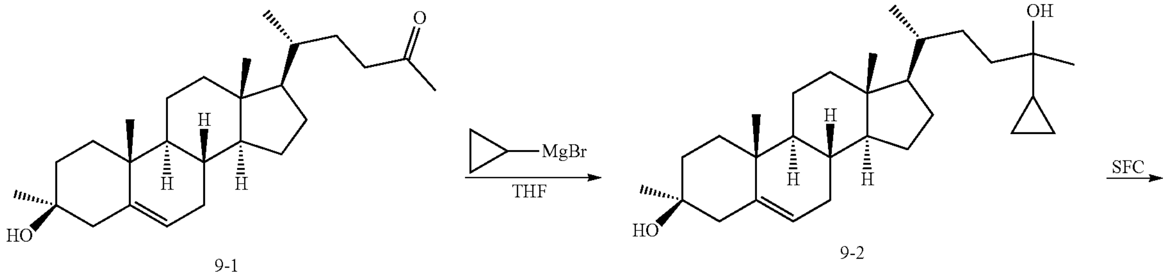

9-1

9-2

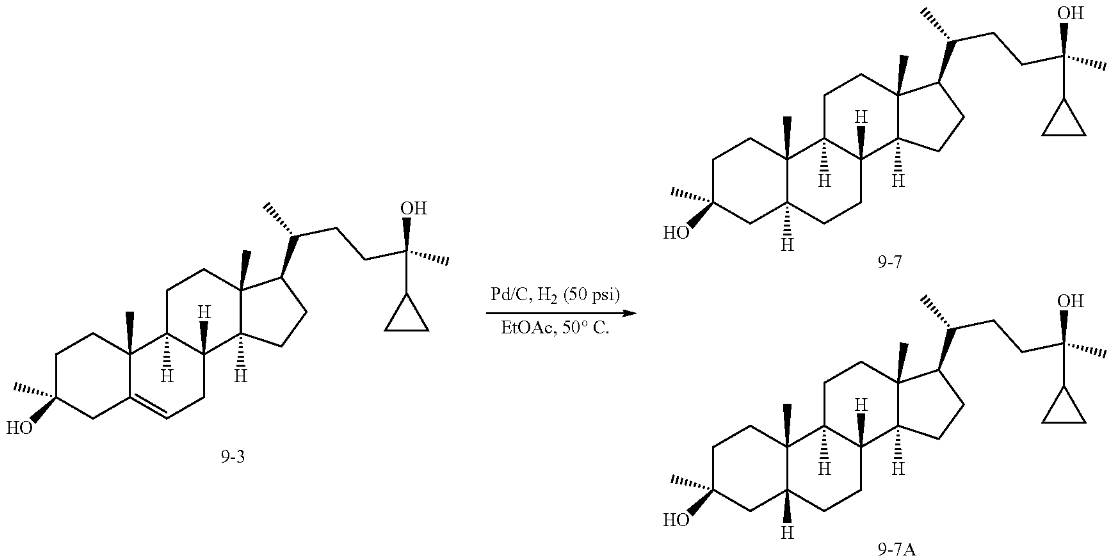

9-3

9-7

9-7A

-continued

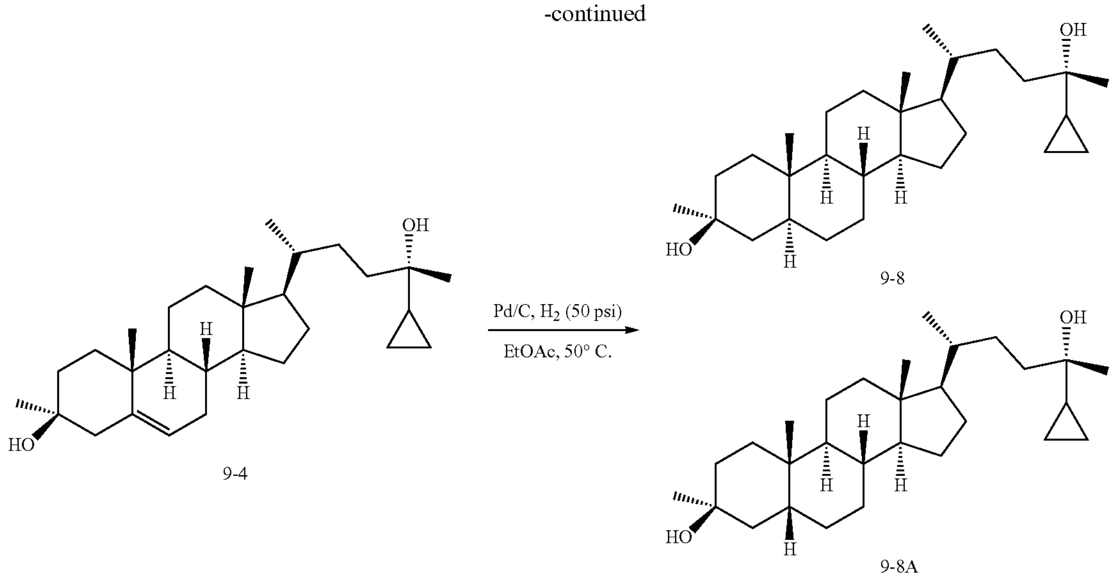

9-4 9-8 9-8A

Preparation of 9-2. To a solution of compound 9-1 (100 mg, 0.25 mmol) in THE (2 mL) was added dropwise a solution of CyclopropylmagnesiumBlromide (2.5 mL, 2.5 mmol, 1 M in THF) at room temperature during a period of 10 min under nitrogen. Then the reaction mixture was stirred at room temperature for 12 h. TLC showed that the starting material was consumed completely. The mixture was poured into aqueous saturated $NH_4Cl$ solution (20 mL) and extracted with EtOAc (50 mL×2). The combined organic phases were dried over $Na_2SO_4$, and the solvent was evaporated to afford crude product. The crude product purified by column chromatography on silica gel (eluent: petroleum ether:ethyl acetate=10:1) to give the product 9-2 (33 mg, 30%) as white powder. $^1$H NMR: (400 MHz, CDC13) δ: 5.31 (d, J=5.2 Hz, 1H), 2.42 (d, J=12.8 Hz, 1H), 2.08-1.93 (m, 3H), 1.90-1.65 (m, 3H), 1.62-1.27 (m, 13H), 1.22-1.08 (m, 11H), 1.01 (s, 3H), 1.00-0.85 (m, 6H), 0.68 (s, 3H), 0.40-0.25 (m, 4H).

Preparation of 9-3 and 9-4 Compound 9-2 (200 mg, 0.46 mmol) was separated by SFC to get 9-3 (90 mg) and 9-4 (100 mg) as white solid, (total yield: 95%). $^1$H NMR: (9-3) (400 MHz, $CDCl_3$) δ 5.31-5.30 (m, 1H), 2.44-2.41 (m, 1H), 2.02-1.99 (m, 3H), 1.95-1.60 (m, 3H), 1.50-1.25 (m, 9H), 1.20-1.05 (m, 11H), 1.02-0.93 (m, 11H), 0.68 (s, 3H), 0.35-0.28 (m, 4H). $^1$H NMR: (9-4) (400 MHz, $CDCl_3$) δ 5.31-5.30 (m, 1H), 2.44-2.41 (m, 1H), 2.02-1.95 (m, 3H), 1.93-1.60 (m, 3H), 1.50-1.25 (m, 10H), 1.20-1.05 (m, 11H), 1.02-0.93 (m, 11H), 0.68 (s, 3H), 0.36-0.24 (m, 4H)

Preparation of 9-7 To a solution of compound 9-3 (100 mg, 0.23 mmol) in EtOAc (8 mL) was added Pd/C (10%, 200 mg) under $N_2$. The suspension was degassed under vacuum and purged with $H_2$ several times. Then the mixture was stirred under $H_2$ (50 psi) at 50° C. for 24 hours. The suspension was filtered through a pad of celite and the pad was washed with EtOAc (30 mL×2). The combined filtrates were concentrated to dryness to give the crude product, which was purified by column chromatography on silica gel (petroleum ether:ethyl acetate=20:1) to afford 9-7 (27.8 mg, 27.8%) as white solid. $^1$H NMR: (9-7) (400 MHz, $CDCl_3$) δ 1.97-1.94 (m, 1H), 1.90-1.80 (m, 1H), 1.64-1.57 (m, 3H), 1.54-1.30 (m, 7H), 1.28-0.85 (m, 25H), 0.80 (s, 3H), 0.65-0.60 (m, 4H), 0.36-0.33 (m, 4H). $^1$H NMR: (9-7A) (400 MHz, $CDCl_3$) δ 1.95-1.83 (m, 4H), 1.70-1.57 (m, 1H), 1.45-1.11 (m, 22H), 1.05-0.85 (m, 17H), 0.65 (s, 3H), 0.36-0.34 (m, 4H)

Preparation of 9-8 To a solution of compound 9-4 (100 mg, 0.23 mmol) in EtOAc (8 mL) was added Pd/C (10%, 200 mg) under $N_2$. The suspension was degassed under vacuum and purged with $H_2$ several times. Then the mixture was stirred under $H_2$ (50 psi) at 50° C. for 24 hours. The suspension was filtered through a pad of celite and the pad was washed with EtOAc (30 mL×2). The combined filtrates were concentrated to dryness to give the crude product, which was purified by HPLC to afford 9-8 (18.3 mg, 18%) as white solid. $^1$H NMR: (9-8) (400 MHz, $CDCl_3$) δ 1.97-1.94 (m, 1H), 1.90-1.80 (m, 1H), 1.60-1.57 (m, 3H), 1.54-1.20 (m, 16H), 1.19-0.82 (m, 16H), 0.80 (s, 3H), 0.65-0.60 (m, 4H), 0.36-0.28 (m, 4H)

Example 10
(a)
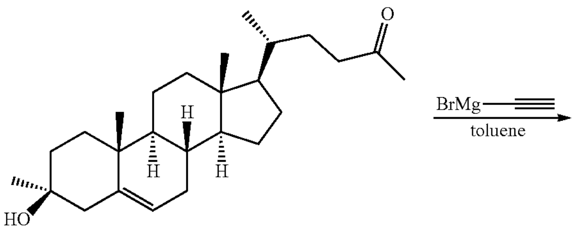
10-1
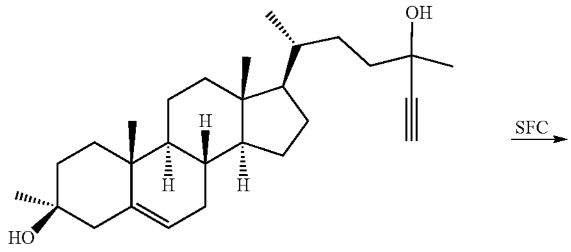
10-2
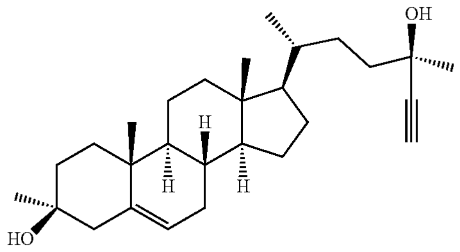
10-3
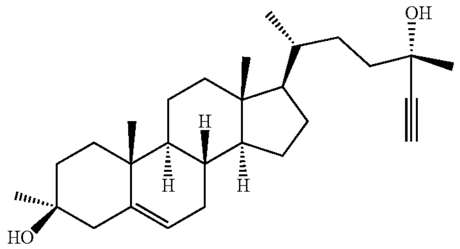
10-4
(b)
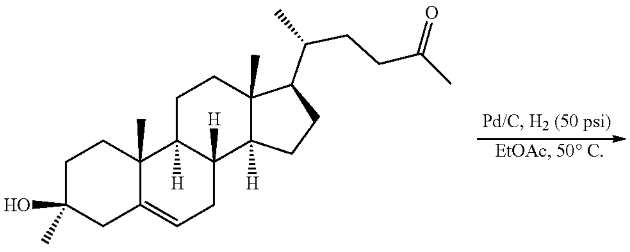
10-1
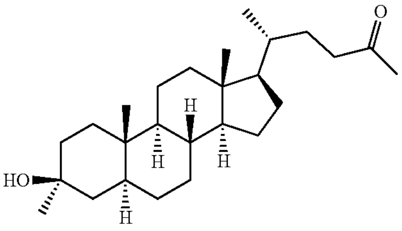
10-5
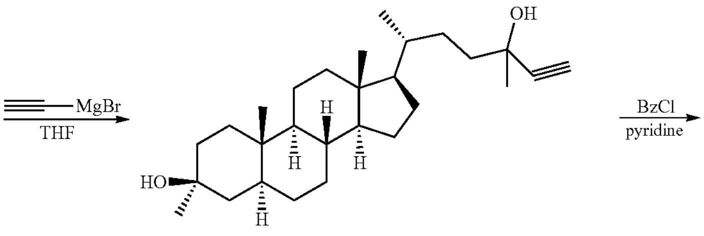
10-6

-continued
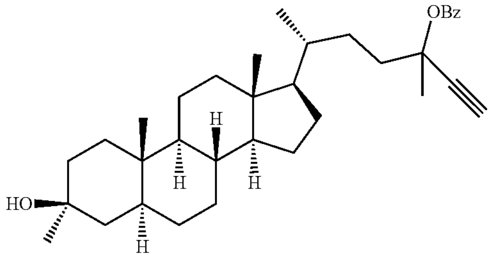
10-6-Bz
SFC
75%
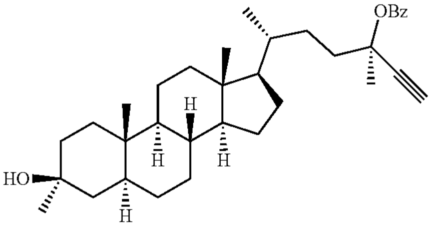
10-8-Bz
LiOH
THF,
MeOH,
$H_2O$
92%
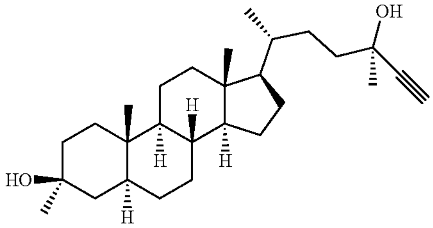
10-8
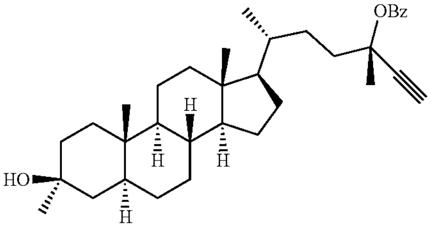
10-9-Bz
LiOH
THF,
MeOH,
$H_2O$
91%
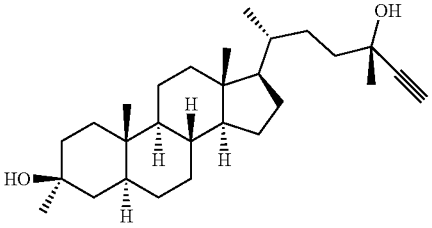
10-9
(c)
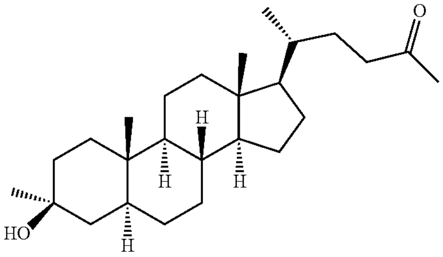
10-5
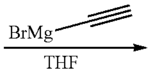
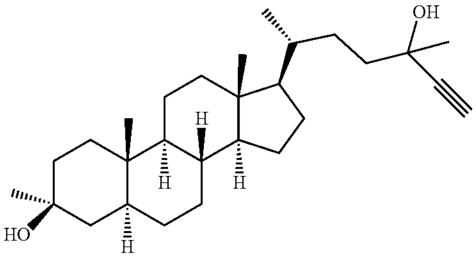
10-6
lindlar cat.
$H_2$(1 atm), EtOAc
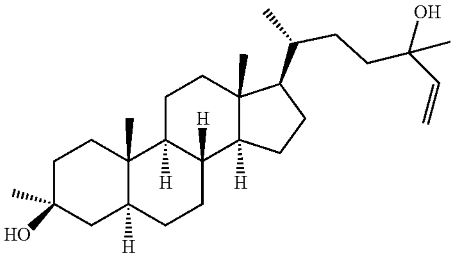
10-7
SFC -continued
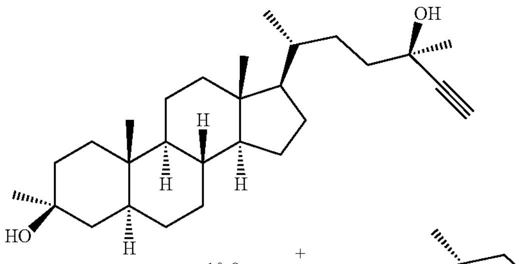
10-8
+
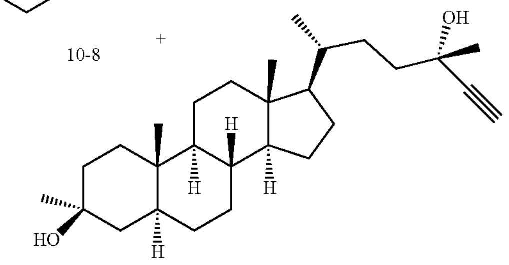
10-9
(d)
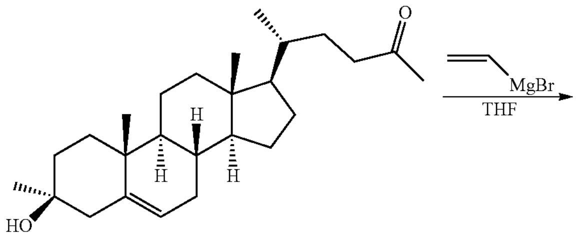
10-1
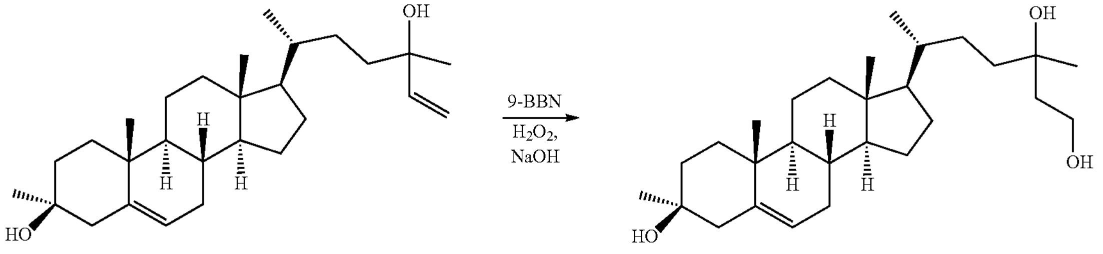
10-12
10-13
(e)
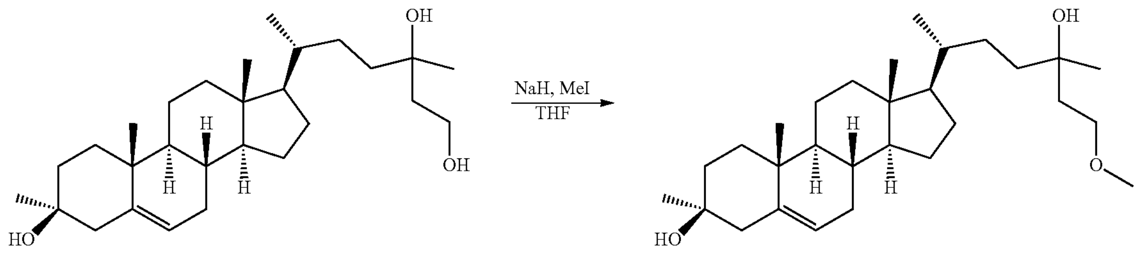
10-13
10-14
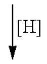

-continued
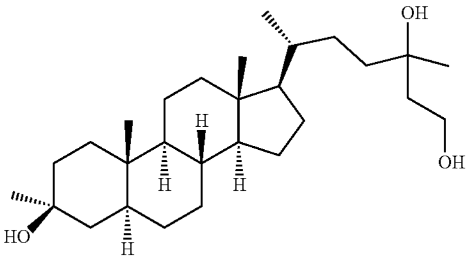
10-15
(f)
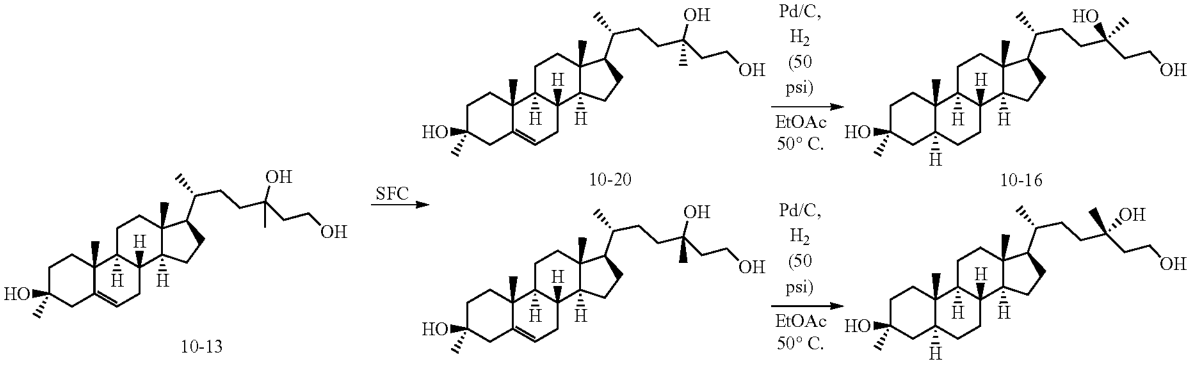
10-13 10-20 10-21 10-16 10-18
(g)
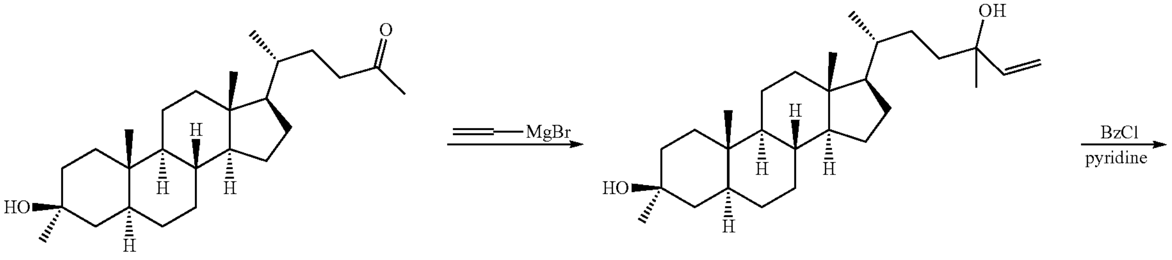
10-5 10-7
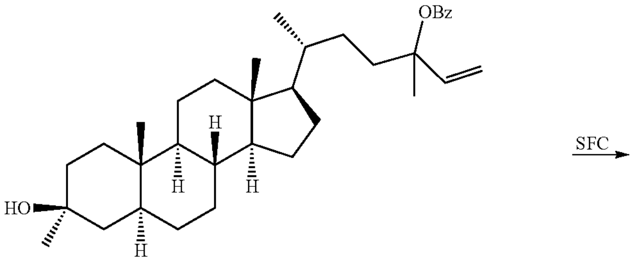
10-7-Bz -continued
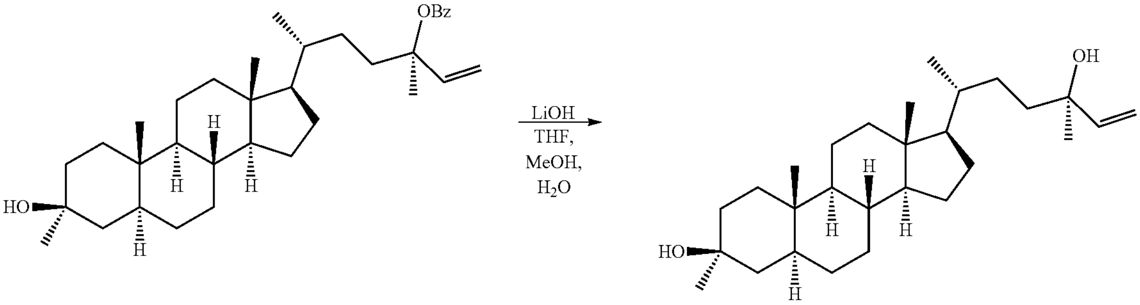
10-10-Bz
10-10
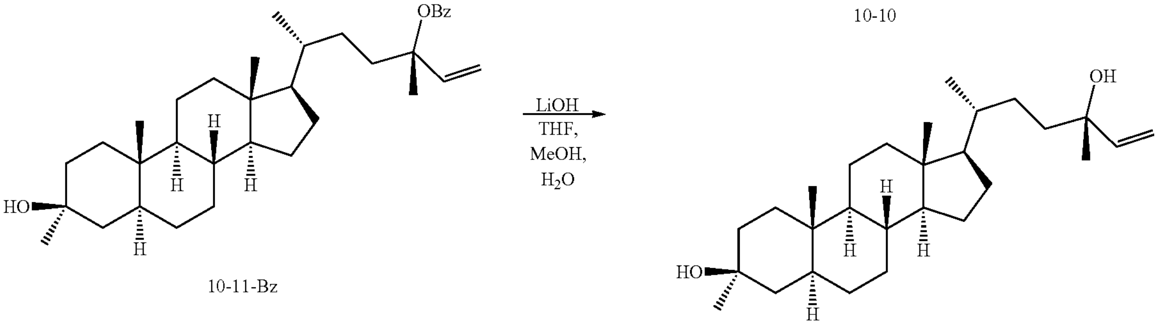
10-11-Bz
10-11
(h)
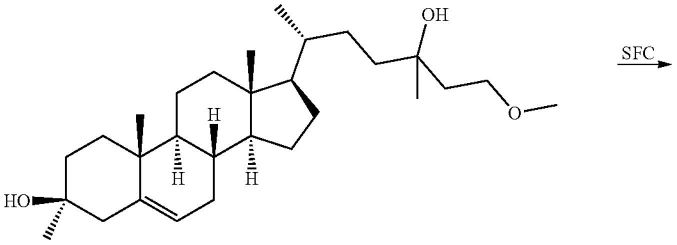
10-14
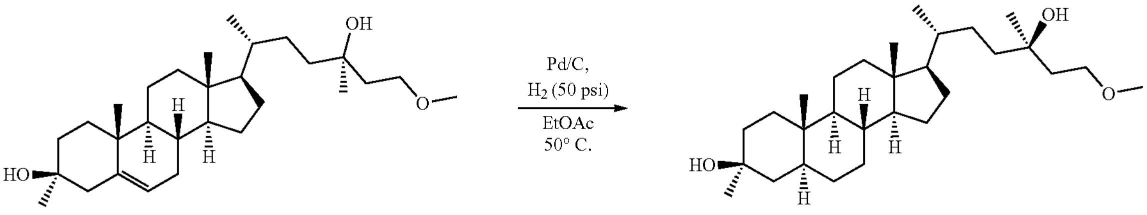
10-22
10-17
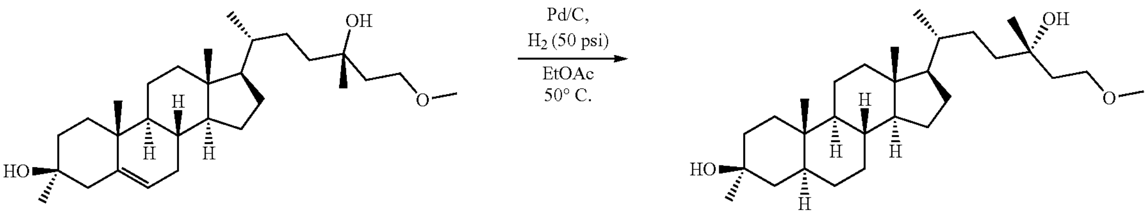
10-23
10-19

-continued (i)

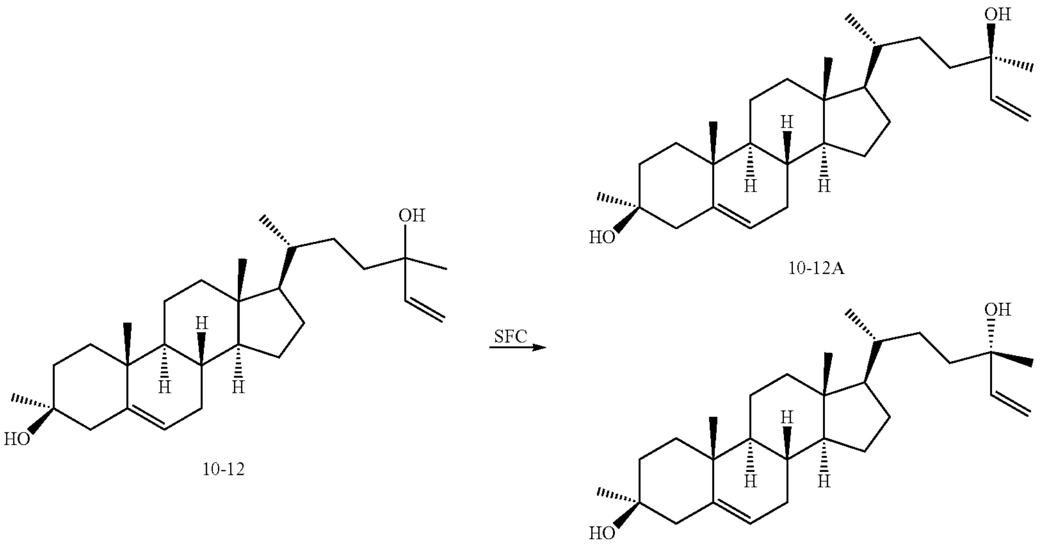

10-12 10-12A 10-12B

Preparation of 10-2. To a solution of compound 10-1 (100 mg, 0.25 mmol) in toluene (8 mL) was added dropwise a solution of ethynylmagnesium bromide (4 mL, 2.0 mmol, 0.5 M in THF) at room temperature during a period of 10 min under nitrogen. Then the reaction mixture was stirred at 50° C. over night. TLC showed that the starting material was consumed completely. The mixture was poured into aqueous saturated $NH_4Cl$ solution (10 mL) and extracted with EtOAc (25 mL×2). The combined organic phases were dried over $Na_2SO_4$, and the solvent was evaporated to afford crude product. The crude product purified by column chromatography on silica gel (eluent: petroleum ether:ethyl acetate=10:1) to give the product 10-2 (80 mg, 74.98%) as white powder. $^1$H NMR: (400 MHz, CDCl3) δ 5.30 (d, J=5.2 Hz, 1H), 2.43-2.40 (m, 2H), 2.06-1.81 (m, 5H), 1.80-1.67 (m, 3H), 1.67-1.59 (m, 2H), 1.49 (s, 3H), 1.48-1.42 (m, 2H), 1.40-1.24 (m, 4H), 1.20-1.13 (m, 2H), 1.10 (s, 3H), 0.96-0.92 (m, 3H), 0.69 (s, 3H).

Preparation of 10-3 and 10-4. Compound 10-2 (350 mg, 0.849 mmol) was split by SFC to get 10-3 (82 mg) and 10-4 (94 mg) as white powder (total yield: 50%). $^1$H NMR ($^a$10-3) (400 MHz, $CDCl_3$), δ 5.29 (d, J=5.2 Hz, 1H), 2.43-2.40 (m, 2H), 2.05-0.95 (m, 38H), 0.68 (s, 3H). $^1$H NMR (10-4) (400 MHz, $CDCl_3$), δ5.29 (d, J=5.2 Hz, 1H), 2.43-2.40 (m, 2H), 2.05-0.95 (m, 38H), 0.68 (s, 3H).

Preparation of 10-5. To a solution of compound 10-1 (3.0 g, 7.76 mmol) in a mixture solvent of EtOAc (20 mL) and EtOH (10 mL) was added Pd/C (33%, 1.0 g) under $N_2$. The suspension was degassed under vacuum and purged with $H_2$ several times. Then the mixture was stirred under $H_2$ (50 psi) at 50° C. for 6 days. The suspension was filtered through a pad of celite and the pad was washed with EtOAc (100 mL×3). The combined filtrates were concentrated to dryness to give the crude product, which was purified by column chromatography on silica gel (petroleum ether:ethyl acetate=20:1) to afford 10-5 (1.7 g, 56%) as a white solid. $^1$H NMR: (400 MHz, $CDCl_3$) δ 2.48-2.44 (m, 1H), 2.43-2.40 (m, 1H), 2.13 (s, 3H), 1.95-1.25 (m, 20H), 1.23 (s, 3H), 1.22-1.00 (m, 8H), 0.90-0.88 (d, J=6.4 Hz, 3H), 0.80 (s, 3H), 0.63-0.60 (m, 4H)

Preparation of 10-6. To a solution of 10-5 (550 mg, 1.41 mmol) in dry THE (10 mL) was added ethynylmagnesium bromide (28.2 mL, 14.1 mmol) dropwise at 0° C. under $N_2$. Then the reaction mixture was stirred at room temperature for 12 hours. TLC showed the starting material was consumed completely. The mixture was quenched by saturated aqueous $NH_4Cl$ (80 mL) and extracted with EtOAc. The organic phase was washed with brine, dried over anhydrous $Na_2SO_4$ then concentrated by vacuum. The residue was purified by column chromatography on silica gel (petroleum ether:ethyl acetate=15:1) to afford 10-6 (380 mg, 64%) as a white solid. $^1$H NMR: (400 MHz, $CDCl_3$) δ 2.42 (s, 1H), 1.97-1.48 (m, 14H), 1.47 (s, 3H), 1.29-1.26 (m, 7H), 1.24 (s, 3H), 1.23-0.94 (m, 7H), 0.93-0.92 (d, J=6.4 Hz, 3H), 0.80 (s, 3H), 0.65-0.62 (m, 4H)

Preparation of 10-6-Bz To a solution of 10-6 (250 mg, 0.60 mmol) in pyridine (3 mL) was added BzCl (168 mg, 1.2 mmol) dropwise at room temperature. Then the reaction mixture was stirred at 45° C. for 12 hours. TLC showed the starting material was consumed completely. The mixture was quenched by saturated aqueous water and extracted with EtOAc. The combined organic phase was washed with 1 M HCl (20 mL) and brine, dried over anhydrous $Na_2SO_4$ then concentrated by vacuum. The residue was purified by column chromatography on silica gel (petroleum ether:ethyl acetate=80:1) to 10-6-Bz (200 mg, 64%) as a white solid.

Preparation of 10-8-Bz and 10-9-Bz Compound 10-6-Bz (200 mg, 0.39 mmol) was split by SFC to afford 10-8-Bz (80 mg, 40%) and 10-9-Bz (70 mg, 35%) as white solid. $^1$H NMR: (10-8-Bz) (400 MHz, $CDCl_3$) δ 7.99-7.98 (d, J=7.6 Hz, 2H), 7.51-7.49 (d, J=7.2 Hz, 1H), 7.42-7.38 (t, J=7.2 Hz, 2H), 2.42 (s, 1H), 2.05-1.68 (m, 8H), 1.65 (s, 3H), 1.60-1.49 (m, 7H), 1.48 (s, 3H), 1.45-1.11 (m, 16H), 0.94-0.92 (d, J=6.4 Hz, 3H), 0.87 (s, 3H), 0.66-0.62 (m, 4H). $^1$H NMR: (10-9-Bz) (400 MHz, $CDCl_3$) δ 7.99-7.98 (d, J=7.6 Hz, 2H), 7.51-7.49 (d, J=7.2 Hz, 1H), 7.42-7.38 (t, J=7.6 Hz, 2H), 2.43 (s, 1H), 2.05-1.67 (m, 8H), 1.65 (s, 3H), 1.60-1.48 (m, 5H), 1.47 (s, 3H), 1.45-1.20 (m, 11H), 1.19-0.95 (m, 9H), 0.94-0.92 (d, J=6.8 Hz), 0.87 (s, 3H), 0.66-0.62 (m, 4H)

Preparation of 10-8 To a solution of compound 10-8-Bz (80 mg, 0.15 mmol) in a mixture solvent of THE (3 mL) and MeOH (1.5 mL) was added a solution of LiOH (180 mg, 7.5 mmol) in $H_2O$ (1.5 mL). The mixture was stirred at 40° C. for 3 days. TLC showed the starting material was consumed completely. The reaction mixture was treated with water and extracted with EtOAc. The combined organic phase was washed with brine, dried over anhydrous $Na_2SO_4$ then concentrated by vacuum. The residue was purified by column chromatography on silica gel (petroleum ether:ethyl acetate=8:1) to afford 10-8 (57 mg, 92%) as a white solid. $^1H$ NMR: (400 MHz, $CDCl_3$) δ 2.42 (s, 1H), 1.93-1.49 (m, 11H), 1.48 (s, 3H), 1.35-1.20 (m, 16H), 1.19-0.94 (m, 5H), 0.93-0.92 (d, J=6.4 Hz, 3H), 0.80 (s, 3H), 0.65-0.62 (m, 4H)

Preparation of 10-9 To a solution of compound 10-9-Bz (70 mg, 0.14 mmol) in a mixture solvent of THE (3 mL) and MeOH (1.5 mL) was added a solution of LiOH (168 mg, 7.0 mmol) in $H_2O$ (1.5 mL). The mixture was stirred at 40° C. for 3 days. TLC showed the starting material was consumed completely. The reaction mixture was treated with water and extracted with EtOAc. The combined organic phase was washed with brine, dried over anhydrous $Na_2SO_4$ then concentrated by vacuum. The residue was purified by column chromatography on silica gel (petroleum ether:ethyl acetate=8:1) to afford 10-9 (53 mg, 91%) as a white solid. $^1H$ NMR: (400 MHz, $CDCl_3$) δ 2.42 (s, 1H), 1.93-1.49 (m, 11H), 1.48 (s, 3H), 1.29-0.94 (m, 21H), 0.93-0.92 (d, J=6.4 Hz, 3H), 0.80 (s, 3H), 0.65-0.62 (m, 4H)

Preparation of 10-7 To a solution of 10-5 (550 mg, 1.41 mmol) in dry THE (10 mL) was added vinylmagnesium bromide (9.87 mL, 9.87 mmol) dropwise at 0° C. under $N_2$. Then the reaction mixture was stirred at room temperature for 12 hours. TLC showed the starting material was consumed completely. The mixture was quenched by saturated aqueous $NH_4Cl$ (30 mL) and extracted with EtOAc. The organic phase was washed with brine, dried over anhydrous $Na_2SO_4$ then concentrated by vacuum. The residue was purified by column chromatography on silica gel (petroleum ether:ethyl acetate=15:1) to afford 10-7 (300 mg, 51%) as a white solid. $^1H$ NMR: (400 MHz, $CDCl_3$) δ 5.93-5.86 (m, 1H), 5.20-5.16 (d, J=17.6 Hz, 1H), 5.05-5.02 (d, J=10.8 Hz, 1H), 1.96-193 (m, 1H), 1.60-1.57 (m, 4H), 1.51-1.20 (m, 20H), 1.19-1.00 (m, 8H), 0.91-0.89 (d, J=6 Hz, 3H), 0.80 (s, 3H), 0.64-0.60 (m, 4H)

Preparation of 10-7-Bz. To a solution of 10-7 (220 mg, 0.53 mmol) in pyridine (3 mL) was added BzCl (150 mg, 1.06 mmol) dropwise at room temperature. Then the reaction mixture was stirred at 40° C. for 12 hours. TLC showed the starting material was consumed completely. The mixture was quenched by saturated aqueous water and extracted with EtOAc. The combined organic phase was washed with 1 M HCl (30 mL) and brine, dried over anhydrous $Na_2SO_4$ then concentrated by vacuum. The residue was purified by column chromatography on silica gel (petroleum ether:ethyl acetate=80:1) to afford 10-7-Bz (150 mg, 54%) as a white solid.

Preparation of 10-10-Bz and 10-11-Bz Compound 10-7-Bz (190 mg, 0.37 mmol) was split by SFC to get 10-10-Bz (75 mg, 39%) and 10-11-Bz (70 mg, 37%) as white solid. $^1H$ NMR: (10-10-Bz) (400 MHz, $CDCl_3$) δ 7.99-7.97 (d, J=7.2 Hz, 1H), 7.51-7.49 (d, J=7.6 Hz, 1H), 7.42-7.38 (t, J=8.0 Hz, 2H), 5.93-5.86 (dd, $J_1$=11.2 Hz, $J_2$=17.2, 1H), 5.21-5.16 (d, J=17.6 Hz, 1H), 5.05-5.02 (d, J=10.4 Hz, 1H), 2.05-1.75 (m, 8H), 1.65-1.27 (m, 19H), 1.26 (s, 3H), 1.25-0.93 (m, 10H), 0.91-0.90 (d, 6.0 Hz, 3H), 0.86 (s, 3H), 0.70-0.64 (m, 4H) $^1H$ NMR: (10-11-Bz) (400 MHz, $CDCl_3$) δ 7.99-7.97 (d, J=7.2 Hz, 1H), 7.51-7.49 (d, J=7.6 Hz, 1H), 7.42-7.38 (t, J=8.0 Hz, 2H), 5.93-5.86 (dd, $J_1$=10.8 Hz, $J_2$=17.6, 1H), 5.20-5.16 (d, J=17.2 Hz, 1H), 5.05-5.02 (d, J=10.4 Hz, 1H), 2.05-1.75 (m, 8H), 1.65-1.27 (m, 10H), 1.26 (s, 3H), 1.25-0.93 (m, 10H), 0.91-0.90 (d, 6.4 Hz, 3H), 0.86 (s, 3H), 0.70-0.64 (m, 4H)

Preparation of 10-10. To a solution of compound 10-10-Bz (75 mg, 0.14 mmol) in a mixture solvent of THE (3 mL) and MeOH (1.5 mL) was added a solution of LiOH (168 mg, 7.0 mmol) in $H_2O$ (1.5 mL). The mixture was stirred at 40° C. for 3 days. TLC showed the starting material was consumed completely. The reaction mixture was treated with water and extracted with EtOAc. The combined organic phase was washed with brine, dried over anhydrous $Na_2SO_4$ then concentrated by vacuum. The residue was purified by column chromatography on silica gel (petroleum ether:ethyl acetate=8:1) to afford 10-10 (55 mg, 94%) as a white solid. $^1H$ NMR: (400 MHz, $CDCl_3$) δ 1.96-1.92 (m, 1H), 1.90-1.70 (m, 2H), 1.69-1.57 (m, 5H), 1.55-1.20 (m, 18H), 1.19-0.81 (m, 10H), 0.80 (s, 3H), 0.70-0.60 (m, 4H)

Preparation of 10-11-Bz. To a solution of compound 10-11-Bz (70 mg, 0.13 mmol) in a mixture solvent of THE (3 mL) and MeOH (1.5 mL) was added a solution of LiOH (168 mg, 7.0 mmol) in $H_2O$ (1.5 mL). The mixture was stirred at 40° C. for 3 days. TLC showed the starting material was consumed completely. The reaction mixture was treated with water and extracted with EtOAc. The combined organic phase was washed with brine, dried over anhydrous $Na_2SO_4$ then concentrated by vacuum. The residue was purified by column chromatography on silica gel (petroleum ether:ethyl acetate=8:1) to afford 10-11 (49 mg, 91%) as a white solid. $^1H$ NMR: (400 MHz, $CDCl_3$) δ 1.96-1.92 (m, 1H), 1.90-1.70 (m, 2H), 1.69-1.57 (m, 5H), 1.55-1.20 (m, 18H), 1.19-0.81 (m, 10H), 0.80 (s, 3H), 0.70-0.60 (m, 4H)

Preparation of 10-22 and 10-23. To a solution of 10-14 (550 mg, 1.27 mmol) in THF (10 mL) was added NaH (254 mg, 6.36 mmol) at 0° C., and stirred at the same temperature for 30 minutes. Then $CH_3I$ (127 mg, 0.770 mmol) was added dropwise to the mixture. The reaction was monitored by TLC. After 1 h, 127 mg of $CH_3I$ was added in two portions. After stirring at room temperature for 1.5 h, the reaction mixture was quenched with aqueous $NH_4Cl$ (20 mL), extracted with EtOAc (20 mL×3), dried over $Na_2SO_4$ and concentrated to give crude product. The crude product was purified by column chromatography on silica gel (petroleum ether/ethyl acetate=15/1) to give 10-14 as a white powder. The diastereomeric pairs (340 mg) were separated by prep-SFC to give 10-22 (130 mg, 22.9%) as a white power and 10-23 (135 mg, 23.8%) as a white power. $^1H$ NMR (10-22): (400 MHz, $CDCl_3$) δ 5.30 (s, 1H), 3.65-3.53 (m, 2H), 3.35 (s, 3H), 3.04 (br, 1H), 2.44-2.40 (d, 1H, J=13.6 Hz), 2.02-1.95 (m, 3H), 1.86-1.64 (m, 5H), 1.62-1.58 (m, 1H), 1.52-1.23 (m, 9H), 1.17-1.05 (m, 11H), 1.04-0.98 (m, 4H), 0.95-0.93 (d, 4H, J=6.8 Hz), 0.68 (s, 3H). $^1H$ NMR (10-23): (400 MHz, $CDCl_3$) δ5.30 (s, 1H), 3.61 (t, 2H, J=6.0 Hz), 3.35 (s, 3H), 3.04 (br, 1H), 2.44-2.40 (d, 1H, J=12.8 Hz), 2.02-1.95 (m, 3H), 1.86-1.64 (m, 5H), 1.57-1.25 (m, 12H), 1.16-0.93 (m, 17H), 0.68 (s, 3H).

Preparation of 10-17. A mixture of 10-22 (100 mg, 0.224 mmol) and Pd/C (50 mg, cat.) in EtOAc (10 mL) was hydrogenated under 50 psi of hydrogen for 48 h at 50° C. The reaction mixture was filtered through a celite pad. The pad was washed with EtOAc (40 mL). The filtrate was concentrated in vacuum and the residue was purified by silica gel column eluted with PE/EtOAc=15/1 to give 10-17 (68.4 mg, 68.1%) as a white solid. $^1H$ NMR (10-17) (400 MHz, $CDCl_3$), δ 3.62-3.58 (m, 2H), 3.35 (s, 3H), 3.07 (br, 1H), 1.97-1.93 (d, 1H, J=12.8 Hz), 1.83-1.74 (m, 2H), 1.69-1.55 (m, 5H), 1.50-1.43 (m, 3H), 1.37-1.23 (m, 12H), 1.16-0.97 (m, 10H), 0.93-0.91 (d, 1H, J=6.0 Hz), 0.80 (s, 3H), 0.68-0.64 (m, 3H).

Preparation of 10-19. A mixture of 10-23 (100 mg, 0.224 mmol) and Pd/C (50 mg, cat.) in EtOAc (10 mL) was hydrogenated under 50 psi of hydrogen for 48 h at 50° C. The reaction mixture was filtered through a celite pad. The pad was washed with EtOAc (40 mL). The filtrate was concentrated in vacuum and the residue was purified by silica gel column eluted with PE/EtOAc=15/1 to give 10-19 (68.6 mg, 68.3%) as a white solid. $^1$H NMR (10-19) (400 MHz, $CDCl_3$), δ 3.60 (t, 2H, J=6.0 Hz), 3.35 (s, 3H), 3.07 (br, 1H), 1.97-1.94 (d, 1H, J=12.8 Hz), 1.81-1.57 (m, 6H), 1.54-1.43 (m, 4H), 1.36-1.22 (m, 12H), 1.16-0.97 (m, 10H), 0.92-0.91 (d, 1H, J=6.0 Hz), 0.80 (s, 3H), 0.68-0.61 (m, 3H).

Preparation of 10-7. To a solution of 10-6 (60 mg, 0.14 mmol) in EtOAc (2 mL) was added lindlar cat (24 mg). Then the mixture was stirred under hydrogen (1 atm) at room temperature for 1.5 hours. The mixture was filtered through a pad of celite and the filtrate was evaporated under reduced pressure. The residue was purified by column chromatography on silica gel (eluent: petroleum ether:ethyl acetate 10:1) to afford the pure product 10-7 (26 mg, 43.0%) as white powder. $^1$H NMR: (400 MHz, CDCl3) δ 5.93-5.85 (m, 1H), 5.20-5.16 (d, J=17.2 Hz, 1H), 5.05-5.02 (d, J=10.8 Hz, 1H), 1.96-1.93 (m, 1H), 1.79-1.67 (m, 1H), 1.66-1.57 (m, 4H), 1.55-1.36 (m, 11H), 1.35-1.27 (m, 9H), 1.26-0.97 (m, 8H), 0.96-0.89 (m, 3H), 0.81 (s, 3H), 0.68-0.62 (m, 4H).

Preparation of Compound 10-12. To a solution of 10-1 (50 mg, 0.13 mmol) in THE (2 mL), vinyl magnesium bromide solution (1 mmol, 1 M in THF, 1 mL) was added drop-wise at −50° C. The reaction mixture was warmed to room temperature and stirred at room temperature for 16 hours. TLC (petroleum ether:ethyl acetate=3:1) showed the reaction was finished, the reaction mixture was quenched with aq. saturated $NH_4Cl$ solution (10 mL) and then extracted with EtOAc (10 mL×3). The combined organic layer was washed with brine (10 mL×2), dried over anhydrous $Na_2SO_4$ and concentrated in vacuum. The residue was purified by column chromatography on silica gel (eluent: petroleum ether:ethyl acetate=15/1) to afford 10-12 (27 mg, 54%) as white powder. $^1$H NMR: (400 MHz, CDCl3) δ 5.94-5.86 (m, 1H), 5.30 (d, J=5.2 Hz, 1H), 5.19 (d, J=17.2 Hz, 1H), 5.04 (d, J=10.4 Hz, 1H), 2.42 (d, J=12.8 Hz, 1H), 2.01-1.95 (m, 3H), 1.80-1.61 (m, 4H), 1.56-1.37 (m, 10H), 1.27 (s, 3H), 1.18-1.13 (m, 3H), 1.11 (s, 3H), 1.10-1.04 (m, 3H), 1.01 (s, 3H), 1.00-0.95 (m, 2H), 0.92 (d, J=6.4 Hz, 3H), 0.67 (s, 3H).

Preparation of 10-12A and 10-12B. Compound 10-12 (350 mg, 0.84 mmol) was split by SFC to give 10-12A (160 mg) and 10-12B (110 mg) as a white solid (total yield: 77%). $^1$H NMR (10-12-A): (400 MHz, $CDCl_3$) δ 5.94-5.86 (m, 1H), 5.30 (d, J=5.2 Hz, 1H), 5.19 (d, J=17.2 Hz, 1H), 5.04 (d, J=10.4 Hz, 1H), 2.50-2.40 (m, 1H), 2.05-0.85 (m, 36H), 0.67 (s, 3H). $^1$H NMR (10-12-B): (400 MHz, $CDCl_3$) δ 5.94-5.86 (m, 1H), 5.30 (d, J=5.2 Hz, 1H), 5.19 (d, J=17.2 Hz, 1H), 5.04 (d, J=10.4 Hz, 1H), 2.50-2.40 (m, 1H), 2.05-0.85 (m, 36H), 0.67 (s, 3H).

Preparation of Compound 10-13. To a solution of 10-12 (500 mg, 1.21 mmol) in THF (5 mL) was added 9-BBN (24.2 mL, 12.1 mmol) gradually at 0° C. under $N_2$ protection. The mixture was stirred at 60° C. for 16 hours. Then the reaction mixture was cooled to 0° C., and 10% aqueous NaOH (10 mL), 30% $H_2O_2$ (5 mL) was added. The resulting mixture was stirred at 0° C. for 2 hours. The reaction mixture was quenched with aqueous $Na_2S_2O_3$ (10 mL), extracted with EtOAc (10 mL×3), dried over $Na_2SO_4$ and concentrated to give crude product. The crude product was purified by pre-HPLC to give 10-13 (100 mg, 19.2%) as white solid. $^1$H NMR: (300 MHz, $CD_3OD$) δ 5.32 (d, J=5.2 Hz, 1H), 3.70 (d, J=6.4 Hz, 2H), 2.51-2.35 (m, 1H), 2.14-1.84 (m, 4H), 1.82-1.26 (m, 16H), 1.24-1.10 (m, 7H), 1.08-1.00 (m, 7H), 1.00-0.93 (m, 4H), 0.73 (s, 3H).

Preparation of Compound 10-14. To a solution of 10-13 (50 mg, 0.11 mmol) in THF (5 mL) was added NaH (13.2 mg, 0.55 mmol) at 0° C., and stirred at the same temperature for 30 minutes. Then $CH_3I$ (78 mg, 0.55 mmol) was added drop-wise to the mixture. The mixture was stirred at room temperature for 1 hour. The reaction mixture was quenched with aqueous $NH_4Cl$ (10 mL), extracted with EtOAc (10 mL×3), dried over $Na_2SO_4$ and concentrated to give crude product. The crude product was purified by column chromatography on silica gel (petroleum ether:ethyl acetate=5:1) to give 10-14 (13 mg, 25.2%) as white powder. $^1$H NMR: (300 MHz, $CDCl_3$) δ 5.23 (d, J=5.2 Hz, 1H), 3.54 (d, J=6.4 Hz, 2H), 3.29 (s, 3H), 2.38-2.34 (m, 1H), 1.95-1.88 (m, 3H), 1.74-1.58 (m, 5H), 1.52-1.19 (m, 14H), 1.10 (s, 3H), 1.09-1.05 (m, 1H), 1.04 (s, 3H), 1.02-0.94 (m, 2H), 0.91 (s, 3H), 0.87 (d, J=6.4 Hz, 3H), 0.61 (s, 3H).

Preparation of 10-20 and 10-21. The crude product 10-13 was washed with EtOAc (30 mL) to give the diastereomeric pair (900 mg, 53.9%) as a white solid. The mixture (400 mg) was separated by SFC to give 10-20 (30 mg, 4.0%) as a white solid and 10-21 (68 mg, 9.2%) as a white solid. $^1$H NMR (10-20): (400 MHz, Methanol-d4) δ 5.28 (s, 1H), 3.69 (t, 2H, J=7.2 Hz), 2.42-2.39 (d, 1H, J=11.6 Hz), 2.04-1.90 (m, 5H), 1.78-1.28 (m, 17H), 1.17-1.02 (m, 12H), 0.95-0.93 (d, 4H, J=6.8 Hz), 0.71 (s, 3H). $^1$H NMR (10-21): (400 MHz, Methanol-d4) δ 5.28 (s, 1H), 3.68 (t, 2H, J=7.2 Hz), 2.42-2.39 (d, 1H, J=11.6 Hz), 2.04-1.90 (m, 5H), 1.78-1.28 (m, 16H), 1.18-0.98 (m, 13H), 0.95-0.93 (d, 4H, J=7.0 Hz), 0.71 (s, 3H).

Preparation of 10-16. A mixture of 10-20 (20 mg, 0.046 mmol) and Pd/C (20 mg, cat.) in EtOAc (5 mL) was hydrogenated under 50 psi of hydrogen for 48 h at 50° C. The reaction mixture was filtered through a celite pad. The pad was washed with EtOAc (50 mL). The filtrate was concentrated in vacuum and the residue was purified by silica gel column eluted with PE/EtOAc=5/1 to give 10-16 (7.6 mg, 39.3%) as a white solid. $^1$H NMR (10-16) (400 MHz, Methanol-d4), δ 3.70 (t, 2H, J=7.2 Hz), 2.01-1.98 (d, 1H, J=12.4 Hz), 1.93-1.82 (m, 1H), 1.72-1.57 (m, 5H), 1.53-1.39 (m, 5H), 1.35-0.99 (m, 22H), 0.96-0.94 (d, 4H, J=6.4 Hz), 0.84 (s, 3H), 0.70-0.66 (m, 4H).

Preparation of 10-18. A mixture of 10-21 (40 mg, 0.092 mmol, 1.0 eq) and Pd/C (20 mg, cat.) in EtOAc (5 mL) was hydrogenated under 50 psi of hydrogen for 48 h at 50° C. The reaction mixture was filtered through a celite pad. The pad was washed with EtOAc (50 mL). The filtrate was concentrated in vacuum and the residue was purified by silica gel column eluted with PE/EtOAc=5/1 to give 10-18 (12.9 mg, 32.1%) as a white solid. $^1$H NMR (10-18) (400 MHz, Methanol-d4), δ 3.68 (t, 2H, J=7.2 Hz), 1.99-1.96 (d, 1H, J=12.4 Hz), 1.92-1.82 (m, 1H), 1.68-1.58 (m, 5H), 1.52-1.41 (m, 5H), 1.37-0.97 (m, 22H), 0.94-0.92 (d, 4H, J=6.4 Hz), 0.82 (s, 3H), 0.67-0.65 (m, 4H).

Example 11
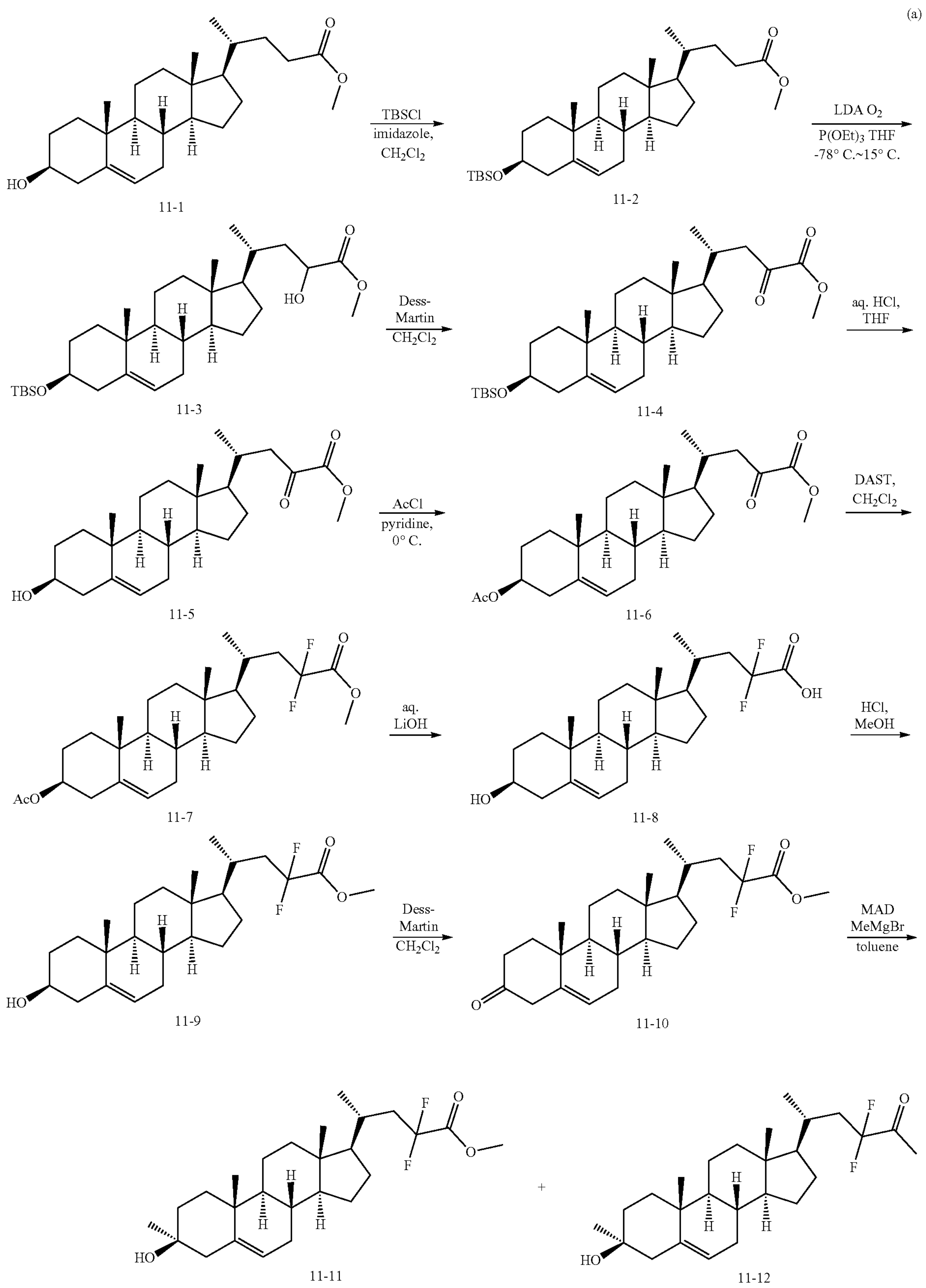
11-1 11-2 11-3 11-4 11-5 11-6 11-7 11-8 11-9 11-10 11-11 11-12

-continued (b)

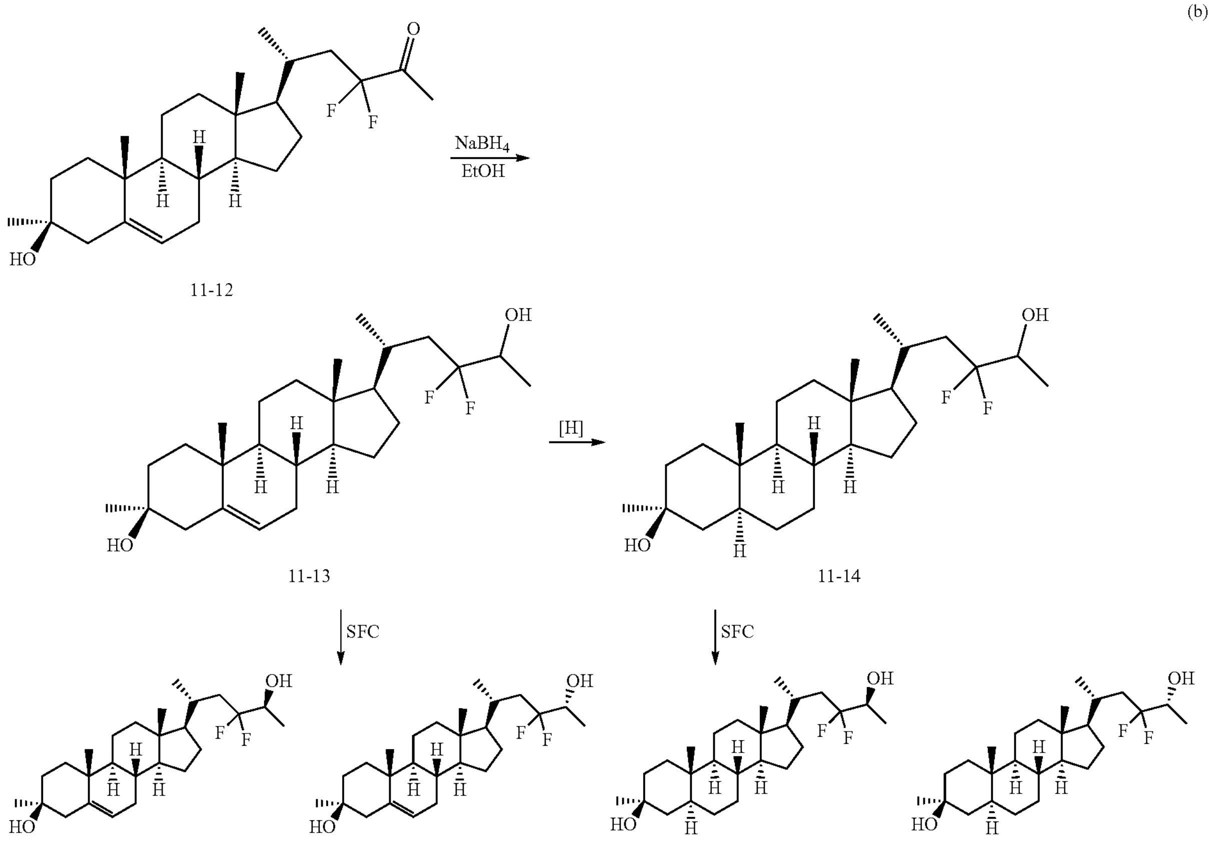

11-12

11-13

11-14

11-15 11-16 11-17 11-18

(c)

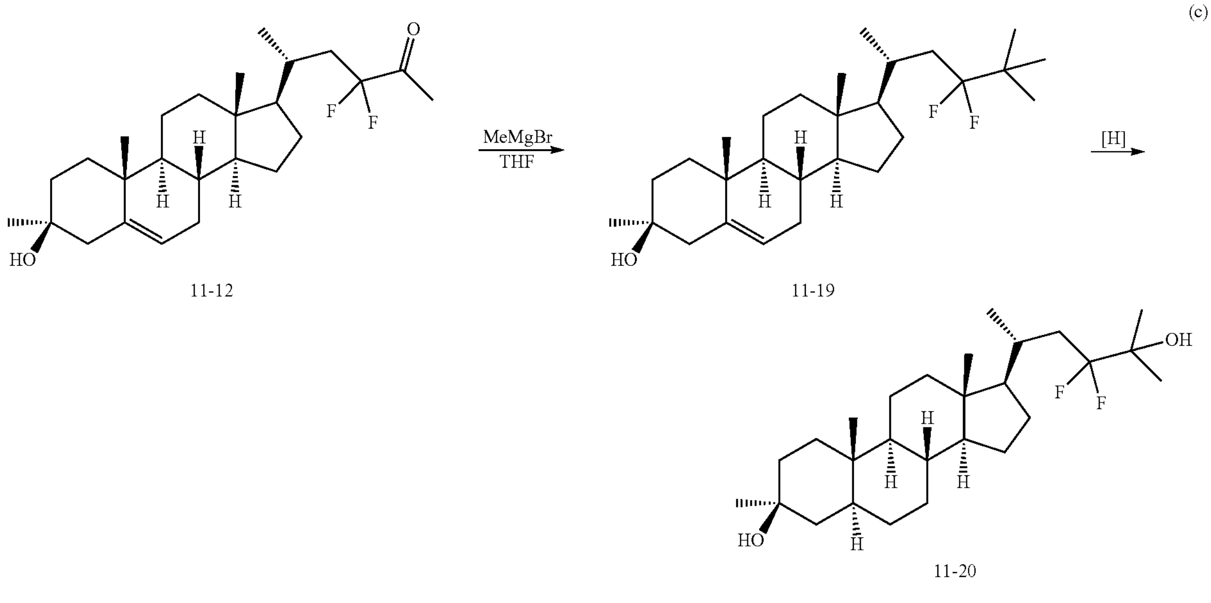

11-12

11-19

11-20

Preparation of Compound 11-2. To a solution of crude compound 11-1 (30 g, 77 mmol) in dichloromethane (200 mL) was added imidazole (10.4 g, 154 mmol) and tert-butylchlorodimethylsilane (13.8 g, 92 mmol). The mixture was then stirred at 15° C. for 16 h. The mixture was washed with water, dried over anhydrous $Na_2SO_4$ and concentrated. The residue was purified by column chromatography on silica gel (petroleum ether:ethyl acetate=150:1 to 80:1) to give crude product of 11-2 (38 g, 98%) as white solid.

Preparation of Compound 11-3. To a solution of diisopropylamine (34.3 g, 340 mmol) in THE (1 L) was added butyl lithium (136 mL, 340 mmol, 2.5 M in hexane) under nitrogen atmosphere at −78° C. The mixture was then stirred at −78° C. for 10 minutes and then 25° C. for 10 minutes and at last −78° C. for 10 minutes. A solution of crude compound 11-2 (34 g, 68 mmol) in THF (100 mL) was then added and stirred for 1 h at −78° C. To the mixture was then added triethyl phosphite (22.6 g, 136 mmol), the mixture was then stirred under oxygen atmosphere for 3 h at −78° C. and then 16 h at 25° C. To the mixture was then added ammonium chloride (aq.). The organic layer was separated, purified by column chromatography on silica gel (petroleum ether:ethyl acetate=10:1 to 3:1) to give crude product of 11-3 (10 g, 28%) as yellow solid.

Preparation of Compound 11-4. To a solution of crude 11-3 (10 g, 19 mmol) in dichloromethane (100 mL) was added Dess-Matin reagent (16 g, 38 mmol) at 0° C. under nitrogen atmosphere. The mixture was then stirred at 30° C. for 3 h. To the mixture was then added a mixed solution of sodium bicarbonate and sodium thiosulfate in water. The organic layer was separated, washed with water, dried over anhydrous sodium sulfate, concentrated under vacuum to give crude compound 11-4 as (5.9 g, 59%) white solid.

Preparation of Compound 11-5. To a solution of crude 11-4 (5.9 g, 11 mmol) in THF (60 mL) was added hydrogen chloride (aq., 6 mL, 6 mmol, 1M). The mixture was stirred at 15° C. for 16 h. To the mixture was then added sodium bicarbonate (aq.). The organic layer was separated, dried over anhydrous sodium sulfate, concentrated under vacuum to give crude 11-5 (3.2 g, yield: 70%) as white solid.

Preparation of Compound 11-6. To a solution of crude 11-5 (3.2 g, 7.9 mmol) in pyridine (50 mL), acetyl chloride (1.5 g, 19 mmol) was added dropwise at 0° C. as monitored by TLC until the reaction was completed. To the mixture was then added water, concentrated under vacuum. To the residue was added water, extracted with dichloromethane. The organic layer was dried over anhydrous sodium sulfate, purified by column chromatography on silica gel (eluent: petroleum ether:ethyl acetate=100:1) to give crude 11-6 (2.8 g, 79%) as white solid.

Preparation of Compound 11-7. To a solution of crude 11-6 (2.8 g, 6.3 mmol) in dichloromethane (10 mL) was added diethylaminosulfur trifluoride (8 g, 50 mmol) at 0° C. dropwise. The mixture was then stirred for 16 h at 30° C. The mixture was then added to sodium bicarbonate (aq.). The organic layer was separated, dried over anhydrous sodium sulfate, purified by column chromatography on silica gel (eluent: petroleum ether:ethyl acetate=100:1 to 33:1) to give crude 11-7 (2 g, 68%) as white solid.

Preparation of Compound 11-8. To a solution of crude 11-7 (2 g, 4.2 mmol) in THF (10 mL) wad added a solution of lithium hydroxide monohydrate (900 mg, 21 mmol) in water (10 mL) and then was added methanol (5 mL). The mixture was then stirred at 30° C. for 16 h. The mixture was then concentrated under vacuum. To the residue was added water, filtered. The solid was washed with water, dried under vacuum to give 11-8 (1.5 g, 85%) as white solid. $^1$H NMR: (400 MHz, methanol-d4) δ 5.34 (d, J=5.2 Hz, 1H), 3.45-3.35 (m, 1H), 2.30-2.10 (m, 3H), 2.10-1.68 (m, 7H), 1.68-1.44 (m, 6H), 1.35-1.28 (m, 2H), 1.28-1.12 (m, 3H), 1.12-0.98 (m, 8H), 0.74 (s, 3H).

Preparation of Compound 11-9. To a solution of 11-8 (1 g, 2.4 mmol) in methanol (15 mL) was added hydrogen chloride (5 mL, 4 M in methanol). The mixture was stirred at 30° C. for 15 minutes. Sodium bicarbonate (aq.) was added till pH=7. The mixture was then concentrated under vacuum. To the residue was added water, extracted with ethyl acetate, The organic layer was separated, dried over anhydrous sodium sulfate, concentrated under vacuum, purified by column chromatography on silica gel (eluent: petroleum ether:ethyl acetate=10:1 to 5:1) to give 11-9 (970 mg, 93%) as white solid. $^1$H NMR: (400 MHz, CDCl3) δ 5.34 (d, J=5.2 Hz, 1H), 3.87 (s, 3H), 3.60-3.48 (m, 1H), 2.32-2.15 (m, 2H), 2.10-1.95 (m, 2H), 1.95-1.70 (m, 5H), 1.65-1.40 (m, 8H), 1.30-0.90 (m, 13H), 0.70 (s, 3H).

Preparation of Compound 11-10. To a solution of 11-9 (0.97 g, 2.3 mmol) in dichloromethane (50 mL) was added Dess-Matin reagent (2.3 g, 5.4 mmol) at 0° C. under nitrogen atmosphere. The mixture was then stirred at 30° C. for 3 h. To the mixture was then added a mixed solution of sodium bicarbonate and sodium thiosulfate in water. The organic layer was separated, washed with water, dried over anhydrous sodium sulfate, concentrated under vacuum to give crude compound of 11-10 (1 g, 100%) as yellow oil.

Preparation of Compound 11-11 and 11-12. To a solution of butylated hydroxytoluene (3.1 g, 14.2 mmol) in toluene (20 mL) was added $Me_3Al$ (3.6 mL, 7.2 mmol, 2 M in toluene) at 15° C. The mixture was then stirred at 15° C. for 30 minutes. A solution of 11-11 (0.9 g, 2.4 mmol) in toluene (5 mL) was added at −78° C. The mixture was then stirred at −78° C. for 1 h. methylmagnesium bromide (2.4 mL, 7.2 mmol, 3M in ether) was then added at −78° C. The mixture was then stirred at −78° C. for 1 hour. To the mixture was then added ammonium chloride (aq.), filtered. The organic layer was separated and the aqueous phase was extracted with ethyl acetate. The combined organic layer was dried over anhydrous sodium sulfate, concentrated under vacuum, purified by column chromatography on silica gel (eluent: petroleum ether:ethyl acetate=20:1 to 10:1) to give 240 mg of crude 11-11 (yield: 28%) and 210 mg of crude 11-12 (yield: 25%). $^1$H NMR (400 MHz, CDCl3): δ 5.33-5.25 (m, 1H), 3.87 (s, 3H), 2.50-0.75 (m, 33H), 0.70 (s, 3H). $^1$H NMR: (400 MHz, CDCl3) δ 5.35-5.27 (m, 1H), 2.50-2.37 (m, 1H), 2.32 (s, 3H), 2.20-0.75 (m, 32H), 0.70 (s, 3H).

Preparation of Compound 11-13. To a solution of 11-12 (70 mg, 0.16 mmol) in ethanol (2 mL) was added sodium borohydride (100 mg, 2.6 mmol) at 15° C. The mixture was stirred at 15° C. for 30 minutes. To the mixture was then added ammonium chloride (aq.), concentrated under vacuum. To the residue was added water, extracted with ethyl acetate. The organic layer was separated, dried over anhydrous sodium sulfate, concentrated under vacuum, purified by column chromatography on silica gel (eluent: petroleum ether:ethyl acetate=10:1 to 8:1) to give 11-13 (40 mg, 57%) as white solid. $^1$H NMR: (400 MHz, methanol-d4) δ 5.35-5.28 (m, 1H), 3.88-3.68 (m, 1H), 2.49-2.37 (m, 1H), 2.18-1.22 (m, 20H), 1.19 (d, J=6.0 Hz, 3H), 1.18-1.14 (m, 1H), 1.11-1.08 (m, 3H), 1.06 (s, 3H), 1.04 (s, 3H), 1.02-0.95 (m, 1H), 0.76 (s, 3H).

Preparation of Compound 11-15 and 11-16. Diastereomeric mixture 11-13 (30 mg, 0.071 mmol) was split by SFC to get 11-15 (12.2 mg) and 11-16 (14.7 mg) as white powder (total yield: 90%). $^1$H NMR (11-15): (400 MHz, MeOD) δ 5.32 (d, J=5.2 Hz, 1H), 3.85-3.72 (m, 1H), 2.50-2.40 (m, 1H), 2.20-1.57 (m, 11H), 1.52-0.85 (m, 23H), 0.78 (s, 3H). $^1$H NMR (11-16): (400 MHz, MeOD) δ 5.32 (d, J=5.2 Hz, 1H), 3.85-3.72 (m, 1H), 2.50-2.40 (m, 1H), 2.20-1.45 (m, 15H), 1.40-0.85 (m, 20H), 0.78 (s, 3H).

Preparation of Compound 11-19. To a solution of 11-12 (70 mg, 0.16 mmol) in THF (2 mL) was added methylmagnesium bromide (1 mL, 3 mmol, 3M in ether) at −78° C. The mixture was stirred at 15° C. for 30 minutes. To the mixture was then added ammonium chloride (aq.), concentrated under vacuum. To the residue was added water, extracted with ethyl acetate. The organic layer was separated, dried over anhydrous sodium sulfate, concentrated under vacuum, purified by column chromatography on silica gel (eluent: petroleum ether:ethyl acetate=10:1 to 8:1) to give 11-19 (39 mg, 55%) as white solid. $^1$H NMR: (400 MHz, methanol-d4)

δ 5.33-5.28 (m, 1H), 2.48-2.38 (m, 1H), 2.12-1.70 (m, 17H), 1.23 (s, 6H), 1.20-1.12 (m, 3H), 1.10 (d, J=6.4 Hz, 3H), 1.06 (s, 3H), 1.04 (s, 3H), 1.03-0.91 (m, 2H), 0.76 (s, 3H).

Example 12. Preparation of Intermediate 0-9

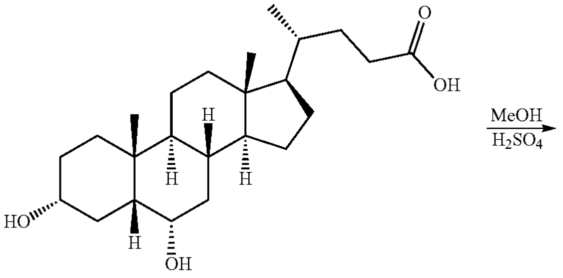

0-1

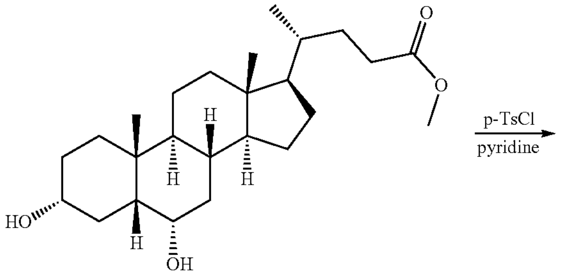

0-2

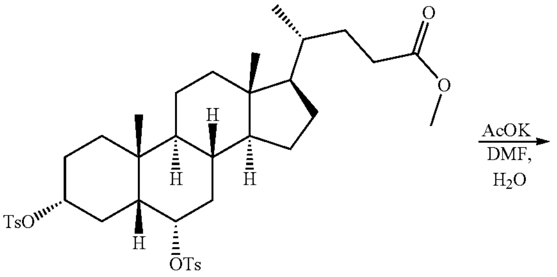

0-3

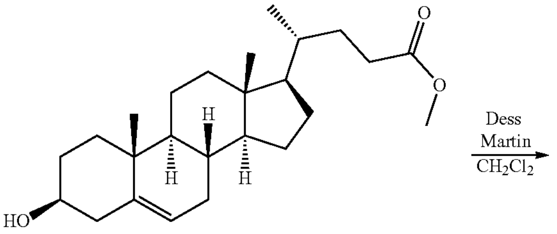

0-4

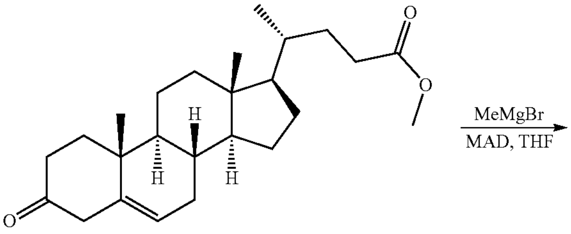

0-5

-continued

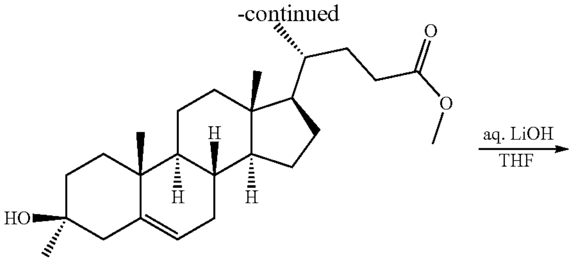

0-6

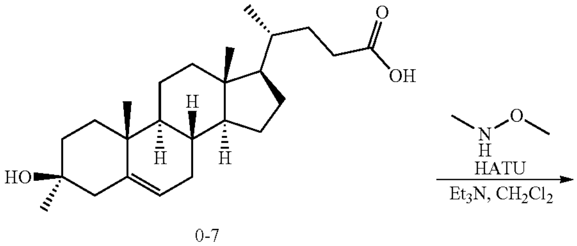

0-7

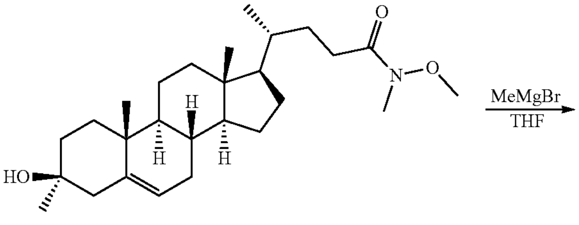

0-8

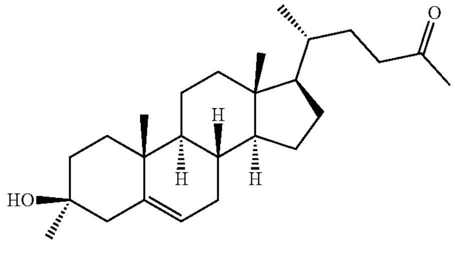

0-9

Preparation of 0-2. To a solution of compound 0-1 (100 g, 255 mmol, 1.0 eq) in dry MeOH (500 mL) was added concentrated $H_2SO_4$ (14 mL). The mixture was heated to reflux overnight and then cooled to room temperature. The mixture was quenched with aq. saturated $NaHCO_3$ solution (0.5 L) and then evaporated to remove MeOH. The residue mixture was extracted with EtOAc (300 mL×3). The combined organic layers were washed with brine (200 mL), dried over $Na_2SO_4$ and evaporated to give the product (100 g crude, 96%) as off-white powder. $^1$H NMR: (400 MHz, CDCl3) δ 4.09-4.02 (m, 1H), 3.66 (s, 3H), 3.63-3.58 (m, 1H), 2.39-2.31 (m, 1H), 2.25-2.15 (m, 1H), 1.97-1.91 (m, 1H), 1.91-1.55 (m, 10H), 1.52-1.02 (m, 14H), 0.95-0.88 (m, 6H), 0.62 (s, 3H).

Preparation of 0-3. To a solution of compound 0-2 (250 g, 615 mmol, 1.0 eq) in dry pyridine (0.8 L) was added a solution of TsCl (352 g, 1844 mmol, 3.0 eq) in dry pyridine (200 mL). The mixture was stirred at room temperature for 18 h. Ice chips were added gradually to the mixture, and the precipitated solid was filtered, washed with aq. 10% HCl solution (400 mL×3) and water (400 mL×2), and then evaporated to dryness to give crude product (500 g, crude) as a off-white powder, which was used to next step directly Preparation of 0-4. A mixture of compound 0-3 (250 g crude), $CH_3COOK$ (24 g, 245 mmol, 0.77 eq), water (150 mL) and DMF (900 mL) was heated at reflux for 24 h. The solution was cooled to room temperature, with ice chips added gradually. The precipitated solid was filtered off and washed with water (100 mL×2). The crude solid was purified on silica gel column (PE/EtOAc=8/1) to give compound 0-4 (40 g, yield 34.3% of two steps) as white solid. $^1$H NMR (400 MHz, $CDCl_3$) δ 5.32-5.38 (m, 1H), 3.66 (s, 3H), 3.47-3.57 (m, 1H), 2.16-2.41 (m, 4H), 1.93-2.04 (m, 2H), 1.74-1.92 (m, 4H), 1.30-1.59 (m, 9H), 0.90-1.19 (m, 12H), 0.68 (s, 3H)

Preparation of 0-5. To a solution of compound 0-4 (33 g, 85 mmol, 1.0 eq) in dry $CH_2Cl_2$ (700 mL) was added Dess-Martin reagent (72 g, 170 mmol, 2.0 eq) in portions at 0° C. Then the reaction mixture was stirred at room temperature for 1 h. TLC (PE:EA=3:1) showed the starting material was consumed completely. The reaction mixture were quenched with a saturated aqueous solution of $NaHCO_3/Na_2S_2O_3$=1:3 (250 mL). The organic phase was washed with brine (200 mL×2) and dried over $Na_2SO_4$, and the solvent was evaporated to afford desired product (35 g, crude), which was used in the next step without further purification.

Preparation of 0-6. To a solution of MAD (0.42 mol, 3.0 eq) in toluene, freshly prepared by addition of a solution of $Me_3Al$ (210 mL, 0.42 mmol, 2 M in hexane) to a stirred solution of 2,6-di-tert-butyl-4-methylphenol (185 g, 0.84 mol) in toluene (200 mL) followed by stirring for 1 h at room temperature, was added dropwise a solution of compound 0-5 (54 g, 0.14 mol, 1.0 eq) in toluene (200 mL) at −78° C. under nitrogen. Then the reaction mixture was stirred for 30 min, a solution of MeMgBr (140 mL, 0.42 mol, 3.0 eq, 3 M in ether) was added dropwise at −78° C. The reaction mixture was warmed to −40° C. and stirred at this temperature for 3 h. TLC (PE:EA=3:1) showed that the starting material was consumed completely. The mixture was poured into aqueous saturated $NH_4Cl$ solution (100 mL) and extracted with EtOAc (300 mL×2). The combined organic phases were dried over $Na_2SO_4$, and the solvent was evaporated to afford crude product. The crude product was purified on silica gel chromatography eluted with PE:EA=10:1 to give the pure target (30 g, 53%) as white powder. $^1$H NMR: (400 MHz, CDCl3) δ 5.31-5.29 (m, 1H), 3.66 (s, 3H), 2.39-2.33 (m, 2H), 2.24-2.22 (m, 1H), 1.99-1.95 (m, 3H), 1.85-1.68 (m, 4H), 1.59-1.40 (m, 8H), 1.31-1.26 (m, 2H), 1.17-1.01 (m, 11H), 0.93-0.91 (m, 4H), 0.67 (s, 3H).

Preparation of 0-7. To a solution of compound 0-6 (30.0 g, 74.51 mmol) in THF/$H_2O$ (800 mL, 1/1) was added LiOH·$H_2O$ (17.51 g, 417.28 mmol). The reaction was stirred at room temperature for 18 h. TLC (PE/EA=2/1) showed that compound 0-6 was consumed completely. The mixture was concentrated in vacuum, diluted with water (2 L), and then acidified to pH=4 with 1 M aqueous HCl. The precipitate was collected by filtration and dried in vacuum to give the product compound 0-7 (33 g, crude) as off-white solid. $^1$H NMR: (400 MHz, CDCl3) δ 5.31-5.30 (m, 1H), 2.44-2.36 (m, 2H), 2.29-2.24 (m, 1H), 2.01-1.95 (m, 3H), 1.87-1.71 (m, 5H), 1.61-1.56 (m, 2H), 1.50-1.32 (m, 8H), 1.17-1.09 (m, 7H), 1.01 (s, 3H), 0.95-0.93 (m, 4H), 0.68 (s, 3H).

Preparation of 0-8. A mixture of compound 0-7 (32.0 g, 82.35 mmol), N,O-dimethylhydroxylamine (16.07 g, 164.70 mmol), HATU (37.57 g, 98.82 mmol) and $Et_3N$ (46.0 mL, 329.40 mmol) in 500 mL anhydrous $CH_2Cl_2$ was stirred for 18 h at room temperature. TLC showed the reaction was completed. Then $CH_2Cl_2$ was added to the mixture and the resulting solution was washed with water, 1 N HCl aqueous, saturated aqueous $NaHCO_3$ and brine, dried over anhydrous $Na_2SO_4$, filtered and concentrated, purified by silica gel (PE:EtOAc=10:1 to 3:1) to afford the target compound 0-8 (17.0 g, yield: 47.8%) as off-white solid. $^1$H NMR: (400 MHz, CDCl3) δ 5.31-5.29 (m, 1H), 3.69 (s, 3H), 3.17 (s, 3H), 3.03 (s, 2H), 2.47-2.29 (m, 3H), 2.04-1.68 (m, 7H), 1.60-1.43 (m, 7H), 1.38-1.30 (m, 2H), 1.20-1.08 (m, 6H), 1.03-0.91 (m, 8H), 0.68 (s, 3H).

Preparation of Key Intermediate 0-9. To a solution of compound 0-8 (17.0 g, 39.38 mmol) in 300 mL anhydrous THE was added dropwise MeMgBr (65.6 mL, 196.92 mmol, 3 M in ether) under $N_2$ at 0° C. After the addition was completed, the reaction mixture was stirred for 2 h at room temperature. TLC showed the reaction was completed. Then saturated aqueous $NH_4Cl$ was slowly added to the mixture at 0° C., then the mixture was poured to water, extracted with EtOAc (2*200 mL), the organic layers were washed with brine, dried over anhydrous $Na_2SO_4$, filtered and concentrated, purified on silica gel (PE:EtOAc=20:1 to 6:1) to afford the target compound 0-9 (11.0 g, yield: 72%) as white solid. $^1$H NMR: (400 MHz, CDCl3) δ 5.31-5.30 (m, 1H), 2.50-2.30 (m, 3H), 2.17 (s, 2H), 2.14 (s, 3H), 2.02-1.94 (m, 3H), 1.88-1.67 (m, 4H), 1.61-1.58 (m, 1H), 1.56-1.49 (m, 5H), 1.47-1.41 (m, 2H), 1.31-1.11 (m, 7H), 1.08-0.91 (m, 8H), 0.68 (s, 3H).

Assay Methods

Compounds of the present invention can be evaluated using various in vitro and in vivo assays described in the literature; examples of which are described below.

The following examples are offered to illustrate the biological activity of the compounds, pharmaceutical compositions, and methods provided herein and are not to be construed in any way as limiting the scope thereof.

NMDA Potentiation

NMDA potentiation was assessed using either whole cell patch clamp of mammalian cells which expressed NMDA receptors, or using two-electrode voltage clamp (TEVC) of *Xenopus Laevis* oocytes expressing NMDA receptors.

Whole-cell Patch Clamp of Mammalian Cells

The whole-cell patch-clamp technique was used to investigate the effects of compounds (0.1 mM and 1.0 mM) on the NMDA receptor (GRIN1/GRIN2A subunits) expressed in HEK cells. NMDA/Glycine peak and steady-state currents were recorded from stably transfected cells expressing the NMDA receptor and the modulatory effects of the test items on these currents were investigated. Results are shown on Table 1.

Cells were stably transfected with human GRIN1 (variant NR1-3). These cells were transiently transfected (Lipofectamine™) with GRIN2A cDNA and CD8 (pLeu) antigene cDNA. About 24-72 hours following transfection 1 μl Dynabeads M-45 CD8 was added to identify successfully transfected cells (Jurman et al., *Biotechniques* (1994) 17:876-881). Cells were passaged to a confluence of 50-80%. Cells were seeded onto Poly-L-Lysine coated cover slips covered with culture complete medium in a 35 mm culture dish. Confluent clusters of cells are electrically coupled (Pritchett et al., Science (1988), 242:1306-8). Because responses in distant cells are not adequately voltage clamped and because of uncertainties about the extent of coupling (Verdoorn et al., *Neuron* (1990), 4:919-28), cells were cultivated at a density that enables single cells (without visible connections to neighboring cells) to be measured. Cells were incubated at 37° C. in a humidified atmosphere with 5% $CO_2$ (rel. humidity about 95%). The cells were continuously maintained in and passaged in sterile culture flasks containing a 1:1 mixture of Dulbecco's modified eagle medium and nutrient mixture F-12 (D-MEM/F-12 1×, liquid, with L-Glutamine) supplemented with 9% fetal bovine serum and 0.9% Penicillin/Streptomycin solution. The complete medium was supplemented with 3.0 μg/ml Puromycin.

Whole cell currents were measured with HEKA EPC-10 amplifiers using PatchMaster software. Cell culture dishes for recordings were placed on the dish holder of the microscope and continuously perfused (1 ml/min) with "bath solution" (NaCl 137 mM, KCl 4 mM, $CaCl_2$ 1.8 mM, $MgCl_2$ 1 mM, HEPES 10 mM, D-Glucose 10 mM, pH (NaOH) 7.4). All solutions applied to cells including the pipette solution were maintained at room temperature (19° C.-30° C.). After formation of a Gigaohm seal between the patch electrodes and transfected individual HEK 293 cells (pipette resistance range: 2.5 MΩ-6.0 MΩ; seal resistance range: >1 GQ) the cell membrane across the pipette tip was ruptured to assure electrical access to the cell interior (whole-cell patch-configuration). At this point the bath solution is switched to "NMDA bath solution" (NaCl 137 mM, KCl 4 mM, $CaCl_2$ 2.8 mM, HEPES 10 mM, D-Glucose 10 mM, Cremophore 0.02%, pH (NaOH) 7.4). NMDA inward currents were measured upon application of 30 μM NMDA (and 5.0 μM Glycine) to patch-clamped cells (2 applications) for 5 s. The cells were voltage clamped at a holding potential of −80 mV. For the analysis of test articles, NMDA receptors were stimulated by 30 μM NMDA and 5.0 μM Glycine after sequential pre-incubation of increasing concentrations of the test article. Pre-incubation duration was 30 s. Stimulation duration was 5 s Test articles were dissolved in DMSO to form stock solutions of 0.1 mM and 1 mM. Test articles were diluted to 0.1 μM and 1 μM in "NMDA bath solution". Both concentrations of test articles were tested on each cell. The same concentration was applied at least three times or until the steady state current amplitude was reached. Every day one cell was tested with 50 μM PREGS (positive control) using the same application protocol to test whether cells were successfully transfected with NMDA receptors.

TABLE 1

| Structure | NMDA 1a2A (%) Potentiation 0.1 uM | NMDA 1a2A (%) Potentiation 1 uM |
|---|---|---|
| 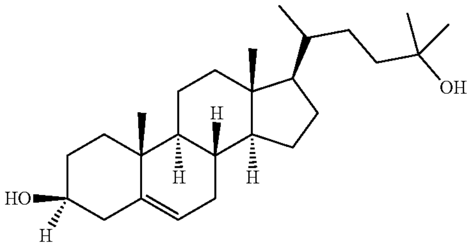 Org-1 | A | C |
| 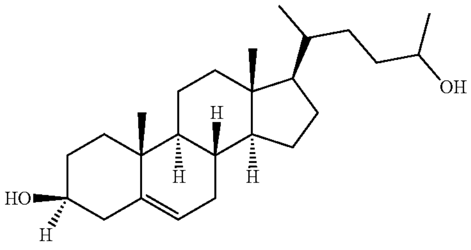 Comparison compound 1 | A | B |
| 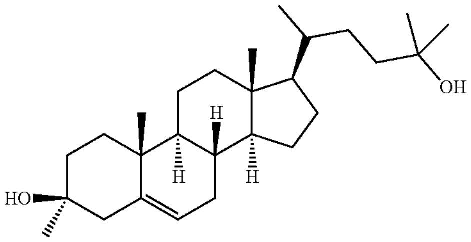 Comparison compound 2 | B | D |

TABLE 1-continued
| Structure | NMDA 1a2A (%) Potentiation 0.1 uM | NMDA 1a2A (%) Potentiation 1 uM |
|---|---|---|
| 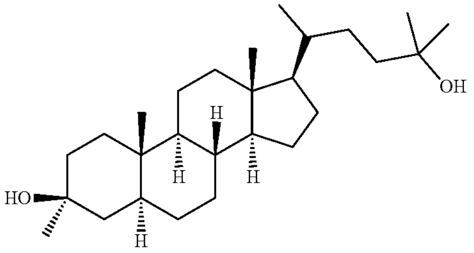 Comparison compound 3 | B | C |
| 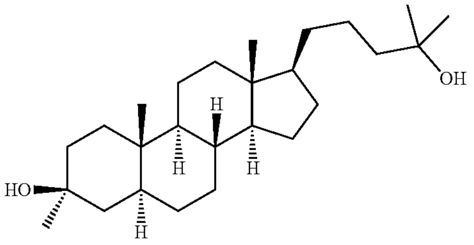 Comparison compound 4 | A | B |
| 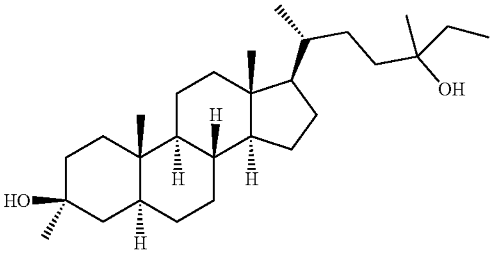 Comparison compound 5 | A | A |
| 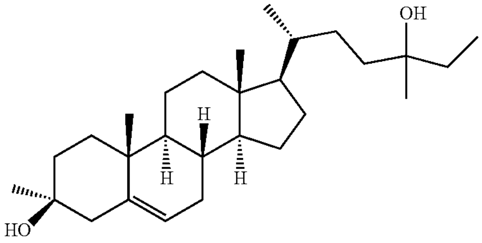 4-6 | C | C |
| 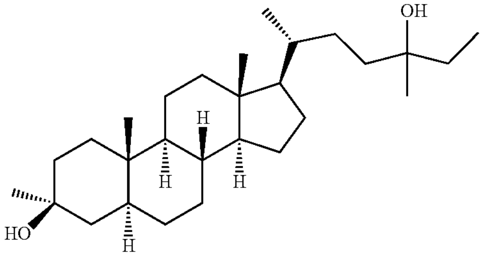 4-7 | B | C |

TABLE 1-continued
| Structure | NMDA 1a2A (%) Potentiation 0.1 uM | NMDA 1a2A (%) Potentiation 1 uM |
|---|---|---|
| 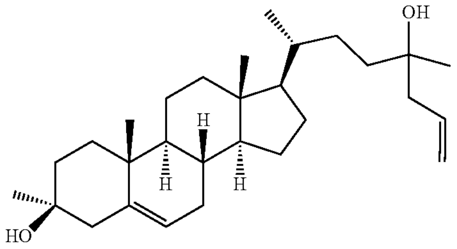 6-2 | B | C |
| 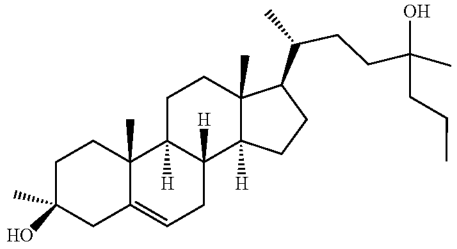 5-2 | B | C |
| 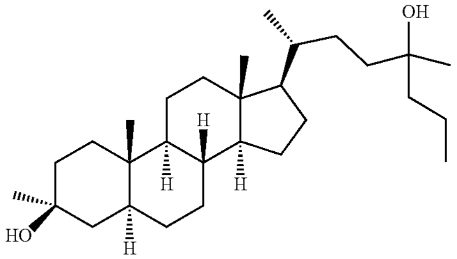 5-3 | A | B |
| 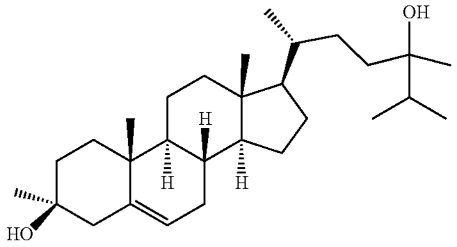 8-2 | B | C |
| 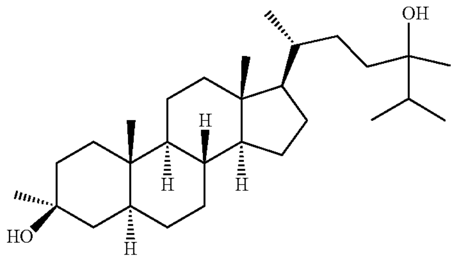 8-3 | B | D |

TABLE 1-continued
| Structure | NMDA 1a2A (%) Potentiation 0.1 uM | NMDA 1a2A (%) Potentiation 1 uM |
|---|---|---|
| 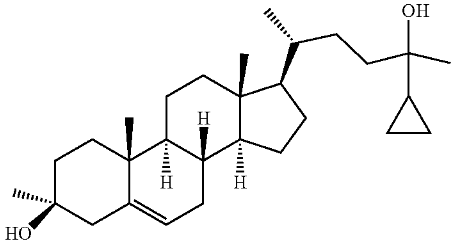 9-2 | C | C |
| 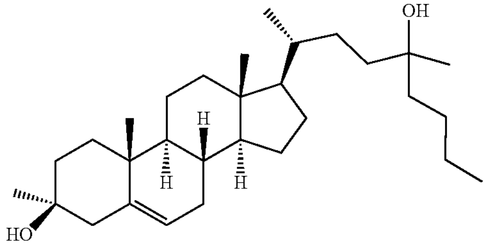 7-2 | A | B |
| 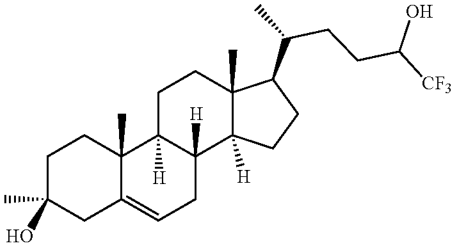 1-11 | C | C |
| 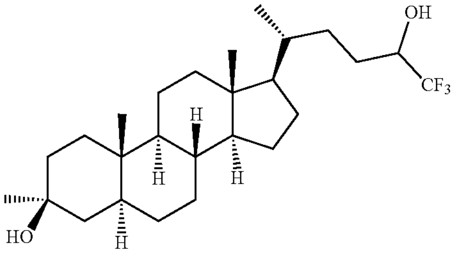 1-12 | A | B |
| 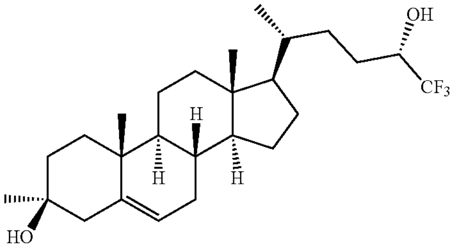 1-15 | B | C |

TABLE 1-continued

| Structure | NMDA 1a2A (%) Potentiation 0.1 uM | NMDA 1a2A (%) Potentiation 1 uM |
|---|---|---|
| 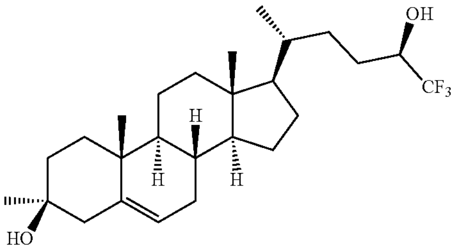 1-17 | C | C |

For Table 1, "A" indicates 10-75% potentiation, "B" indicates potentiation of >75% to 150%, and "C" indicates potentiation of >150 to 250%; and "D indicates potentiation of >250%.

Oocytes

The Two Electrode Voltage Clamp (TEVC) technique was used to investigate the effects of compounds (10 μM) on the NMDA receptor (GRIN1/GRIN2A) expressed in *Xenopus* oocytes. Glutamate/Glycine peak and steady-state currents were recorded from oocytes that expressed the NMDA receptor and the modulatory effects of the test items on these currents were investigated. Results are shown on Table 2.

Ovaries were harvested from *Xenopus Laevis* females that had been deeply anesthetized by cooling at 4° C. and immersion in Tricaine methanesulfonate (MS-222 at a concentration of 150 mg/L) in sodium bicarbonate (300 mg/L). Once anesthetized the animal was decapitated and pithed following the rules of animal rights from the Geneva canton. A small piece of ovary was isolated for immediate preparation while the remaining part was placed at 4° C. in a sterile Barth solution containing in mM NaCl 88, KCl 1, $NaHCO_3$ 2.4, HEPES 10, $MgSO_4 \cdot 7H_2O$ 0.82, Ca$(NO_3)_2 \cdot 4H_2O$ 0.33, $CaCl_2 \cdot 6H_2O$ 0.41, at pH 7.4, and supplemented with 20 μg/ml of kanamycin, 100 unit/ml penicillin and 100 μg/ml streptomycin. All recordings were performed at 18° C. and cells were super-fused with medium containing in mM: NaCl 82.5, KCl 2.5, HEPES 5, $CaCl_2 \cdot 2H_2O$, $\cdot 6H_2O$ 1, pH 7.4.

Oocytes were injected with either cDNAs encoding for the human GRIN1 and GRIN2A subunits, using a proprietary automated injection device (Hogg et al., *J. Neurosci. Methods*, (2008) 169: 65-75) and receptor expression was assessed using electrophysiology at least two days later. The ratio of cDNA injection for GRIN1 and GRIN2A was 1:1. Electrophysiological recordings were made using an automated process equipped with standard TEVC and data were captured and analyzed using a proprietary data acquisition and analysis software running under Matlab (Mathworks Inc.). The membrane potential of the oocytes was maintained at −80 mV throughout the experiments. To explore the effects of proprietary compounds, currents were evoked by applying 3 μM Glutamate and 10 M Glycine for 10 s. Oocytes were then washed for 90 s before being exposed to the test article at a concentration of 10 μM for 120 s. Following this, 3 μM Glutamate and 10 M Glycine were immediately reapplied for 10 s. Potentiation of both the peak current and the steady state current was assessed. For statistical analysis values were computed either with Excel (Microsoft) or Matlab (Mathworks Inc.). To obtain mean measurements with standard deviations, all experiments were carried out using at least three cells.

Glutamate was prepared as a concentrated stock solution (101 M) in water and then diluted in the recording medium to obtain the desired test concentration. Glycine was prepared as a stock solution at 1 M in water. Compounds were prepared as stock solution (102 M) in DMSO and then diluted in the recording medium to obtain the desired test concentration. Residual DMSO did not exceed the concentration of 1% a concentration that has been shown to have no effects on *Xenopus* oocytes function.

TABLE 2

| Structure | % Potentiation at 10 μM |
|---|---|
| 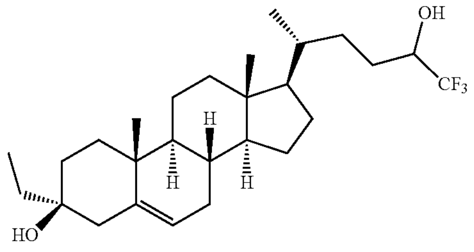 2-4 | C |

TABLE 2-continued
| Structure | % Potentiation at 10 μM |
| --- | --- |
| 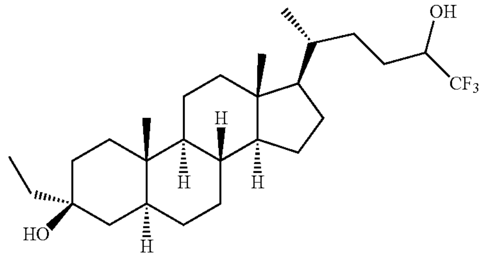 2-5 | B |
| 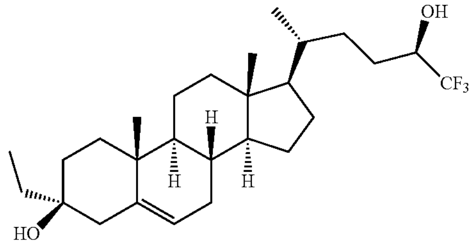 2-7 | C |
| 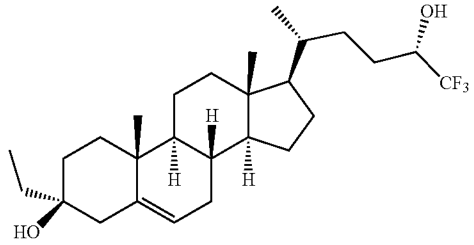 2-8 | B |
| 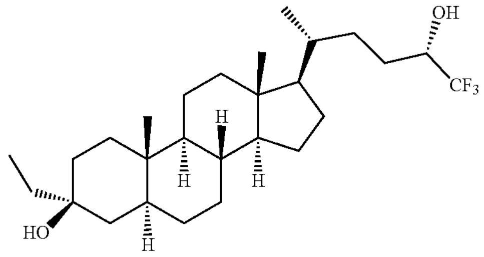 2-10 | A |
| 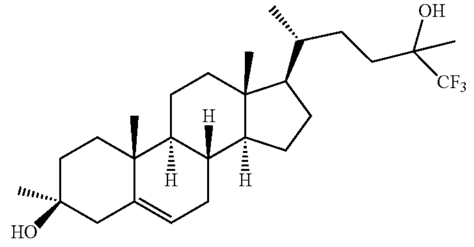 3-2 | C |

TABLE 2-continued
| Structure | % Potentiation at 10 μM |
|---|---|
| 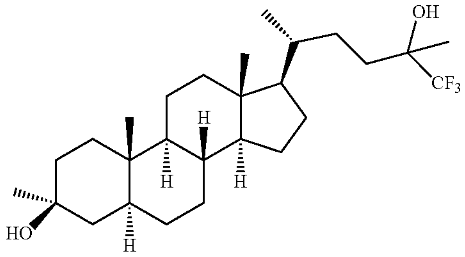 3-3 | B |
| 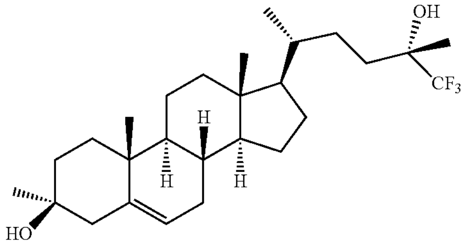 3-5 | A |
| 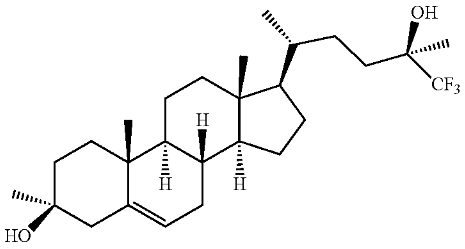 3-6 | B |
| 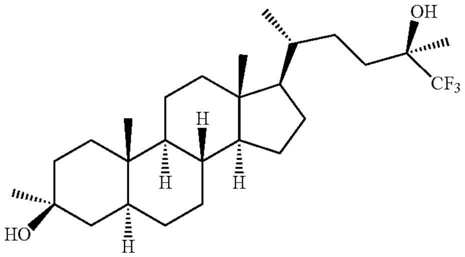 3-7 | A |
| 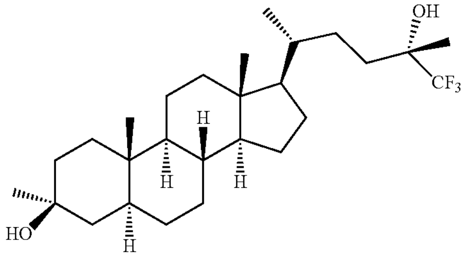 3-8 | B |

TABLE 2-continued
| Structure | % Potentiation at 10 μM |
| --- | --- |
| 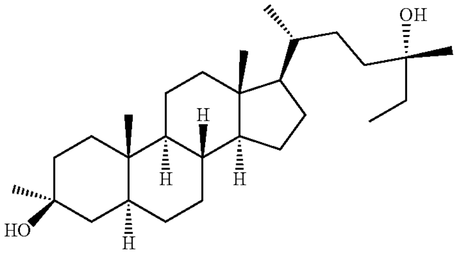 4-9 | A |
| 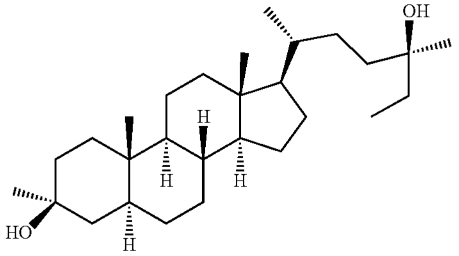 4-10 | A |
| 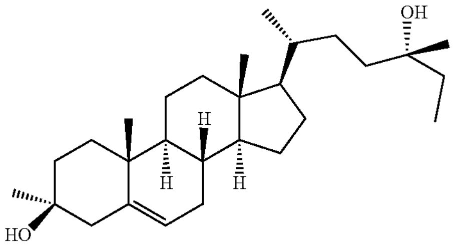 4-11 | C |
| 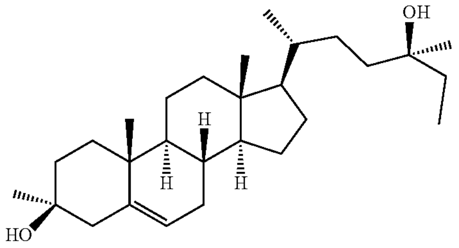 4-12 | B |
| 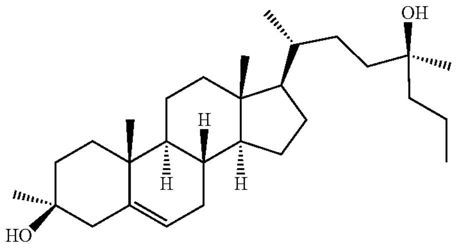 5-5 | A |

TABLE 2-continued
| Structure | % Potentiation at 10 μM |
| --- | --- |
| 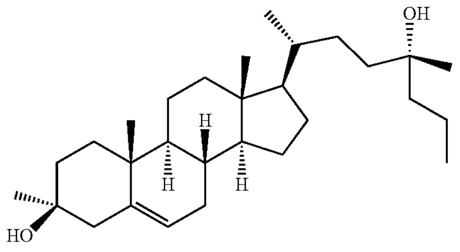 5-6 | A |
| 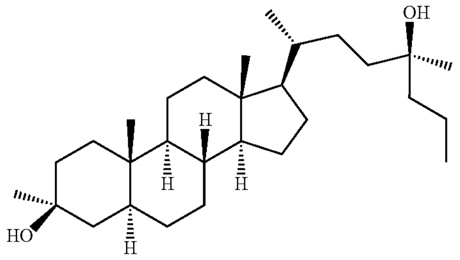 5-7 | B |
| 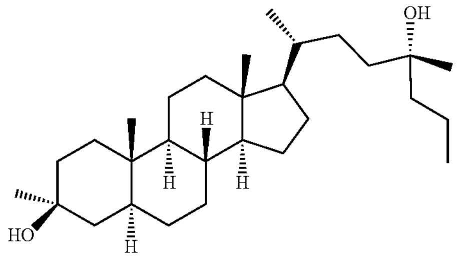 5-8 | B |
| 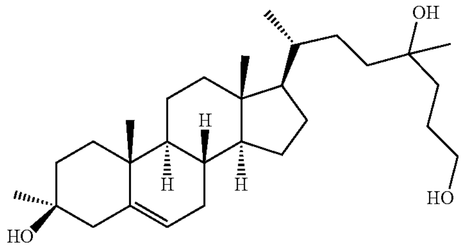 6-3 | B |
| 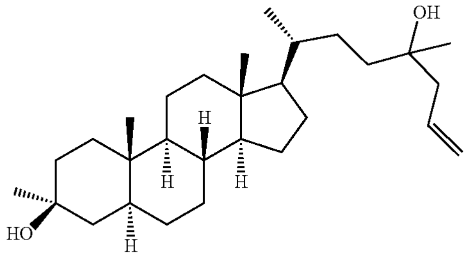 6-6 | B |

TABLE 2-continued
| Structure | % Potentiation at 10 μM |
|---|---|
| 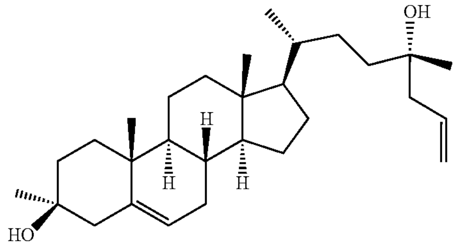 6-8 | A |
| 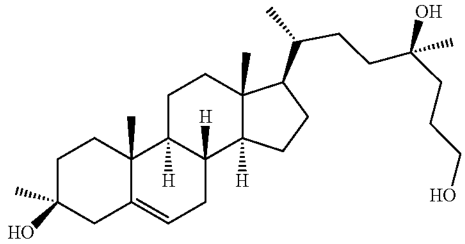 6-9 | A |
| 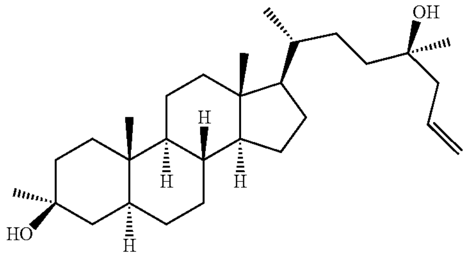 6-11 | A |
| 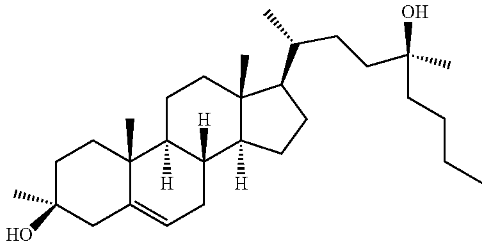 7-4 | B |
| 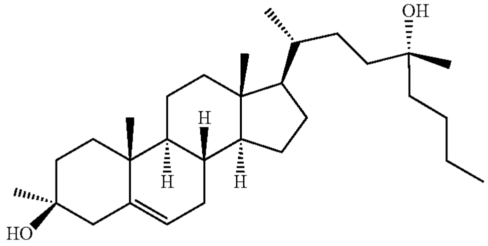 7-5 | A |

TABLE 2-continued
| Structure | % Potentiation at 10 μM |
|---|---|
| 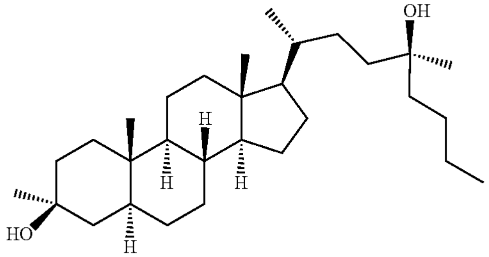 7-6 | C |
| 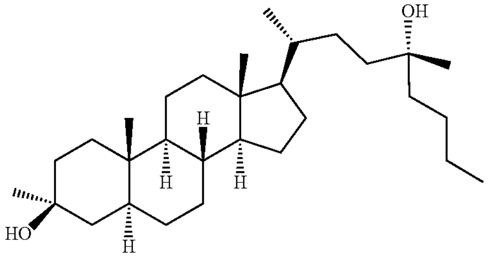 7-7 | A |
| 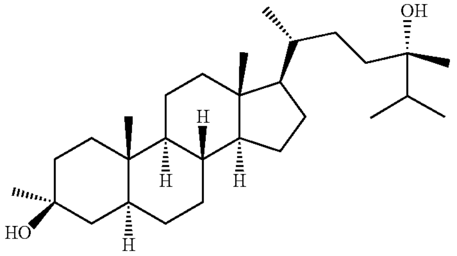 8-5 | A |
| 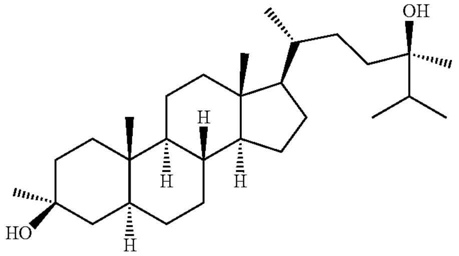 8-6 | A |
| 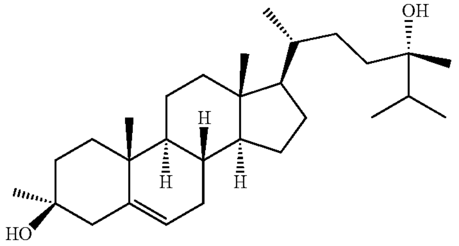 8-7 | B |

TABLE 2-continued
| Structure | % Potentiation at 10 μM |
|---|---|
| 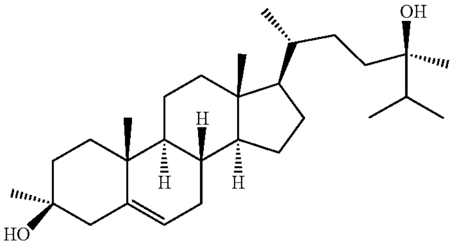 8-8 | C |
| 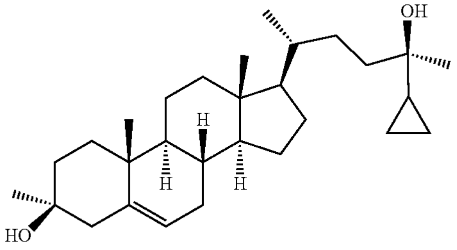 9-3 | B |
| 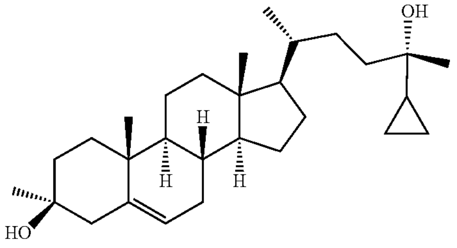 9-4 | B |
| 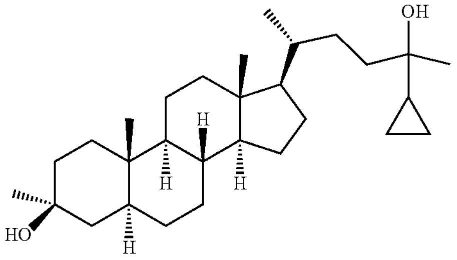 9-6 | B |
| 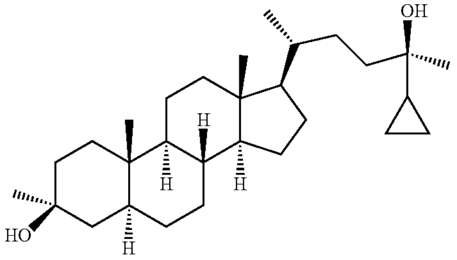 9-7 | A |

TABLE 2-continued
| Structure | % Potentiation at 10 μM |
|---|---|
| 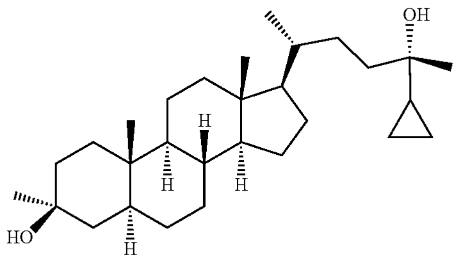 9-8 | A |
| 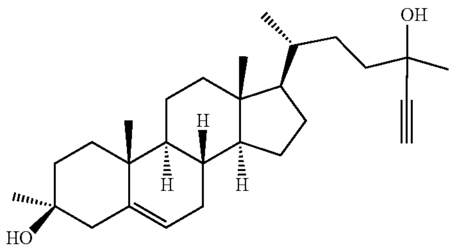 10-2 | B |
| 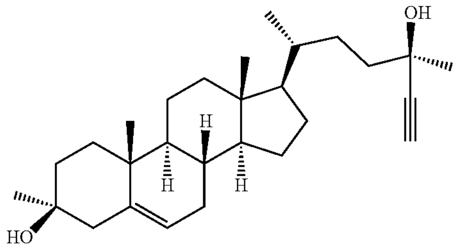 10-3 | A |
| 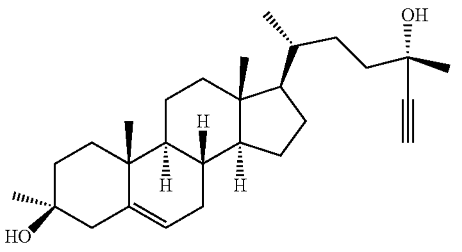 10-4 | A |
| 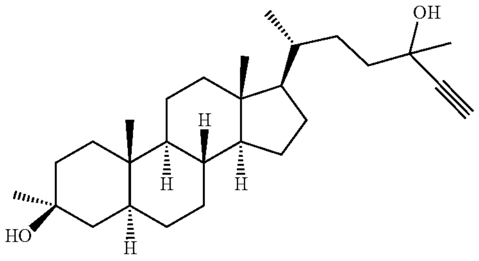 10-6 | B |

TABLE 2-continued
| Structure | % Potentiation at 10 μM |
|---|---|
| 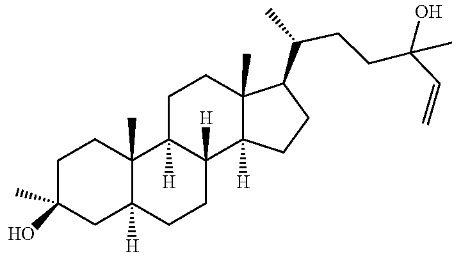 10-7 | B |
| 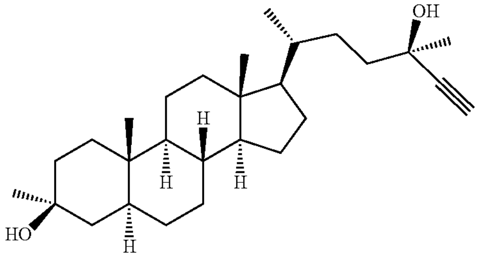 10-8 | B |
| 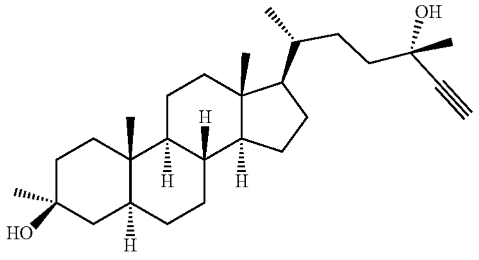 10-9 | A |
| 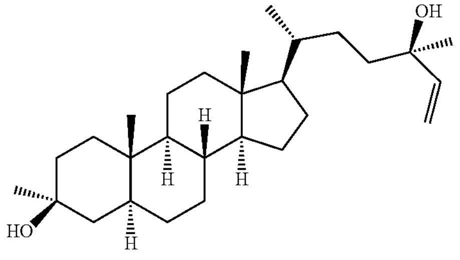 10-10 | A |
| 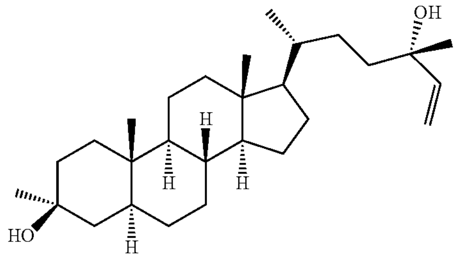 10-11 | A |

TABLE 2-continued
| Structure | % Potentiation at 10 μM |
|---|---|
| 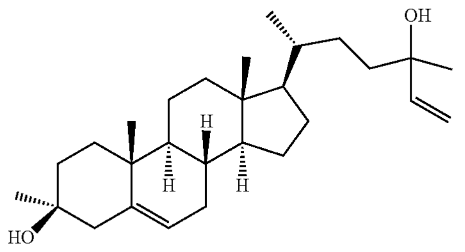 10-12 | A |
| 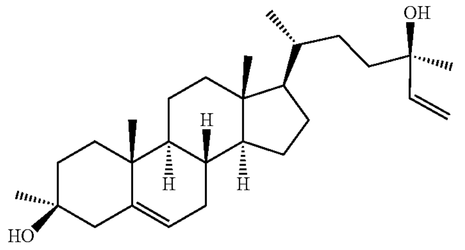 10-12A | A |
| 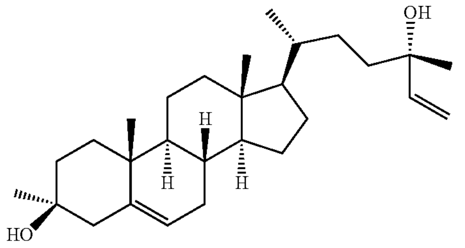 10-12B | A |
| 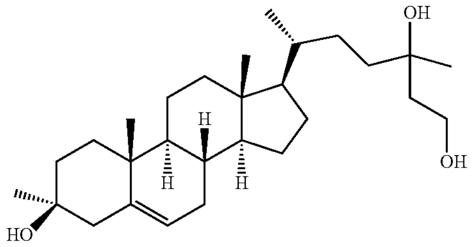 10-13 | B |
| 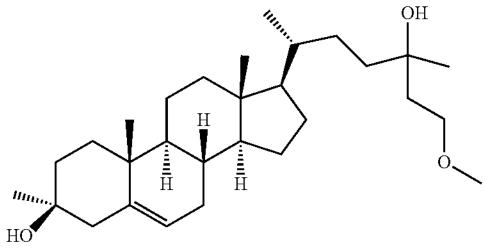 10-14 | B |

TABLE 2-continued
| Structure | % Potentiation at 10 μM |
|---|---|
| 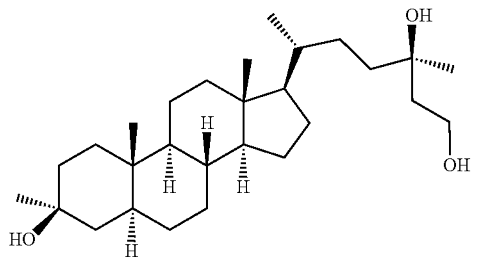 10-16 | A |
| 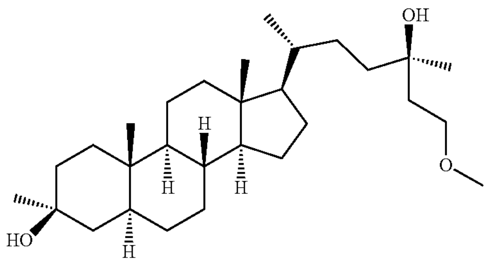 10-17 | C |
| 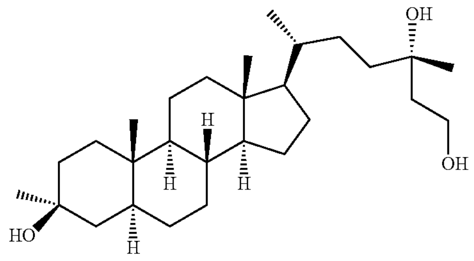 10-18 | B |
| 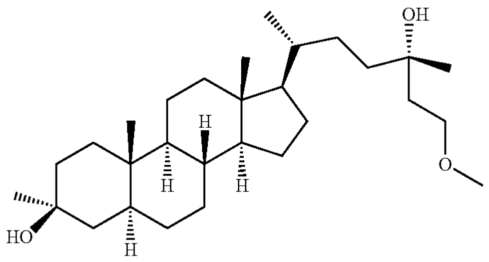 10-19 | A |
| 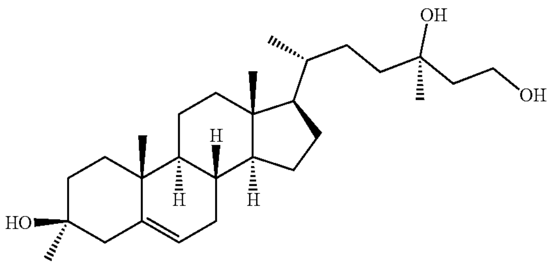 10-20 | A |

TABLE 2-continued
| Structure | % Potentiation at 10 μM |
| --- | --- |
| 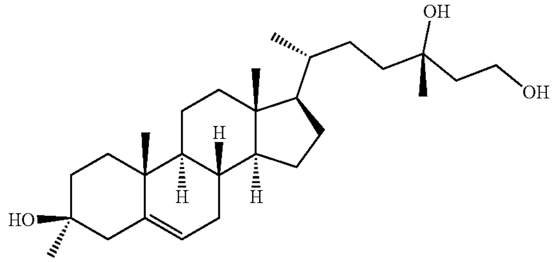 10-21 | A |
| 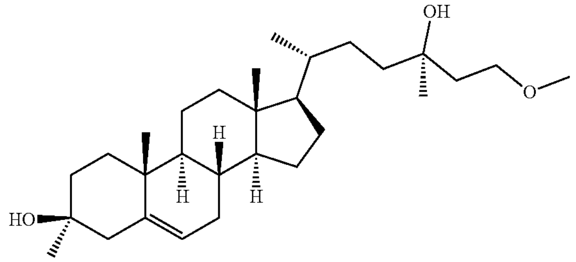 10-22 | B |
| 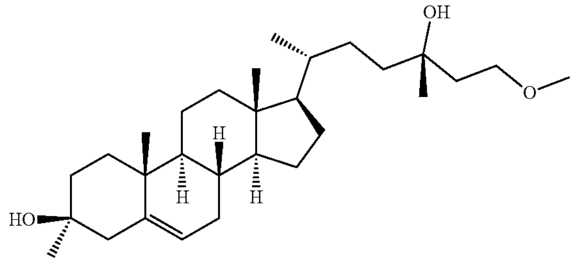 10-23 | A |
| 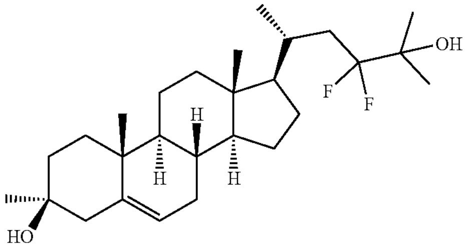 11-19 | A |
| 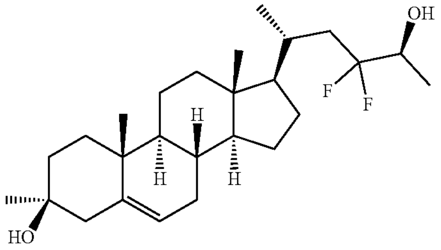 11-15 | A |

TABLE 2-continued

| Structure | % Potentiation at 10 μM |
|---|---|
| 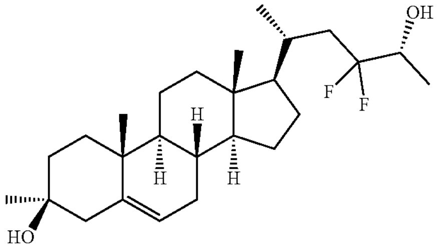 11-16 | A |
| 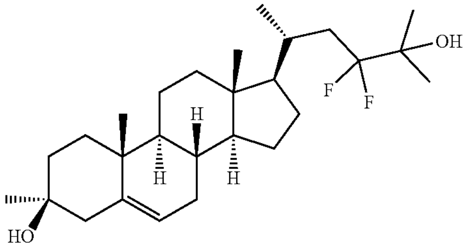 11-19 | A |

For Table 2, "A" indicates 10-50% potentiation, "B" indicates potentiation of >50% to 100%, and "C" indicates potentiation of >100%.

As shown in Table 1, compounds bearing a beta-hydrogen at $C_5$ are disfavored compared to compounds bearing either alpha-hydrogen $C_5$ or double bond across $C_5$-$C_6$ due to loss of potentiation of the NMDA receptor. This is illustrated by Comparison Compound 5 vs 4-6 and 4-7. The removal of the methyl at $C_{21}$ also results in significant loss of NMDA potentiation, for example Comparison Compound 4 lost five fold potentiation compared to Comparison Compound 3 when measured at 0.1 μM concentration. Therefore the compounds in this selection bear both a methyl group in $C_{21}$ and either a double bond across $C_5$-$C_6$ or an alpha-hydrogen in $C_5$. In addition, compounds in this selection showed improved potency and limited maximum potentiation of the NMDA receptor when tested as high as 1 μM concentrations of compound (for example Comparison Compound 2 vs 4-6 and 1-11). Such properties are expected limit the risk of inducing glutamate driven neurotoxicity relative to compounds that achieve a greater maximum potentiation of the NMDA receptor.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for treating a CNS-related condition in a subject, comprising administering to the subject an effective amount of a compound selected from the group consisting of:

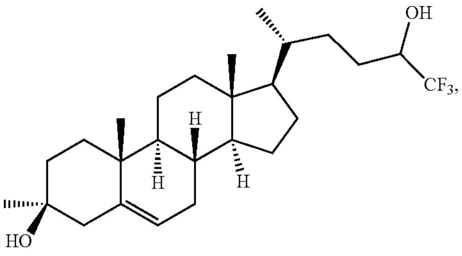
1-11

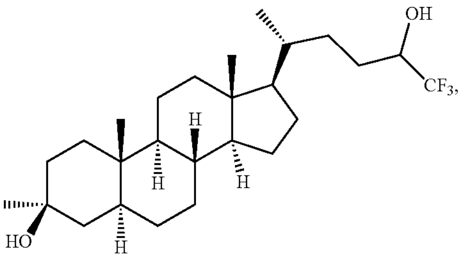
1-12

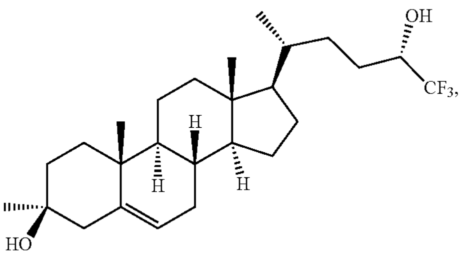
1-15

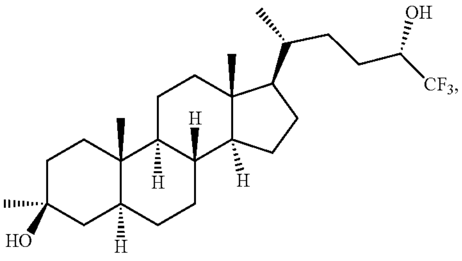
1-16

-continued

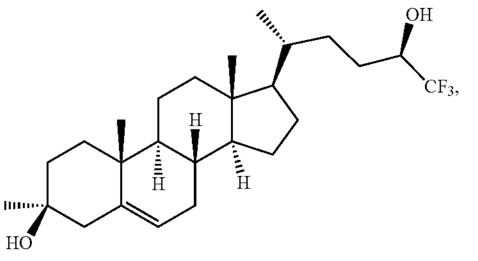
1-17

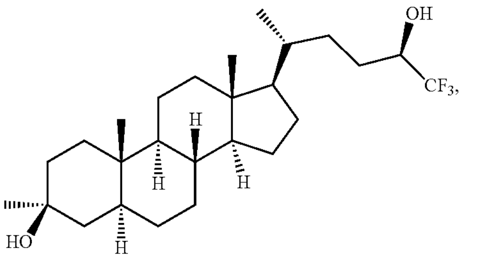
1-18

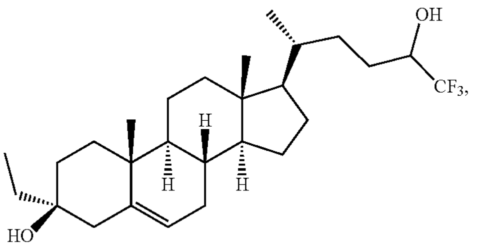
2-4

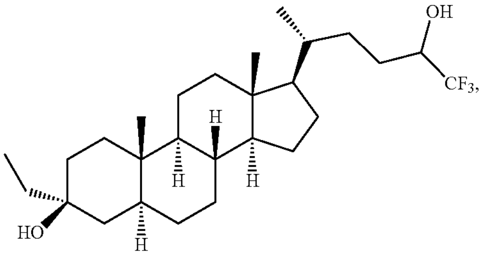
2-5

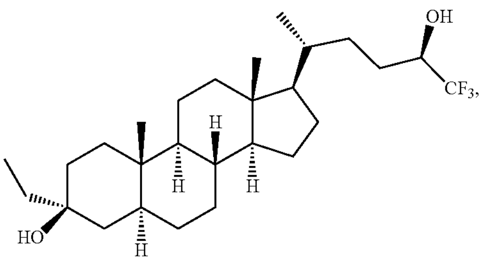
2-9

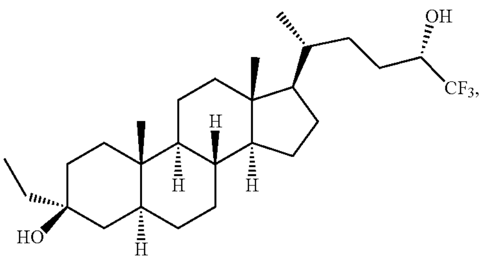
2-10

-continued
3-2
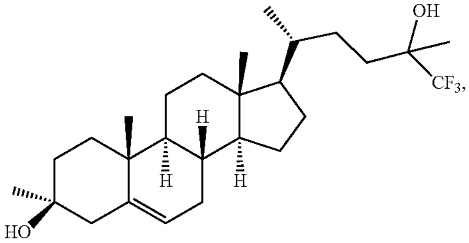,
3-3
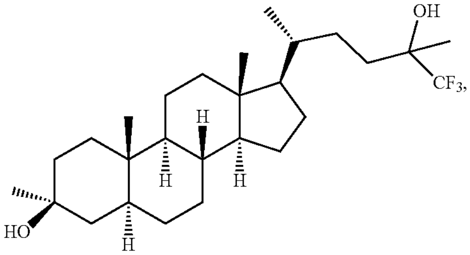,
3-7
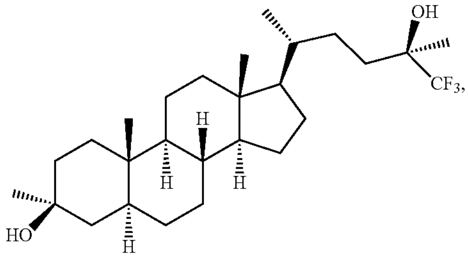,
3-8
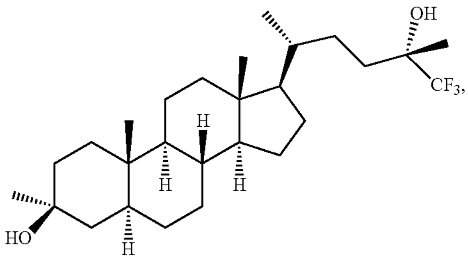,
4-6
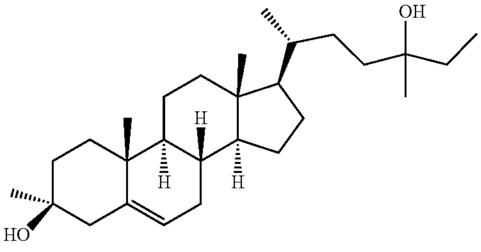,
4-7
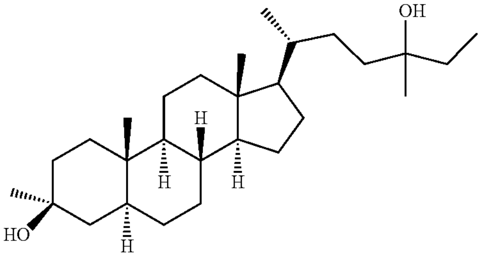,
-continued
4-9
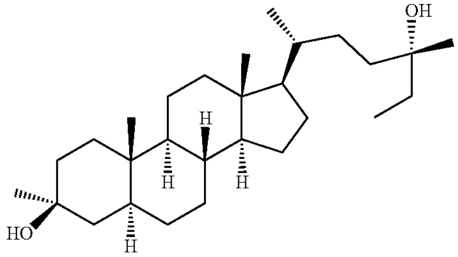,
4-10
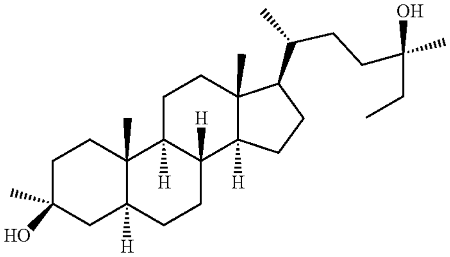,
5-2
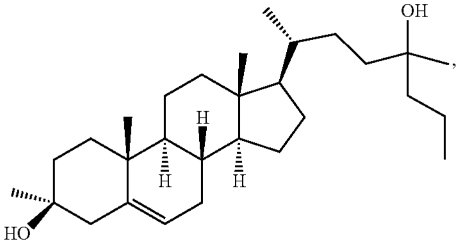,
5-3
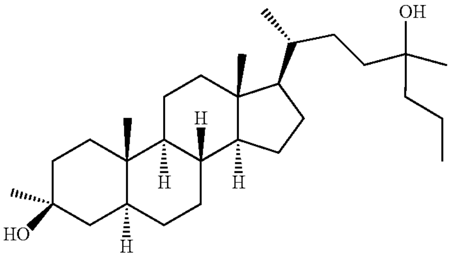,
5-5
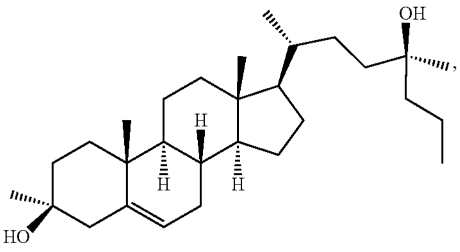,
5-6
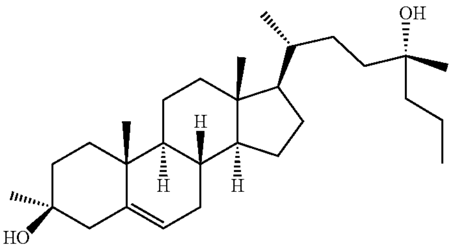, -continued
5-7
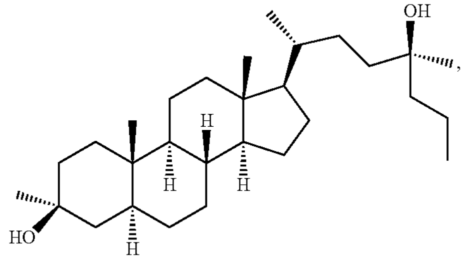
,
5-8
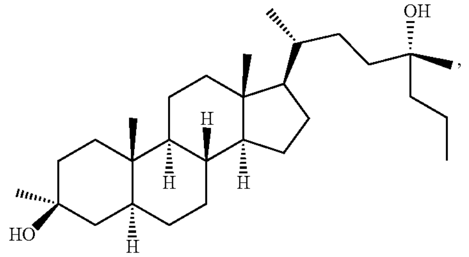
,
6-2
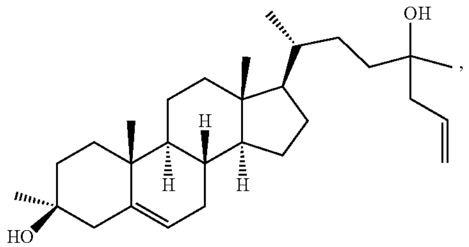
,
6-3
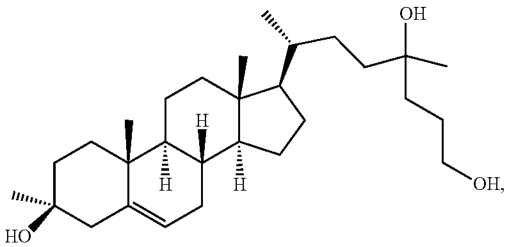
,
6-6
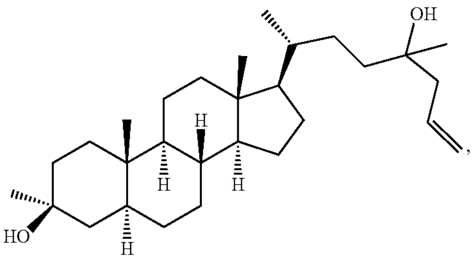
,
6-7
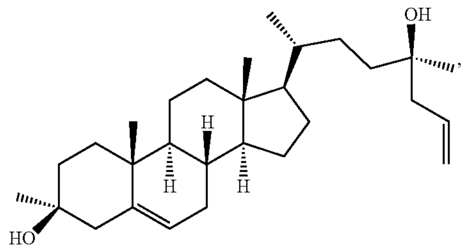
,
-continued
6-8
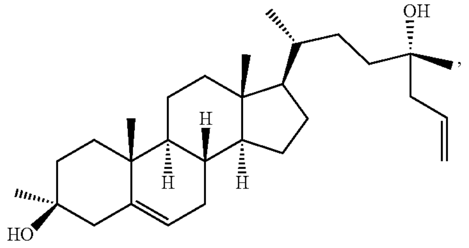
,
6-9
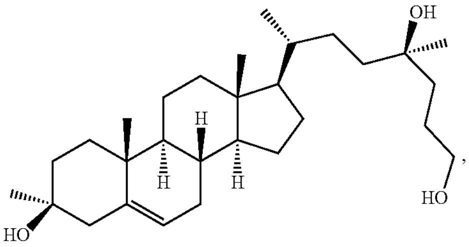
,
6-10
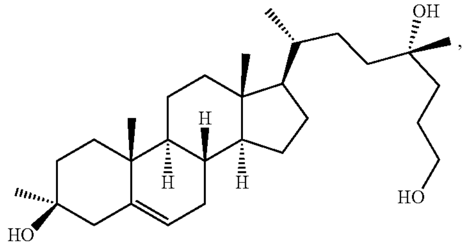
,
6-11
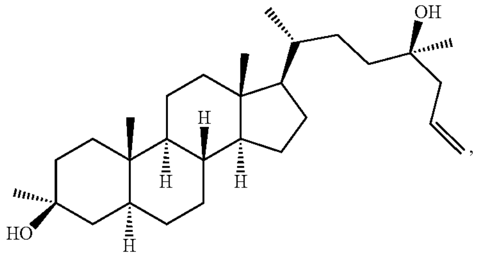
,
6-12
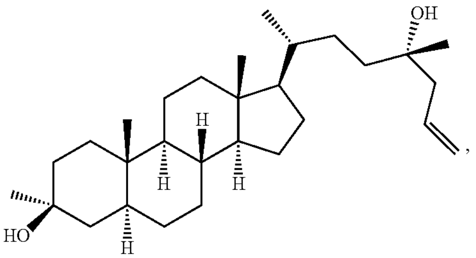
,
6-13
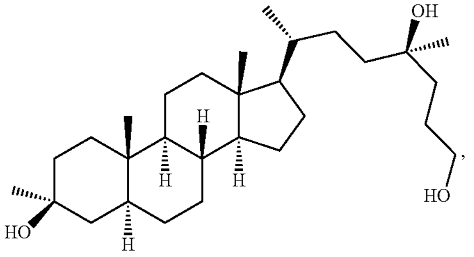
, -continued
6-14
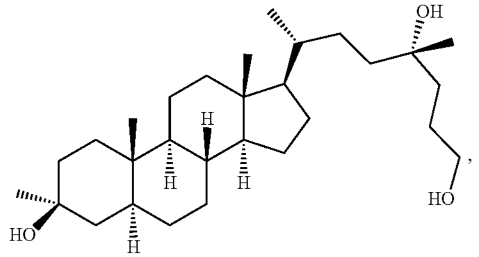,
6-15
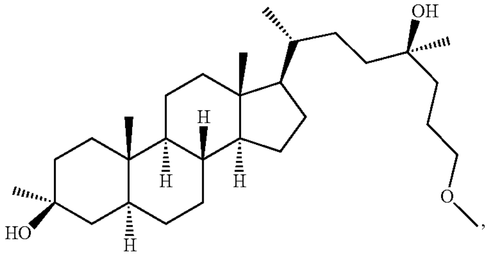,
6-16
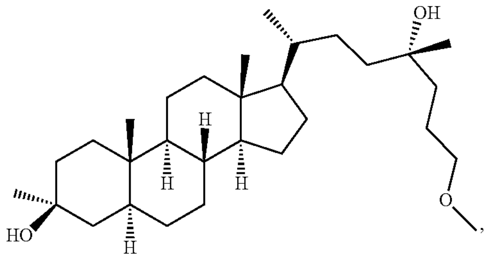,
6-17
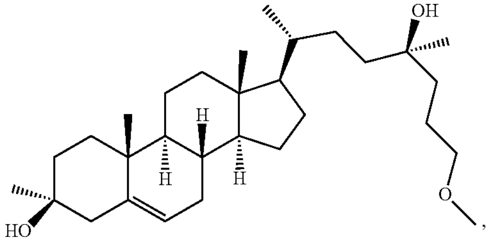,
6-18
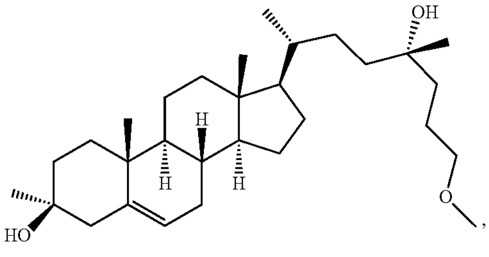,
7-2
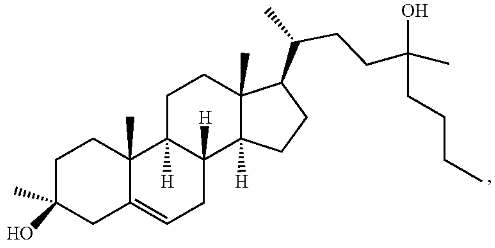,
-continued
7-3
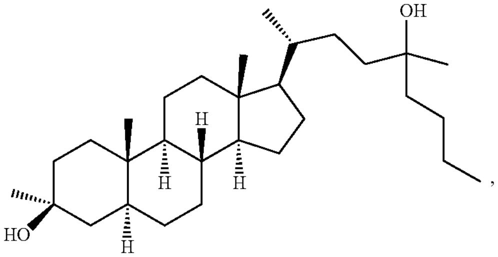,
7-4
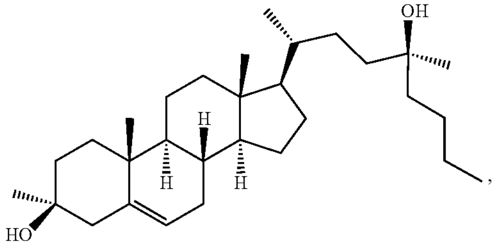,
7-5
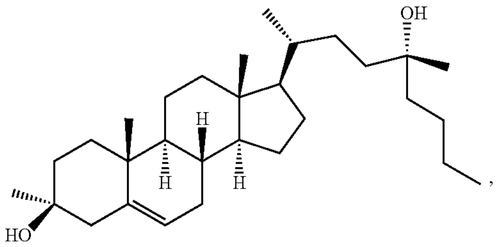,
7-6
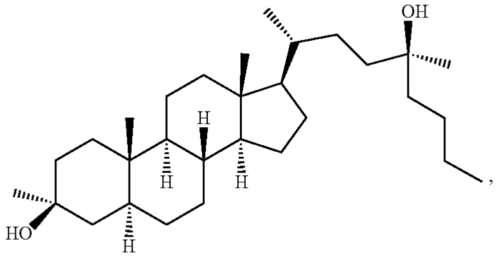,
7-7
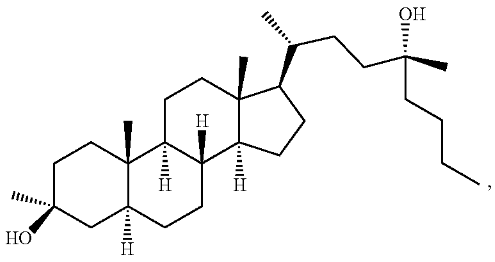,
8-2
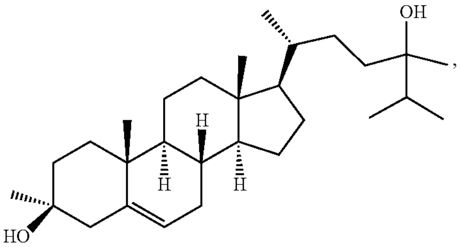, -continued
8-3
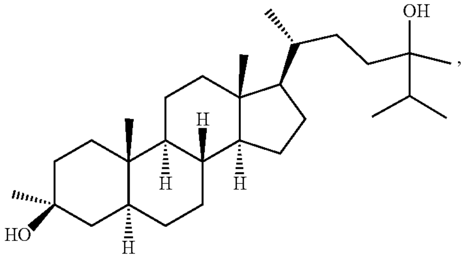
8-5
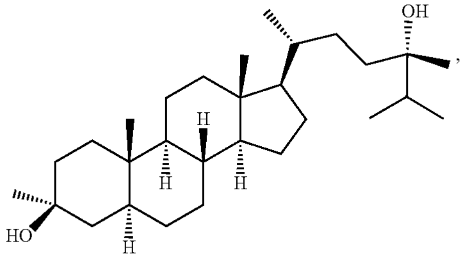
8-6
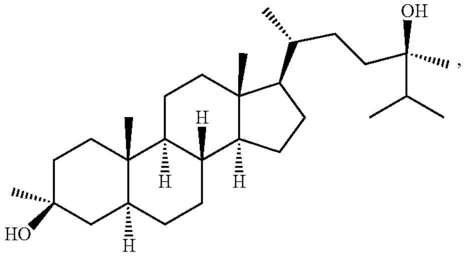
9-2
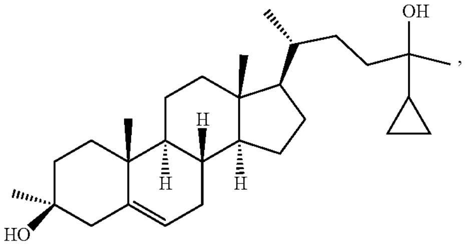
9-3
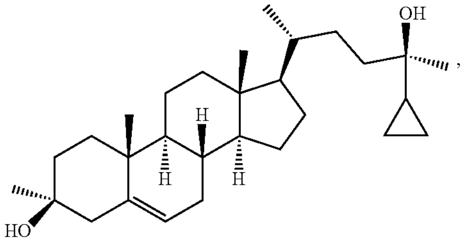
9-4
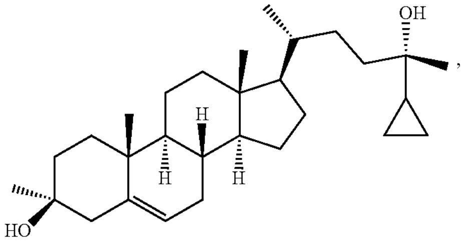
-continued
9-6
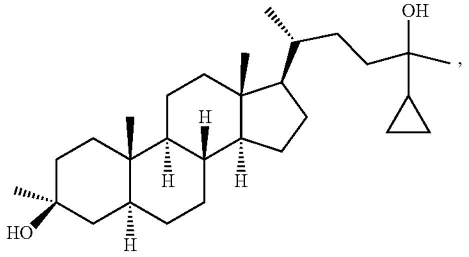
9-7
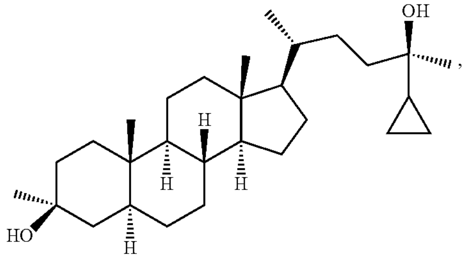
9-8
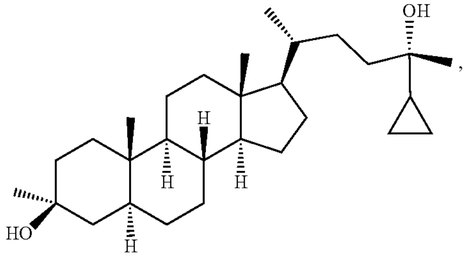
10-2
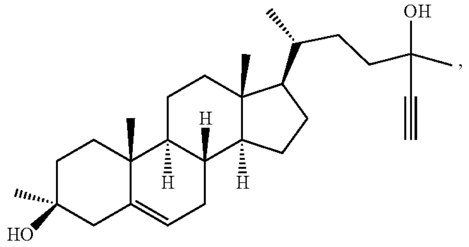
10-3
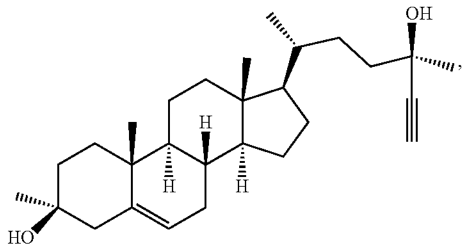
10-4
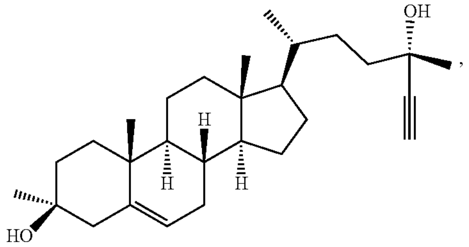

-continued
10-6
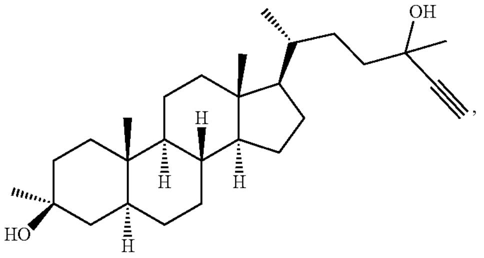
10-8
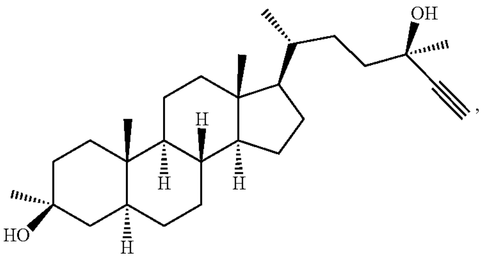
10-9
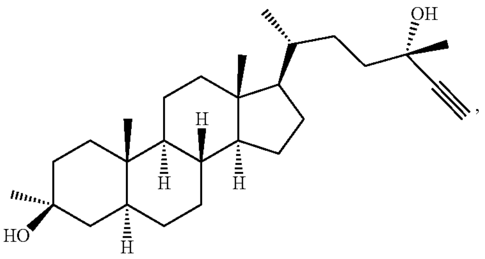
10-7
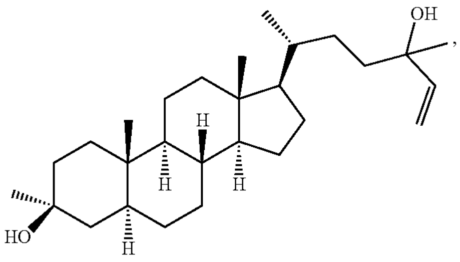
10-10
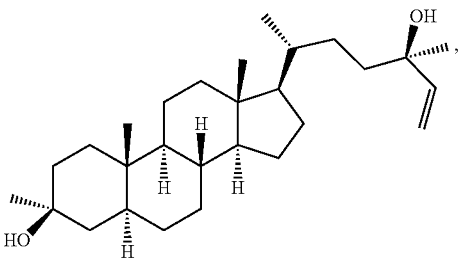
10-11
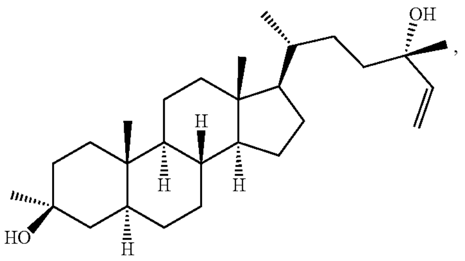
-continued
10-12
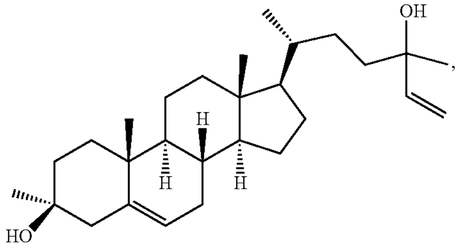
10-12A
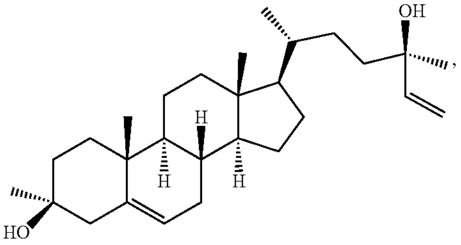
10-12B
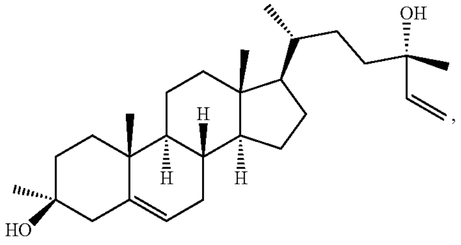
10-13
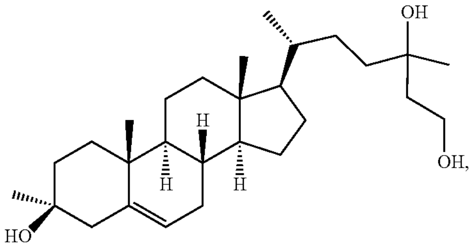
10-14
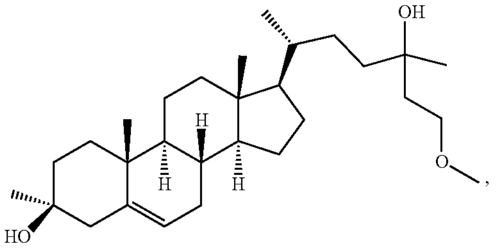
10-16
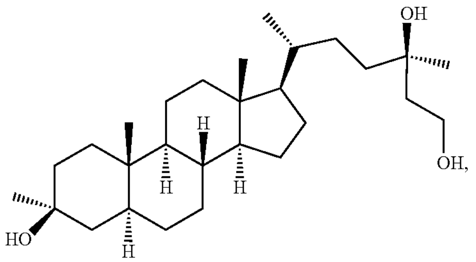

-continued
10-15
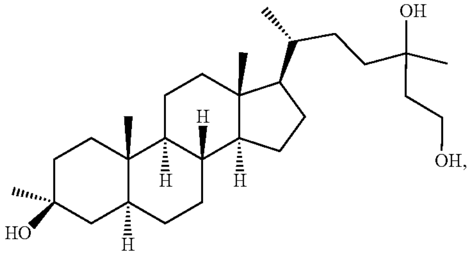
10-17
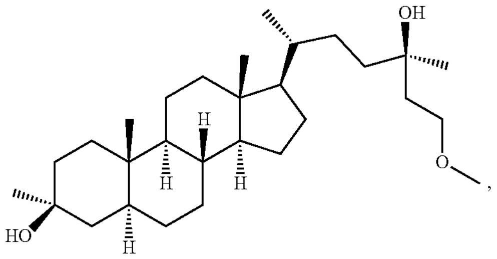
10-18
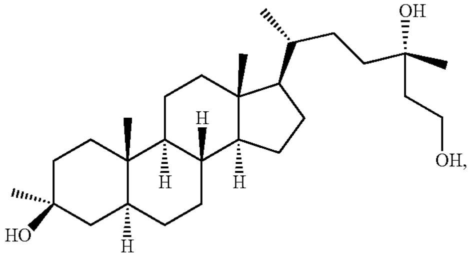
10-19
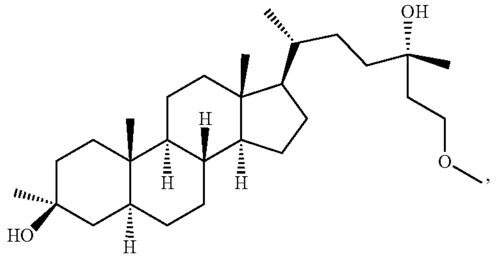
10-20
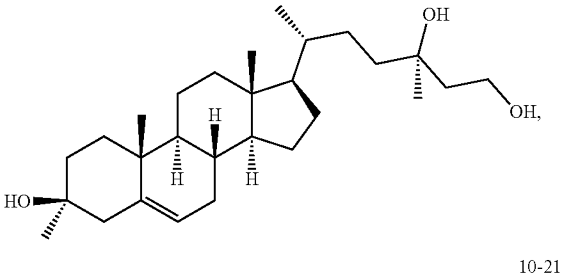
10-21
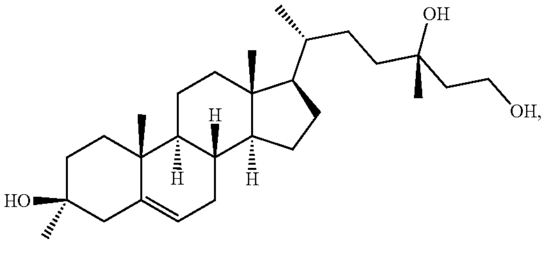
-continued
10-22
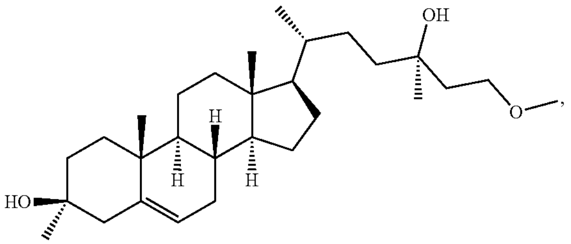
10-23
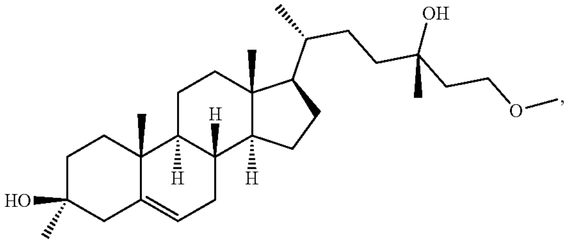
11-13
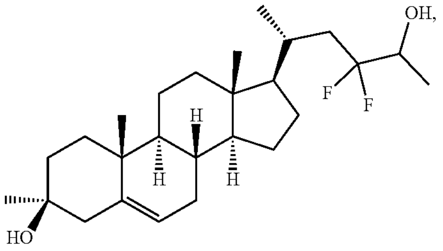
11-14
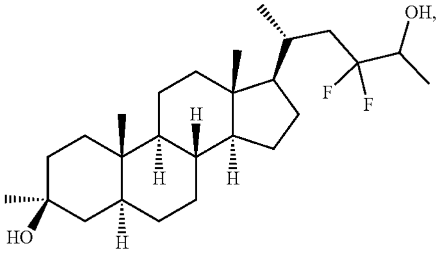
11-17
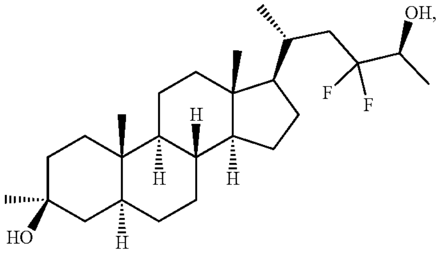
11-18
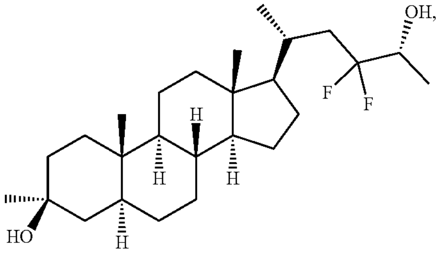

-continued 11-19

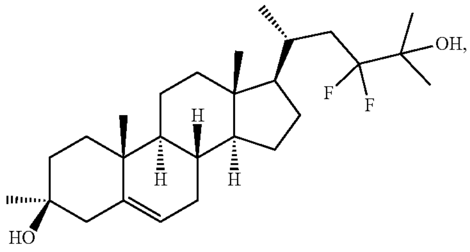

and 11-20

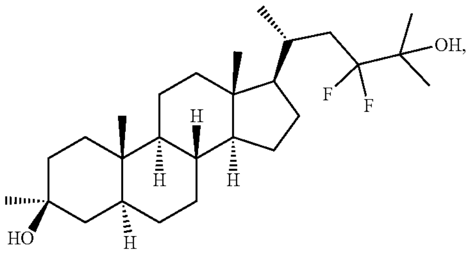

wherein the CNS-related condition is an adjustment disorder, an anxiety disorder, an obsessive-compulsive disorder, a posttraumatic stress disorder, social phobia, a cognitive disorder, a dissociative disorder, an eating disorder, a mood disorder, schizophrenia, a schizoaffective disorder, a sleep disorder, a substance abuse-related disorder, a personality disorder, autism spectrum disorder, a neurodevelopmental disorder, pain, a seizure disorder, stroke, traumatic brain injury, a movement disorder or tinnitus.

2. The method of claim 1, wherein the compound is selected from the group consisting of:

1-11

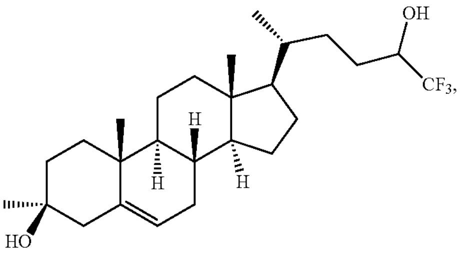

1-12

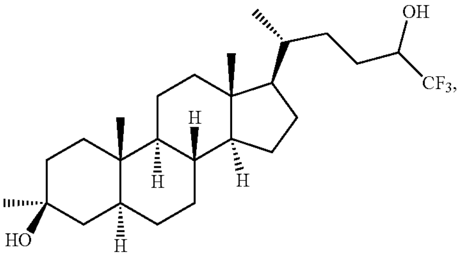

-continued 1-15

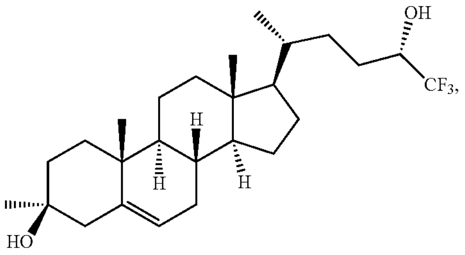

1-16

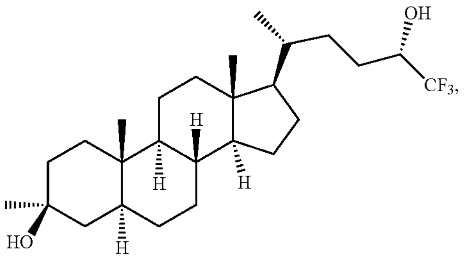

1-17

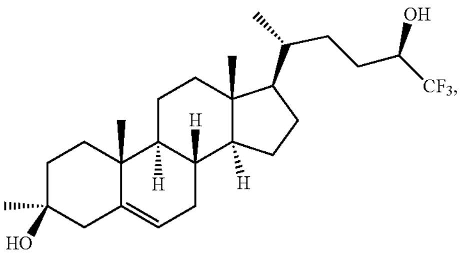

and 1-18

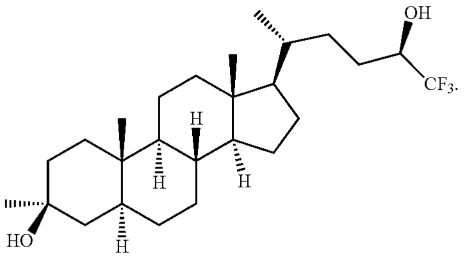

3. The method of claim 1, wherein the compound is selected from the group consisting of:

2-4

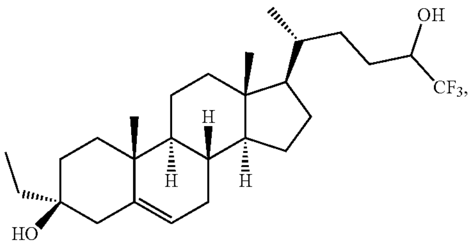

-continued
2-5
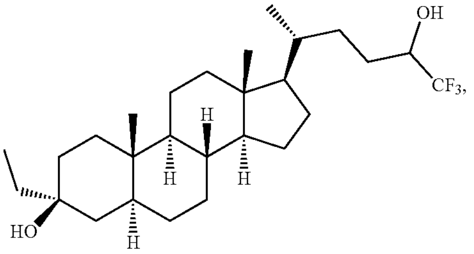
,
2-9
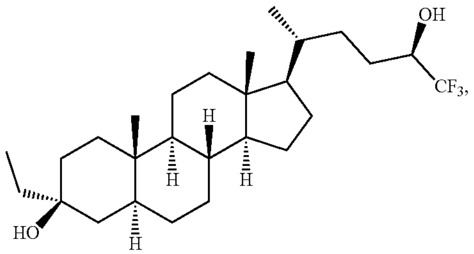
, and
2-10
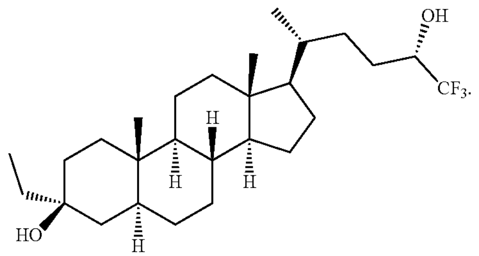
.
4. The method of claim 1, wherein the compound is selected from the group consisting of
3-2
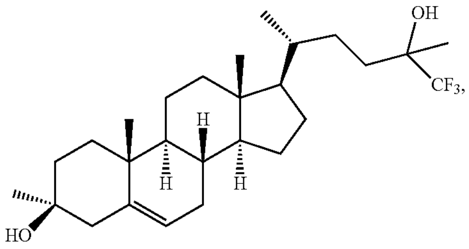
,
3-3
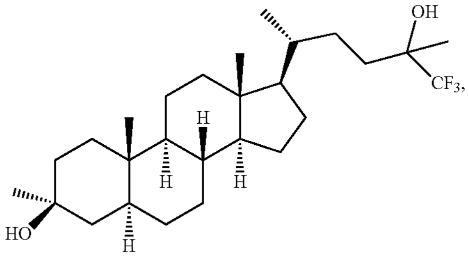
,
-continued
3-7
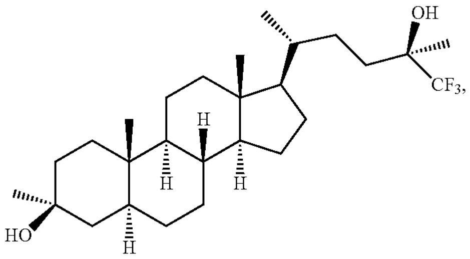
, and
3-8
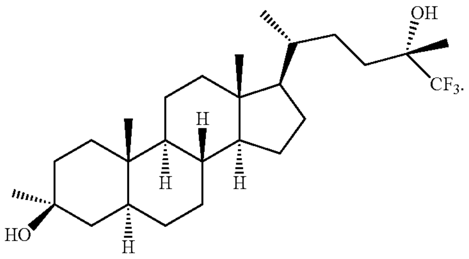
.
5. The method of claim 1, wherein the compound is selected from the group consisting of:
4-6
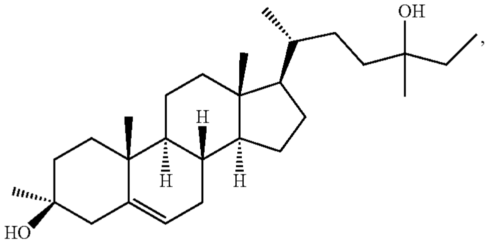
,
4-7
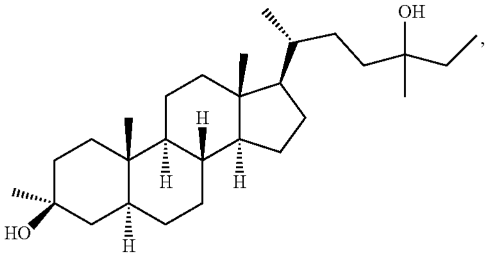
,
4-9
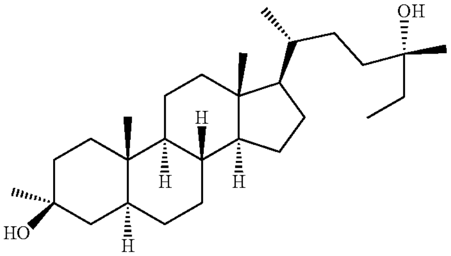
, and -continued
4-10
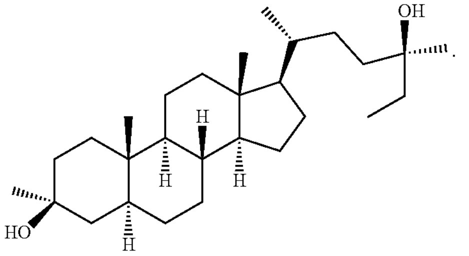
6. The method of claim 1, wherein the compound is selected from the group consisting of:
5-2
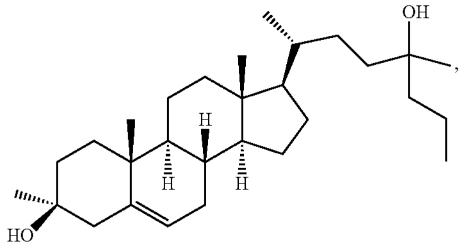
5-3
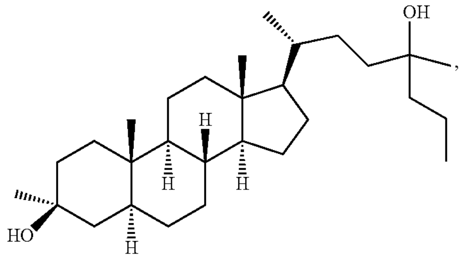
5-5
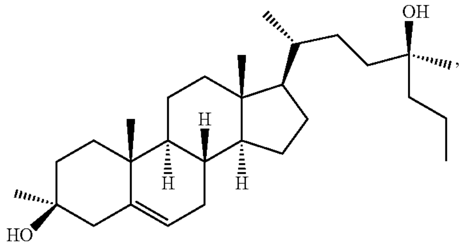
5-6
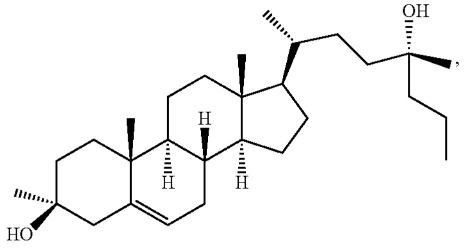
-continued
5-7
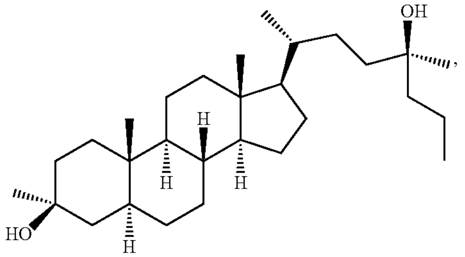
and
5-8
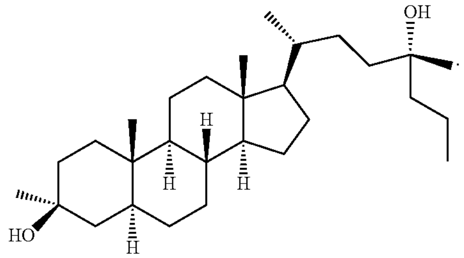
7. The method of claim 1, wherein the compound is selected from the group, consisting of:
6-2
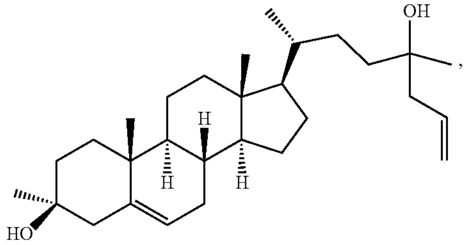
6-3
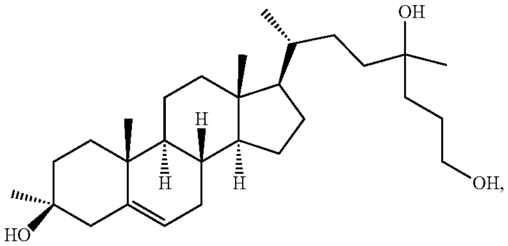
6-6
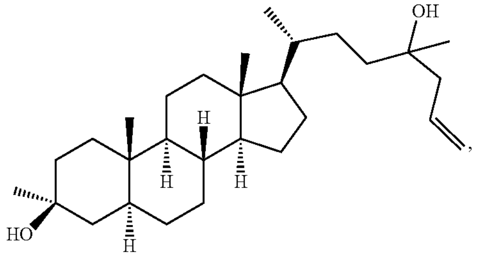

-continued
6-7
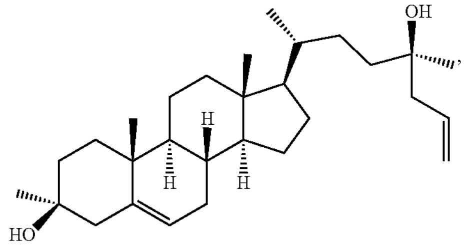
6-8
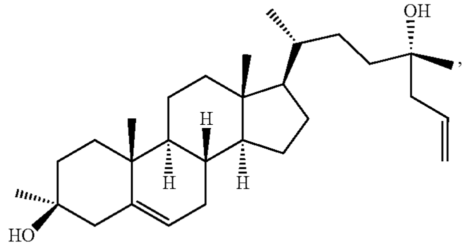
6-9
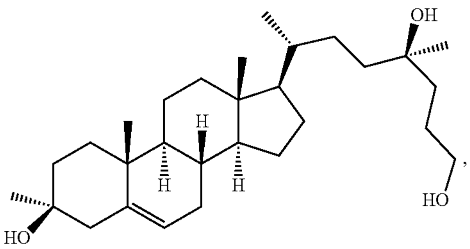
6-10
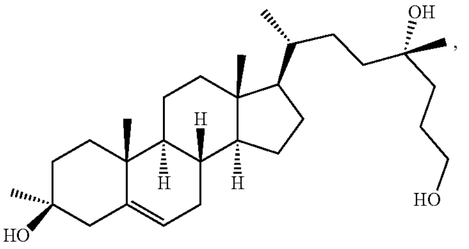
6-11
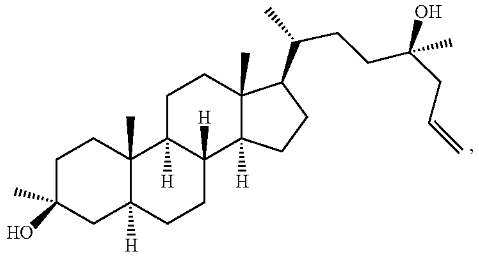
6-12
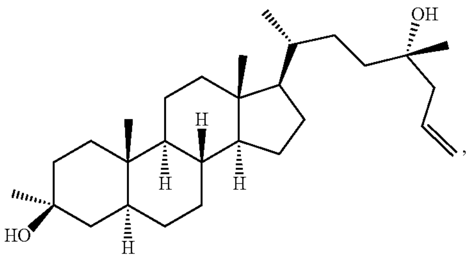
-continued
6-13
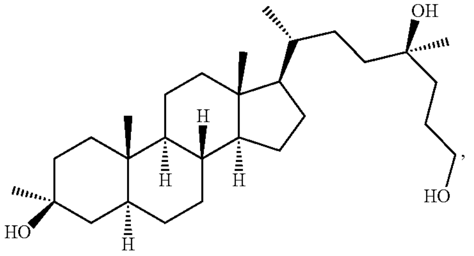
6-14
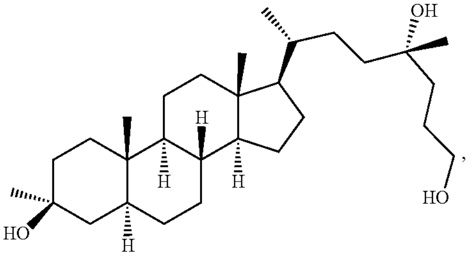
6-15
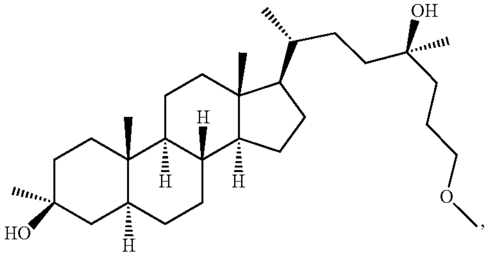
6-16
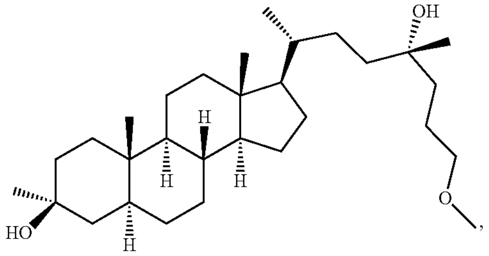
6-17
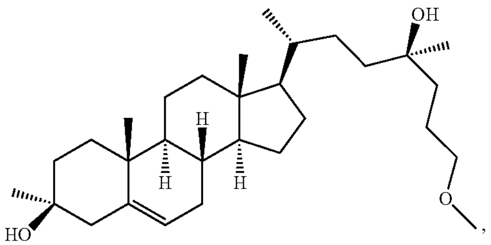
and
6-18
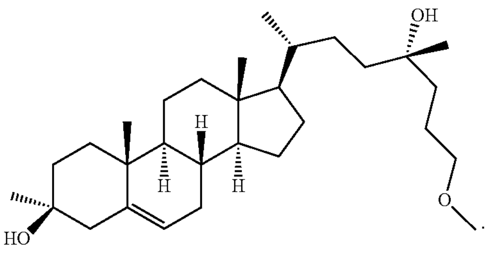
8. The method of claim 1, wherein the compound is selected from the group consisting of:

7-2
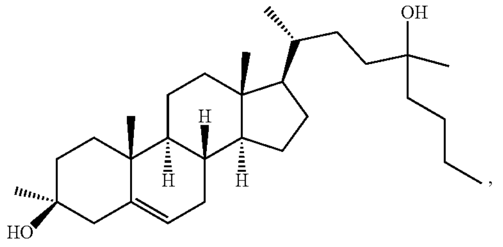
7-3
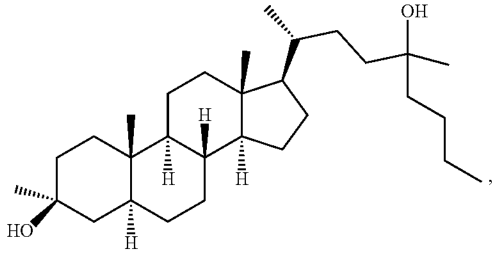
7-4
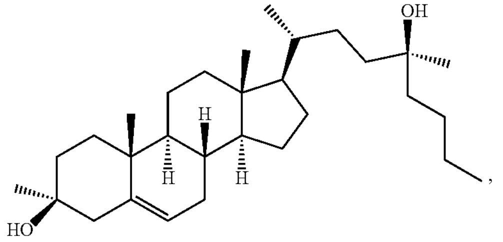
7-5
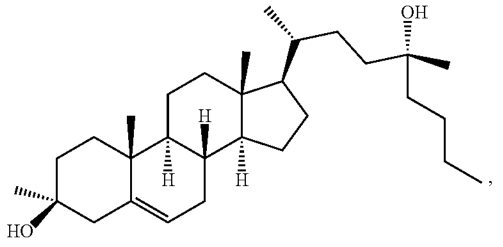
7-6
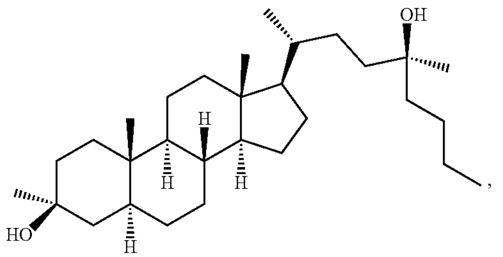
and
7-7
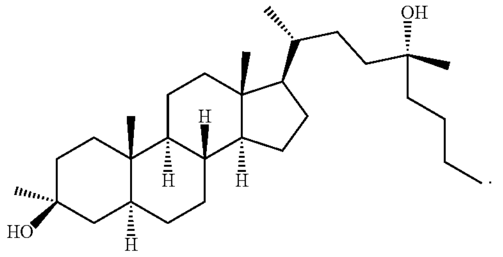
9. The method of claim 1, wherein the compound is selected from the group consisting of:
8-2
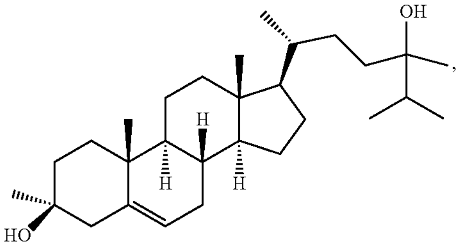
8-3
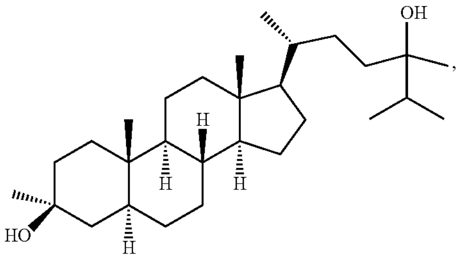
8-5
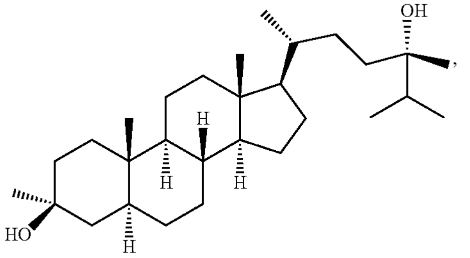
and
8-6
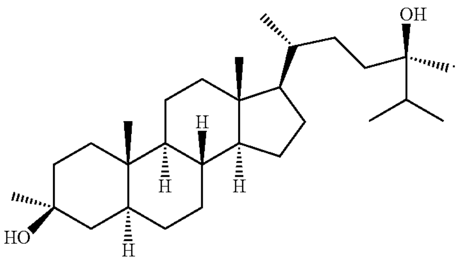
10. The method of claim 1, wherein the compound is selected from the group consisting of:
9-2
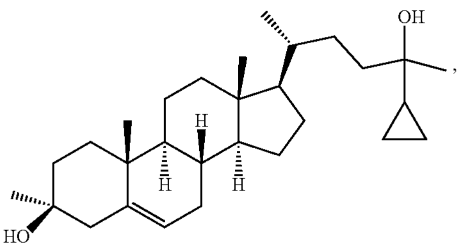

-continued
9-3
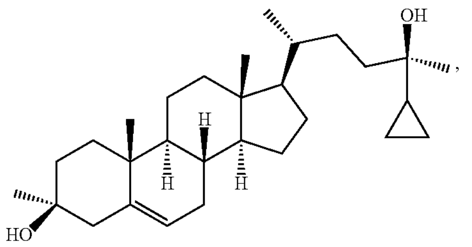
9-4
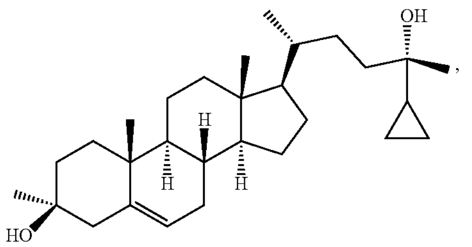
9-6
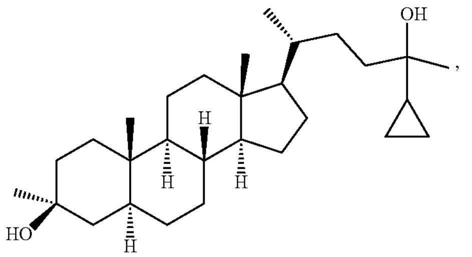
9-7
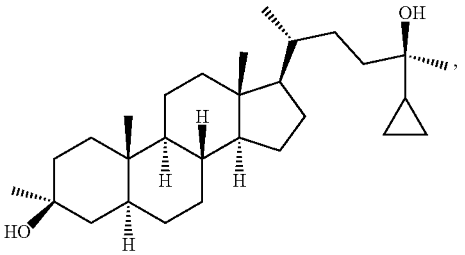
and
9-8
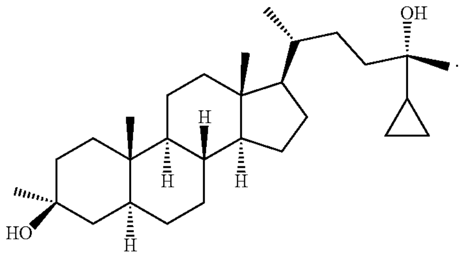
11. The method of claim 1, wherein the compound is selected from the group consisting of:
10-2
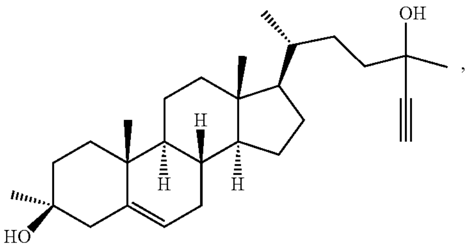
10-3
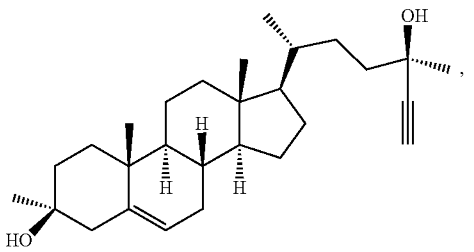
10-4
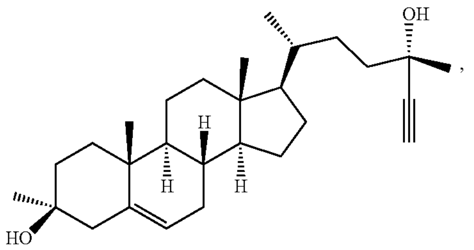
10-6
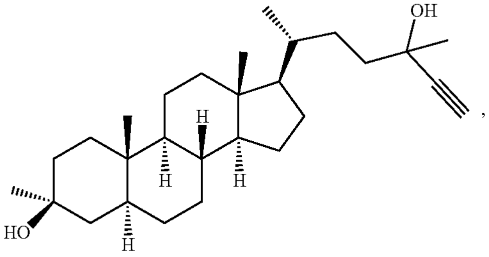
10-8
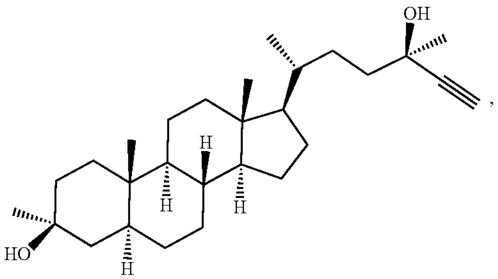
10-9
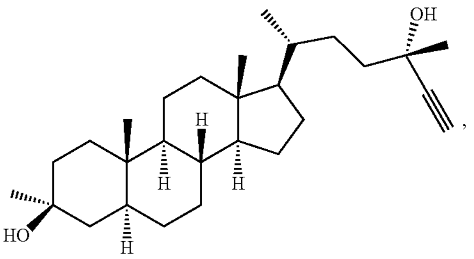

-continued
10-7
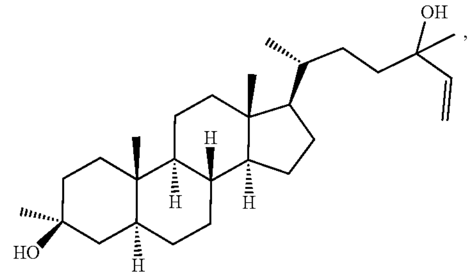,
10-10
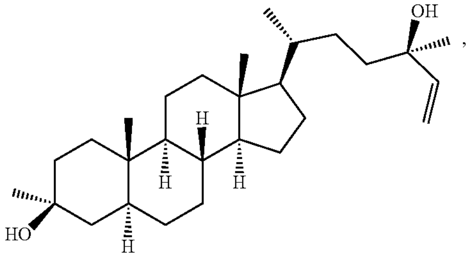,
10-11
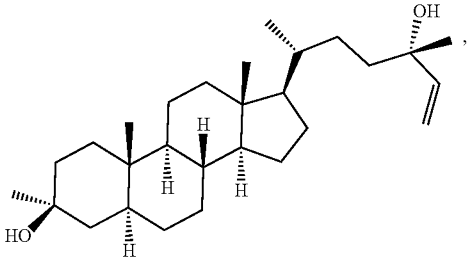,
10-12
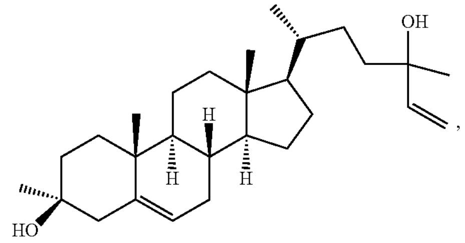,
10-12A
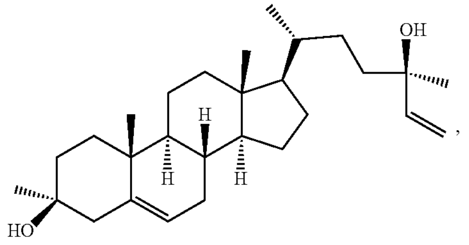,
10-12B
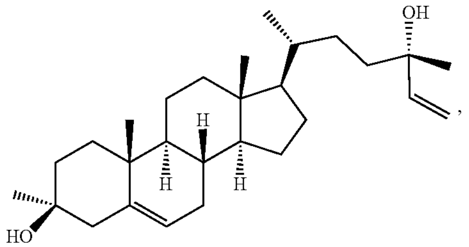,
-continued
10-13
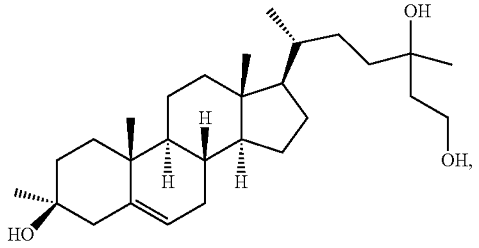,
10-14
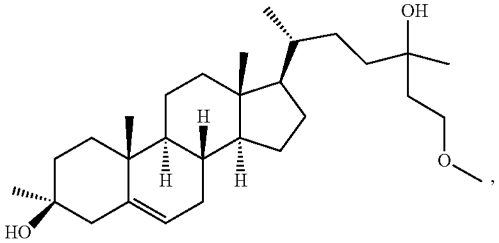,
10-16
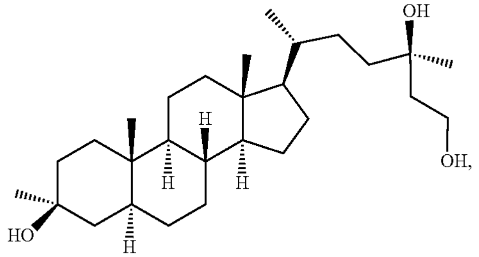,
10-15
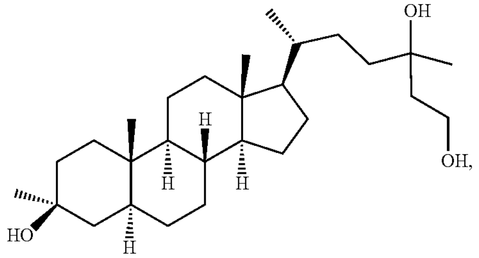,
10-17
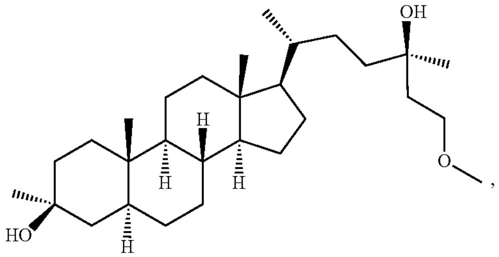,
10-18
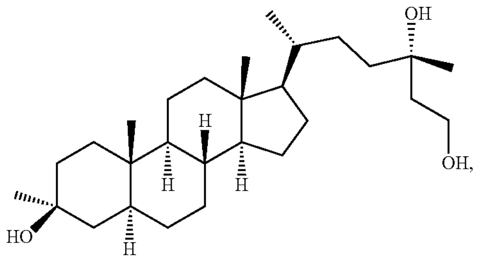, -continued
10-19
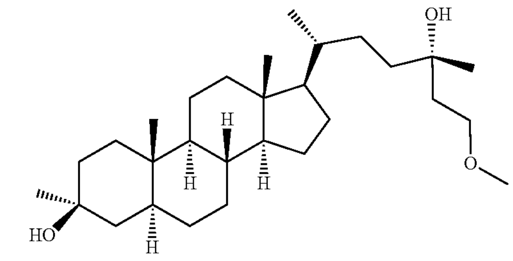
,
10-20
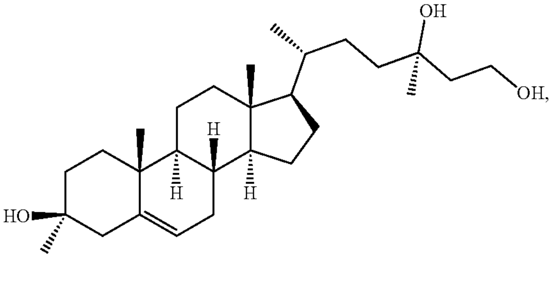
10-21
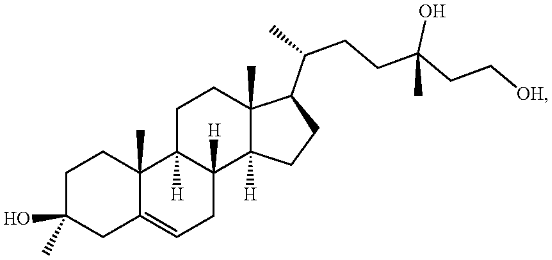
10-22
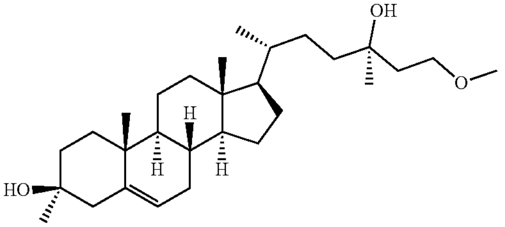
, and
10-23
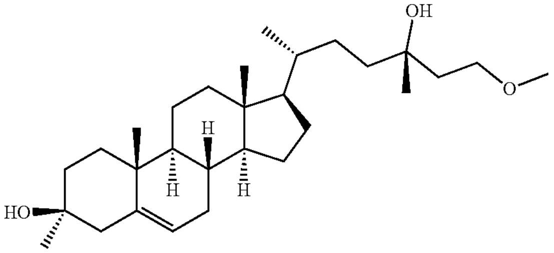
.
11-13
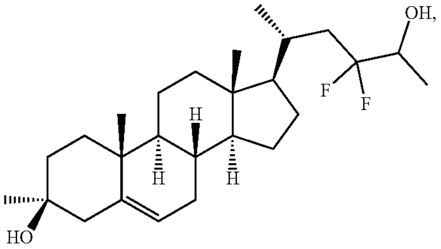
11-14
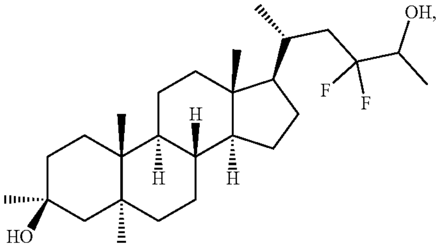
11-17
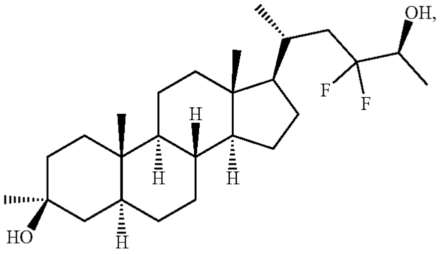
11-18
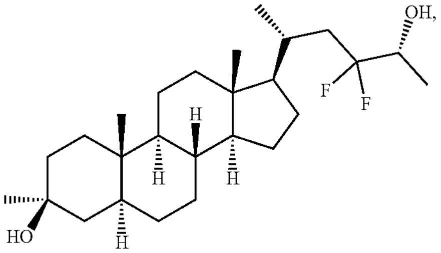
11-19
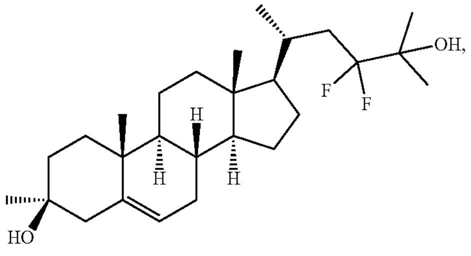
and
11-20
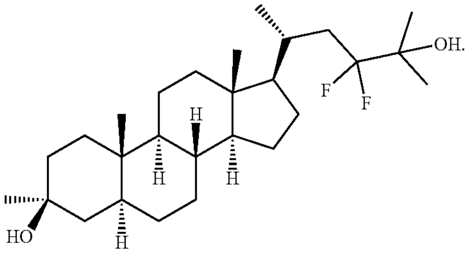
12. The method of claim 1, wherein the compound is selected from the group consisting of:
* * * * *